US008674095B2

(12) United States Patent
Campbell et al.

(10) Patent No.: US 8,674,095 B2
(45) Date of Patent: *Mar. 18, 2014

(54) COMPOUNDS FOR TREATING NEUROPSYCHIATRIC CONDITIONS

(75) Inventors: David Campbell, San Diego, CA (US); Sergio G. Durón, San Diego, CA (US); Benedikt Vollrath, San Diego, CA (US); Warren Wade, San Diego, CA (US)

(73) Assignee: Afraxis Holdings, Inc., La Jolla, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/140,694

(22) PCT Filed: Dec. 18, 2009

(86) PCT No.: PCT/US2009/068855
§ 371 (c)(1),
(2), (4) Date: Sep. 29, 2011

(87) PCT Pub. No.: WO2010/071846
PCT Pub. Date: Jun. 24, 2010

(65) Prior Publication Data
US 2012/0046283 A1 Feb. 23, 2012

Related U.S. Application Data

(60) Provisional application No. 61/286,317, filed on Dec. 14, 2009, provisional application No. 61/250,262, filed on Oct. 9, 2009, provisional application No. 61/139,498, filed on Dec. 19, 2008, provisional application No. 61/139,477, filed on Dec. 19, 2008.

(51) Int. Cl.
*C07D 487/00* (2006.01)

(52) U.S. Cl.
USPC .......................................................... 544/279

(58) Field of Classification Search
None
See application file for complete search history.

(56) References Cited

U.S. PATENT DOCUMENTS

| | | | |
|---|---|---|---|
| 5,945,422 | A | 8/1999 | Doherty et al. |
| 8,372,970 | B2 * | 2/2013 | Vollrath et al. ............... 544/117 |
| 2002/0107171 | A1 | 8/2002 | Price et al. |
| 2005/0182078 | A1 | 8/2005 | Barvian et al. |
| 2010/0317715 | A1 | 12/2010 | Vollrath et al. |
| 2011/0217280 | A1 | 9/2011 | Vollrath et al. |
| 2012/0184547 | A1 | 7/2012 | Lichter et al. |
| 2012/0270844 | A1 | 10/2012 | Lichter et al. |
| 2012/0283296 | A1 | 11/2012 | Campbell et al. |
| 2013/0035335 | A1 | 2/2013 | Vollrath et al. |
| 2013/0059824 | A1 | 3/2013 | Lichter et al. |

FOREIGN PATENT DOCUMENTS

| | | |
|---|---|---|
| WO | WO-96-34867 | 11/1996 |
| WO | WO-01-44258 | 6/2001 |
| WO | WO 02-064594 | 8/2002 |
| WO | WO-2005-034869 | 4/2005 |
| WO | WO-2006-082492 | 8/2006 |
| WO | WO-2007-076092 | 7/2007 |
| WO | WO-2008-034008 | 3/2008 |
| WO | WO-2008-051757 | 5/2008 |
| WO | WO-2008-055842 | 5/2008 |
| WO | WO-2009/086202 A2 | 7/2009 |
| WO | WO-2009/086202 A3 | 7/2009 |
| WO | WO-2009/086204 A2 | 7/2009 |
| WO | WO-2011/009097 A2 | 1/2011 |
| WO | WO-2011/009097 A9 | 1/2011 |
| WO | WO-2011/044264 A2 | 4/2011 |
| WO | WO-2011/044264 A9 | 4/2011 |
| WO | WO-2011-044535 | 4/2011 |
| WO | WO-2011/044537 A2 | 4/2011 |
| WO | WO-2011/044537 A9 | 4/2011 |
| WO | WO-2011/063415 A2 | 5/2011 |
| WO | WO-2011/063415 A9 | 5/2011 |
| WO | WO-2011/090666 A2 | 7/2011 |
| WO | WO-2011/090666 A9 | 7/2011 |
| WO | WO-2011/156640 A2 | 12/2011 |
| WO | WO-2011/156640 A3 | 12/2011 |
| WO | WO-2011/156646 A2 | 12/2011 |
| WO | WO-2011/156646 A3 | 12/2011 |
| WO | WO-2011/156775 A2 | 12/2011 |
| WO | WO-2011/156775 A3 | 12/2011 |
| WO | WO-2011/156780 A2 | 12/2011 |
| WO | WO-2011/156780 A3 | 12/2011 |
| WO | WO-2011/156786 A2 | 12/2011 |
| WO | WO-2011/156786 A3 | 12/2011 |
| WO | WO-2011/156786 A8 | 12/2011 |
| WO | WO-2011/159945 A2 | 12/2011 |
| WO | WO-2011/159945 A9 | 12/2011 |
| WO | WO-2013/043232 A2 | 3/2013 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Black et al., "Pathology of layer V pyramidal neurons in the prefrontal cortex of patients with schizophrenia," Am J Psychiatry, (2004) 161:742-744.
Costa et al., "Learning deficits, but normal development and tumor predisposition, in mice lacking exon 23a of Nf1," Nature Genet. 27, 399-405 (2001).
Dickstein et al., "Changes in the structural complexity of the aged brain," Aging Cell (2007) 6:275-284.
Hajszan et al., "Short-term treatment with the antidepressant fluoxetine triggers pyramidal dendritic spine synapse formation in rat hippocampus," Eur J Neurosci, (2005) 21 :1299-1303.
Hayashi et al., "Altered cortical synaptic morphology and impaired memory consolidation in forebrain-specific dominant-negative PAK transgenic mice," Neuron (2004) 42(5):773-787.

(Continued)

*Primary Examiner* — Jeffrey Murray
(74) *Attorney, Agent, or Firm* — Morrison & Foerster LLP

(57) ABSTRACT

Provided herein are pyrido[2,3-D]pyrimidin-7(8H)-one compounds and compositions useful as PAK inhibitors. Also provided herein are methods of utilizing these compounds for the treatment of neuropsychiatric conditions. The compounds modulate dendritic spine morphology and/or synaptic function.

7 Claims, 1 Drawing Sheet

(56) References Cited

OTHER PUBLICATIONS

Hikida et al., "Dominant-negative DISC1 transgenic mice display schizophrenia-associated phenotypes detected by measures translatable to humans," (2007), Proc Natl Acad Sci USA 104(36):14501-14506.

Knafo et al., Widespread changes in dendritic spines in a model of Alzheimer's disease, Cerebral Cortex 19(3):586-92 (2009).

Kreis et al., "The p21-activated kinase 3 implicated in mental retardation regulates spine morphogenesis through a Cdc42-dependent pathway," J Biol Chem (2007) 282(29):21497-21506.

Neely et al., "Cortical regulation of dopamine depletion-induced dendritic spine loss in striatal medium spiny neurons," Neuroscience (2007) 149(2): 457-464.

Penzes et al., "Rapid induction of dendritic spine morphogenesis by trans-synaptic ephrinB-EphB receptor activation of the Rho-GEF kalirin," Neuron (2003) 37:263-274.

Science IP Search Report dated Oct. 27, 2011.

Van Riezen et al. "Effects of psychotropic drugs on the behavior and neurochemistry of olfactory bulbectomized rats," (1990), Pharmacol Ther, 47(1):21-34.

Wong, "Modulation of dendritic spines in epilepsy: cellular mechanisms and functional implications," Epilepsy and Behavior (2005) 7:569-577.

Young et al., "Progressive impairment in olfactory working memory in a mouse model of Mild Cognitive Impairment," (2009), Neurobiology of Aging, 30:1430-1443.

Yu et al., "Enzyme-linked immunosorbent assay for the determination of p21-activated kinase activity," (2001) J. Biochem (Tokyo) 129(2): 243-251.

PCT/US2009/068855 Search Report dated Jun. 30, 2011.

PCT/US2010/052106 Search Report dated Jun. 23, 2011.

Written Opinion of the International Searching Authority mailed Sep. 14, 2010 for PCT Application PCT/US2009/068855 filed on Dec. 18, 2009, five pages.

U.S. Appl. No. 13/519,299, filed Dec. 21, 2010, by Lichter et al.
U.S. Appl. No. 13/703,326, filed Jun. 16, 2011, by Lichter et al.
U.S. Appl. No. 13/702,572, filed Jun. 9, 2011, by Campbell et al.
U.S. Appl. No. 13/702,573, filed Jun. 10, 2011, by Campbell et al.
U.S. Appl. No. 13/702,963, filed Jun. 10, 2011, by Campbell et al.
U.S. Appl. No. 13/702,560, filed Jun. 9, 2011, by Campbell et al.
U.S. Appl. No. 13/702,969, filed Jun. 10, 2011, by Campbell et al.
U.S. Appl. No. 13/708,886, filed Dec. 7, 2012, by Campbell et al.
U.S. Appl. No. 13/668,079, filed Nov. 2, 2012, by Campbell et al.

\* cited by examiner

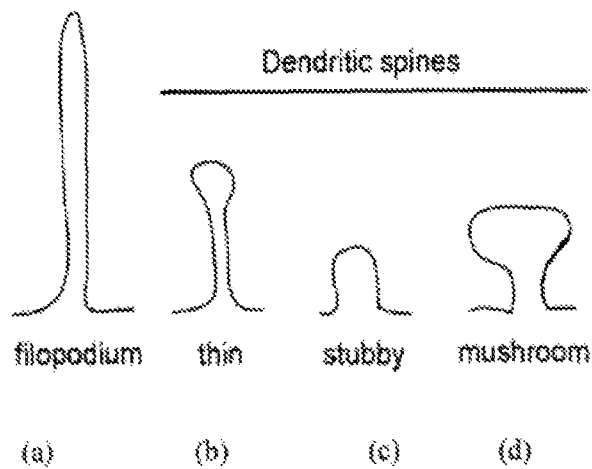
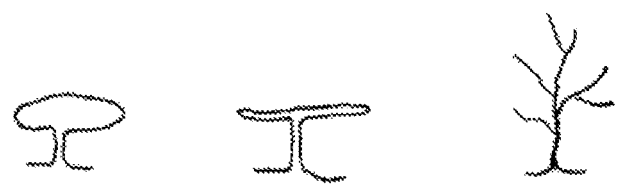

COMPOUNDS FOR TREATING NEUROPSYCHIATRIC CONDITIONS

CROSS-REFERENCE

This application is filed pursuant to 35 U.S.C. §371 as a United States National Phase Application of International Application No. PCT/US09/68855, filed Dec. 18, 2009, which claims the benefit of U.S. Provisional Application No. 61/139,477, filed Dec. 19, 2008, U.S. Provisional Application No. 61/139,498, filed Dec. 19, 2008, U.S. Provisional Application No. 61/250,262, filed Oct. 9, 2009; and U.S. Provisional Application No. 61/286,317, filed Dec. 14, 2009; each of which is incorporated herein by reference in its entirety.

BACKGROUND OF THE INVENTION

Neuropsychiatric conditions (NCs) are characterized by a variety of debilitating affective and cognitive impairments. For example, in schizophrenia, one of the most common psychotic disorders, individuals may suffer from hallucinations, disorders of movement, and the inability to initiate plans, speak, or express emotion. Cognitive deficits in schizophrenia include problems with attention, memory, and the executive functions that allow us to plan and organize. Other NCs include, e.g., mood disorders, age-related cognitive decline, and neurological disorders (e.g., epilepsy and Huntington's disease). The effects of NCs are devastating to the quality of life of those afflicted as well as that of their families. Moreover, NCs impose an enormous health care burden on society. A number of NCs, as well as other conditions that affect cognitive function, have been associated with alterations in the morphology and/or density of dendritic spines, membranous protrusions from dendritic shafts of neurons that serve as highly specialized structures for the formation, maintenance, and function of synapses.

SUMMARY OF THE INVENTION

Described herein are compounds, compositions and methods for treating an individual suffering from a neuropsychiatric condition (e.g., schizophrenia, Fragile X Syndrome (FXS), clinical depression, age-related cognitive decline, Mild Cognitive Impairment, Huntington's disease, Parkinson's disease, Alzheimer's disease, epilepsy, autism spectrum disorders, mental retardation, Down's syndrome or the like) by administering to an individual a pharmaceutical composition comprising a therapeutically effective amount of an inhibitor of a p21-activated kinase (PAK), e.g., an inhibitor of PAK1, PAK2, PAK3 or PAK-4, as described herein. PAK activation is shown to play a key role in spine morphogenesis. In some instances, attenuation of PAK activity reduces, prevents or reverses defects in spine morphogenesis. In some embodiments, inhibitors of one or more of Group I PAKs (PAK1, PAK2 and/or PAK3) and/or Group II PAKs (PAK-4, PAK5 and/or PAK6) are administered to rescue defects in spine morphogenesis in individuals suffering from a condition in which dendritic spine morphology, density, and/or function are aberrant, including but not limited to abnormal spine density, spine size, spine shape, spine plasticity, spine motility or spine plasticity.

Provided herein, in some embodiments, are compounds having the structure of Formula V or pharmaceutically acceptable salt or N-oxide thereof:

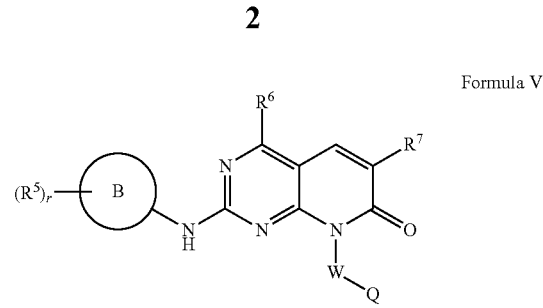

Formula V wherein:

W is a bond;

$R^6$ is H, or halogen;

$R^7$ is H, halogen, CN, OH, substituted or unsubstituted alkyl, substituted or unsubstituted alkoxy, —C(=O)N$(R^{10})_2$, $CO_2R^{10}$, $N(R^{10})_2$, acyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Q is substituted or unsubstituted cycloalkyl or heterocycloalkyl fused to ring A;

ring A is substituted or unsubstituted aryl or heteroaryl substituted with 0-4 $R^4$;

each $R^4$ is independently halogen, —CN, —NO$_2$, —OH, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$), —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

$R^8$ is H or substituted or unsubstituted alkyl;

$R^9$ is substituted or unsubstituted alkyl, substituted or unsubstituted cycloalkyl, substituted or unsubstituted aryl or substituted or unsubstituted heteroaryl each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;

ring B is aryl or heteroaryl substituted with $R^5$;

each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

r is 0-8;

provided that when Q is unsubstituted indane, tetrahydronaphthalene or fluorene, and $R^6$ is H, ring B is not unsubstituted phenyl and $R^5$ is not para substituted piperidinyl, pyrazolyl or methylpiperazinyl.

In some embodiments, the compound of Formula V has the structure of Formula VI:

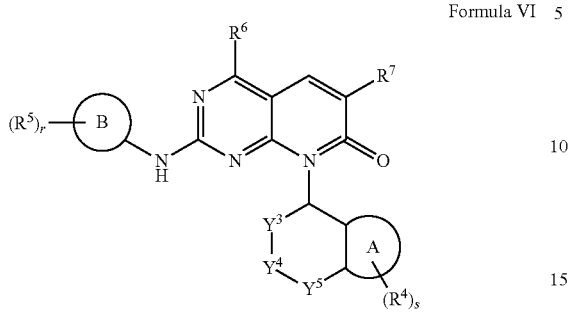

Formula VI wherein:
each of $Y^3$, $Y^4$ and $Y^5$ are independently a bond, O, N—$R^{1a}$, $CR^1R^2$, $SO_2$, or C=O;
$R^{1a}$ is H or substituted or unsubstituted alkyl;
$R^1$ and $R^2$ are each independently H, halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
s is 0-4.

In some embodiments, the compound of Formula V has the structure of Formula VII:

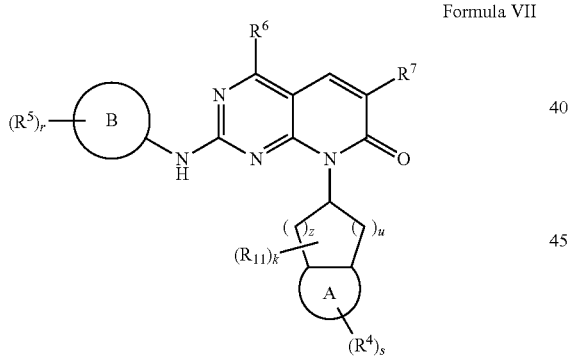

Formula VII wherein:
ring A is an aryl or heteroaryl substituted with $R^4$;
each $R^4$ is independently halogen, —CN, —NO$_2$, —OH, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^9$, —NR$^{10}$C(=O)OR$^9$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
$R^8$ is H or substituted or unsubstituted alkyl;
$R^9$ is substituted or unsubstituted alkyl, substituted or unsubstituted cycloalkyl, substituted or unsubstituted aryl or substituted or unsubstituted heteroaryl;

each $R^{10}$ is independently H, substituted or unsubstituted alkyl, substituted or unsubstituted cycloalkyl, substituted or unsubstituted aryl or substituted or unsubstituted heteroary, or two $R^{10}$ together with the nitrogen to which they are attached form a heterocycle;
each $R^{11}$ is independently hydrogen, halogen, —CN, —NO$_2$, —OH, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^9$, —NR$^{10}$C(=O)OR$^9$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl; or two $R^{11}$ together with the carbon atom to which they are attached form C=O;
s is 0-4;
k is 1-4;
z is 0 or 1;
u is 1, 2 or 3;
provided that z+u≠1;
ring B is an aryl or heteroaryl substituted with $R^5$;
each $R^5$ is independently halogen, —CN, —NO$_2$, —OH, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^9$, —NR$^{10}$C(=O)OR$^9$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
r is 0-8;
$R^6$ is H, or halogen;
$R^7$ is H, halogen, CN, OH, substituted or unsubstituted alkyl, substituted or unsubstituted alkoxy, —C(=O)N(R$^{10}$)$_2$, CO$_2$R$^{10}$, N(R$^{10}$)$_2$, acyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments of Formula V, VI or VII, ring A is heteroaryl ring comprising 1-3 nitrogen atoms, an oxygen atom, a sulfur atom, or any combination thereof. In some embodiments of Formula V, VI or VII, ring A is a phenyl ring.

In some embodiments, a compound of Formula VII has a structure of Formula VIIA, Formula VIIB, Formula VIIC, Formula VIID, Formula VIIE, Formula VIIF, Formula VIIG or Formula VIIH:

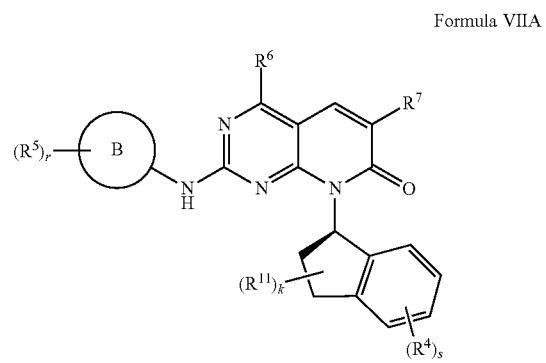

Formula VIIA

Formula VIIB
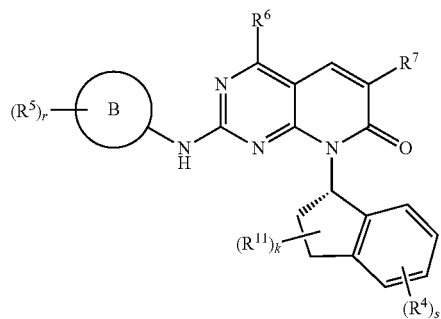

Formula VIIC
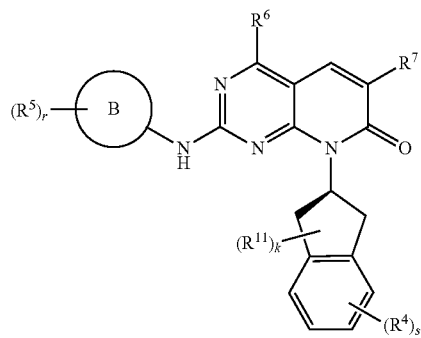

Formula VIID
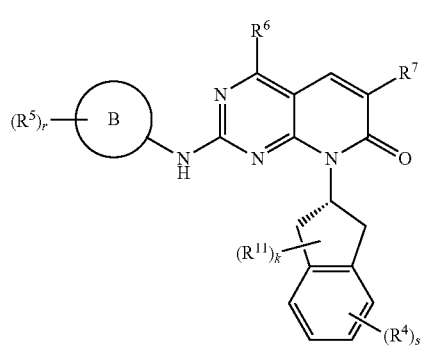

Formula VIIE
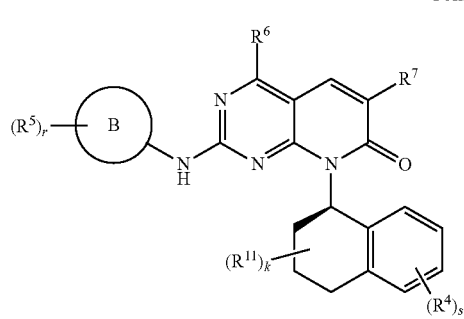

Formula VIIF
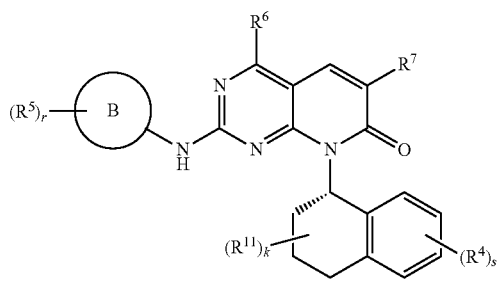

Formula VIIG
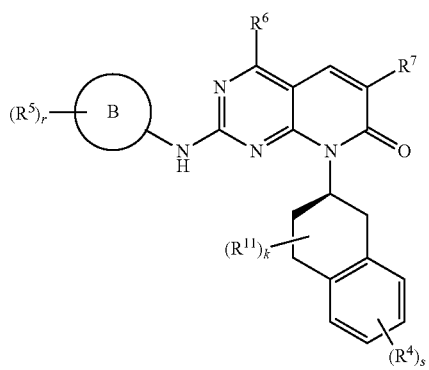

Formula VIIH
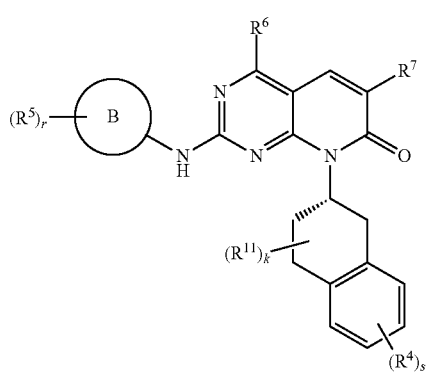

In some embodiments of Formula VII, $R^{11}$ is H, halogen, substituted or unsubstituted alkyl, substituted or unsubstituted alkoxy or)$N(R^{10})_2$. In some embodiments of Formula VII, $R^{11}$ is H. In some embodiments of Formula VII, each $R^4$ is independently halogen, substituted or unsubstituted alkyl, substituted or unsubstituted alkoxy, substituted or unsubstituted cycloalkyl or substituted or unsubstituted heterocycloalkyl. In some embodiments of Formula VII, each $R^4$ is independently Cl, F, $CF_3$ or OMe.

Provided herein, in some embodiments, are compound having the structure of Formula VIII or pharmaceutically acceptable salt or N-oxide thereof:

Formula VIII

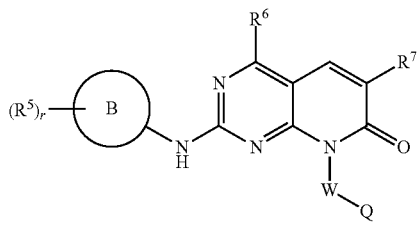

W is a bond;
R⁶ is H, halogen, —CN, —OH, substituted or unsubstituted alkoxy, —N(R¹⁰)₂, substituted or unsubstituted heteroalkyl, substituted or unsubstituted cycloalkyl, substituted or unsubstituted aryl or substituted or unsubstituted heteroaryl;
R⁷ is H, halogen, —CN, —OH, substituted or unsubstituted alkyl, substituted or unsubstituted alkoxy, —C(=O)N(R¹⁰)₂, —CO₂R¹⁰, —N(R¹⁰)₂, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
Q is

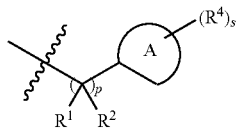

R¹ is H or substituted or unsubstituted alkyl;
R² is substituted or unsubstituted alkyl, or R¹ and R² together with the carbon to which they are attached form a C₃-C₆ cycloalkyl ring;
p is 1, 2 or 3;
ring A is aryl substituted with R⁴;
each R⁴ is independently halogen, —CN, —NO₂, —OH, —OCF₃, —OCF₂H, —CF₃, —SR⁸, —S(=O)R⁹, —S(=O)₂R⁹, —NR¹⁰S(=O)₂R⁹, —S(=O)₂N(R¹⁰)₂, —C(=O)R⁹, —OC(=O)R⁹, —CO₂R¹⁰, —N(R¹⁰)₂, —C(=O)N(R¹⁰)², —NR¹⁰C(=O)R¹⁰, —N R¹⁰C(=O)OR¹⁰, —NR¹⁰C(=O)N(R¹⁰)₂, substituted or unsubstituted alkyl, substituted or unsubstituted alkoxy, substituted or unsubstituted heteroalkyl, substituted or unsubstituted cycloalkyl or substituted or unsubstituted heterocycloalkyl;
R⁸ is H or substituted or unsubstituted alkyl;
R⁹ is substituted or unsubstituted alkyl, substituted or unsubstituted cycloalkyl, substituted or unsubstituted aryl or substituted or unsubstituted heteroaryl
each R¹⁰ is independently H, substituted or unsubstituted alkyl, substituted or unsubstituted cycloalkyl, substituted or unsubstituted aryl or substituted or unsubstituted heteroaryl, or two R¹⁰ together with the atoms to which they are attached form a heterocycle;
s is 0-4;
ring B is aryl or heteroaryl substituted with R⁵;
each R⁵ is independently halogen, —CN, —NO₂, —OH, —SR⁸, —S(=O)R⁹, —S(=O)₂R⁹, NR¹⁰S(=O)₂R⁹, —S(=O)₂N(R¹⁰)₂, —C(=O)R⁹, —OC(=O)R⁹, —CO₂R¹⁰, —N(R¹⁰)₂, —C(=O)N(R¹⁰)₂, —NR¹⁰C(=O)R¹⁰, —NR¹⁰C(=O)OR¹⁰, —NR¹⁰C(=O)N(R¹⁰)₂, substituted or unsubstituted alkyl, substituted or unsubstituted alkoxy, substituted or unsubstituted heteroalkyl, substituted or unsubstituted cycloalkyl or substituted or unsubstituted heterocycloalkyl;
r is 0-8;
provided that when s is zero, then R² is not methyl.
In some embodiments of Formula VIII,
W is a bond;
R⁶ is H, halogen, —CN, —OH, substituted or unsubstituted alkoxy, —N(R¹⁰)₂, substituted or unsubstituted heteroalkyl, substituted or unsubstituted cycloalkyl, substituted or unsubstituted aryl or substituted or unsubstituted heteroaryl;
R⁷ is H, halogen, —CN, —OH, substituted or unsubstituted alkyl, substituted or unsubstituted alkoxy, —C(=O)N(R¹⁰)₂, —CO₂R¹⁰, —N(R¹⁰)₂, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
Q is

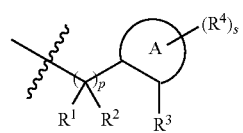

R¹ is H or substituted or unsubstituted alkyl;
R² is substituted or unsubstituted alkyl, or R¹ and R² together with the carbon to which they are attached form a C₃-C₆ cycloalkyl ring;
p is 1, 2 or 3;
ring A is aryl substituted with R³ and R⁴;
R³ is halogen, —CN, —NO₂, —OH, —OCF₃, —OCF₂H, —CF₃, —SR⁸, —S(=O)R⁹, —S(=O)₂R⁹, —NR¹⁰S(=O)₂R⁹, —S(=O)₂N(R¹⁰)₂, —C(=O)R⁹, —OC(=O)R⁹, —CO₂R¹⁰—N(R¹⁰)₂, —C(=O)N(R¹⁰)₂, —NR¹⁰C(=O)R⁹, NR¹⁰C(=O)OR⁹, —NR¹⁰C(=O)N(R¹⁰)₂, substituted or unsubstituted alkyl, substituted or unsubstituted alkoxy, substituted or unsubstituted heteroalkyl, substituted or unsubstituted cycloalkyl or substituted or unsubstituted heterocycloalkyl;
each R⁴ is independently halogen, —CN, —NO₂, —OH, —OCF₃, —OCF₂H, —CF₃, —SR⁸, —S(=O)R⁹, —S(=O)₂R⁹, —NR¹⁰S(=O)₂R⁹, —S(=O)₂N(R¹⁰)₂, —C(=O)R⁹, —OC(=O)R⁹, —CO₂R¹⁰, —N(R¹⁰)₂, —C(=O)N(R¹⁰)₂, —NR¹⁰C(=O)R¹⁰, —NR¹⁰C(=O)OR¹⁰, —NR¹⁰C(=O)N(R¹⁰)₂, substituted or unsubstituted alkyl, substituted or unsubstituted alkoxy, substituted or unsubstituted heteroalkyl, substituted or unsubstituted cycloalkyl or substituted or unsubstituted heterocycloalkyl;
R⁸ is H or substituted or unsubstituted alkyl;
R⁹ is substituted or unsubstituted alkyl, substituted or unsubstituted cycloalkyl, substituted or unsubstituted aryl or substituted or unsubstituted heteroaryl
each R¹⁰ is independently H, substituted or unsubstituted alkyl, substituted or unsubstituted cycloalkyl, substituted or unsubstituted aryl or substituted or unsubstituted heteroaryl, or two R¹⁰ together with the atoms to which they are attached form a heterocycle;

s is 0-4;

ring B is aryl or heteroaryl substituted with $R^5$;

each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

r is 0-8.

In some embodiments of Formula VIII, $R^3$ is halogen, —CN, —NO$_2$, —OH, —OCF$_3$, —OCF$_2$H, —CF$_3$, —SR$^8$, —S(=O)R$^9$, —S(=O)$_2$R$^9$, substituted or unsubstituted alkyl, substituted or unsubstituted alkoxy, substituted or unsubstituted heteroalkyl, substituted or unsubstituted cycloalkyl or substituted or unsubstituted heterocycloalkyl. In some embodiments of Formula VIII, $R^3$ is a chiral sulfoxide and Q is:

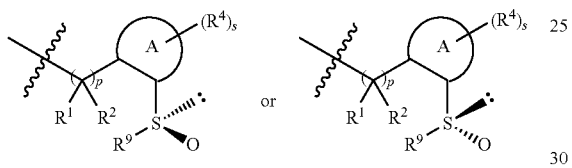

In some embodiments, a compound of Formula VIII has the structure of Formula VIIIA or Formula VIIIB:

Formula VIIIA

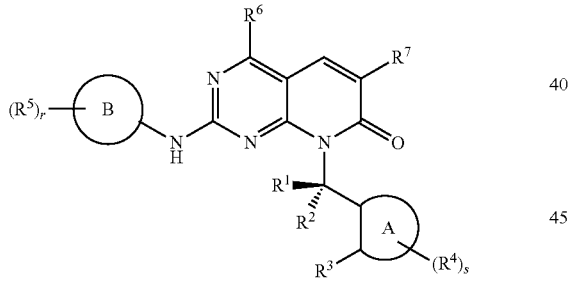

Formula VIIIB

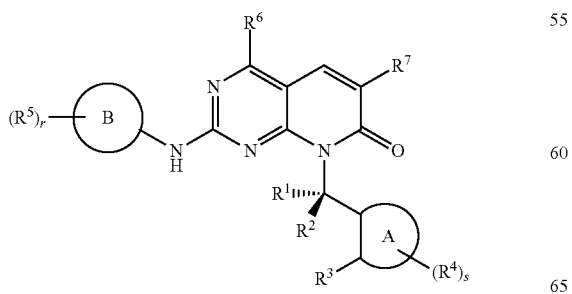

In some embodiments, the compound of Formula VIII has the structure of Formula (IX):

Formula IX

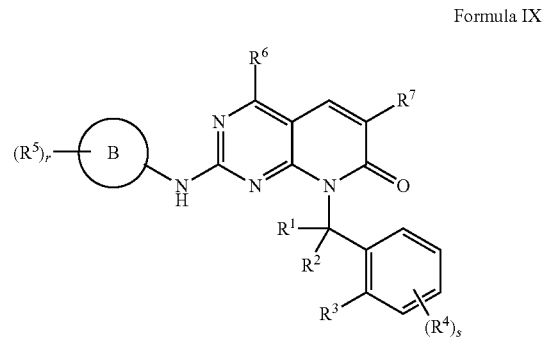

wherein:
  $R^1$ is H or substituted or unsubstituted alkyl;
  $R^2$ is substituted or unsubstituted alkyl; and
  $R^3$ is halogen, alkyl, fluoroalkyl, alkoxy, fluoroalkoxy, SR$^8$, —S(=O)R$^9$, or —S(=O)$_2$R$^9$, substituted or unsubstituted cycloalkyl, substituted or unsubstituted heterocycloalkyl.

In some embodiments of Formula VIII, $R^3$ is F, Cl, SCF$_3$, CF$_3$, OMe, (R) or (S)—S(=O)R$^9$ or —S(O)$_2$R$^9$.

In some embodiments, the compound of Formula IX has the structure of Formula (IXA) or Formula (IXB):

Formula (IXA)

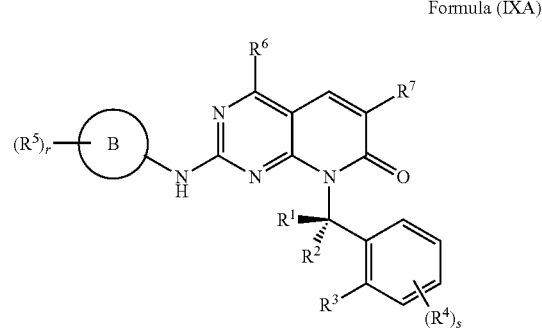

Formula (IXB)

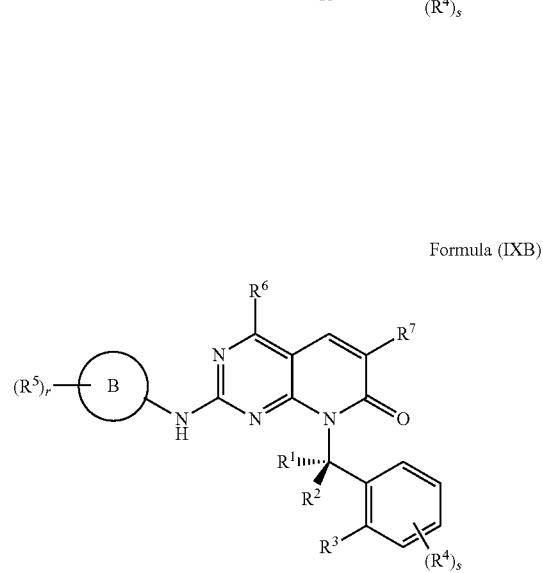

Also provided herein, in some embodiments, are compound having the structure of Formula X or pharmaceutically acceptable salt or N-oxide thereof:

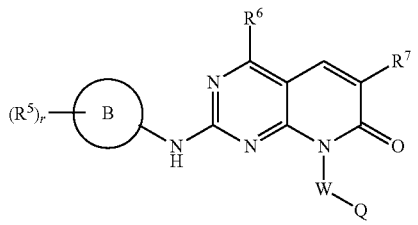

Formula X wherein:
W is a bond;
$R^6$ is H, halogen, —CN, —OH, substituted or unsubstituted alkyl, substituted or unsubstituted alkoxy, —N($R^{10}$)$_2$, substituted or unsubstituted heteroalkyl, substituted or unsubstituted cycloalkyl, substituted or unsubstituted aryl or substituted or unsubstituted heteroaryl;
$R^7$ is H, halogen, —CN, —OH, substituted or unsubstituted alkyl, substituted or unsubstituted alkoxy, —C(=O)N($R^{10}$)$_2$, —CO$_2$$R^{10}$, —N($R^{10}$)$_2$, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
Q is

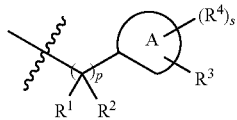

$R^1$ and $R^2$ are each independently H or substituted or unsubstituted alkyl; or $R^1$ and $R^2$ together with the carbon to which they are attached form a $C_3$-$C_6$ cycloalkyl ring;
p is 1, 2 or 3;
ring A is aryl substituted with $R^3$ and $R^4$;
$R^3$ is a substituted or unsubstituted heteroaryl, substituted or unsubstituted cycloalkyl or substituted or unsubstituted heterocycloalkyl attached to ring A via a carbon atom;
each $R^4$ is independently halogen, —CN, —NO$_2$, —OH, —OCF$_3$, —OCF$_2$H, —CF$_3$, —S$R^8$, —S(=O)$R^9$, —S(=O)$_2$$R^9$, —N$R^{10}$S(=O)$_2$$R^9$, —S(=O)$_2$N($R^{10}$)$_2$, —C(=O)$R^9$, —OC(=O)$R^9$, —CO$_2$$R^{10}$, —N($R^{10}$)$_2$, —C(=O)N($R^{10}$)$_2$, —N$R^{10}$C(=O)$R^{10}$, —N$R^{10}$C(=O)O$R^{10}$, —N$R^{10}$C(=O)N($R^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
$R^8$ is H or substituted or unsubstituted alkyl;
$R^9$ is substituted or unsubstituted alkyl, substituted or unsubstituted cycloalkyl, substituted or unsubstituted aryl or substituted or unsubstituted heteroaryl each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;
s is 0-4;
ring B is aryl or heteroaryl substituted with $R^5$;
each $R^5$ is independently halogen, —CN, —NO$_2$, —OH, —S$R^8$, —S(=O)$R^9$, —S(=O)$_2$$R^9$, NR$^{10}$S(=O)$_2$$R^9$, —S(=O)$_2$N($R^{10}$)$_2$, —C(=O)$R^9$, —OC(=O)$R^9$, —CO$_2$$R^{10}$, —N($R^{10}$)$_2$, —C(=O)N($R^{10}$)$_2$, —N$R^{10}$C(=O)$R^{10}$, —N$R^{10}$C(=O)O$R^{10}$, —N$R^{10}$C(=O)N($R^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
r is 0-8.
In some embodiments of Formula X, Q is:

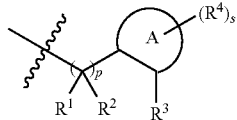

In some embodiments of Formula X, Q is

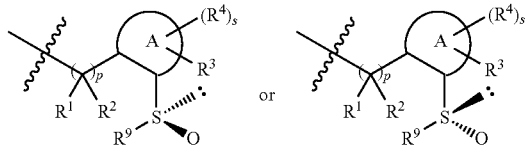

In some embodiments of Formula X, $R^3$ is a $C_3$-$C_6$ cycloalkyl ring, a 5-6-membered heteroaryl ring comprising 1-3 nitrogen atoms, an oxygen atom, a sulfur atom, or any combination thereof, or a 3-6-membered heterocycloalkyl ring comprising 1-3 nitrogen atoms, an oxygen atom, a sulfur atom, or any combination thereof, that is attached to ring via a carbon atom and wherein $R^3$ is further substituted by halogen, cyano, alkyl, alkoxy, —S$R^8$, (R) or (S)—S(O)$R^9$ or —S(O)$_2$$R^9$. In some embodiments of Formula X, $R^1$ and $R^2$ are H.

Also provided herein are methods for treating neuropsychiatric conditions comprising administering to an individual in need thereof a therapeutically effective amount of a compound of Formula VA or pharmaceutically acceptable salt or N-oxide thereof:

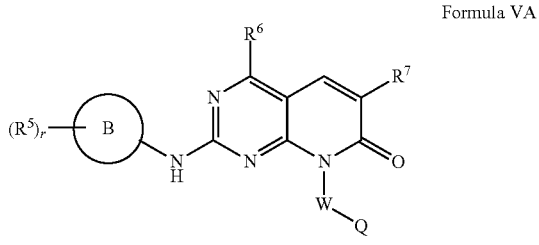

Formula VA wherein:

W is a bond;

R⁶ is H, or halogen;

R⁷ is H, halogen, CN, OH, substituted or unsubstituted alkyl, substituted or unsubstituted alkoxy, —C(=O)N(R¹⁰)₂, CO₂R¹⁰, N(R¹⁰)₂, acyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Q is substituted or unsubstituted cycloalkyl or heterocycloalkyl fused to ring A;

ring A is substituted or unsubstituted aryl or heteroaryl substituted with 0-4 R⁴;

each R⁴ is independently halogen, —CN, —NO₂, —OH, —SR⁸, —S(=O)R⁹, —S(=O)₂R⁹, —NR¹⁰S(=O)₂R⁹, —S(=O)₂N(R¹⁰)₂, —C(=O)R⁹, —OC(=O)R⁹, —CO₂R¹⁰, —N(R¹⁰)₂, —C(=O)N(R¹⁰)₂, —NR¹⁰C(=O)R¹⁰, —NR¹⁰C(=O)OR¹⁰, —NR¹⁰C(=O)N(R¹⁰)₂, substituted or unsubstituted alkyl, substituted or unsubstituted alkoxy, substituted or unsubstituted heteroalkyl, substituted or unsubstituted cycloalkyl or substituted or unsubstituted heterocycloalkyl;

R⁸ is H or substituted or unsubstituted alkyl;

R⁹ is substituted or unsubstituted alkyl, substituted or unsubstituted cycloalkyl, substituted or unsubstituted aryl or substituted or unsubstituted heteroaryl each R¹⁰ is independently H, substituted or unsubstituted alkyl, substituted or unsubstituted cycloalkyl, substituted or unsubstituted aryl or substituted or unsubstituted heteroaryl, or two R¹⁰ together with the atoms to which they are attached form a heterocycle;

ring B is aryl or heteroaryl substituted with R⁵;

each R⁵ is independently halogen, —CN, —NO₂, —OH, —SR⁸, —S(=O)R⁹, —S(=O)₂R⁹, NR¹⁰S(=O)₂R⁹, —S(=O)₂N(R¹⁰)₂, —C(=O)R⁹, —OC(=O)R⁹, —CO₂R¹⁰, —N(R¹⁰)₂, —C(=O)N(R¹⁰)₂, —NR¹⁰C(=O)R¹⁰, —NR¹⁰C(=O)OR¹⁰, —NR¹⁰C(=O)N(R¹⁰)₂, substituted or unsubstituted alkyl, substituted or unsubstituted alkoxy, substituted or unsubstituted heteroalkyl, substituted or unsubstituted cycloalkyl or substituted or unsubstituted heterocycloalkyl; and r is 0-8.

Also provided herein are methods for treating neuropsychiatric conditions comprising administering to an individual in need thereof a therapeutically effective amount of a compound of Formula VIIIC or pharmaceutically acceptable salt or N-oxide thereof:

Formula VIIIC

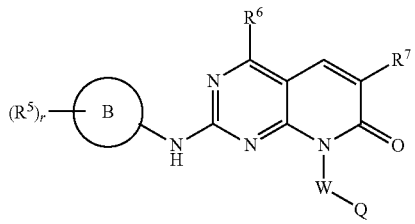

W is a bond;

R⁶ is H, halogen, —CN, —OH, substituted or unsubstituted alkoxy, —N(R¹⁰)₂, substituted or unsubstituted heteroalkyl, substituted or unsubstituted cycloalkyl, substituted or unsubstituted aryl or substituted or unsubstituted heteroaryl;

R⁷ is H, halogen, —CN, —OH, substituted or unsubstituted alkyl, substituted or unsubstituted alkoxy, —C(=O)N(R¹⁰)₂, —CO₂R¹⁰, —N(R¹⁰)₂, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

Q is

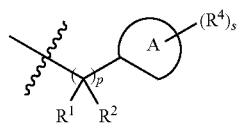

R¹ is H or substituted or unsubstituted alkyl;

R² is substituted or unsubstituted alkyl, or R¹ and R² together with the carbon to which they are attached form a C₃-C₆ cycloalkyl ring;

p is 1, 2 or 3;

ring A is aryl substituted with R⁴;

each R⁴ is independently halogen, —CN, —NO₂, —OH, —OCF₃, —OCF₂H, —CF₃, —SR⁸, —S(=O)R⁹, —S(=O)₂R⁹, —NR¹⁰S(=O)₂R⁹, —S(=O)₂N(R¹⁰)₂, —C(=O)R⁹, —OC(=O)R⁹, —CO₂R¹⁰, —N(R¹⁰)₂, —C(=O)N(R¹⁰)₂, —NR¹⁰C(=O)R¹⁰, —NR¹⁰C(=O)OR¹⁰, —NR¹⁰C(=O)N(R¹⁰)₂, substituted or unsubstituted alkyl, substituted or unsubstituted alkoxy, substituted or unsubstituted heteroalkyl, substituted or unsubstituted cycloalkyl or substituted or unsubstituted heterocycloalkyl;

R⁸ is H or substituted or unsubstituted alkyl;

R⁹ is substituted or unsubstituted alkyl, substituted or unsubstituted cycloalkyl, substituted or unsubstituted aryl or substituted or unsubstituted heteroaryl each R¹⁰ is independently H, substituted or unsubstituted alkyl, substituted or unsubstituted cycloalkyl, substituted or unsubstituted aryl or substituted or unsubstituted heteroaryl, or two R¹⁰ together with the atoms to which they are attached form a heterocycle;

s is 0-4;

ring B is aryl or heteroaryl substituted with R⁵;

each R⁵ is independently halogen, —CN, —NO₂, —OH, —SR⁸, —S(=O)R⁹, —S(=O)₂R⁹, NR¹⁰S(=O)₂R⁹, —S(=O)₂N(R¹⁰)₂, —C(=O)R⁹, —OC(=O)R⁹, —CO₂R¹⁰, —N(R¹⁰)₂, —C(=O)N(R¹⁰)₂, —NR¹⁰C(=O)R¹⁰, —NR¹⁰C(=O)OR¹⁰, —NR¹⁰C(=O)N(R¹⁰)₂, substituted or unsubstituted alkyl, substituted or unsubstituted alkoxy, substituted or unsubstituted heteroalkyl, substituted or unsubstituted cycloalkyl or substituted or unsubstituted heterocycloalkyl; and r is 0-8.

Also provided herein are methods for treating neuropsychiatric conditions comprising administering to an individual in need thereof a therapeutically effective amount of a compound of Formula X or pharmaceutically acceptable salt or N-oxide thereof:

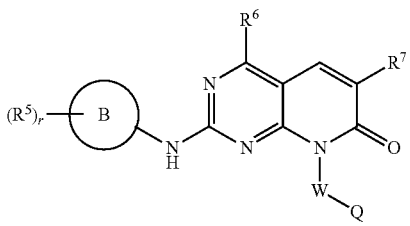

Formula X wherein:

W is a bond;

$R^6$ is H, halogen, —CN, —OH, substituted or unsubstituted alkyl, substituted or unsubstituted alkoxy, —N($R^{10}$)$_2$, substituted or unsubstituted heteroalkyl, substituted or unsubstituted cycloalkyl, substituted or unsubstituted aryl or substituted or unsubstituted heteroaryl;

$R^7$ is H, halogen, —CN, —OH, substituted or unsubstituted alkyl, substituted or unsubstituted alkoxy, —C(=O)N($R^{10}$)$_2$, —CO$_2$$R^{10}$, —N($R^{10}$)$_2$, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

Q is

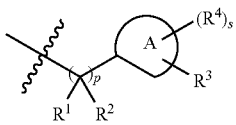

$R^1$ and $R^2$ are each independently H or substituted or unsubstituted alkyl; or $R^1$ and $R^2$ together with the carbon to which they are attached form a $C_3$-$C_6$ cycloalkyl ring;

p is 1, 2 or 3;

ring A is aryl substituted with $R^3$ and $R^4$;

$R^3$ is a substituted or unsubstituted heteroaryl, substituted or unsubstituted cycloalkyl or substituted or unsubstituted heterocycloalkyl attached to ring A via a carbon atom;

each $R^4$ is independently halogen, —CN, —NO$_2$, —OH, —OCF$_3$, —OCF$_2$H, —CF$_3$, —S$R^8$, —S(=O)$R^9$, —S(=O)$_2$$R^9$, —N$R^{10}$S(=O)$_2$$R^9$, —S(=O)$_2$N($R^{10}$)$_2$, —C(=O)$R^9$, —OC(=O)$R^9$, —CO$_2$$R^{10}$, —N($R^{10}$)$_2$, —C(=O)N($R^{10}$)$_2$, —N$R^{10}$C(=O)$R^{10}$, —N$R^{10}$C(=O)O$R^{10}$, —N$R^{10}$C(=O)N($R^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

$R^8$ is H or substituted or unsubstituted alkyl;

$R^9$ is substituted or unsubstituted alkyl, substituted or unsubstituted cycloalkyl, substituted or unsubstituted aryl or substituted or unsubstituted heteroaryl each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;

s is 0-4;

ring B is aryl or heteroaryl substituted with $R^5$;

each $R^5$ is independently halogen, —CN, —NO$_2$, —OH, —S$R^8$, —S(=O)$R^9$, —S(=O)$_2$$R^9$, N$R^{10}$S(=O)$_2$$R^9$, —S(=O)$_2$N($R^{10}$)$_2$, —C(=O)$R^9$, —OC(=O)$R^9$, —CO$_2$$R^{10}$, —N($R^{10}$)$_2$, —C(=O)N($R^{10}$)$_2$, —N$R^{10}$C(=O)$R^{10}$, —N$R^{10}$C(=O)O$R^{10}$, —N$R^{10}$C(=O)N($R^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

r is 0-8.

Provided herein are pharmaceutical compositions comprising a therapeutically effective amount of a compound of Formula I, or a pharmaceutically acceptable salt or N-oxide thereof, and a pharmaceutically acceptable carrier, wherein the compound of Formula I is as described herein.

Provided herein are pharmaceutical compositions comprising a therapeutically effective amount of a compound of Formula II, or a pharmaceutically acceptable salt or N-oxide thereof, and a pharmaceutically acceptable carrier, wherein the compound of Formula II is as described herein.

Provided herein are pharmaceutical compositions comprising a therapeutically effective amount of a compound of Formula III, or a pharmaceutically acceptable salt or N-oxide thereof, and a pharmaceutically acceptable carrier, wherein the compound of Formula III is as described herein.

Provided herein are pharmaceutical compositions comprising a therapeutically effective amount of a compound of Formula IIIA, or a pharmaceutically acceptable salt or N-oxide thereof, and a pharmaceutically acceptable carrier, wherein the compound of Formula IIIA is as described herein.

Provided herein are pharmaceutical compositions comprising a therapeutically effective amount of a compound of Formula IV, or a pharmaceutically acceptable salt or N-oxide thereof, and a pharmaceutically acceptable carrier, wherein the compound of Formula IV is as described herein.

Provided herein are pharmaceutical compositions comprising a therapeutically effective amount of a compound of Formula V, or a pharmaceutically acceptable salt or N-oxide thereof, and a pharmaceutically acceptable carrier, wherein the compound of Formula V is as described above.

Provided herein are pharmaceutical compositions comprising a therapeutically effective amount of a compound of Formula VA, or a pharmaceutically acceptable salt or N-oxide thereof, and a pharmaceutically acceptable carrier, wherein the compound of Formula VA is as described above.

Provided herein are pharmaceutical compositions comprising a therapeutically effective amount of a compound of Formula VIII, or a pharmaceutically acceptable salt or N-oxide thereof, and a pharmaceutically acceptable carrier, wherein the compound of Formula VIII is as described above.

Provided herein are pharmaceutical compositions comprising a therapeutically effective amount of a compound of Formula VIIIC, or a pharmaceutically acceptable salt or N-oxide thereof, and a pharmaceutically acceptable carrier, wherein the compound of Formula VIIIC is as described above.

Provided herein are pharmaceutical compositions comprising a therapeutically effective amount of a compound of Formula X, or a pharmaceutically acceptable salt or N-oxide thereof, and a pharmaceutically acceptable carrier, wherein the compound of Formula X is as described above.

Provided herein, in some embodiments, are methods for treating neuropsychiatric conditions comprising administering to an individual in need thereof a therapeutically effective amount of a compound of Formula I wherein compounds of Formula I are as described herein. Provided herein, in some embodiments, are methods for treating neuropsychiatric conditions comprising administering to an individual in need thereof a therapeutically effective amount of a compound of Formula II wherein compounds of Formula II are as described herein. Provided herein, in some embodiments, are methods for treating neuropsychiatric conditions comprising administering to an individual in need thereof a therapeutically effective amount of a compound of Formula III wherein compounds of Formula III are as described herein. Provided herein, in some embodiments, are methods for treating neuropsychiatric conditions comprising administering to an individual in need thereof a therapeutically effective amount of a compound of Formula IIIA wherein compounds of Formula IIIA are as described herein. Provided herein, in some embodiments, are methods for treating neuropsychiatric conditions comprising administering to an individual in need thereof a therapeutically effective amount of a compound of Formula IV wherein compounds of Formula IV are as described herein.

In some embodiments of any of the above methods, compounds of any of Formulae I-X are inhibitors of p21-activated kinase. In some embodiments, compounds of any of Formulae I-X inhibit one or more of PAK1, PAK2, PAK3, PAK4, PAK5 or PAK6. In some embodiments of any of the above methods compounds of any of Formulae I-X inhibit one or more of PAK1, PAK2 or PAK3. In some embodiments of any of the above methods, compounds of any of Formulae I-X inhibit PAK1 and PAK3. In some embodiments of any of the above methods, compounds of any of Formulae I-X inhibit PAK1 and PAK2. In some embodiments of any of the above methods, compounds of any of Formulae I-X inhibit PAK1, PAK2 and PAK3. In some embodiments of any of the above methods, compounds of any of Formulae I-X inhibit PAK1 and PAK4. In some embodiments of any of the above methods, compounds of any of Formulae I-X inhibit PAK1, PAK2, PAK3 and PAK4.

In some embodiments of any of the above methods, compounds of any of Formulae I-X inhibit PAK1. In some embodiments of any of the above methods, compounds of any of Formulae I-X inhibit PAK2. In some embodiments of any of the above methods, compounds of any of Formulae I-X inhibit PAK3. In some embodiments of any of the above methods, compounds of any of Formulae I-X inhibit PAK4.

In some embodiments of any of the above methods, a therapeutically effective amount compounds of any of Formulae I-X causes substantially complete inhibition of one or more Group I p21-activated kinases.

In some embodiments of any of the above methods, a therapeutically effective amount of compounds of any of Formulae I-X causes partial, inhibition of one or more Group I p21-activated kinases.

In some embodiments of any of the above methods, the neuropsychiatric condition is a psychotic disorder, a mood disorder or cognitive impairment.

In some embodiments of any of the above methods, the neuropsychiatric condition is schizophrenia, Alzheimer's disease, mild cognitive impairment, age-related cognitive decline, Parkinson's disease, Fragile X Syndrome, autism spectrum disorder, clinical depression, epilepsy, Huntington's disease, mental retardation, Down's syndrome, Niemann-Pick disease, spongiform encephalitis, Lafora disease, Maple syrup urine disease, maternal phenylketonuria, Rett's syndrome, atypical phenylketonuria, cognitive decline associated with menopause or tuberous sclerosis In some embodiments of any of the above methods, compounds of any of Formulae I-X modulate dendritic spine morphology or synaptic function. In some embodiments of any of the above methods, compounds of any of Formulae I-X modulate dendritic spine density. In some embodiments of any of the above methods, compounds of any of Formulae I-X modulate dendritic spine length. In some embodiments of any of the above methods, compounds of any of Formulae I-X modulate dendritic spine neck diameter. In some embodiments of any of the above methods, compounds of any of Formulae I-X modulate dendritic spine head volume. In some embodiments of any of the above methods, compounds of any of Formulae I-X modulate the ratio of the number of mature spines to the number of immature spines. In some embodiments of any of the above methods, compounds of any of Formulae I-X modulate the ratio of the spine head diameter to spine length. In some embodiments of any of the above methods, compounds of any of Formulae I-X modulate synaptic function.

In some embodiments of any of the above methods, compounds of any of Formulae I-X normalize or partially normalize aberrant baseline synaptic transmission associated with a neuropsychiatric condition. In some embodiments of any of the above methods, compounds of any of Formulae I-X normalize or partially normalize aberrant synaptic plasticity associated with a neuropsychiatric condition. In some embodiments of any of the above methods, compounds of any of Formulae I-X normalize or partially normalize aberrant long term depression (LTD) associated with a neuropsychiatric condition. In some embodiments of any of the above methods, compounds of any of Formulae I-X normalize or partially normalize aberrant long term potentiation (LTP) associated with a neuropsychiatric condition.

In some embodiments of any of the above methods, compounds of any of Formulae I-X normalize or partially normalize aberrant sensorimotor gating associated with a neuropsychiatric condition. In some embodiments of any of the above methods, compounds of any of Formulae I-X reduce or reverse negative symptoms associated with a neuropsychiatric condition. In some of such embodiments, the negative symptoms associated with a neuropsychiatric condition are asociality, blunted affect, avolition, alogia, anhedonia or dysphoric mood.

In some embodiments of any of the above methods, compounds of any of Formulae I-X reduce or reverse cognitive symptoms associated with a neuropsychiatric condition. In some of such embodiments, the cognitive symptoms associated with a neuropsychiatric condition are impairment in executive function, comprehension, inference, decision-making, planning, learning or memory.

In some embodiments of any of the above methods compounds of any of Formulae I-X halt or delay progression of cognitive impairment associated with a neuropsychiatric condition. In some of such embodiments, the cognitive impairment is mild cognitive impairment. In some embodiments, the cognitive impairment is associated with Alzheimer's disease.

In some embodiments of any of the above methods, the method further comprises administration of a second therapeutic agent that alleviates one or more symptoms associated with a neuropsychiatric condition.

In some embodiments, the second therapeutic agent is an antipsychotic agent, a cognition enhancer, a Group I mGluR antagonist, a mGluR5 antagonist, a mGluR5 potentiator, a nootropic agent, an alpha7 nicotinic receptor agonist, an allosteric alpha7 nicotinic receptor potentiator, a nootropic agent, a trophic agent, an antioxidant, a neuroprotectant, a beta secretase inhibitor, a gamma secretase inhibitor or an Abeta antibody.

In some embodiments, administration of a therapeutically effect amount of compounds of any of Formulae I-X to an individual in need thereof improves one or more of MATRICS cognition scores, Wisconsin Card Sort test scores, Mini-Mental State Exam (MMSE) scores, Alzheimer Disease Assessment Scale-Cognitive (ADAS-cog) scale scores, ADAS-Behav scores, or Hopkins Verbal Learning Test Revised scores for the individual.

Provided herein are methods for reversing cortical hypofrontality associated with a neuropsychiatric condition comprising administering to an individual in need thereof a therapeutically effective amount of a compound of any of Formulae I-X. Provided herein are methods for reducing, stabilizing, or reversing neuronal withering and/or loss of synaptic function associated a neuropsychiatric condition comprising administering to an individual in need thereof a therapeutically effective amount of a compound of any of Formulae I-X. Provided herein are methods for reducing, stabilizing or reversing atrophy or degeneration of nervous tissue in the brain associated with a neuropsychiatric condition comprising administering to an individual in need thereof a therapeutically effective amount of a compound of any of Formulae I-X.

Provided herein are methods of inhibiting the activity of one or more p21-activated kinases comprising contacting the one or more p21-activated kinases with a compound of any of Formulae I-X. In some embodiments, the one or more p21-activated kinase is contacted with a compound of any of Formulae I-X in vitro. In some embodiments, the one or more p21-activated kinase is contacted with a compound of any of Formulae I-X in vivo.

Provided herein is the use of compounds of any of Formulae I-X in the manufacture of a medicament for the treatment of a neuropsychiatric condition.

As used herein, compounds of any of Formulae I-X or compound of Formula I-X includes compounds of Formula I, II, III, IIIA, IV, V, VA, VI, VII, VIII, VIIIA, VIIIB, VIIIC, IX, and X.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 describes illustrative shapes of dendritic spines.

DETAILED DESCRIPTION OF THE INVENTION

Provided herein are methods for treatment of neuropsychiatric conditions by administration of inhibitors of certain p21 activated kinases to individuals in need thereof. Such kinase inhibitors are inhibitors of one or more of PAK1, PAK2, PAK3, PAK4, PAK5 or PAK6 kinases. In certain embodiments, the individual has been diagnosed with or is suspected of suffering from a neuropsychiatric and/or neurodegenerative disease or condition that is mediated by p21 activated kinases. In some instances, provided herein are methods for treating conditions characterized by abnormal dendritic spine morphology and/or spine density and/or spine length and/or spine thickness.comprising.inhibiting PAK activity by administration of a therapeutically effective amount of a PAK inhibitor to an individual diagnosed with or suspected of suffering from a NC (e.g., pscyhotic disorders, mood disorders, age-related cognitive decline, epilepsy, Huntington's disease, schizophrenia, Alzheimer's disease, Parkinson's disease, mental retardation, Down's syndrome, Niemann-Pick disease, spongiform encephalitis, Lafora disease, Maple syrup urine disease, maternal phenylketonuria, atypical phenylketonuria, cognitive decline associated with menopause, Rett's syndrome and tuberous sclerosis).

A number of NCs are characterized by abnormal dendritic spine morphology, spine size, spine plasticity and/or spine density as described in a number of studies referred to herein. PAK kinase activity has been implicated in spine morphogenesis, maturation, and maintenance. See, e.g., Kreis et al (2007), *J Biol Chem,* 282(29):21497-21506; Hayashi et al (2007), *Proc Natl Acad Sci USA.,* 104(27):11489-11494, Hayashi et al (2004), *Neuron,* 42(5):773-787; Penzes et al (2003), *Neuron,* 37:263-274. In some embodiments, inhibition or partial inhibition of one or more PAKs normalizes aberrant dendritic spine morphology and/or synaptic function. NCs that are treated by the methods described herein include, but are not limited to, schizophrenia, psychotic disorders, mood disorders, age-related cognitive decline, epilepsy, Huntington's disease, Alzheimer's disease, Parkinson's disease, mental retardation, Down's syndrome, Niemann-Pick disease, spongiform encephalitis, Lafora disease, Maple syrup urine disease, maternal phenylketonuria, atypical phenylketonuria, cognitive decline associated with menopause, Rett's syndrome and tuberous sclerosis.

In some instances, NCs are associated with abnormal dendritic spine morphology, spine size, spine plasticity, spine motility, spine density and/or abnormal synaptic function. In some instances, activation of one or more of PAK1, PAK2, PAK3, PAK4, PAK5 and/or PAK6 kinases is implicated in defective spine morphogenesis, maturation, and maintenance. Described herein are methods for suppressing or reducing PAK activity (e.g., by administering a PAK inhibitor for rescue of defects in spine morphology, size, plasticity spine motility and/or density) associated with neuropsychiatric conditions as described herein. Accordingly, in some embodiments, the methods described herein are used to treat an individual suffering from a neuropsychiatric disorder wherein the disease is associated with abnormal dendritic spine density, spine size, spine plasticity, spine morphology, spine plasticity, or spine motility.

In some embodiments, any inhibitor of one or more p21-activated kinases described herein modulates abnormalities in dendritic spine morphology and/or synaptic function that are associated with neuropsychiatric conditions. In some embodiments, modulation of dendritic spine morphology and/or synaptic function alleviates or reverses cognitive impairment and/or negative behavioral symptoms (e.g., social withdrawal, anhedonia or the like) associated with NCs. In some embodiments, modulation of dendritic spine morphology and/or synaptic function halts or delays progression of cognitive impairment and/or loss of bodily functions associated with NCs.

In some instances, cellular changes in brain cells contribute to pathogenesis of a neuropsychiatric condition. In some instances, an abnormality in dendritic spine density in the brain contributes to the pathogenesis of a neuropsychiatric condition. In some instances, an abnormality in dendritic spine morphology contributes to the pathogenesis of a neuropsychiatric condition. In some instances, an abnormality in the pruning of dendritic spines or synapses during puberty contributes to the pathogenesis of a neuropsychiatric condition. In some instances, an abnormality in synaptic function contributes to the pathogenesis of a neuropsychiatric condition. In some instances, activation of one or more PAKs is associated with an abnormality in dendritic spine density and/or dendritic morphology and/or synaptic function and contributes to the pathogenesis of a neuropsychiatric condition. In some instances, modulation of PAK activity (e.g., attenuation, inhibition or partial inhibition of PAK activity) reverses or reduces abnormalities in dendritic spine morphology and/or dendritic spine density and/or synaptic function. In certain embodiments, modulation of activity of one or more Group I PAKs (one or more of PAK1, PAK2 and/or PAK3) reverses or reduces abnormalities in dendritic spine morphology and/or dendritic spine density and/or synaptic function associated with neuropsychiatric conditions.

Abnormal dendritic spine morphology and/or density have been found in a number of NCs as described below. Accordingly, in some embodiments, the methods described herein are used to treat an individual suffering from a neuropsychiatric condition that is associated with abnormal dendritic spine density, spine size, spine plasticity, spine morphology, spine plasticity, or spine motility. In some embodiments, the methods described herein are used to treat an individual suffering from a psychotic disorder, as described in, by way of example, Example 124 and Example 128 herein. Examples of psychotic disorders include, but are not limited to, schizophrenia, schizoaffective disorder, schizophreniform disorder, brief psychotic disorder, delusional disorder, shared psychotic disorder (Folie a Deux), substance induced psychosis, and psychosis due to a general medical condition. See, e.g., Black et al. (2004), *Am J Psychiatry*, 161:742-744; Broadbelt et al. (2002), *Schizophr Res*, 58:75-81; Glantz et al. (2000), *Arch Gen Psychiatry* 57:65-73; and Kalus et al. (2000), *Neuroreport*, 11:3621-3625. In some instances, aberrant spine morphogenesis is associated with negative symptoms (e.g., asociality, blunted affect, avolition, alogia, anhedonia or dysphoric mood), and/or cognitive impairment symptomatic of schizophrenia. In some instances, aberrant spine morphogenesis is associated with positive symptoms and behavioral changes (e.g., social withdrawal, depersonalization, loss of appetite, loss of hygiene, delusions, hallucinations, the sense of being controlled by outside forces or the like)symptomatic of schizophrenia.

In some embodiments, the methods described herein are used to treat an individual suffering from a mood disorder. Examples of mood disorders include, but are not limited to, clinical depression as described in, for example, Example 126 herein, bipolar disorder, cyclothymia, and dysthymia. See, e.g., Hajszan et al (2005), *Eur J Neurosci*, 21:1299-1303; Law et al (2004) *Am J Psychiatry*, 161(10):1848-1855; Norrholm et al. (2001), *Synapse*, 42:151-163; and Rosoklija et al. (2000), *Arch Gen Psychiatry*, 57:349-356.

In some embodiments, the methods described herein are used to treat an individual suffering from neurodegenerative disorders (e.g., age-related cognitive decline, Parkinson's disease, Alzheimer's disease (as described in, for example, Example 130 herein) or the like). See, e.g., Dickstein et al (2007), *Aging Cell*, 6:275-284; and Page et al. (2002), *Neuroscience Letters*, 317:37-41. In some embodiments, the methods described herein are used to treat an individual suffering from or suspected of having mild cognitive impairment (MCI). In some embodiments, the methods described herein are used to halt or delay progression of mild cognitive impairment (MCI) to early dementia, mid-stage dementia or late stage dementia in an individual suffering from or suspected of having mild cognitive impairment (MCI). In some instances, Alzheimer's disease is associated with abnormal dendritic spine morphology, spine size, spine plasticity, spine motility, spine density and/or abnormal synaptic function. In some instances, soluble Abeta dimers and/or oligomers increase PAK kinase activity at the synapse. In some instances, Abeta plaques and/or insoluble Abeta aggregates increase PAK kinase activity at the synapse. In some instances, increased PAK kinase activity is associated with defective spine morphogenesis, maturation, and maintenance. In some instances, PAK inhibitors reverse defects in synaptic function and plasticity in a patient diagnosed with Alzheimer's disease before Abeta plaques can be detected. In some embodiments, PAK inhibitors reverse defects in synaptic morphology, synaptic transmission and/or synaptic plasticity induced by soluble Abeta dimers and/or oligomers. In some embodiments, PAK inhibitors reverse defects in synaptic morphology, synaptic transmission and/or synaptic plasticity induced by Abeta oligomers and/or Abeta-containing plaques.

In some embodiments, the methods described herein are used to treat an individual suffering from epilepsy as described in, for example, Example 127 herein. See, e.g., Wong (2005), *Epilepsy and Behavior*, 7:569-577; Swann et al (2000), *Hippocampus*, 10:617-625; and Jiang et al (1998), *J Neurosci*, 18(20):8356-8368.

In some embodiments, the methods described herein are used to treat an individual suffering from Parkinson's Disease or Huntington's Disease. See, e.g., Neely et al (2007), *Neuroscience*, 149(2):457-464; Spires et al (2004), *Eur J Neurosci*, 19:2799-2807; Klapstein et al (2001), *J Neurophysiol*, 86:2667-2677; Ferrante et al (1991), *J Neurosci*, 11:3877-3887; and Graveland et al (1985), *Science*, 227:770-773.

In some embodiments, the methods described herein are used to treat an individual suffering from mental retrdation, Fragile X syndrome, autism spectrum disorders or the like.

In some embodiments, the methods described herein are used to treat an individual suffering from mental retardation, Down's syndrome, Epilepsy, Niemann-Pick disease, spongiform encephalitis, Lafora disease, Maple syrup urine disease, maternal to phenylketonuria, atypical phenylketonuria, cognitive decline associated with menopause, Rett's syndrome and tuberous sclerosis.

In some instances, development of an NC is associated with a genetic component. Certain risk alleles and genes that have been identified for NCs. For example, for Alzheimer's disease, risk alleles and genes include mutations in Amyloid Precursor Protein (APP), mutations in presenilin 1 and 2, the epsilon4 allele, the 91 bp allele in the telomeric region of 12q, Apolipoprotein E-4 (APOE4) gene, SORL1 gene, reelin gene or the like. For example, in some instances, development of schizophrenia is associated with mutations in the DISC1 gene. In some instances, several risk alleles or genes are involved in etiology of a NC. In some instances, NCs run in families and there is a predisposition or vulnerability to the illness. In some instances, a combination of genetic, familial and environmental factors play a role in manifestation of disease symptoms. In some instances, mutations in genes resulting in a predisposition to a NC leads to early-onset of the disease.

Dendritic Spines

A dendritic spine is a small membranous protrusion from a neuron's dendrite that serves as a specialized structure for the formation, maintenance, and/or function of synapses. Dendritic spines vary in size and shape. In some instances, spines have a bulbous head (the spine head) of varying shape, and a thin neck that connects the head of the spine to the shaft of the dendrite. In some instances, spine numbers and shape are regulated by physiological and pathological events. In some instances, a dendritic spine head is a site of synaptic contact. In some instances, a dendritic spine shaft is a site of synaptic contact.

In some instances, mature spines have variably-shaped bulbous tips or heads, ~0.5-2 μm in diameter, connected to a parent dendrite by thin stalks 0.04-1 μm long. In some instances, spine density ranges from 1 to 10 spines per micrometer length of dendrite, and varies with maturational stage of the spine and/or the neuronal cell. In some instances, dendritic spine density ranges from 1 to 40 spines per 10 micrometer in medium spiny neurons. In some instances, small-headed spines have head volume <0.05 μm$^3$) medium-size headed spines have head volumes of 0.05 μm$^3$-0.1 μm$^3$ and large-headed spines have head volumes of >0.1 μm$^3$.

FIG. 1 shows examples of different shapes of dendritic spines. Dendritic spines are "plastic." In other words, spines are dynamic and continually change in shape, volume, and number. In some instances, spines change in shape, volume, length, thickness or number in a few hours. In some instances, spines change in shape, volume, length, thickness or number occurs within a few minutes. In some instances, spines change in shape, volume, length, thickness or number occurs in response to synaptic transmission and/or induction of synaptic plasticity. By way of example, dendritic spines are headless (filopodia as shown, for example, in FIG. 1a), thin (for example, as shown in FIG. 1b), stubby (for example as shown in FIG. 1c), mushroom-shaped (have door-knob heads with thick necks, for example as shown in FIG. 1d), ellipsoid (have prolate spheroid heads with thin necks, for example as shown in FIG. 1e), flattened (flattened heads with thin neck, for example as shown in FIG. 10 or branched (for example as shown in FIG. 1g). In some instances, the shape of the dendritic spine head determines synpatic function. In some instances, dendritic spines with larger spine head diameter form more stable synapses compared with dendritic spines with smaller head diameter. In some instances, a mushroom-shaped spine head is associated with normal or partially normal synaptic function. In some instances, a mushroom-shaped spine head is a healthier spine head (e.g., having normal or partially normal synapses) compared to a spine head that is stubby or flat or thin. In some instances, inhibition or partial inhibition of PAK activity results in an increase in spine head diameter and/or spine head volume and/or reduction of spine length, thereby normalizing or partially normalizing synaptic function in individuals suffering or suspected of suffering from a neuropsychiatric condition.

p21-Activated Kinases (PAKs)

The PAKs constitute a family of serine-threonine kinases that is composed of "conventional", or Group I PAKs, that includes PAK1, PAK2, and PAK3, and "non-conventional", or Group II PAKs, that includes PAK4, PAK5, and PAK6. See, e.g., Zhao et al., (2005), *Biochem J*, 386:201-214. These kinases function downstream of the small GTPases Rac and/or Cdc42 to regulate multiple cellular functions, including dendritic morphogenesis and maintenance (see, e.g., Ethell et al (2005), *Prog in Neurobiol*, 75:161-205; Penzes et al (2003), *Neuron*, 37:263-274), motility, morphogenesis, angiogenesis, and apoptosis, (see, e.g., Bokoch et al., 2003, *Annu. Rev. Biochem.*, 72:743; and Hofmann et al., 2004, *J. Cell Sci.*, 117:4343). GTP-bound Rac and/or Cdc42 bind to inactive PAK, releasing steric constraints imposed by a PAK autoinhibitory domain and/or permitting PAK phosphorylation and/or activation. Numerous phosphorylation sites have been identified that serve as markers for activated PAK.

In some instances, upstream effectors of PAK include, but are not limited to, TrkB receptors; NMDA receptors; adenosine receptors; estrogen receptors; integrins, EphB receptors; CDK5, FMRP; Rho-family GTPases, including Cdc42, Rac (including but not limited to Rac1 and Rac2), Chp, TC10, and Wrnch-1; guanine nucleotide exchange factors ("GEFs"), such as but not limited to GEFT, α-p-21-activated kinase interacting exchange factor (αPIX), Kalirin-7, and Tiam1; G protein-coupled receptor kinase-interacting protein 1 (GIT1), and sphingosine.

In some instances, downstream effectors of PAK include, but are not limited to, substrates of PAK kinase, such as Myosin light chain kinase (MLCK), regulatory Myosin light chain (R-MLC), Myosins I heavy chain, myosin II heavy chain, Myosin VI, Caldesmon, Desmin, Op18/stathmin, Merlin, Filamin A, LIM kinase (LIMK), Ras, Raf, Mek, p47phox, BAD, caspase 3, estrogen and/or progesterone receptors, RhoGEF, NETI, Gαz, phosphoglycerate mutase-B, RhoGD1, prolactin, p41Arc, cortactin and/or Aurora-A (See, e.g., Bokoch et al., 2003, *Annu. Rev. Biochem.*, 72:743; and Hofmann et al., 2004, *J. Cell Sci.*, 117:4343). Other substances that bind to PAK in cells include CIB; sphingolipids; lysophosphatidic acid, G-protein β and/or γ subunits; PIX/COOL; GIT/PKL; Nef; Paxillin; NESH; SH3-containing proteins (e.g. Nck and/or Grb2); kinases (e.g. Akt, PDK1, PI 3-kinase/p85, Cdk5, Cdc2, Src kinases, Abl, and/or protein kinase A (PKA)); and/or phosphatases (e.g. phosphatase PP2A, POPX1, and/or POPX2).

PAK Inhibitors

Described herein are PAK inhibitors that treat one or more symptoms associated with neuropsychiatric conditions. Also described herein are pharmaceutical compositions comprising a PAK inhibitor (e.g., a PAK inhibitor compound described herein) for reversing or reducing one or more of cognitive impairment and/or dementia and/or negative symptoms and/or positive symptoms associated with NCs. Also described herein are pharmaceutical compositions comprising a PAK inhibitor (e.g., a PAK inhibitor compound described herein) for halting or delaying the progression of cognitive impairment and/or dementia and/or negative symptoms and/or positive symptoms associated with NCs. Described herein is the use of a PAK inhibitor for manufacture of a medicament for treatment of one or more symptoms of a neuropsychiatric condition.

In some embodiments, the PAK inhibitor is a Group I PAK inhibitor that inhibits, for example, one or more Group I PAK polypeptides, for example, PAK1, PAK2, and/or PAK3. In some embodiments, the PAK inhibitor is a PAK1 inhibitor (e.g., compound 2, 7, 12, 36, 49, 55, 56, 58, 75, 80, 98 or the like). In some embodiments, the PAK inhibitor is a PAK2 inhibitor. In some embodiments, the PAK inhibitor is a PAK3 inhibitor. In some embodiments, the PAK inhibitor is a mixed PAK1/PAK3 inhibitor. In some embodiments, the PAK inhibitor is a mixed PAK1/PAK2 inhibitor (e.g., compound 21, 33, 43 or the like). In some embodiments, the PAK inhibitor is a mixed PAK1/PAK-4 inhibitor (e.g., compound 18, 59, 61, 94, 106, 111, 113 or the like). In some embodiments, the PAK inhibitor is a mixed PAK1/PAK2/PAK-4 inhibitor (e.g., compound 22, 51, 57, 66 or the like). In some embodiments, the PAK inhibitor is a mixed PAK1/PAK2/PAK3/PAK-4 inhibitor (e.g., compound 13, 14, 15, 19, 23, 27, 44, 45, 46, 53, 60, 62, 63, 65, 69, 71, 72, 73, 74, 78, 79, 81, 91 or the like). In some embodiments, the PAK inhibitor inhibits all three Group I PAK isoforms (PAK1, 2 and PAK3) with equal or similar potency (e.g., compound 64, 68, 77, 84, 86, 119, 120, 121 or the like). In some embodiments, the PAK inhibitor is a Group II PAK inhibitor that inhibits one or more Group II PAK polypeptides, for example PAK-4, PAK5, and/or PAK6. In some embodiments, the PAK inhibitor is a PAK4 inhibitor.

In some embodiments, the PAK inhibitor is a PAK5 inhibitor. In some embodiments, the PAK inhibitor is a PAK6 inhibitor.

In certain embodiments, a PAK inhibitor described herein reduces or inhibits the activity of one or more of PAK1, PAK2, PAK3, and/or PAK4 while not affecting the activity of PAK5 and PAK6. In some embodiments, a PAK inhibitor described herein reduces or inhibits the activity of one or more of PAK1, PAK2 and/or PAK3 while not affecting the activity of PAK4, PAK5 and/or PAK6. In some embodiments, a PAK inhibitor described herein reduces or inhibits the activity of one or more of PAK1, PAK2, PAK3, and/or one or more of PAK4, PAK5 and/or PAK6. In some embodiments, a PAK inhibitor described herein is a substantially complete inhibitor of one or more PAKs. As used herein, "substantially complete inhibition" means, for example, >95% inhibition of one or more targeted PAKs. In other embodiments, "substantially complete inhibition" means, for example, >90% inhibition of one or more targeted PAKs. In some other embodiments, "substantially complete inhibition" means, for example, >80% inhibition of one or more targeted PAKs. In some embodiments, a PAK inhibitor described herein is a partial inhibitor of one or more PAKs. As used herein, "partial inhibition" means, for example, between about 40% to about 60% inhibition of one or more targeted PAKs. In other embodiments, "partial inhibition" means, for example, between about 50% to about 70% inhibition of one or more targeted PAKs. As used herein, where a PAK inhibitor substantially inhibits or partially inhibits the activity of a certain PAK isoform while not affecting the activity of another isoform, it means, for example, less than about 10% inhibition of the non-affected to isoform when the isoform is contacted with the same concentration of the PAK inhibitor as the other substantially inhibited or partially inhibited isoforms. In other instances, where a PAK inhibitor substantially inhibits or partially inhibits the activity of a certain PAK isoform while not affecting the activity of another isoform, it means, for example, less than about 5% inhibition of the non-affected isoform when the isoform is contacted with the same concentration of the PAK inhibitor as the other substantially inhibited or partially inhibited isoforms. In yet other instances, where a PAK inhibitor substantially inhibits or partially inhibits the activity of a certain PAK isoform while not affecting the activity of another isoform, it means, for example, less than about 1% inhibition of the non-affected isoform when the isoform is contacted with the same concentration of the PAK inhibitor as the other substantially inhibited or partially inhibited isoforms.

Provided herein, in certain embodiments, are compounds of Formula I:

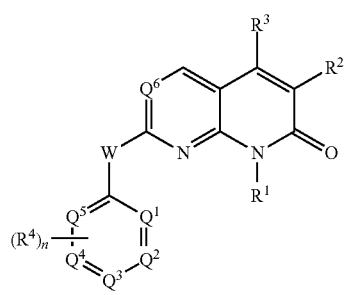

Formula I wherein:

$R^1$ is H, substituted or unsubstituted alkyl, substituted or unsubstituted cycloalkyl; or substituted or unsubstituted heterocycloalkyl;

$R^2$, $R^3$ are independently H, halo, hydroxy, cyano, amino or substituted or unsubstituted alkyl;

each $R^4$ is halo, hydroxy, cyano, substituted or unsubstituted alkyl, substituted or unsubstituted alkoxy, substituted or unsubstituted alkylamino, substituted or unsubstituted heteroalkyl, substituted or unsubstituted aryl, substituted or unsubstituted heteroaryl, substituted or unsubstituted cycloalkyl, or substituted or unsubstituted heterocycloalkyl;

n is 0-5;

$Q^1$, $Q^2$, $Q^3$, $Q^4$, $Q^5$ are each independently N or C—$R^{4a}$; wherein $R^{4a}$ is H or $R^4$; provided that at least two of $Q^1$, $Q^2$, $Q^3$, $Q^4$, $Q^5$ are C—$R^{4a}$;

$Q^6$ is N or C—$R^{4b}$; wherein $R^{4b}$ is H, halo, hydroxy, cyano, substituted or unsubstituted alkyl, or substituted or unsubstituted alkoxy;

W is O, N—$R^5$ or C($R^5$)$_2$, wherein each $R^5$ is independently H, hydroxy, substituted or unsubstituted alkyl; or two $R^5$ taken together are (=O) or (=N$R^6$); wherein $R^6$ is H, hydroxy, substituted or unsubstituted alkyl, or substituted or unsubstituted alkoxy;

provided that when $R^2$ and $R^3$ are H, $R^1$ is cyclopentyl, W is NH, n is 1, $Q^1$, $Q^2$, $Q^4$, $Q^5$ are CH, $Q^3$ is C$R^4$ and $Q^6$ is N, $R^4$ is not p4-methylpiperazin-1-yl;

or a pharmaceutically acceptable salt thereof.

In some embodiments, W is N—$R^5$. In some embodiments, $Q^3$ is C—$R^{4a}$. In some embodiments, $R^2$ and $R^3$ are independently H, or halo. In some embodiments, $R^1$ is H or substituted or unsubstituted cycloalkyl. In some embodiments, $R^1$ is substituted or unsubstituted cyclopropane, substituted or unsubstituted cyclobutane, substituted or unsubstituted cyclopentane, or substituted or unsubstituted cyclohexane. In some embodiments, each $R^4$ is halo, cyano, substituted or unsubstituted alkyl, substituted or unsubstituted alkoxy, substituted or unsubstituted alkylamino or substituted or unsubstituted heteroalkyl. In some embodiments, $R^4$ is substituted or unsubstituted cycloalkyl, or substituted or unsubstituted heterocycloalkyl. In some embodiments, $R^4$ is substituted or unsubstituted cyclopropane, substituted or unsubstituted cyclobutane, substituted or unsubstituted cyclopentane, substituted or unsubstituted cyclohexane, substituted or unsubstituted pyran, substituted or unsubstituted tetrahydrofuran, substituted or unsubstituted pyrrolidine, substituted or unsubstituted piperidine, substituted or unsubstituted morpholine, substituted or unsubstituted pyrrolidinone or substituted or unsubstituted piperidinone.

In some embodiments, $Q^6$ is N. In some embodiments of Formula I, W is NH. In some embodiments, compounds of Formula I are p21-activated kinase inhibitors.

In certain embodiments, compounds of Formula I are as described in Table 1.

TABLE 1

[Structure: pyrido-pyrimidinone core with substituents R¹, R², R³, R⁴, W, Q¹–Q⁶]

| Compound No. | Q¹ | Q² | Q⁴ | Q⁵ | Q⁶ | W | R¹ | R² | R³ | R⁴ |
|---|---|---|---|---|---|---|---|---|---|---|
| 1-1 | N | CH | CH | CH | N | NH | cyclobutyl | H | OH | CH₃NH-CH₂CH₂-C(CH₃)₂-OH |
| 1-2 | CH | CH | CH | CH | N | NH | cyclopentyl | H | H | morpholinyl |
| 1-3 | CH | CH | CH | CH | N | NH | cyclobutyl | H | H | 4-methylpiperazinyl |
| 1-4 | CH | N | CH | CH | N | NH | 4-hydroxycyclohexyl | Me | H | 4-(morpholino)butyl |
| 1-5 | N | N | CH | CH | N | O | cyclopropyl | H | Me | -OCH₂-(cyclopentyl-CH₂OH) |
| 1-6 | CH | CH | CH | CH | N | NH | cyclopentyl | H | H | -OCH₂CH₂-N(CH₃)₂ |
| 1-7 | CH | CH | CH | CH | N | NH | cyclopentyl | H | Me | 4-methylpiperazinyl |
| 1-8 | CH | CH | CH | CH | N | NH | cyclopentyl | H | H | piperazinyl |
| 1-9 | CH | N | N | CH | N | NH | cyclopropylmethyl | Cl | H | -N(CH₃)-CH₂-(4-acetylpiperazinyl) |
| 1-10 | CH | CH | CH | CH | N | NH | Me | H | H | 4-methylpiperazinyl |

TABLE 1-continued
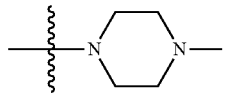 [SMILES: *N1CCN(C)CC1]
| Compound No. | Q¹ | Q² | Q⁴ | Q⁵ | Q⁶ | W | R¹ | R² | R³ | R⁴ |
|---|---|---|---|---|---|---|---|---|---|---|
| 1-11 | CH | CH | CH | CH | N | NH | H | H | H | 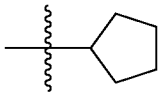 [SMILES: *C1CCCC1] |
| 1-12 | CH | CH | CH | CH | N | NH | 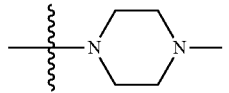 [SMILES: *N1CCN(C)CC1] | Me | H | 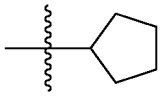 [SMILES: *C1CCCC1] |
| 1-13 | CH | CH | CH | CH | N | NH | 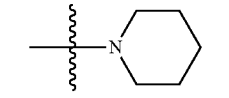 | H | H | 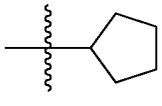 |
| 1-14 | CH | CH | CH | CH | N | NH | 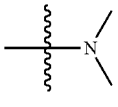 | H | H | 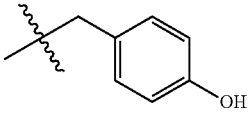 [SMILES: *Cc1ccc(O)cc1] |
| 1-15 | N | CH | CH | N | CH | NH | 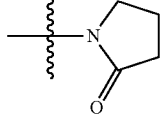 | H | CN | 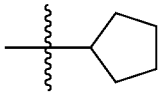 [SMILES: *C1CCCC1] |
| 1-16 | CH | CH | CH | CH | N | NH | 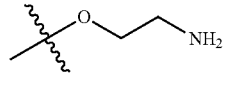 [SMILES: *OCCN] | H | H | 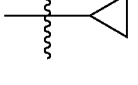 |
| 1-17 | CH | CH | CH | CH | N | NH | 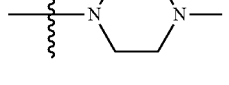 | H | H | 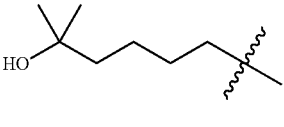 [SMILES: *CCCCC(C)(C)O] |
| 1-18 | CH | N | CH | CH | N | O | 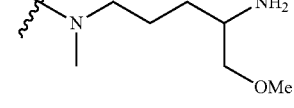 | Me | H | 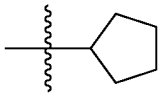 [SMILES: *C1CCCC1] |
| 1-19 | CH | CH | CH | CH | N | NH | 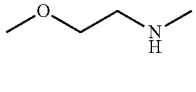 | H | H | 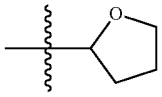 [SMILES: *C1CCCO1] |
| 1-20 | CH | C—F | CH | CH | N | C=O | 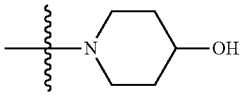 | H | Me |  |

TABLE 1-continued

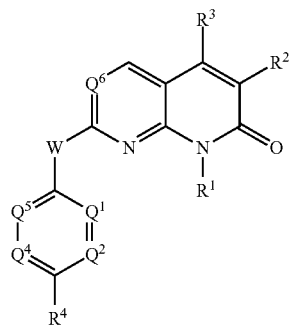

| Compound No. | Q¹ | Q² | Q⁴ | Q⁵ | Q⁶ | W | R¹ | R² | R³ | R⁴ |
|---|---|---|---|---|---|---|---|---|---|---|
| 1-21 | CH | C—F | CH | CH | N | NH | ![piperidinylmethyl] | Me | H | ![OCH2CH2NH2] |
| 1-22 | CH | CH | CH | CH | N | NH | ![cyclopentyl] | H | H | ![piperazinyl-methyl] |

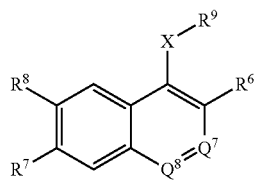

Also provided herein, in certain embodiments, are compounds of Formula II:

$$\text{Formula II}$$

[Structure of Formula II showing a bicyclic ring with substituents $R^6$, $R^7$, $R^8$, $R^9$, $X$, $Q^7$, $Q^8$]

wherein:

$R^6$ is H, halo, hydroxy, cyano, substituted or unsubstituted alkyl, or substituted or unsubstituted alkoxy, $R^7$ is substituted or unsubstituted alkyl, substituted or unsubstituted alkoxy, substituted or unsubstituted alkylamino, C(=O)—N(R$^{10}$)$_2$, C(=O)—O(R$^{10}$)$_2$, S(O)$_m$—N(R$^{10}$)$_2$, N(R$^{10}$)$_2$C(=O)R$^{10}$, OC(=O)(R$^{10}$), N(R$^{10}$)$_2$S(O)$_m$R$^{10}$, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each R$^{10}$ is independently H, substituted or unsubstituted alkyl; substituted or unsubstituted cycloalkyl, or substituted or unsubstituted alkylcycloalkyl; and m is 1-2;

$R^8$ is H, halo, hydroxy, cyano, substituted or unsubstituted alkyl, substituted or unsubstituted alkoxy, substituted or unsubstituted alkylamino, C(=O)—N(R$^{10}$)$_2$, C(=O)—O(R$^{10}$), S(O)$_m$—NR$^{10}$)$_2$, N(R$^{10}$)$_2$C(=O)R$^{10}$, OC(=O)(R$^{10}$), N(R$^{10}$)$_2$S(O)$_m$R$^{10}$;

$R^9$ is substituted or unsubstituted aryl, substituted or unsubstituted heteroaryl, substituted or unsubstituted cycloalkyl, or substituted or unsubstituted heterocycloalkyl;

$Q^7$, $Q^8$ are independently N or C—R$^6$;

X is O, N—R$^{11}$ or C(R$^{11}$)$_2$, wherein each R$^{11}$ is independently H, hydroxy, substituted or unsubstituted alkyl; or two R$^{11}$ taken together are (=O) or (=NR$^{12}$); wherein R$^{12}$ is H, hydroxy, substituted or unsubstituted alkyl, or substituted or unsubstituted alkoxy;

provided that when Q$^8$ is N, Q$^7$ is CH, R$^7$, R$^8$ are alkoxy, and R$^6$ is cyano, R$^9$ is not 2,4-dichloroanilino;

or a pharmaceutically acceptable salt thereof.

In some embodiments of Formula II, X is N—R$^{11}$. In some embodiments, one of Q$^2$ and Q$^3$ is N and the other is CH. In some embodiments, R$^6$ is H, halo, hydroxy, or cyano. In some embodiments, R$^7$ is substituted or unsubstituted alkyl, substituted or unsubstituted alkoxy, substituted or unsubstituted alkylamino, C(=O)—N(R$^{10}$)$_2$, S(O)$_m$—N(R$^{10}$)$_2$, or substituted or unsubstituted heteroalkyl. In some embodiments, R$^7$ is substituted or unsubstituted alkoxy, substituted or unsubstituted alkylamino, or substituted or unsubstituted heteroalkyl. In some embodiments, R$^8$ is H, halo, cyano, or substituted or unsubstituted alkoxy.

In some embodiments, R$^9$ is substituted or unsubstituted aryl, substituted or unsubstituted heteroaryl, substituted or unsubstituted cycloalkyl, or substituted or unsubstituted heterocycloalkyl. In some embodiments, R$^9$ is substituted or unsubstituted aryl, substituted or unsubstituted heteroaryl. In some embodiments, R$^9$ is substituted or unsubstituted phenyl, substituted or unsubstituted pyridinyl, substituted or unsubstituted pyrimidinyl, substituted or unsubstituted pyrazinyl, substituted or unsubstituted thienyl, substituted or unsubstituted pyrazolyl, substituted or unsubstituted imidazolyl, substituted or unsubstituted triazolyl, substituted or unsubstituted oxazolyl, substituted or unsubstituted isoxazolyl, or substituted or unsubstituted thiazolyl.

In some embodiments of Formula II, Q$^7$ is CH and Q$^8$ is N. In some embodiments, Q$^7$ is N and Q$^8$ is CH. In some embodiments, X is NH. In some embodiments, compounds of Formula II are p21-activated kinase inhibitors.

In certain embodiments, compounds of Formula II are as described in Table 2.

TABLE 2

[Structure: bicyclic core with substituents R⁸, R⁷ on one ring; R⁶, X-R⁹ on the other; Q⁷, Q⁸ positions in ring]

| Compound No. | Q⁷ | Q⁸ | R⁶ | R⁷ | R⁸ | R⁹ | X |
|---|---|---|---|---|---|---|---|
| 2-1 | N | CH | Cl | -O-CH₂CH₂-N(Me)₂ | OMe | 4-fluorophenyl | NH |
| 2-2 | N | CH | OMe | -NH-CH₂CH₂-(pyrrolidin-2-yl-CH₂OH) | O(isopropyl) | 2-fluorophenyl | NH |
| 2-3 | CH | N | CN | -O-(CH₂)₃-morpholinyl | OMe | 2,4-dichlorophenyl | NH |
| 2-4 | CH | N | CN | -O-(CH₂)₃-N(Me)₂ | OMe | 2,4-dichlorophenyl | NH |
| 2-5 | CH | N | CN | -O-(CH₂)₃-(2-methylpiperidin-1-yl) | OMe | 2,4-dichlorophenyl | NH |
| 2-6 | N | CH | CN | -NH-(cyclohexyl-NHC(=O)CH₃) | (C=O)NH₂ | 6-methoxypyridin-3-yl | NH |
| 2-7 | CH | N | CN | -O-(CH₂)₃-(4-methylpiperidin-1-yl) | OMe | 2,4-dichlorophenyl | NH |
| 2-8 | CH | N | OH | -NH-(4-hydroxycyclohexyl) | CN | pyrimidin-2-yl | O |
| 2-9 | CH | N | H | -O-(CH₂)₄-OH | N(Me)₂ | 2-chloro-4-methylphenyl | O |

TABLE 2-continued

[Structure: benzene ring with substituents R8, R7 (bottom), R6, X-R9, and fused ring with Q7=Q8]

| Compound No. | Q7 | Q8 | R6 | R7 | R8 | R9 | X |
|---|---|---|---|---|---|---|---|
| 2-10 | CH | N | CN | [3-methylpiperidin-1-yl group connected via -O-CH2CH2CH2-] | OMe | 2,4-dichlorophenyl | NH |
| 2-11 | CH | N | Me | [tert-butyl ketone/pivaloyl group] | Cl | 2-methylpyridin-3-yl | NH |
| 2-12 | CH | N | CN | [4-methylpiperazin-1-yl connected via -O-CH2CH2CH2-] | OMe | 2,4-dichlorophenyl | NH |
| 2-13 | CH | N | CN | [-O-CH2CH2CH2-NH2] | OMe | 2,4-dichlorophenyl | NH |
| 2-14 | CH | N | H | [4-methylpiperazin-1-yl connected via -O-CH2CH2-] | (C=O)NH2 | pyrimidin-2-yl | O |
| 2-15 | N | CH | Cl | [-O-CH2CH2CH2-C(CH3)2-OH] | OEt | 2,4-difluorophenyl | NH |

Also provided herein, in certain embodiments, are compounds of Formula III:

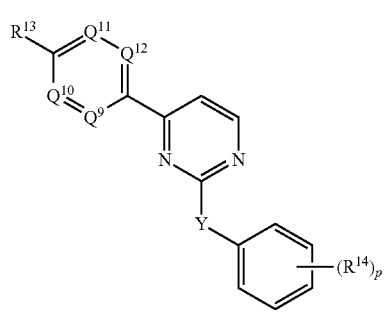

Formula III wherein:

R$^{13}$ is H, halo, hydroxy, cyano, substituted or unsubstituted alkyl, substituted or unsubstituted alkoxy, substituted or unsubstituted alkylamino, substituted or unsubstituted heteroalkyl, substituted or unsubstituted aryl, substituted or unsubstituted heteroaryl, substituted or unsubstituted cycloalkyl, or substituted or unsubstituted heterocycloalkyl;

each R$^{14}$ is independently halo, hydroxy, cyano, substituted or unsubstituted alkyl, substituted or unsubstituted alkoxy, substituted or unsubstituted alkylamino, substituted or unsubstituted heteroalkyl, substituted or unsubstituted aryl, substituted or unsubstituted heteroaryl, substituted or unsubstituted cycloalkyl, or substituted or unsubstituted heterocycloalkyl;

p is 0-5;

Q$^9$, Q$^{10}$, Q$^{11}$, Q$^{12}$ are independently N or C—R$^{15}$; wherein R$^{15}$ is H, halo, hydroxy, cyano, substituted or unsubstituted alkyl or substituted or unsubstituted alkoxy; provided that at least one of $Q^9$, $Q^{10}$, $Q^{11}$, $Q^{12}$ is C—$R^{15}$.

Y is O, N—$R^{16}$ or C($R^{16}$)$_2$, wherein each $R^{16}$ is independently H, hydroxy, substituted or unsubstituted alkyl; or two $R^{16}$ taken together are (=O) or (=N$R^{17}$); wherein $R^{17}$ is H, hydroxy, substituted or unsubstituted alkyl, or substituted or unsubstituted alkoxy;

provided that when $Q^{11}$ is N, $Q^9$, $Q^{10}$, $Q^{12}$ are C—H, and Y is NH, $R^{13}$ is not 2-aminoethylamino;

or a pharmaceutically acceptable salt thereof.

In some embodiments of Formula III, Y is N—$R^{16}$. In some embodiments, each of $Q^9$, $Q^{10}$, $Q^{11}$, and $Q^{12}$ are independently N or CH. In some embodiments, $R^{13}$ is substituted or unsubstituted alkoxy, substituted or unsubstituted alkylamino, substituted or unsubstituted heteroalkyl, substituted or unsubstituted aryl, substituted or unsubstituted heteroaryl, or substituted or unsubstituted heterocycloalkyl. In some embodiments, $R^{13}$ is substituted or unsubstituted alkoxy, or substituted or unsubstituted alkylamino, substituted or unsubstituted heterocycloalkyl, substituted or unsubstituted aryl or substituted or unsubstituted heteroaryl. In some embodiments, $R^{13}$ is substituted or unsubstituted alkylamino or heterocycloalkylamino.

In certain embodiments, each $R^{14}$ is independently halo, hydroxy, cyano, substituted or unsubstituted alkyl, substituted or unsubstituted alkoxy, or substituted or unsubstituted alkylamino. In certain embodiments, $Q^{11}$ is N and $Q^9$, $Q^{10}$ and $Q^{12}$ are CH. In some embodiments, Y is NH. In some embodiments, compounds of Formula III are p21-activated kinase inhibitors.

In certain embodiments, compounds of Formula III are as described in Table 3.

TABLE 3

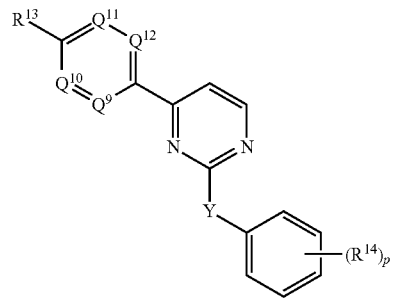

| Compound No. | $Q^9$ | $Q^{10}$ | $Q^{11}$ | $Q^{12}$ | Y | $R^{13}$ | $R^{14}$ |
|---|---|---|---|---|---|---|---|
| 3-1 | N | CH | CH | CH | NH | —O—(CH2)4—OH | m,p-difluoro |
| 3-2 | N | CH | N | CH | O | tetrahydropyranyl-CH2OH | p-Cl |
| 3-3 | CH | N | CH | CH | NH | —NH—CH2CH2—NH2 | 3,4,5-trimethoxy |
| 3-4 | CH | N | CH | CH | NH | piperidinyl | m-CF3 |
| 3-5 | CH | N | CH | CH | NH | —NH—(CH2)3—NH2 | m-CF3 |
| 3-6 | CH | N | CH | CH | NH | —O—CH2CH2—N(CH3)2 | 3,4,5-trimethoxy |
| 3-7 | CH | N | CH | CH | NH | 4-methylpiperazinyl | 3,4,5-trimethoxy |
| 3-8 | CH | N | CH | CH | NH | —NH—CH2CH2—NH2 | o-F |
| 3-9 | CH | N | CH | CH | NH | —NH—CH2CH2—NH2 | o-Me |
| 3-10 | CH | N | CH | CH | NH | 4-methylpiperazinyl | 3,4,5-trimethoxy |
| 3-11 | CH | N | CH | CH | NH | —NH—CH2CH2—NH2 | o-Cl |
| 3-12 | CH | N | N | CH | O | —NH—(CH2)3—OCH3 | m-CH2OH |
| 3-13 | CH | N | CH | CH | NH | —NH—CH2CH2—pyrrolidinyl | o-F |
| 3-14 | CH | N | CH | CH | NH | —NH—CH2CH2—NH2 | m-F |
| 3-15 | CH | N | CH | CH | NH | —O—(CH2)3—N(CH3)2 | m-CF3 |

TABLE 3-continued

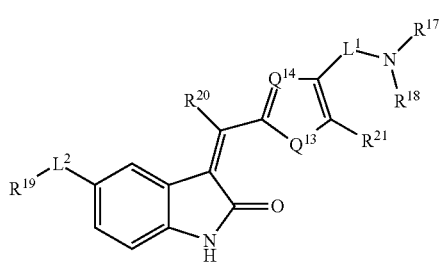

| Compound No. | $Q^9$ | $Q^{10}$ | $Q^{11}$ | $Q^{12}$ | Y | $R^{13}$ | $R^{14}$ |
|---|---|---|---|---|---|---|---|
| 3-16 | CH | N | CH | CH | NH | [piperazinyl group] | m-$CF_3$ |
| 3-17 | CH | N | CH | CH | NH | [N-H, propyl-NH$_2$ group] | m-$CF_3$ |

Also provided herein, in certain embodiments, are compounds of Formula IIIA or pharmaceutically acceptable salt or N-oxide thereof:

Formula IIIA

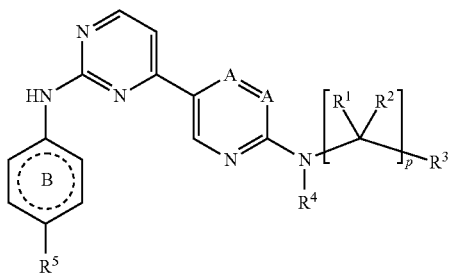

wherein:
- $R^1$ and $R^2$ are each independently H, or substituted or unsubstituted alkyl;
- $R^3$ is H, —OH, —$OR^6$, —$SR^6$, —$S(=O)_2R^7$, —$CO_2R^8$, —$N(R^8)_2$, substituted or unsubstituted alkyl, substituted or unsubstituted cycloalkyl, substituted or unsubstituted heterocycloalkyl;
- $R^6$ is H or substituted or unsubstituted alkyl;
- $R^7$ is substituted or unsubstituted alkyl, substituted or unsubstituted cycloalkyl, substituted or unsubstituted aryl or substituted or unsubstituted heteroaryl;
- each $R^8$ is independently H, substituted or unsubstituted alkyl, substituted or unsubstituted alkylaryl, substituted or unsubstituted alkylheteroaryl, substituted or unsubstituted alkylcycloalkyl, substituted or unsubstituted alkylheterocyclyl, or two $R^8$ together with the nitrogen to which they are attached form a substituted or unsubstituted heterocycle;
- each A is independently N or C—H;
- ring B is aryl or heteroaryl substituted with $R^5$;
- $R^5$ is —$N(R^9)_2$,
- $R^9$ is H, substituted or unsubstituted alkyl, substituted or unsubstituted alkylaryl, substituted or unsubstituted alkylheteroaryl, substituted or unsubstituted alkylcycloalkyl, substituted or unsubstituted alkylheterocyclyl, or two $R^9$ together with the nitrogen to which they are attached form a substituted or unsubstituted heterocycle; and
- p is 1-5.

In some embodiments of Formula IIIA, ring B is an aryl ring. In some embodiments of Formula IIIA, ring B is a heteroaryl ring. In some embodiments of Formula IIIA, $R^3$ is OH, —$OR^6$ or —$N(R^8)_2$. In some embodiments of Formula IIIA, $R^3$ is —$N(R^8)_2$. In some embodiments of Formula IIIA, $R^4$ is H. In some embodiments of Formula IIIA, $R^5$ is a substituted or unsubstituted piperidinyl, pyrrolidinyl or piperazinyl ring. In some embodiments of Formula IIIA, $R^5$ is a substituted or unsubstituted alkylaryl ring. In some embodiments, compounds of Formula IIIA are p21-activated kinase inhibitors.

Also provided herein, in certain embodiments, are compounds of Formula IV:

Formula IV

[Structure of Formula IV]

wherein:
- $R^{17}$, $R^{18}$ are independently H, substituted or unsubstituted alkyl, $C(=O)$—$N(R^{22})_2$, $S(O)_q$—$N(R^{22})_2$, substituted or unsubstituted heteroalkyl, substituted or unsubstituted aryl, substituted or unsubstituted heteroaryl, substituted or unsubstituted cycloalkyl, or substituted or unsubstituted heterocycloalkyl; wherein each $R^{22}$ is independently H, substituted or unsubstituted alkyl; substituted or unsubstituted cycloalkyl, or substituted or unsubstituted alkylcycloalkyl; and q is 1-2; or $R^{17}$ and $R^{18}$ together with the nitrogen to which they are attached from a heterocycle;
- $R^{19}$ is substituted or unsubstituted alkyl, substituted or unsubstituted alkoxy, substituted or unsubstituted alkylamino, substituted or unsubstituted heteroalkyl, substituted or unsubstituted aryl, substituted or unsubstituted heteroaryl, substituted or unsubstituted cycloalkyl, or substituted or unsubstituted heterocycloalkyl;
- $R^{20}$, $R^{21}$ is H, substituted or unsubstituted alkyl or substituted or unsubstituted alkylcycloalkyl;
- $L^1$, $L^2$ are independently O, $S(O)_t$, N—$R^{23}$ or $C(R^{23})_2$, wherein each $R^{23}$ is independently H, hydroxy, substituted or unsubstituted alkyl; or two $R^{23}$ taken together are (=O) or (=$NR^{24}$); $R^{24}$ is H, hydroxy, substituted or unsubstituted alkyl, or substituted or unsubstituted alkoxy; t is 1-2;
- $Q^{13}$ is O, N—$R^{25}$ or C—$R^{26}$; wherein $R^{25}$ is H or substituted or unsubstituted alkyl; $R^{26}$ is H, halo, substituted or unsubstituted alkyl or substituted or unsubstituted alkoxy;

$Q^{14}$ is N, O, S, or $CR^{26}$;

provided that when $R^{20}$ is H, $R^{21}$ is methyl, $Q^{14}$ is C—$CH_3$, $L^1$, and $L^2$ are C=O, and $R^{17}$ and $R^{18}$ together with the nitrogen to which they are attached form a heterocycle, $R^{19}$ is not (-methylbenzylamino;

or a pharmaceutically acceptable salt thereof.

In some embodiments of Formula IV, $L^1$ and $L^2$ are each independently C=O. In some embodiments, $Q^{13}$ is NH or O. In some embodiments, $Q^{14}$ is C—$R^{26}$. In some embodiments, $R^{17}$ and $R^{18}$ are each independently H or substituted or unsubstituted alkyl. In some embodiments, $R^{17}$ and $R^{18}$ together with the nitrogen to which they are attached form a heterocycle. In some embodiments, $R^{19}$ is substituted or unsubstituted alkyl, substituted or unsubstituted alkylamino, substituted or unsubstituted heteroalkyl, substituted or unsubstituted aryl or substituted or unsubstituted heteroaryl. In some embodiments, $R^{19}$ is substituted or unsubstituted alkylaryl or substituted or unsubstituted alkylheteroaryl.

In some embodiments, $R^{20}$ is H. In some embodiments, $R^{21}$ is substituted or unsubstituted alkyl. In some embodiments, $L^1$ is C=O. In some embodiments, $L^2$ is C=O. In some embodiments, $L^1$ and $L^2$ are C=O. In some embodiments, compounds of Formula IV are p21-activated kinase inhibitors.

In certain embodiments, compounds of Formula IV are as described in Table 4.

TABLE 4

| Compound No. | $Q^{13}$ | $R^{19}$ | $R^{20}$ | $R^{21}$ | $L^2$ | $NR^{17}R^{18}$ |
|---|---|---|---|---|---|---|
| 4-1 | NH | (1-phenyl-1-methylethyl)amino | H | H | C=O | N,N-diethylamino |
| 4-2 | NMe | (2-phenylethyl)amino | H | Me | C=O | pyrrolidinyl |
| 4-3 | O | (4-fluorophenyl)(hydroxy)methylamino | Me | Me | C=O | morpholinyl |
| 4-4 | NH | (6-fluoropyridin-3-yl)methylamino | H | H | $SO_2$ | 2-(1-methylpiperidin-3-yl)ethoxy |
| 4-5 | NH | N-methyl-2-(benzofuran-6-yl)ethylamino | Me | Me | $SO_2$ | (2-methoxyethyl)amino |
| 4-6 | NH | (S)-N-methyl-1-phenylethylamino | H | Me | C=O | 4-methylpiperazin-1-yl |

TABLE 4-continued

[Structure shown with R17, R18, R19, R20, R21, L2, Q13 substituents on an indolinone-furan scaffold]

| Compound No. | Q13 | R19 | R20 | R21 | L2 | NR17R18 |
|---|---|---|---|---|---|---|
| 4-7 | NH | 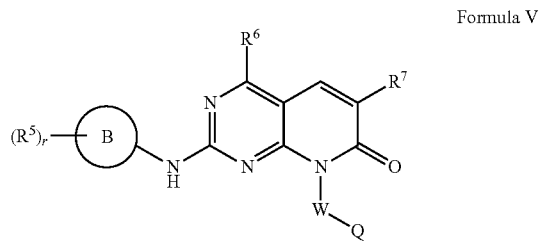 | H | Me | C=O | [N-methylpiperazinyl group] |

Provided herein, in some embodiments, are compounds having the structure of Formula V or pharmaceutically acceptable salt or N-oxide thereof:

Formula V

[Structure of Formula V with R5, B, R6, R7, W, Q substituents on pyrido-pyrimidinone core]

wherein:
W is a bond;
$R^6$ is H, or halogen;
$R^7$ is H, halogen, CN, OH, substituted or unsubstituted alkyl, substituted or unsubstituted alkoxy, —C(=O)N($R^{10}$)$_2$, CO$_2$$R^{10}$, N($R^{10}$)$_2$, acyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
Q is substituted or unsubstituted cycloalkyl or heterocycloalkyl fused to ring A;
ring A is substituted or unsubstituted aryl or heteroaryl substituted with 0-4 $R^4$;
each $R^4$ is independently halogen, —CN, —NO$_2$, —OH, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
$R^8$ is H or substituted or unsubstituted alkyl;
$R^9$ is substituted or unsubstituted alkyl, substituted or unsubstituted cycloalkyl, substituted or unsubstituted aryl or substituted or unsubstituted heteroaryl each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;
ring B is aryl or heteroaryl substituted with $R^5$;
each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
r is 0-8;
provided that when Q is unsubstituted indane, tetrahydronaphthalene or fluorene, and $R^6$ is H, ring B is not unsubstituted phenyl and $R^5$ is not para substituted piperidinyl, pyrazolyl or methylpiperazinyl.

In some embodiments, the compound of Formula V has the structure of Formula VI:

Formula VI

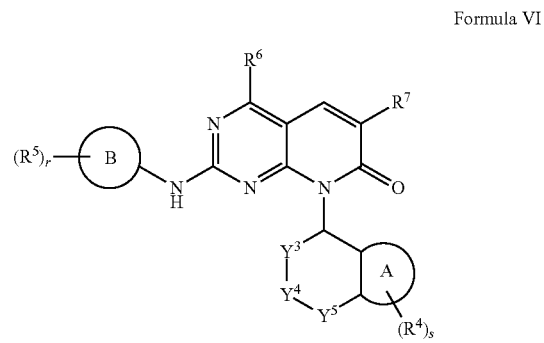

wherein:
each of $Y^3$, $Y^4$ and $Y^5$ are independently a bond, O, N—$R^{1a}$, CR$^1$R$^2$, SO$_2$, or C=O;

$R^{1a}$ is H or substituted or unsubstituted alkyl;

$R^1$ and $R^2$ are each independently H, halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

s is 0-4.

In some embodiments, the compound of Formula V has the structure of Formula VII:

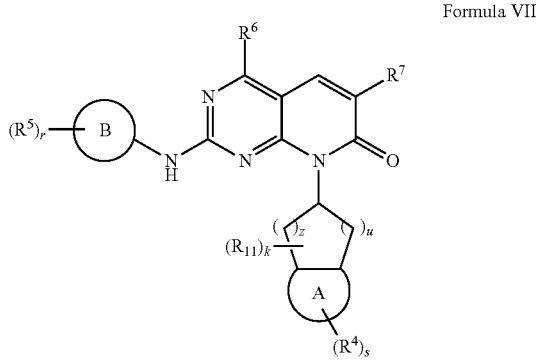

Formula VII wherein:

ring A is an aryl or heteroaryl substituted with R$^4$;

each R$^4$ is independently halogen, —CN, —NO$_2$, —OH, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^9$, —NR$^{10}$C(=O)OR$^9$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

R$^8$ is H or substituted or unsubstituted alkyl;

R$^9$ is substituted or unsubstituted alkyl, substituted or unsubstituted cycloalkyl, substituted or unsubstituted aryl or substituted or unsubstituted heteroaryl;

each R$^{10}$ is independently H, substituted or unsubstituted alkyl, substituted or unsubstituted cycloalkyl, substituted or unsubstituted aryl or substituted or unsubstituted heteroary, or two R$^{10}$ together with the nitrogen to which they are attached form a heterocycle;

each R$^{11}$ is independently hydrogen, halogen, —CN, —NO$_2$, —OH, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^9$, —NR$^{10}$C(=O)OR$^9$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl; or two R$^{11}$ together with the carbon atom to which they are attached form C=O;

s is 0-4;

k is 1-4;

z is 0 or 1;

u is 1, 2 or 3;

provided that z+u≠1;

ring B is an aryl or heteroaryl substituted with R$^5$;

each R$^5$ is independently halogen, —CN, —NO$_2$, —OH, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^9$, —NR$^{10}$C(=O)OR$^9$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

r is 0-8;

R$^6$ is H, or halogen;

R$^7$ is H, halogen, CN, OH, substituted or unsubstituted alkyl, substituted or unsubstituted alkoxy, —C(=O)N(R$^{10}$)$_2$, CO$_2$R$^{10}$, N(R$^{10}$)$_2$, acyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments of Formula V, VI or VII, ring A is heteroaryl ring comprising 1-3 nitrogen atoms, an oxygen atom, a sulfur atom, or any combination thereof. In some embodiments of Formula V, VI or VII, ring A is a phenyl ring.

In some embodiments, a compound of Formula VII has a structure of Formula VIIA, Formula VIIB, Formula VIIC, Formula VIID, Formula VIIE, Formula VIIF, Formula VIIG or Formula VIIH:

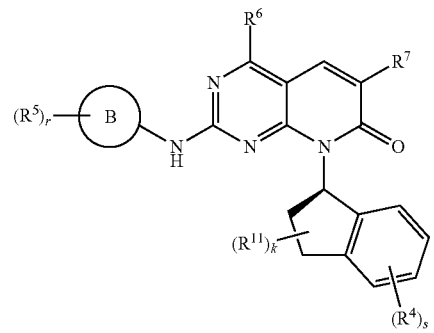

Formula VIIA

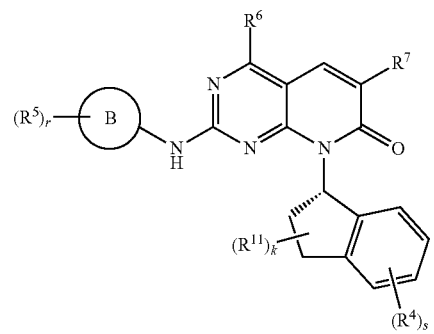

Formula VIIB

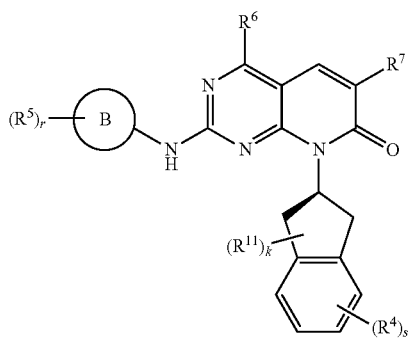

Formula VIIC

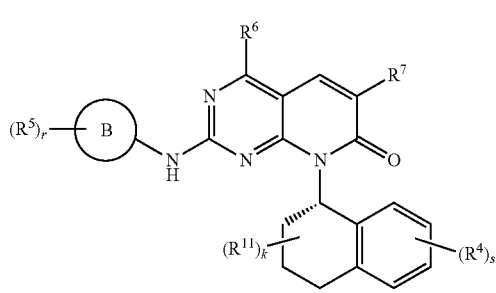

Formula VIIF

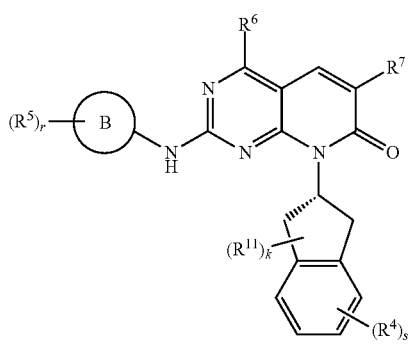

Formula VIID

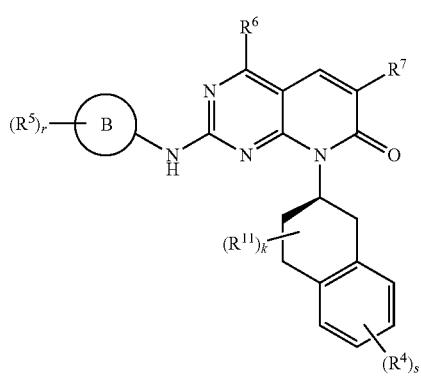

Formula VIIG

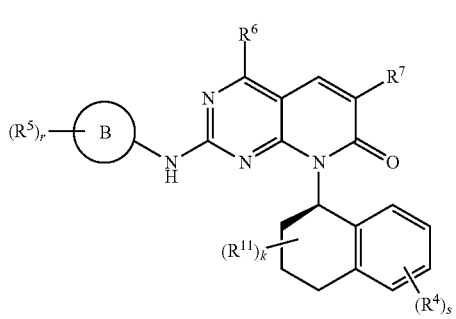

Formula VIIE

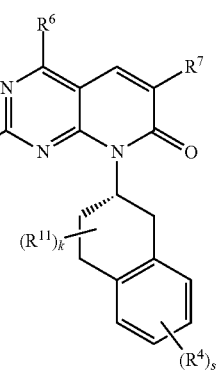

Formula VIIH

In some embodiments of Formula VII, $R^{11}$ is H, halogen, substituted or unsubstituted alkyl, substituted or unsubstituted alkoxy or $N(R^{10})_2$. In some embodiments of Formula VII, $R^{11}$ is H. In some embodiments of Formula VII, each $R^4$ is independently halogen, substituted or unsubstituted alkyl, substituted or unsubstituted alkoxy, substituted or unsubstituted cycloalkyl or substituted or unsubstituted heterocycloalkyl. In some embodiments of Formula VII, each $R^4$ is independently Cl, F, $CF_3$ or OMe.

In some embodiments, compounds of Formula V are as described in the Example section and Table 5:

TABLE 5
| Compound No. | B | Q | R⁶ | R⁷ | R⁵ |
|---|---|---|---|---|---|
| 5-1 | 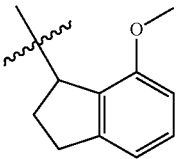 [SMILES: *C1CCc2cccc(OC)c21] | 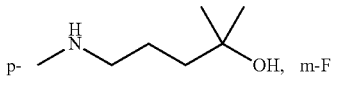 | H | OH |  p-, m-F |
| 5-2 | 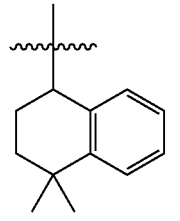 [SMILES: *C1CCC(C)(C)c2ccccc21] | 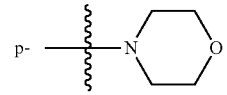 | H | Me |  p- |
| 5-3 | 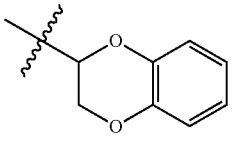 [SMILES: *C1COc2ccccc2O1] | 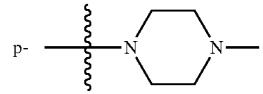 | H | H |  p- |
| 5-4 | 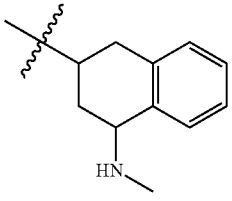 [SMILES: *C1Cc2ccccc2C(NC)C1] | 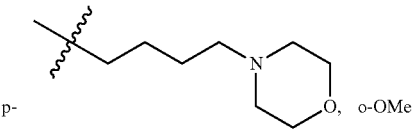 [SMILES: *CCCCN1CCOCC1] | Cl | H |  p-, o-OMe |
| 5-5 | 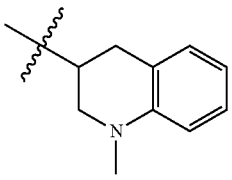 [SMILES: *C1Cc2ccccc2N(C)C1] | 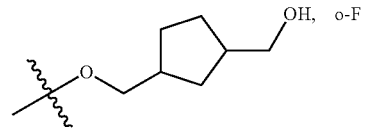 | H | H |  p-, o-F |
| 5-6 | 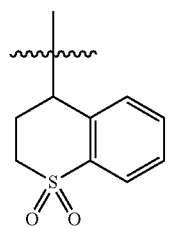 [SMILES: *C1CCS(=O)(=O)c2ccccc21] | 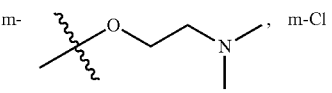 [SMILES: *OCCN(C)C] | H | H | m-, m-Cl |

TABLE 5-continued

| Compound No. | B | Q | R6 | R7 | R5 |
|---|---|---|---|---|---|
| 5-7 | phenyl | 4-chroman-2-one | H | CONH2 | m-, N-methylpiperazinyl |
| 5-8 | phenyl | 4-(3,4-dihydroquinolin-2(1H)-one) | H | cyclopentyl | p-, piperazinyl, o-Cl |
| 5-9 | phenyl | 1-(8-methoxy-1,2,3,4-tetrahydronaphthalen-1-yl) | Cl | cyclopropylcarbonyl | p-, N-methyl-N-((4-acetylpiperazin-1-yl)methyl)amino |
| 5-10 | phenyl | 1-(8-methylthio-1,2,3,4-tetrahydronaphthalen-1-yl) | H | H | p-, 1-methylpyrrolidin-3-yl |
| 5-11 | phenyl | 3-(1-acetylindolin-3-yl) | H | Cl | p-, N-cyclopropylisobutyramide, o-Me |
| 5-12 | phenyl | 4-(6,7-dihydro-5H-cyclopenta[b]pyridin-4-yl) | Me | H | p-, piperazinyl, o-F |

TABLE 5-continued

| Compound No. | B | Q | R⁶ | R⁷ | R⁵ |
|---|---|---|---|---|---|
| 5-13 | phenyl | 1-acetamido-indan-3-yl | H | OMe | p-piperidinyl, m-CN |
| 5-14 | phenyl | 5-fluoro-indan-2-yl | H | H | p-C(CH₃)₂SO₂NHcyclopropyl |
| 15-15 | phenyl | indanyl-methylsulfinyl | H | CN | p-(2-oxopyrrolidin-1-yl) |
| 5-16 | phenyl | 7-cyano-tetralin-1-yl | H | H | m-OCH₂CH₂NH₂, p-SO₂Me |
| 5-17 | pyridyl | tetralinyl-methylsulfinyl | H | isopropyl | m-(4-methylpiperazin-1-yl) |
| 5-18 | pyridyl | 6-chloro-tetralin-1-yl | Cl | H | p-SO₂Me |
| 5-20 | phenyl | 8-methoxy-tetralin-1-yl | F | pyrrolidin-1-yl | p-N(Me)CH₂CH₂CH₂CH(NH₂)CH₂OMe |

TABLE 5-continued

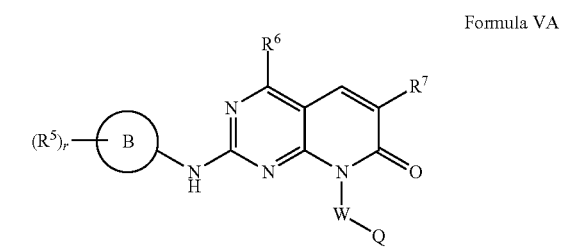

| Compound No. | B | Q | R⁶ | R⁷ | R⁵ |
|---|---|---|---|---|---|
| 5-21 | phenyl | chloro-indanyl | H | p-(N-isopropyl benzamide) | m-methoxyethylamino, p-Cl |
| 5-22 | phenyl | methoxy-tetrahydronaphthyl | H | methylthiophenyl | p-(4-hydroxypiperidinyl), o-Me |
| 5-23 | phenyl | chloro-indanyl | H | H | p-(N-phenylurea), m-OMe |
| 5-24 | phenyl | methoxy-tetrahydronaphthyl | H | H | p-(1H-1,2,4-triazolyl) |

Provided herein, in some embodiments, are compounds having the structure of Formula VA or pharmaceutically acceptable salt or N-oxide thereof:

Formula VA wherein:
W is a bond;
$R^6$ is H, or halogen;
$R^7$ is H, halogen, CN, OH, substituted or unsubstituted alkyl, substituted or unsubstituted alkoxy, —C(=O)N$(R^{10})_2$, CO$_2R^{10}$, N$(R^{10})_2$, acyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Q is substituted or unsubstituted cycloalkyl or heterocycloalkyl fused to ring A;
ring A is substituted or unsubstituted aryl or heteroaryl substituted with 0-4 $R^4$;
each $R^4$ is independently halogen, —CN, —NO$_2$, —OH, —SR$^8$, —S(=O)R$^9$, —S(=O)$_2R^9$, —NR$^{10}$S(=O)$_2R^9$, —S(=O)$_2$N$(R^{10})_2$, —C(=O)R$^9$, —OC(=O)R$^9$, —CO$_2R^{10}$, —N$(R^{10})_2$, —C(=O)N$(R^{10})_2$, —NR$^{10}$C(=O)R$^{10}$, —NR$^{10}$C(=O)OR$^{10}$, —NR$^{10}$C(=O)N$(R^{10})_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
$R^8$ is H or substituted or unsubstituted alkyl;
$R^9$ is substituted or unsubstituted alkyl, substituted or unsubstituted cycloalkyl, substituted or unsubstituted aryl or substituted or unsubstituted heteroaryl
each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;

ring B is aryl or heteroaryl substituted with $R^5$;
each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

r is 0-8.

Provided herein, in some embodiments, are compounds having the structure of Formula VIII or pharmaceutically acceptable salt or N-oxide thereof:

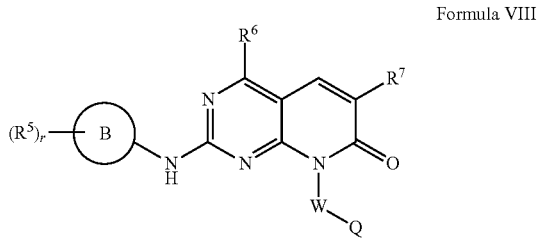

Formula VIII

W is a bond;
$R^6$ is H, halogen, —CN, —OH, substituted or unsubstituted alkoxy, —N(R$^{10}$)$_2$, substituted or unsubstituted heteroalkyl, substituted or unsubstituted cycloalkyl, substituted or unsubstituted aryl or substituted or unsubstituted heteroaryl;
$R^7$ is H, halogen, —CN, —OH, substituted or unsubstituted alkyl, substituted or unsubstituted alkoxy, —C(=O)N(R$^{10}$)$_2$, —CO$_2$R$^{10}$, —N(R$^{10}$)$_2$, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
Q is

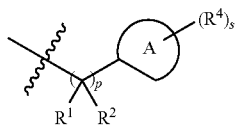

$R^1$ is H or substituted or unsubstituted alkyl;
$R^2$ is substituted or unsubstituted alkyl, or $R^1$ and $R^2$ together with the carbon to which they are attached form a C$_3$-C$_6$ cycloalkyl ring;
p is 1, 2 or 3;
ring A is aryl substituted with $R^4$;
each $R^4$ is independently halogen, —CN, —NO$_2$, —OH, —OCF$_3$, —OCF$_2$H, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

$R^8$ is H or substituted or unsubstituted alkyl;
$R^9$ is substituted or unsubstituted alkyl, substituted or unsubstituted cycloalkyl, substituted or unsubstituted aryl or substituted or unsubstituted heteroaryl
each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;
s is 0-4;
ring B is aryl or heteroaryl substituted with $R^5$;
each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;
r is 0-8;
provided that when s is zero, then $R^2$ is not methyl.

In some embodiments of Formula VIII, $R^1$ is H or $C_1$-$C_5$ alkyl. In some embodiments of Formula VIII, $R^2$ is $C_1$-$C_5$ alkyl. In some embodiments of Formula VIII, $R^2$ is $C_2$-$C_5$ alkyl. In some embodiments of Formula VIII, $R^2$ is ethyl, propyl or isopropyl.

In some embodiments of Formula VIII,
W is a bond;
$R^6$ is H, halogen, —CN, —OH, substituted or unsubstituted alkoxy, —N(R$^{10}$)$_2$, substituted or unsubstituted heteroalkyl, substituted or unsubstituted cycloalkyl, substituted or unsubstituted aryl or substituted or unsubstituted heteroaryl;
$R^7$ is H, halogen, —CN, —OH, substituted or unsubstituted alkyl, substituted or unsubstituted alkoxy, —C(=O)N(R$^{10}$)$_2$, —CO$_2$R$^{10}$, —N(R$^{10}$)$_2$, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
Q is

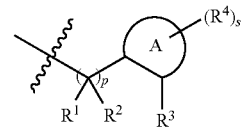

$R^1$ is H or substituted or unsubstituted alkyl;
$R^2$ is substituted or unsubstituted alkyl, or $R^1$ and $R^2$ together with the carbon to which they are attached form a C$_3$-C$_6$ cycloalkyl ring;
p is 1, 2 or 3;
ring A is aryl substituted with $R^3$ and $R^4$;
$R^3$ is halogen, —CN, —NO$_2$, —OH, —OCF$_3$, —OCF$_2$H, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^9$, NR$^{10}$C(=O)OR$^9$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

each $R^4$ is independently halogen, —CN, —NO$_2$, —OH, —OCF$_3$, —OCF$_2$H, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

$R^8$ is H or substituted or unsubstituted alkyl;

$R^9$ is substituted or unsubstituted alkyl, substituted or unsubstituted cycloalkyl, substituted or unsubstituted aryl or substituted or unsubstituted heteroaryl each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;

s is 0-4;

ring B is aryl or heteroaryl substituted with $R^5$;

each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

r is 0-8.

In some embodiments, a compound of Formula VIII has the structure of Formula VIIIA or Formula VIIIB:

Formula VIIIA

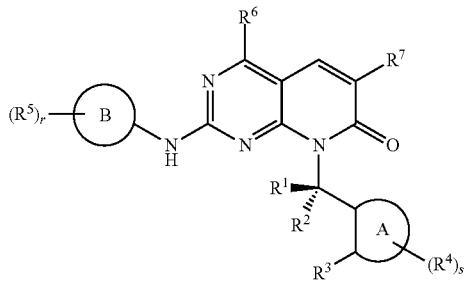

Formula VIIIB

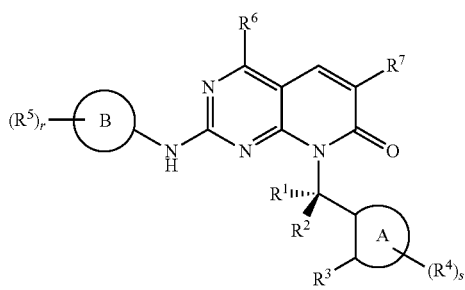

In some embodiments, the compound of Formula VIII has the structure of Formula (IX):

Formula IX

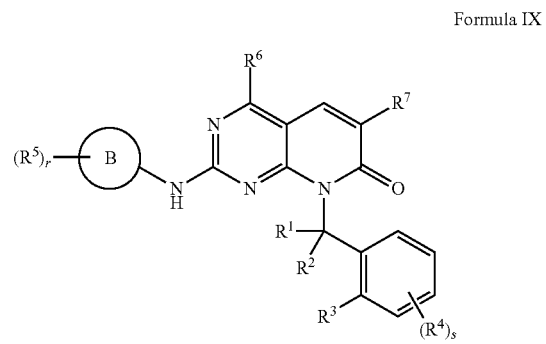

wherein:
$R^1$ is H or substituted or unsubstituted alkyl;
$R^2$ is substituted or unsubstituted alkyl; and
$R^3$ is halogen, alkyl, fluoroalkyl, alkoxy, fluoroalkoxy, SR$^8$, —S(=O)R$^9$, or —S(=O)$_2$R$^9$, substituted or unsubstituted cycloalkyl, substituted or unsubstituted heterocycloalkyl.

In some embodiments of Formula VIII, $R^3$ is F, Cl, SCF$_3$, CF$_3$, OMe, (R) or (S)—S(=O)R$^9$ or —S(O)$_2$R$^9$.

In some embodiments, the compound of Formula IX has the structure of Formula (IXA) or Formula (IXB):

Formula (IXA)

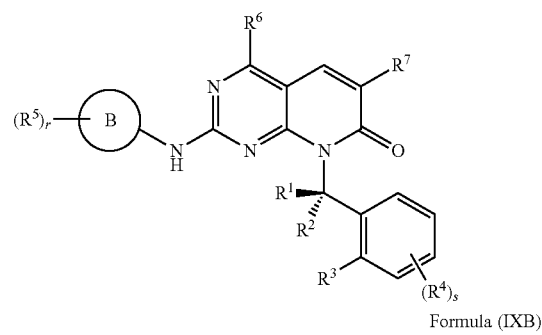

Formula (IXB)

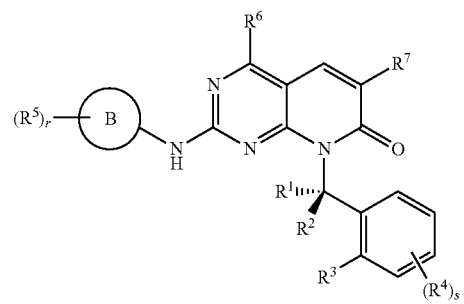

In some embodiments of Formula IX, $R^1$ is H or C$_1$-C$_5$ alkyl. In some embodiments of Formula IX, $R^2$ is C$_1$-C$_5$ alkyl. In some embodiments of Formula IX, $R^2$ is C$_2$-C$_5$ alkyl. In some embodiments of Formula IX, $R^2$ is ethyl, propyl or isopropyl.

In some embodiments, compounds of Formula VIII, VIIIA, VIIIB, IX, IXA and/or IXB are as described in the Examples section and in Table 6.

TABLE 6
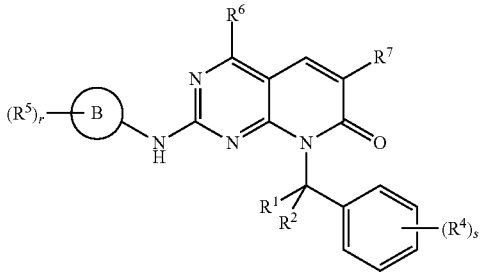
| Compound No. | B |  | R⁶ | R⁷ | R⁵ |
|---|---|---|---|---|---|
| 6-1 | 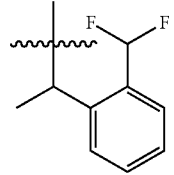 [SMILES: *C(C)c1ccccc1C(F)F] | 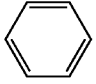 | H | OH | 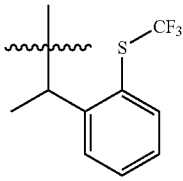 [SMILES: *C(C)c1ccccc1SC(F)(F)F] p-, m-F |
| 6-2 |  | 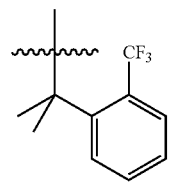 [SMILES: *C(C)(C)c1ccccc1C(F)(F)F] | H | Me |  p- |
| 6-3 | 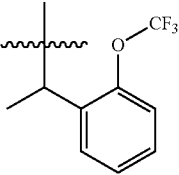 [SMILES: *C(C)c1ccccc1OC(F)(F)F] |  | H | H | 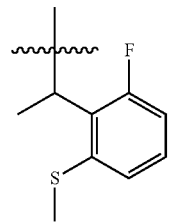 [SMILES: *C(C)c1c(F)cccc1SC] p- |
| 6-4 | (benzene) | (2-OCF₃, iPr-phenyl) | Cl | H | (morpholinopentyl) p-, o-OMe |
| 6-5 | (benzene) | (2-F, 6-SMe, iPr-phenyl) | H | H | (cyclopentyl-CH₂-O-) p-, o-F, OH |

TABLE 6-continued

| Compound No. | B | (R¹R² substituted benzyl group with (R⁴)ₛ) | R⁶ | R⁷ | R⁵ |
|---|---|---|---|---|---|
| 6-6 | phenyl | 2-F, 6-OMe, α-isopropyl phenyl | H | H | m-OCH₂CH₂N(CH₃)₂, m-Cl |
| 6-7 | phenyl | 2-S(O)CH₃, α-isopropyl phenyl | H | CONH₂ | m-(4-methylpiperazin-1-yl) |
| 6-8 | phenyl | 2-F, 6-S(O)CH₃, α-isopropyl phenyl | H | cyclopentyl | p-(piperazin-1-yl), o-Cl |
| 6-9 | phenyl | 2-F, 6-S(O)CH₃, α-sec-butyl phenyl | Cl | C(O)-cyclopropyl | p-CH₂N(CH₃)CH₂-(4-acetylpiperazin-1-yl) |
| 6-10 | phenyl | 2-F, 6-CH₃, α-isopropyl phenyl | H | H | p-(1-methylpyrrolidin-3-yl) |

TABLE 6-continued
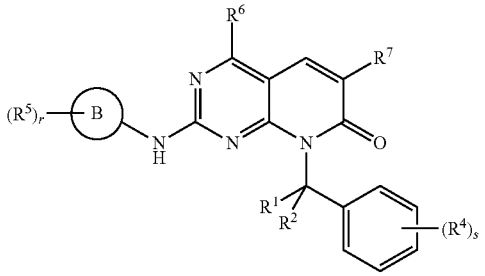
| Compound No. | B |  | R⁶ | R⁷ | R⁵ |
|---|---|---|---|---|---|
| 6-11 | 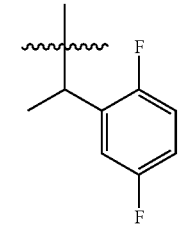 [SMILES: *C(C)c1cc(F)ccc1F] | 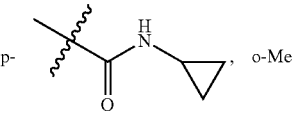 [SMILES: *C(=O)NC1CC1] | H | Cl | p-  , o-Me |
| 6-12 | 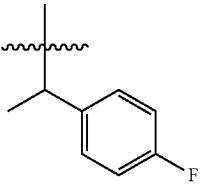 [SMILES: *C(C)c1ccc(F)cc1] | 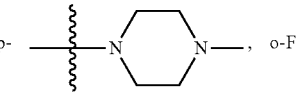 | Me | H | p-  , o-F |
| 6-13 | 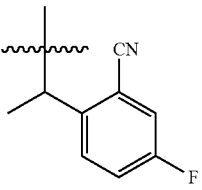 [SMILES: *C(C)c1ccc(F)cc1C#N] | 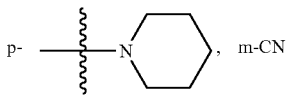 | H | OMe | p-  , m-CN |
| 6-14 | 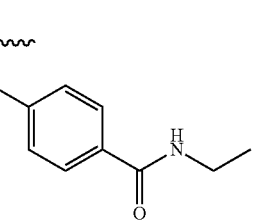 | 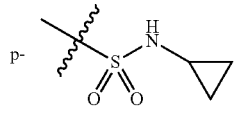 [SMILES: *S(=O)(=O)NC1CC1] | H | H | p-  |
| 6-15 | 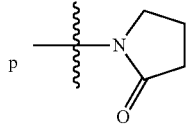 [SMILES: *N1CCCC1=O] | | H | CN | p  |

TABLE 6-continued

| Compound No. | B | R¹R²/(R⁴)s | R⁶ | R⁷ | R⁵ |
|---|---|---|---|---|---|
| 6-16 | phenyl | 4-isopropylphenyl with –OCH₂CH₂NH-iPr | H | H | m- –O-CH₂CH₂NH₂, p-SO₂Me |
| 6-17 | pyridyl | 3-isopropylphenyl with NHC(O)NHMe | H | isopropyl | m- 4-methylpiperazin-1-yl |
| 6-18 | pyridyl | (S)-1-(2,5-difluorophenyl)ethyl | Cl | H | p-SO₂Me |
| 6-20 | phenyl | (S)-1-(3-fluoro-4-methylsulfonylphenyl)ethyl | F | pyrrolidin-1-yl | p- –N(Me)CH₂CH₂CH₂CH(NH₂)CH₂OMe |
| 6-21 | phenyl | 2-(trifluoromethyl)phenyl, CF₃ | H | 4-(N-isopropylcarbamoyl)phenyl | m- –OCH₂CH₂NHMe, p-Cl |

TABLE 6-continued

| Compound No. | B | R⁶ | R⁷ | R⁵ |
|---|---|---|---|---|
| 6-22 | phenyl | H | 5-methylthiophen-2-yl | p- piperidin-N-yl-4-OH, o-Me |
| 6-23 | phenyl | H | H | p- NHC(O)NH-phenyl, m-OMe |
| 6-24 | phenyl | H | H | p- 1H-1,2,4-triazol-3-yl |

Provided herein, in some embodiments, are compounds having the structure of Formula VIIIC or pharmaceutically acceptable salt or N-oxide thereof:

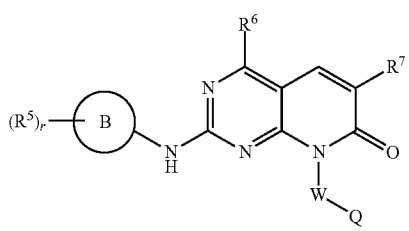

Formula VIIIC

W is a bond;

R⁶ is H, halogen, —CN, —OH, substituted or unsubstituted alkoxy, —N(R¹⁰)₂, substituted or unsubstituted heteroalkyl, substituted or unsubstituted cycloalkyl, substituted or unsubstituted aryl or substituted or unsubstituted heteroaryl;

R⁷ is H, halogen, —CN, —OH, substituted or unsubstituted alkyl, substituted or unsubstituted alkoxy, —C(=O)N(R¹⁰)₂, —CO₂R¹⁰, —N(R¹⁰)₂, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

Q is

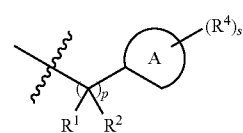

$R^1$ is H or substituted or unsubstituted alkyl;

$R^2$ is substituted or unsubstituted alkyl, or $R^1$ and $R^2$ together with the carbon to which they are attached form a $C_3$-$C_6$ cycloalkyl ring;

p is 1, 2 or 3;

ring A is aryl substituted with $R^4$;

each $R^4$ is independently halogen, —CN, —NO$_2$, —OH, —OCF$_3$, —OCF$_2$H, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

$R^8$ is H or substituted or unsubstituted alkyl;

$R^9$ is substituted or unsubstituted alkyl, substituted or unsubstituted cycloalkyl, substituted or unsubstituted aryl or substituted or unsubstituted heteroaryl each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;

s is 0-4;

ring B is aryl or heteroaryl substituted with $R^5$;

each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

r is 0-8.

Also provided herein, in some embodiments, are compound having the structure of Formula X or pharmaceutically acceptable salt or N-oxide thereof:

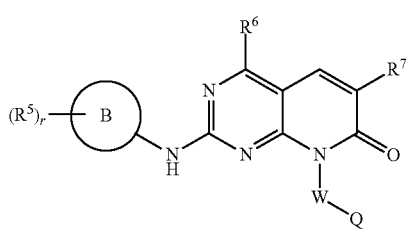

Formula X wherein:

W is a bond;

$R^6$ is H, halogen, —CN, —OH, substituted or unsubstituted alkyl, substituted or unsubstituted alkoxy, —N(R$^{10}$)$_2$, substituted or unsubstituted heteroalkyl, substituted or unsubstituted cycloalkyl, substituted or unsubstituted aryl or substituted or unsubstituted heteroaryl;

$R^7$ is H, halogen, —CN, —OH, substituted or unsubstituted alkyl, substituted or unsubstituted alkoxy, —C(=O)N(R$^{10}$)$_2$, —CO$_2$R$^{10}$, —N(R$^{10}$)$_2$, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

Q is

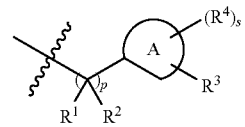

$R^1$ and $R^2$ are each independently H or substituted or unsubstituted alkyl; or $R^1$ and $R^2$ together with the carbon to which they are attached form a $C_3$-$C_6$ cycloalkyl ring;

p is 1, 2 or 3;

ring A is aryl substituted with $R^3$ and $R^4$;

$R^3$ is a substituted or unsubstituted heteroaryl, substituted or unsubstituted cycloalkyl or substituted or unsubstituted heterocycloalkyl attached to ring A via a carbon atom;

each $R^4$ is independently halogen, —CN, —NO$_2$, —OH, —OCF$_3$, —OCF$_2$H, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

$R^8$ is H or substituted or unsubstituted alkyl;

$R^9$ is substituted or unsubstituted alkyl, substituted or unsubstituted cycloalkyl, substituted or unsubstituted aryl or substituted or unsubstituted heteroaryl each $R^{10}$ is independently H, substituted or unsubstituted alkyl, substituted or unsubstituted cycloalkyl, substituted or unsubstituted aryl or substituted or unsubstituted heteroaryl, or two $R^{13}$ together with the atoms to which they are attached form a heterocycle;

s is 0-4;

ring B is aryl or heteroaryl substituted with $R^5$;

each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

r is 0-8.

In some embodiments of Formula X, $R^3$ is located at the ortho position on ring A, relative to the position of the group

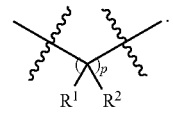

In some embodiments of Formula X, $R^3$ is located at the meta position on ring A, relative to the position of the group

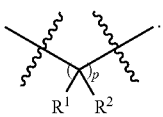

In some embodiments of Formula X, R³ is located at the para position on ring A, relative to the position of the group

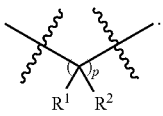

In some embodiments of Formula X, Q is:

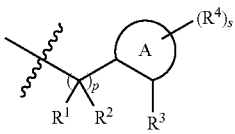

In some embodiments of Formula X, Q is

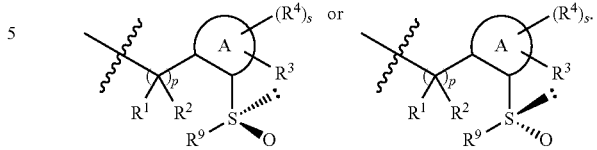

In some embodiments of Formula X, R³ is a $C_3$-$C_6$ cycloalkyl ring, a 5-6-membered heteroaryl ring comprising 1-3 nitrogen atoms, an oxygen atom, a sulfur atom, or any combination thereof, or a 3-6-membered heterocycloalkyl ring comprising 1-3 nitrogen atoms, an oxygen atom, a sulfur atom, or any combination thereof, that is attached to ring via a carbon atom and wherein R³ is further substituted by halogen, cyano, alkyl, alkoxy, —SR⁸, (R) or (S)—S(O)R⁹ or —S(O)₂R⁹.

In some embodiments of Formula X, R¹ and R² are H. In some embodiments of Formula X, one of R¹ and R² is H, and the other of R¹ and R² is $C_1$-$C_5$ alkyl.

In some embodiments, compounds of Formula X are as described in the Examples section and Table 7.

TABLE 7
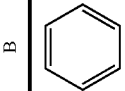
| Compound No. | B | ![A/R structure] | R⁶ | R⁷ | R⁵ |
|---|---|---|---|---|---|
| 7-1 | phenyl | 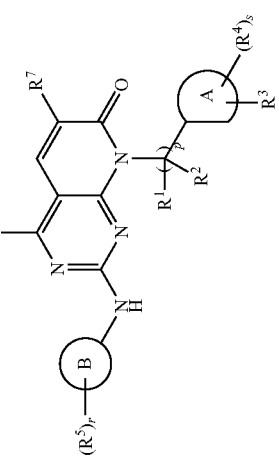 | H | OH | 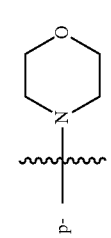 p-, OH, m-F |
| 7-2 | phenyl | 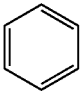 | H | Me | 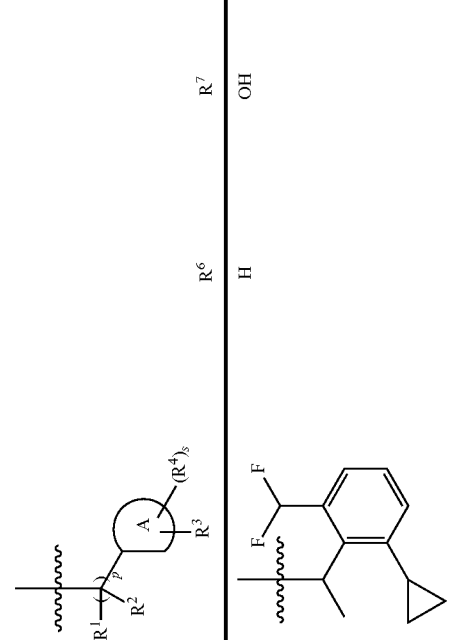 p- |

TABLE 7-continued
| Compound No. | B | 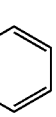 | R⁶ | R⁷ | R⁵ |
|---|---|---|---|---|---|
| 7-3 | 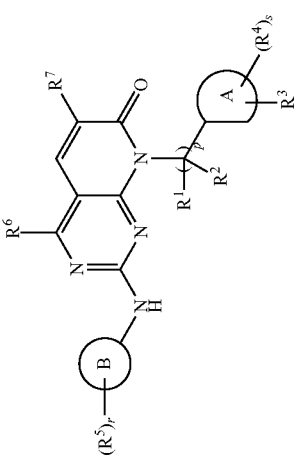 | 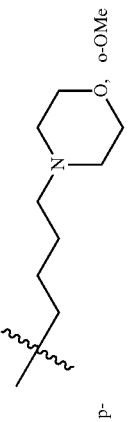 | H | H | 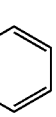 p- |
| 7-4 | 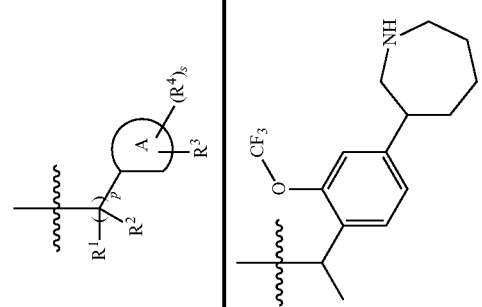 |  | Cl | H |  p- |

TABLE 7-continued

| Compound No. | B | | R6 | R7 | R5 |
|---|---|---|---|---|---|
| 7-5 | phenyl | 2-(1-methylimidazol-5-yl)phenyl-C(CH3)- | H | H | p-, cyclopentyl-CH2-O-C(CH3)- ; OH, o-F |
| 7-6 | phenyl | 4-phenyl-2-(methylsulfinyl)phenyl-C(CH3)- | H | H | m-, -C(CH3)-O-CH2CH2-N(CH3)2 ; m-Cl |

TABLE 7-continued
| Compound No. | B | —C(R¹)(R²)—(A)(R³)(R⁴)ₛ | R⁶ | R⁷ | R⁵ |
|---|---|---|---|---|---|
| 7-7 | 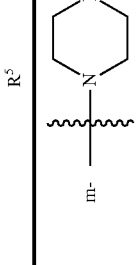 |  (F, cyclobutyl) | H | CONH₂ |  m- (N-methylpiperazine) |
| 7-8 | 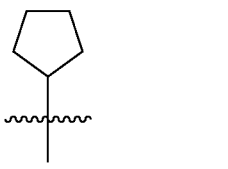 | 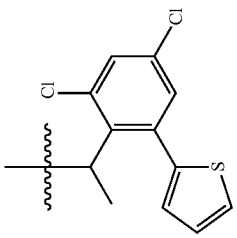 (Cl, Cl, thiophene) | H | 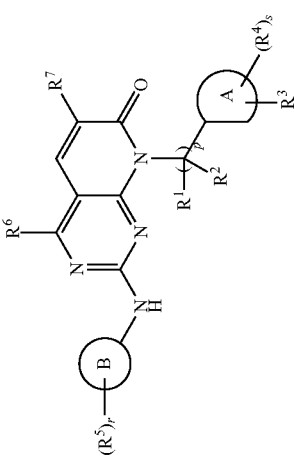 (cyclopentyl) | 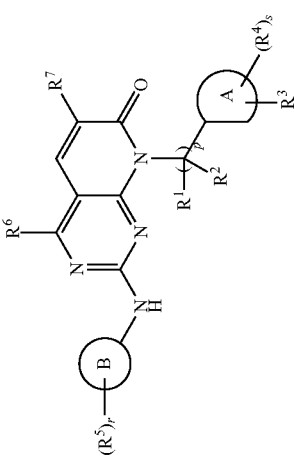 p- (piperazine NH, o-Cl) |

TABLE 7-continued

| Compound No. | B | R³ (A ring substituent) | R⁶ | R⁷ | R⁵ |
|---|---|---|---|---|---|
| 7-9 | phenyl | 4,5-difluoro-2-cyclopropyl-phenyl with isopropyl linker | Cl | cyclopropyl-C(O)- | p- N-methyl-N-(piperazinylmethyl with N-acetyl) |
| 7-10 | phenyl | 4-fluoro-3-(tetrahydropyran-4-yl)phenyl with isopropyl linker | H | H | p- 1-methylpyrrolidin-3-yl |

TABLE 7-continued

| Compound No. | B | $\overset{(R^4)_s}{\underset{R^1\ R^2}{\overset{R^3}{\bigwedge}}}$ | $R^6$ | $R^7$ | $R^5$ |
|---|---|---|---|---|---|
| 7-11 | phenyl | p-(2-methoxy-5-(3-hydroxycyclopentyl)phenyl)isopropyl | H | Cl | p-(N-cyclopropylcarbamoyl-isopropyl), o-Me |
| 7-12 | phenyl | p-(4-(N-ethylcarbamoyl)phenyl)sec-butyl | Me | H | p-(4-fluoropiperazin-1-yl), o-F |

TABLE 7-continued

| Compound No. | B | R¹, R², R³, R⁴, A, p | R⁶ | R⁷ | R⁵ |
|---|---|---|---|---|---|
| 7-13 | phenyl | 2-(5-propoxy-cyclohexylamino-phenyl)propyl | H | OMe | p-(piperidin-1-yl), m-CN |

TABLE 7-continued
| Compound No. | B | $\begin{array}{c}\vdots\\ \text{—}\\ R^1 \;\; R^2 \\ \text{A} \\ R^3 \;\; (R^4)_s\end{array}$ | $R^6$ | $R^7$ | $R^5$ |
|---|---|---|---|---|---|
| 7-14 | 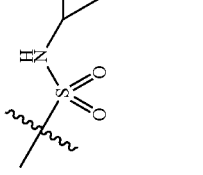 |  | H | H | 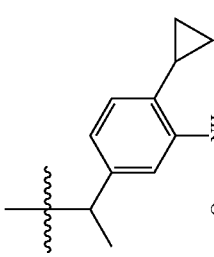 |
| 7-15 | 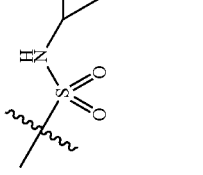 | 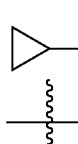 | H | CN | 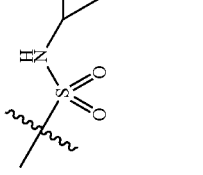 |

TABLE 7-continued
| Compound No. | B | R¹, R², (A)(R³)(R⁴)ₛ | R⁶ | R⁷ | R⁵ |
|---|---|---|---|---|---|
| 7-16 | phenyl | 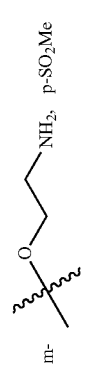 (phenyl with SO₂Me and cyclopropyl) | H | H |  m-, NH₂, p-SO₂Me |
| 7-17 | pyridyl |  (phenyl with CF₃ and cyclopropyl) | H | isopropyl | 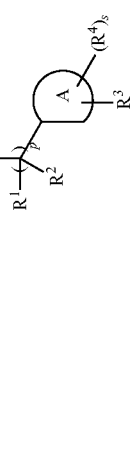 m- (N-methylpiperazine) |

TABLE 7-continued
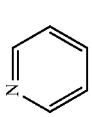
| Compound No. | B | R² R¹ (R⁴)ₛ A R³ | R⁶ | R⁷ | R⁵ |
|---|---|---|---|---|---|
| 7-18 | 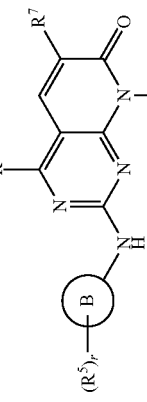 | 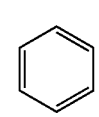 | Cl | H | p-SO₂Me |
| 7-20 | 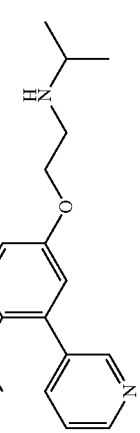 | 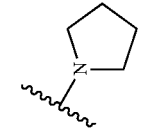 | F | 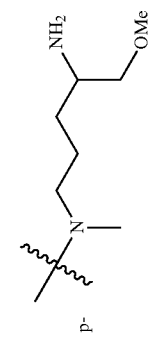 | p- |

TABLE 7-continued
| Compound No. | B | R³<br> | R⁶ | R⁷ | R⁵ |
|---|---|---|---|---|---|
| 7-21 | 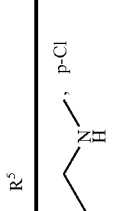 | 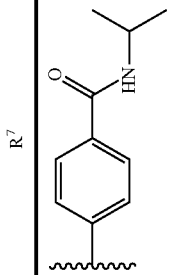 | H | 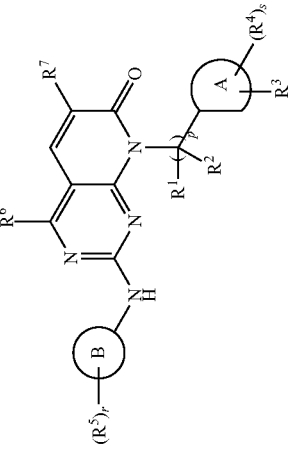 | m- , p-Cl |
| 7-22 | 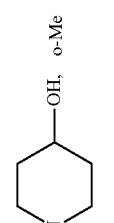 |  | H | 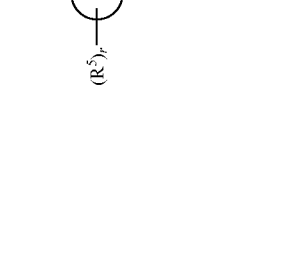 | p- (piperidine-OH), o-Me |

TABLE 7-continued

| Compound No. | B | $\begin{array}{c}\text{R}^2\\ \text{R}^1\overset{\displaystyle\sim}{\underset{\displaystyle p}{\frown}}\overset{\displaystyle A}{\underset{\displaystyle R^3}{\bigcirc}}(R^4)_s\end{array}$ | $R^6$ | $R^7$ | $R^5$ |
|---|---|---|---|---|---|
| 7-23 | phenyl | [triazole-difluorophenyl-isopropyl group] | H | H | p-[NH-C(O)-NH-phenyl], m-OMe |
| 7-24 | phenyl | [pyrrolinone-difluorophenyl-isopropyl group] | H | H | p-[pyrazole] |

In some embodiments, a PAK inhibitor is a small molecule. As referred to herein, a "small molecule" is an organic molecule that is less than about 5 kilodaltons (kDa) in size. In some embodiments, the small molecule is less than about 4 kDa, 3 kDa, about 2 kDa, or about 1 kDa. In some embodiments, the small molecule is less than about 800 daltons (Da), about 600 Da, about 500 Da, about 400 Da, about 300 Da, about 200 Da, or about 100 Da. In some embodiments, a small molecule is less than about 4000 g/mol, less than about 3000 g/mol, 2000 g/mol, less than about 1500 g/mol, less than about 1000 g/mol, less than about 800 g/mol, or less than about 500 g/mol. In some embodiments, small molecules are non-polymeric. Typically, small molecules are not proteins, polypeptides, polynucleotides, oligonucleotides, polysaccharides, glycoproteins, or proteoglycans, but includes peptides of up to about 40 amino acids. A derivative of a small molecule refers to a molecule that shares the same structural core as the original small molecule, but which is prepared by a series of chemical reactions from the original small molecule. As one example, a pro-drug of a small molecule is a derivative of that small molecule. An analog of a small molecule refers to a molecule that shares the same or similar structural core as the original small molecule, and which is synthesized by a similar or related route, or art-recognized variation, as the original small molecule.

In certain embodiments, compounds described herein have one or more chiral centers. As such, all stereoisomers are envisioned herein. In various embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer is utilized as the therapeutic compound described herein. In certain embodiments, compounds described herein contains one or more chiral centers. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

In various embodiments, pharmaceutically acceptable salts described herein include, by way of non-limiting example, a nitrate, chloride, bromide, phosphate, sulfate, acetate, hexafluorophosphate, citrate, gluconate, benzoate, propionate, butyrate, sulfosalicylate, maleate, laurate, malate, fumarate, succinate, tartrate, amsonate, pamoate, p-toluenenesulfonate, mesylate and the like. Furthermore, pharmaceutically acceptable salts include, by way of non-limiting example, alkaline earth metal salts (e.g., calcium or magnesium), alkali metal salts (e.g., sodium-dependent or potassium), ammonium salts and the like.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, $^{35}S$ or the like. In some embodiments, isotopically-labeled compounds are useful in drug and/or substrate tissue distribution studies. In some embodiments, substitution with heavier isotopes such as deuterium affords certain therapeutic advantages resulting from greater metabolic stability (for example, increased in vivo half-life or reduced dosage requirements). In some embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference for such disclosure). General methods for the preparation of compound as described herein are modified by the use of appropriate reagents and conditions, for the introduction of the various moieties found in the formula as provided herein. As a guide the following synthetic methods are utilized.

Compounds described herein are synthesized using any suitable procedures starting from compounds that are available from commercial sources, or are prepared using procedures described herein.

Formation of Covalent Linkages by Reaction of an Electrophile with a Nucleophile The compounds described herein are modified using various electrophiles and/or nucleophiles to form new functional groups or substituents. Table A entitled "Examples of Covalent Linkages and Precursors Thereof" lists selected non-limiting examples of covalent linkages and precursor functional groups which yield the covalent linkages. Table A is used as guidance toward the variety of electrophiles and nucleophiles combinations available that provide covalent linakges. Precursor functional groups are shown as electrophilic groups and nucleophilic groups.

TABLE A

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |

TABLE A-continued

Examples of Covalent Linkages and Precursors Thereof

| Covalent Linkage Product | Electrophile | Nucleophile |
|---|---|---|
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

Use of Protecting Groups

In the reactions described, it is necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. In some embodiments it is contemplated that each protective group be removable by a different means. Protective groups that are cleaved under totally disparate reaction conditions fulfill the requirement of differential removal.

In some embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In some embodiments carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a Pd⁰-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups are selected from:

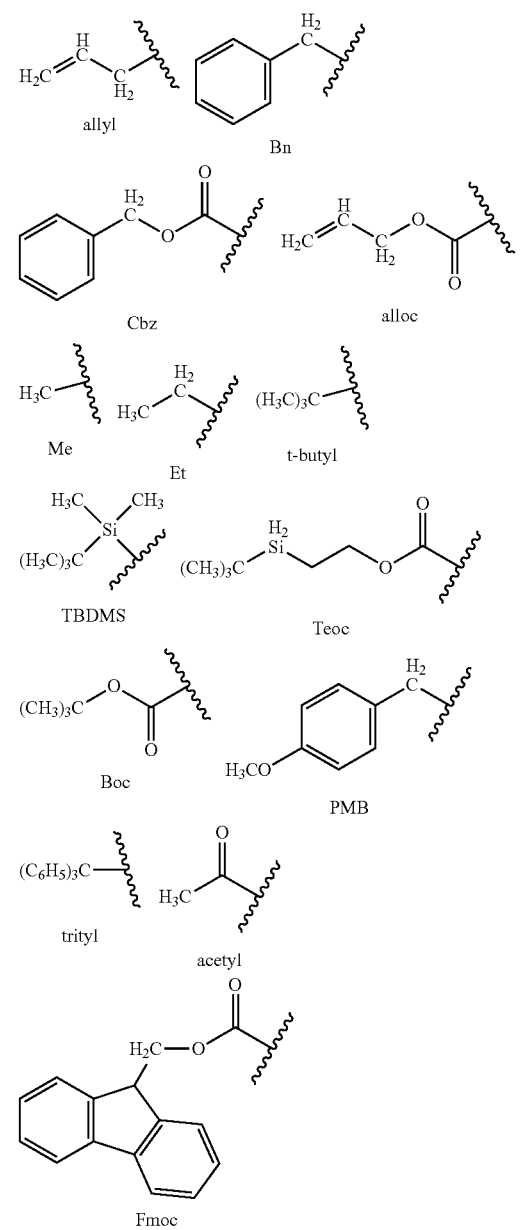

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Certain Definitions

As used herein the term "Treatment" or "treating" includes achieving a therapeutic benefit and/or a prophylactic benefit. By therapeutic benefit is meant eradication or amelioration of the underlying disorder or condition being treated. For example, in an individual with a neuropsychiatric condition, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient is still affected by the condition. A prophylactic benefit of treatment includes prevention of a condition, retarding the progress of a condition, or decreasing the likelihood of occurrence of a condition. As used herein, "treating" or "treatment" includes prophylaxis.

As used herein, the phrase "neuropsychiatric condition" refers to any condition that results in chronic impairment in cognition, affect, and/or motor function. Neuropsychiatiric conditions include and are not limited to schizophrenia, Alzheimer's disease, mild cognitive impairment, age-related cognitive decline, Parkinson's disease, Fragile X Syndrome, autism spectrum disorder, clinical depression, epilepsy, Huntington's disease, mental retardation, Down's syndrome, Niemann-Pick disease, spongiform encephalitis, Lafora disease, Maple syrup urine disease, maternal phenylketonuria, cognitive decline associated with menopause, Rett's syndrome, atypical phenylketonuria, or tuberous sclerosis or the like.

As used herein, the phrase "abnormal spine size" refers to dendritic spine volumes or dendritic spine surface areas (e.g., volumes or surface areas of the spine heads and/or spine necks) associated with a neuropsychiatric condition that deviate significantly relative to spine volumes or surface areas in the same brain region (e.g., the CA1 region, the prefrontal cortex) in a normal individual (e.g., a mouse, rat, or human) of the same age; such abnormalities are determined as appropriate, including, e.g., tissue samples, relevant animal models, post-mortem analyses, or other model systems.

The phrase "defective spine morphology" or "abnormal spine morphology" or "aberrant spine morphology" refers to abnormal dendritic spine shapes, volumes, surface areas, length, width (e.g., diameter of the neck), spine density, spine head diameter, spine head volume, spine head surface area, ratio of mature to immature spines, ratio of spine volume to spine length, ratio of spine head diameter to spine length, or the like that is associated with a neuropsychiatric condition relative to the dendritic spine shapes, volumes, surface areas, length, width (e.g., diameter of the neck), spine density, spine head diameter, spine head volume, spine head surface area, ratio of mature to immature spines, ratio of spine volume to spine length, ratio of spine head diameter to spine length, or the like observed in the same brain region in a normal individual (e.g., a mouse, rat, or human) of the same age; such abnormalities or defects are determined as appropriate, including, e.g., tissue samples, relevant animal models, post-mortem analyses, or other model systems.

The phrase "abnormal spine function" or "defective spine function" or "aberrant spine function" refers to a defect of dendritic spines to undergo stimulus-dependent morphological or functional changes (e.g., calcium entry through NMDA receptors, activation of AMPA receptors, LTP, LTD, etc) associated with a neuropsychiatric condition as compared to dendritic spines in the same brain region in a normal individual of the same age. The "defect" in spine function includes, e.g., a reduction in dendritic spine plasticity, (e.g., an abnormally small change in dendritic spine morphology or actin re-arrangement in the dendritic spine), or an excess level of dendritic plasticity, (e.g., an abnormally large change in dendritic spine morphology or actin re-arrangement in the dendritic spine). Such abnormalities or defects are determined as appropriate, including, e.g., tissue samples, relevant animal models, post-mortem analyses, or other model systems.

The phrase "abnormal spine motility" refers to a significant low or high movement of dendritic spines associated with a neuropsychiatric condition as compared to dendritic spines in the same brain region in a normal individual of the same age. Any defect in spine morphology (e.g., spine length, density or the like) or synaptic plasticity or synaptic function (e.g., LTP, LTD or the like) occurs in any region of the brain, including, for example, the frontal cortex, the hippocampus, the amygdala, the CA I region, the prefrontal cortex or the like. Such abnormalities or defects are determined as appropriate, including, e.g., tissue samples, relevant animal models, post-mortem analyses, or other model systems.

As used herein, the phrase "biologically active" refers to a characteristic of any substance that has activity in a biological system and/or organism. For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

As used herein, the term "effective amount" is an amount, which when administered systemically, is sufficient to effect beneficial or desired results, such as beneficial or desired clinical results, or enhanced cognition, memory, mood, or other desired effects. An effective amount is also an amount that produces a prophylactic effect, e.g., an amount that delays, reduces, or eliminates the appearance of a pathological or undesired condition associated with a neuropsychiatric condition. An effective amount is optionally administered in one or more administrations. In terms of treatment, an "effective amount" of a composition described herein is an amount that is sufficient to palliate, ameliorate, stabilize, reverse or slow the progression of a neuropsychiatric condition, e.g., cognitive decline. An "effective amount" includes any PAK inhibitor used alone or in conjunction with one or more agents used to treat a disease or disorder. An "effective amount" of a therapeutic agent as described herein will be determined by a patient's attending physician or other medical care provider. Factors which influence what a therapeutically effective amount will be include, the absorption profile (e.g., its rate of uptake into the brain) of the PAK inhibitor, time elapsed since the initiation of disease, and the age, physical condition, existence of other disease states, and nutritional status of an individual being treated. Additionally, other medication the patient is receiving, e.g., antipsychotic drugs used in combination with a PAK inhibitor, will typically affect the determination of the therapeutically effective amount of the therapeutic agent to be administered.

As used herein, the term "inhibitor" refers to a molecule which is capable of inhibiting (including partially inhibiting or allosteric inhibition) one or more of the biological activities of a target molecule, e.g., a p21-activated kinase. Inhibitors, for example, act by reducing or suppressing the activity of a target molecule and/or reducing or suppressing signal transduction. In some embodiments, a PAK inhibitor described herein causes substantially complete inhibition of one or more PAKs. In some embodiments, the phrase "partial inhibitor" refers to a molecule which can induce a partial response for example, by partially reducing or suppressing the activity of a target molecule and/or partially reducing or suppressing signal transduction. In some instances, a partial inhibitor mimics the spatial arrangement, electronic properties, or some other physicochemical and/or biological property of the inhibitor. In some instances, in the presence of elevated levels of an inhibitor, a partial inhibitor competes with the inhibitor for occupancy of the target molecule and provides a reduction in efficacy, relative to the inhibitor alone. In some embodiments, a PAK inhibitor described herein is a partial inhibitor of one or more PAKs. In some embodiments, a PAK inhibitor described herein is an allosteric modulator of PAK. In some embodiments, a PAK inhibitor described herein blocks the p21 binding domain of PAK. In some embodiments, a PAK inhibitor described herein blocks the ATP binding site of PAK. In some embodiments, a PAK inhibitor is a "Type II" kinase inhibitor. In some embodiment a PAK inhibitor stabilizes PAK in its inactive conformation. In some embodiments, a PAK inhibitor stabilizes the "DFG-out" conformation of PAK.

In some embodiments, PAK inhibitors reduce, abolish, and/or remove the binding between PAK and at least one of its natural binding partners (e.g., Cdc42 or Rac). In some instances, binding between PAK and at least one of its natural binding partners is stronger in the absence of a PAK inhibitor (by e.g., 90%, 80%, 70%, 60%, 50%, 40%, 30% or 20%) than in the presence of a PAK inhibitor. Alternatively or additionally, PAK inhibitors inhibit the phosphotransferase activity of PAK, e.g., by binding directly to the catalytic site or by altering the conformation of PAK such that the catalytic site becomes inaccessible to substrates. In some embodiments, PAK inhibitors inhibit the ability of PAK to phosphorylate at least one of its target substrates, e.g., LIM kinase 1 (LIMK1), myosin light chain kinase (MLCK), cortactin; or itself. PAK inhibitors include inorganic and/or organic compounds.

In some embodiments, PAK inhibitors described herein increase dendritic spine length. In some embodiments, PAK inhibitors described herein decrease dendritic spine length. In some embodiments, PAK inhibitors described herein increase dendritic neck diameter. In some embodiments, PAK inhibitors described herein decrease dendritic neck diameter. In some embodiments, PAK inhibitors described herein increase dendritic spine head diameter. In some embodiments, PAK inhibitors described herein decrease dendritic spine head diameter. In some embodiments, PAK inhibitors described herein increase dendritic spine head volume. In some embodiments, PAK inhibitors described herein decrease dendritic spine head volume. In some embodiments, PAK inhibitors described herein increase dendritic spine surface area. In some embodiments, PAK inhibitors described herein decrease dendritic spine surface area. In some embodiments, PAK inhibitors described herein increase dendritic spine density. In some embodiments, PAK inhibitors described herein decrease dendritic spine density. In some embodiments, PAK inhibitors described herein increase the number of mushroom shaped spines. In some embodiments, PAK inhibitors described herein decrease the number of mushroom shaped spines.

In some embodiments, a PAK inhibitor suitable for the methods described herein is a direct PAK inhibitor. In some embodiments, a PAK inhibitor suitable for the methods described herein is an indirect PAK inhibitor. In some embodiments, a PAK inhibitor suitable for the methods described herein decreases PAK activity relative to a basal level of PAK activity by about 1.1 fold to about 100 fold, e.g., to about 1.2 fold, 1.5 fold, 1.6 fold, 1.7 fold, 2.0 fold, 3.0 fold, 5.0 fold, 6.0 fold, 7.0 fold, 8.5 fold, 9.7 fold, 10 fold, 12 fold, 14 fold, 15 fold, 20 fold, 30 fold, 40 fold, 50 fold, 60 fold, 70 fold, 90 fold, 95 fold, or by any other amount from about 1.1 fold to about 100 fold relative to basal PAK activity. In some embodiments, the PAK inhibitor is a reversible PAK inhibitor. In other embodiments, the PAK inhibitor is an irreversible PAK inhibitor. Direct PAK inhibitors are optionally used for the manufacture of a medicament for treating a neuropsychiatric condition.

In some embodiments, a PAK inhibitor used for the methods described herein has in vitro $ED_{50}$ for PAK activation of less than 100 µM (e.g., less than 10 µM, less than 5 µM, less than 4 µM, less than 3 µM, less than 1 µM, less than 0.8 µM, less than 0.6 µM, less than 0.5 µM, less than 0.4 µM, less than 0.3 µM, less than less than 0.2 µM, less than 0.1 µM, less than 0.08 µM, less than 0.06 µM, less than 0.05 µM, less than 0.04 µM, less than 0.03 µM, less than less than 0.02 µM, less than 0.01 µM, less than 0.0099 µM, less than 0.0098 µM, less than 0.0097 µM, less than 0.0096 µM, less than 0.0095 µM, less than 0.0094 µM, less than 0.0093 µM, less than 0.00092 µM, or less than 0.0090 µM).

In some embodiments, a PAK inhibitor used for the methods described herein has in vitro $ED_{50}$ for PAK activation of less than 100 µM (e.g., less than 10 µM, less than 5 µM, less than 4 µM, less than 3 µM, less than 1 µM, less than 0.8 µM, less than 0.6 µM, less than 0.5 µM, less than 0.4 µM, less than 0.3 µM, less than less than 0.2 µM, less than 0.1 µM, less than 0.08 µM, less than 0.06 µM, less than 0.05 µM, less than 0.04 µM, less than 0.03 µM, less than less than 0.02 µM, less than 0.01 µM, less than 0.0099 µM, less than 0.0098 µM, less than 0.0097 µM, less than 0.0096 µM, less than 0.0095 µM, less than 0.0094 µM, less than 0.0093 µM, less than 0.00092 µM, or less than 0.0090 µM).

As used herein, synaptic function refers to synaptic transmission and/or synaptic plasticity, including stabilization of synaptic plasticity. As used herein, "defect in synaptic plasticity" or "aberrant synaptic plasticity" refers to abnormal synaptic plasticity following stimulation of that synapse. In some embodiments, a defect in synaptic plasticity is a decrease in LTP. In some embodiments, a defect in synaptic plasticity is an increase in LTD. In some embodiments, a defect in synaptic plasticity is erratic (e.g., fluctuating, randomly increasing or decreasing) synaptic plasticity. In some instances, measures of synaptic plasticity are LTP and/or LTD (induced, for example, by theta-burst stimulation, high-frequency stimulation for LTP, low-frequency (e.g., e.g., 1 Hz) stimulation for LTD) and LTP and/or LTD after stabilization. In some embodiments, stabilization of LTP and/or LTD occurs in any region of the brain including the frontal cortex, the hippocampus, the prefrontal cortex, the amygdala or any combination thereof.

As used herein "stabilization of synaptic plasticity" refers to stable LTP or LTD following induction (e.g., by theta-burst stimulation, high-frequency stimulation for LTP, low-frequency (e.g., e.g., 1 Hz) stimulation for LTD).

"Aberrant stabilization of synaptic transmission" (for example, aberrant stabilization of LTP or LTD), refers to failure to establish a stable baseline of synaptic transmission following an induction paradigm (e.g., by theta-burst stimulation, high-frequency stimulation for LTP, low-frequency (e.g., 1 Hz) stimulation for LTD) or an extended period of vulnerability to disruption by pharmacological or electrophysiological means As used herein "synaptic transmission" or "baseline synaptic transmission" refers to the EPSP and/or IPSP amplitude and frequency, neuronal excitability or population spike thresholds of a normal individual (e.g., an individual not suffering from a neuropsychiatric condition) or that predicted for an animal model for a normal individual. As used herein "aberrant synaptic transmission" or "defective synaptic transmission" refers to any deviation in synaptic transmission compared to synaptic transmission of a normal individual or that predicted for an animal model for a normal individual. In some embodiments, an individual suffering from a neuropsychiatric condition has a defect in baseline synaptic transmission that is a decrease in baseline synaptic transmission compared to the baseline synaptic transmission in a normal individual or that predicted for an animal model for a normal individual. In some embodiments, an individual suffering from a neuropsychiatric condition has a defect in baseline synaptic transmission that is an increase in baseline synaptic transmission compared to the baseline synaptic transmission in a normal individual or that predicted for an animal model for a normal individual.

As used herein "sensorimotor gating" is assessed, for example, by measuring prepulse inhibition (PPI) and/or habituation of the human startle response. In some embodiments, a defect in sensorimotor gating is a deficit in sensorimotor gating. In some embodiments, a defect in sensorimotor gating is an enhancement of sensorimotor gating.

As used herein, "normalization of aberrant synaptic plasticity" refers to a change in aberrant synaptic plasticity in an individual suffering from, suspected of having, or pre-disposed to a neuropsychiatric condition to a level of synaptic plasticity that is substantially the same as the synaptic plasticity of a normal individual or to that predicted from an animal model for a normal individual. As used herein, substantially the same means, for example, about 90% to about 110% of the measured synaptic plasticity in a normal individual or to that predicted from an animal model for a normal individual. In other embodiments, substantially the same means, for example, about 80% to about 120% of the measured synaptic plasticity in a normal individual or to that predicted from an animal model for a normal individual. In yet other embodiments, substantially the same means, for example, about 70% to about 130% of the synaptic plasticity in a normal individual or to that predicted from an animal model for a normal individual. As used herein, "partial normalization of aberrant synaptic plasticity" refers to any change in aberrant synaptic plasticity in an individual suffering from, suspected of having, or pre-disposed to a neuropsychiatric condition that trends towards synaptic plasticity of a normal individual or to that predicted from an animal model for a normal individual. As used herein "partially normalized synaptic plasticity" or "partially normal synaptic plasticity" is, for example, ±about 25%, ±about 35%, ±about 45%, ±about 55%, ±about 65%, or ±about 75% of the synaptic plasticity of a normal individual or to that predicted from an animal model for a normal individual. In some embodiments, normalization or partial normalization of aberrant synaptic plasticity in an individual suffering from, suspected of having, or pre-disposed to a neuropsychiatric condition is lowering of aberrant synaptic plasticity where the aberrant synaptic plasticity is higher than the synaptic plasticity of a normal individual or to that predicted from an animal model for a normal individual. In some embodiments, normalization or partial normalization of aberrant synaptic plasticity in an individual suffering from, suspected of having, or pre-disposed to a neuropsychiatric condition is an increase in aberrant synaptic plasticity where the aberrant synaptic plasticity is lower than the synaptic plasticity of a normal individual or to that predicted from an animal model for a normal individual. In some embodiments, normalization or partial normalization of synaptic plasticity in an individual suffering from, suspected of having, or pre-disposed to a neuropsychiatric condition is a change from an erratic (e.g., fluctuating, randomly increasing or decreasing) synaptic plasticity to a normal (e.g. stable) or partially normal (e.g., less fluctuating) synaptic plasticity compared to the synaptic plasticity of a normal individual or to that predicted from an animal model for a normal individual. In some embodiments, normalization or partial normalization of synaptic plasticity in an individual suffering from, suspected of having, or pre-disposed to a neuropsychiatric condition is a change from a non-stabilizing synaptic plasticity to a normal (e.g., stable) or partially normal (e.g., partially stable) synaptic plasticity compared to the synaptic plasticity of a normal individual or to that predicted from an animal model for a normal individual.

As used herein, "normalization of aberrant baseline synaptic transmission" refers to a change in aberrant baseline synaptic transmission in an individual suffering from, suspected of having, or pre-disposed to a neuropsychiatric condition to a level of baseline synaptic transmission that is substantially the same as the baseline synaptic transmission of a normal individual or to that predicted from an animal model for a normal individual. As used herein, substantially the same means, for example, about 90% to about 110% of the measured baseline synaptic transmission in a normal individual or to that predicted from an animal model for a normal individual. In other embodiments, substantially the same means, for example, about 80% to about 120% of the measured baseline synaptic transmission in a normal individual or to that predicted from an animal model for a normal individual. In yet other embodiments, substantially the same means, for example, about 70% to about 130% of the measured baseline synaptic transmission in a normal individual or to that predicted from an animal model for a normal individual. As used herein, "partial normalization of aberrant baseline synaptic transmission" refers to any change in aberrant baseline synaptic transmission in an individual suffering from, suspected of having, or pre-disposed to a neuropsychiatric condition that trends towards baseline synaptic transmission of a normal individual or to that predicted from an animal model for a normal individual. As used herein "partially normalized baseline synaptic transmission" or "partially normal baseline synaptic transmission" is, for example, ±about 25%, ±about 35%, ±about 45%, ±about 55%, ±about 65%, or ±about 75% of the measured baseline synaptic transmission of a normal individual or to that predicted from an animal model for a normal individual. In some embodiments, normalization or partial normalization of aberrant baseline synaptic transmission in an individual suffering from, suspected of having, or pre-disposed to a neuropsychiatric condition is lowering of aberrant baseline synaptic transmission where the aberrant baseline synaptic transmission is higher than the baseline synaptic transmission of a normal individual or to that predicted from an animal model for a normal individual. In some embodiments, normalization or partial normalization of aberrant baseline synaptic transmission in an individual suffering from, suspected of having, or pre-disposed to a neuropsychiatric condition is an increase in aberrant baseline synaptic transmission where the aberrant baseline synaptic transmission is lower than the baseline synaptic transmission of a normal individual or to that predicted from an animal model for a normal individual. In some embodiments, normalization or partial normalization of baseline synaptic transmission in an individual suffering from, suspected of having, or pre-disposed to a neuropsychiatric condition is a change from an erratic (e.g., fluctuating, randomly increasing or decreasing) baseline synaptic transmission to a normal (e.g. stable) or partially normal (e.g., less fluctuating) baseline synaptic transmission compared to the baseline synaptic transmission of a normal individual or to that predicted from an animal model for a normal individual. In some embodiments, normalization or partial normalization of aberrant baseline synaptic transmission in an individual suffering from, suspected of having, or pre-disposed to a neuropsychiatric condition is a change from a non-stabilizing baseline synaptic transmission to a normal (e.g., stable) or partially normal (e.g., partially stable) baseline synaptic transmission compared to the baseline synaptic transmission of a normal individual or to that predicted from an animal model for a normal individual.

As used herein, "normalization of aberrant synaptic function" refers to a change in aberrant synaptic function in an individual suffering from, suspected of having, or pre-disposed to a neuropsychiatric condition to a level of synaptic function that is substantially the same as the synaptic function of a normal individual or to that predicted from an animal model for a normal individual. As used herein, substantially the same means, for example, about 90% to about 110% of the synaptic function in a normal individual or to that predicted from an animal model for a normal individual. In other embodiments, substantially the same means, for example, about 80% to about 120% of the synaptic function in a normal individual or to that predicted from an animal model for a normal individual. In yet other embodiments, substantially the same means, for example, about 70% to about 130% of the synaptic function in a normal individual or to that predicted from an animal model for a normal individual. As used herein, "partial normalization of aberrant synaptic function" refers to any change in aberrant synaptic function in an individual suffering from, suspected of having, or pre-disposed to a neuropsychiatric condition that trends towards synaptic function of a normal individual or to that predicted from an animal model for a normal individual. As used herein "partially normalized synaptic function" or "partially normal synaptic function" is, for example, ±about 25%, ±about 35%, ±about 45%, ±about 55%, ±about 65%, or ±about 75% of the measured synaptic function of a normal individual or to that predicted from an animal model for a normal individual. In some embodiments, normalization or partial normalization of aberrant synaptic function in an individual suffering from, suspected of having, or pre-disposed to a neuropsychiatric condition is lowering of aberrant synaptic function where the aberrant synaptic function is higher than the synaptic function of a normal individual or to that predicted from an animal model for a normal individual. In some embodiments, normalization or partial normalization of aberrant synaptic function in an individual suffering from, suspected of having, or pre-disposed to a neuropsychiatric condition is an increase in aberrant synaptic function where the aberrant synaptic function is lower than the synaptic function of a normal individual or to that predicted from an animal model for a normal individual. In some embodiments, normalization or partial normalization of synaptic function in an individual suffering from, suspected of having, or pre-disposed to a neuropsychiatric condition is a change from an erratic (e.g., fluctuating, randomly increasing or decreasing) synaptic function to a normal (e.g. stable) or partially normal (e.g., less fluctuating) synaptic function compared to the synaptic function of a normal individual or to that predicted from an animal model for a normal individual. In some embodiments, normalization or partial normalization of aberrant synaptic function in an individual suffering from, suspected of having, or pre-disposed to a neuropsychiatric condition is a change from a non-stabilizing synaptic function to a normal (e.g., stable) or partially normal (e.g., partially stable) synaptic function compared to the synaptic function of a normal individual or to that predicted from an animal model for a normal individual.

As used herein, "normalization of aberrant long term potentiation (LTP)" refers to a change in aberrant LTP in an individual suffering from, suspected of having, or pre-disposed to a neuropsychiatric condition to a level of LTP that is substantially the same as the LTP of a normal individual or to that predicted from an animal model for a normal individual. As used herein, substantially the same means, for example, about 90% to about 110% of the LTP in a normal individual or to that predicted from an animal model for a normal individual. In other embodiments, substantially the same means, for example, about 80% to about 120% of the LTP in a normal individual or to that predicted from an animal model for a normal individual. In yet other embodiments, substantially the same means, for example, about 70% to about 130% of the LTP in a normal individual or to that predicted from an animal model for a normal individual. As used herein, "partial normalization of aberrant LTP" refers to any change in aberrant LTP in an individual suffering from, suspected of having, or pre-disposed to a neuropsychiatric condition that trends towards LTP of a normal individual or to that predicted from an animal model for a normal individual. As used herein "partially normalized LTP" or "partially normal LTP" is, for example, ±about 25%, ±about 35%, ±about 45%, ±about 55%, ±about 65%, or ±about 75% of the measured LTP of a normal individual or to that predicted from an animal model for a normal individual. In some embodiments, normalization or partial normalization of aberrant LTP in an individual suffering from, suspected of having, or pre-disposed to a neuropsychiatric condition is lowering of aberrant LTP where the aberrant LTP is higher than the LTP of a normal individual or to that predicted from an animal model for a normal individual. In some embodiments, normalization or partial normalization of aberrant LTP in an individual suffering from, suspected of having, or pre-disposed to a neuropsychiatric condition is an increase in aberrant LTP where the aberrant LTP is lower than the LTP of a normal individual or to that predicted from an animal model for a normal individual. In some embodiments, normalization or partial normalization of LTP in an individual suffering from, suspected of having, or pre-disposed to a neuropsychiatric condition is a change from an erratic (e.g., fluctuating, randomly increasing or decreasing) LTP to a normal (e.g. stable) or partially normal (e.g., less fluctuating) LTP compared to the LTP of a normal individual or to that predicted from an animal model for a normal individual. In some embodiments, normalization or partial normalization of aberrant LTP in an individual suffering from, suspected of having, or pre-disposed to a neuropsychiatric condition is a change from a non-stabilizing LTP to a normal (e.g., stable) or partially normal (e.g., partially stable) LTP compared to the LTP of a normal individual or to that predicted from an animal model for a normal individual.

As used herein, "normalization of aberrant long term depression (LTD)" refers to a change in aberrant LTD in an individual suffering from, suspected of having, or pre-disposed to a neuropsychiatric condition to a level of LTD that is substantially the same as the LTD of a normal individual or to that predicted from an animal model for a normal individual. As used herein, substantially the same means, for example, about 90% to about 110% of the LTD in a normal individual or to that predicted from an animal model for a normal individual. In other embodiments, substantially the same means, for example, about 80% to about 120% of the LTD in a normal individual or to that predicted from an animal model for a normal individual. In yet other embodiments, substantially the same means, for example, about 70% to about 130% of the LTD in a normal individual or to that predicted from an animal model for a normal individual. As used herein, "partial normalization of aberrant LTD" refers to any change in aberrant LTD in an individual suffering from, suspected of having, or pre-disposed to a neuropsychiatric condition that trends towards LTD of a normal individual or to that predicted from an animal model for a normal individual. As used herein "partially normalized LTD" or "partially normal LTD" is, for example, ±about 25%, ±about 35%, ±about 45%, ±about 55%, ±about 65%, or ±about 75% of the measured LTD of a normal individual or to that predicted from an animal model for a normal individual. In some embodiments, normalization or partial normalization of aberrant LTD in an individual suffering from, suspected of having, or pre-disposed to a neuropsychiatric condition is lowering of aberrant LTD where the aberrant LTD is higher than the LTD of a normal individual or to that predicted from an animal model for a normal individual. In some embodiments, normalization or partial normalization of aberrant LTD in an individual suffering from, suspected of having, or pre-disposed to a neuropsychiatric condition is an increase in aberrant LTD where the aberrant LTD is lower than the LTD of a normal individual or to that predicted from an animal model for a normal individual. In some embodiments, normalization or partial normalization of LTD in an individual suffering from, suspected of having, or pre-disposed to a neuropsychiatric condition is a change from an erratic (e.g., fluctuating, randomly increasing or decreasing) LTD to a normal (e.g. stable) or partially normal (e.g., less fluctuating) LTD compared to the LTD of a normal individual or to that predicted from an animal model for a normal individual. In some embodiments, normalization or partial normalization of aberrant LTD in an individual suffering from, suspected of having, or pre-disposed to a neuropsychiatric condition is a change from a non-stabilizing LTD to a normal (e.g., stable) or partially normal (e.g., partially stable) LTD compared to the LTD of a normal individual or to that predicted from an animal model for a normal individual.

As used herein, "normalization of aberrant sensorimotor gating" refers to a change in aberrant sensorimotor gating in an individual suffering from, suspected of having, or pre-disposed to a neuropsychiatric condition to a level of sensorimotor gating that is substantially the same as the sensorimotor gating of a normal individual or to that predicted from an animal model for a normal individual. As used herein, substantially the same means, for example, about 90% to about 110% of the sensorimotor gating in a normal individual or to that predicted from an animal model for a normal individual. In other embodiments, substantially the same means, for example, about 80% to about 120% of the sensorimotor gating in a normal individual or to that predicted from an animal model for a normal individual. In yet other embodiments, substantially the same means, for example, about 70% to about 130% of the sensorimotor gating in a normal individual or to that predicted from an animal model for a normal individual. As used herein, "partial normalization of aberrant sensorimotor gating" refers to any change in aberrant sensorimotor gating in an individual suffering from, suspected of having, or pre-disposed to a neuropsychiatric condition that trends towards sensorimotor gating of a normal individual or to that predicted from an animal model for a normal individual. As used herein "partially normalized sensorimotor gating" or "partially normal sensorimotor gating" is, for example, ±about 25%, ±about 35%, ±about 45%, ±about 55%, ±about 65%, or ±about 75% of the measured sensorimotor gating of a normal individual or to that predicted from an animal model for a normal individual. In some embodiments, normalization or partial normalization of aberrant sensorimotor gating in an individual suffering from, suspected of having, or pre-disposed to a neuropsychiatric condition is lowering of aberrant sensorimotor gating where the aberrant sensorimotor gating is higher than the sensorimotor gating of a normal individual or to that predicted from an animal model for a normal individual. In some embodiments, normalization or partial normalization of aberrant sensorimotor gating in an individual suffering from, suspected of having, or pre-disposed to a neuropsychiatric condition is an increase in aberrant sensorimotor gating where the aberrant sensorimotor gating is lower than the sensorimotor gating of a normal individual or to that predicted from an animal model for a normal individual. In some embodiments, normalization or partial normalization of sensorimotor gating in an individual suffering from, suspected of having, or pre-disposed to a neuropsychiatric condition is a change from an erratic (e.g., fluctuating, randomly increasing or decreasing) sensorimotor gating to a normal (e.g. stable) or partially normal (e.g., less fluctuating) sensorimotor gating compared to the sensorimotor gating of a normal individual or to that predicted from an animal model for a normal individual. In some embodiments, normalization or partial normalization of aberrant sensorimotor gating in an individual suffering from, suspected of having, or pre-disposed to a neuropsychiatric condition is a change from a non-stabilizing sensorimotor gating to a normal (e.g., stable) or partially normal (e.g., partially stable) sensorimotor gating compared to the sensorimotor gating of a normal individual or to that predicted from an animal model for a normal individual.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; (4) post-translational modification of a polypeptide or protein.

As used herein the term "PAK polypeptide" or "PAK protein" or "PAK" refers to a protein that belongs in the family of p21-activated serine/threonine protein kinases. These include mammalian isoforms of PAK, e.g., the Group I PAK proteins (sometimes referred to as Group A PAK proteins), including PAK1, PAK2, PAK3, as well as the Group II PAK proteins (sometimes referred to as Group B PAK proteins), including PAK4, PAK5, and/or PAK6 Also included as PAK polypeptides or PAK proteins are lower eukaryotic isoforms, such as the yeast Step 20 (Leberter et al., 1992, EMBO J., 11:4805; incorporated herein by reference) and/or the Dictyostelium single-headed myosin I heavy chain kinases (Wu et al., 1996, J. Biol. Chem., 271:31787; incorporated herein by reference). Representative examples of PAK amino acid sequences include, but are not limited to, human PAK1 (GenBank Accession Number AAA65441), human PAK2 (GenBank Accession Number AAA65442), human PAK3 (GenBank Accession Number AAC36097), human PAK 4 (GenBank Accession Numbers NP_005875 and CAA09820), human PAK5 (GenBank Accession Numbers CAC18720 and BAA94194), human PAK6 (GenBank Accession Numbers NP_064553 and AAF82800), human PAK1 (GenBank Accession Number Q9P286), *C. elegans* PAK (GenBank Accession Number BAA 11844), *D. melanogaster* PAK (GenBank Accession Number AAC47094), and rat PAK1 (GenBank Accession Number AAB95646). In some embodiments, a PAK polypeptide comprises an amino acid sequence that is at least 70% to 100% identical, e.g., at least 75%, 80%, 85%, 86%, 87%, 88%, 90%, 91%, 92%, 94%, 95%, 96%, 97%, 98%, or any other percent from about 70% to about 100% identical to sequences of GenBank Accession Numbers AAA65441, AAA65442, AAC36097, NP_005875, CAA09820, CAC18720, BAA94194, NP_064553, AAF82800, Q9P286, BAA 11844, AAC47094, and/or AAB95646. In some embodiments, a Group I PAK polypeptide comprises an amino acid sequence that is at least 70% to 100% identical, e.g., at least 75%, 80%, 85%, 86%, 87%, 88%, 90%, 91%, 92%, 94%, 95%, 96%, 97%, 98%, or any other percent from about 70% to about 100% identical to sequences of GenBank Accession Numbers AAA65441, AAA65442, and/or AAC36097.

Representative examples of PAK genes encoding PAK proteins include, but are not limited to, human PAK1 (GenBank Accession Number U24152), human PAK2 (GenBank Accession Number U24153), human PAK3 (GenBank Accession Number AF068864), human PAK4 (GenBank Accession Number AJ011855), human PAK5, (GenBank Accession Number AB040812), and human PAK6 (GenBank Accession Number AF276893). In some embodiments, a PAK gene comprises a nucleotide sequence that is at least 70% to 100% identical, e.g., at least 75%, 80%, 85%, 86%, 87%, 88%, 90%, 91%, 92%, 94%, 95%, 96%, 97%, 98%, or any other percent from about 70% to about 100% identical to sequences of GenBank Accession Numbers U24152, U24153, AF068864, AJ011855, AB040812, and/or AF276893. In some embodiments, a Group I PAK gene comprises a nucleotide sequence that is at least 70% to 100% identical, e.g., at least 75%, 80%, 85%, 86%, 87%, 88%, 90%, 91%, 92%, 94%, 95%, 96%, 97%, 98%, or any other percent from about 70% to about 100% identical to sequences of GenBank Accession Numbers U24152, U24153, and/or AF068864.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In one embodiment the two sequences are the same length.

To determine percent homology between two sequences, the algorithm of Karlin and Altschul (1990) Proc. Natl. Acad. Sci. USA 87:2264-2268, modified as in Karlin and Altschul (1993) Proc. Natl. Acad. Sci. USA 90:5873-5877 is used. Such an algorithm is incorporated into the NBLAST and XBLAST programs of Altschul, et al. (1990) J. Mol. Biol. 215:403-410. BLAST nucleotide searches are performed with the NBLAST program, score=100, wordlength=12 to obtain nucleotide sequences homologous to a nucleic acid molecules described or disclose herein. BLAST protein searches are performed with the XBLAST program, score=50, wordlength=3. To obtain gapped alignments for comparison purposes, Gapped BLAST is utilized as described in Altschul et al. (1997) Nucleic Acids Res. 25:3389-3402. When utilizing BLAST and Gapped BLAST programs, the default parameters of the respective programs (e.g., XBLAST and NBLAST) are used. See the website of the National Center for Biotechnology Information for further details (on the world wide web at ncbi.nlm.nih.gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein PAK inhibitor described herein. In other embodiments, the altered amino acid sequence is at least 75% identical, e.g., 77%, 80%, 82%, 85%, 88%, 90%, 92%, 95%, 97%, 98%, 99%, or 100% identical to the amino acid sequence of any protein PAK inhibitor described herein. Such sequence-variant proteins are suitable for the methods described herein as long as the altered amino acid sequence retains sufficient biological activity to be functional in the compositions and methods described herein. Where amino acid substitutions are made, the substitutions should be conservative amino acid substitutions. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al (1992), Proc. Natl. Acad. Sci. USA, 89:10915-10919). Accordingly, the BLOSUM62 substitution frequencies are used to define conservative amino acid substitutions that may be introduced into the amino acid sequences described or described herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

As used herein, the term "PAK activity," unless otherwise specified, includes, but is not limited to, at least one of PAK protein-protein interactions, PAK phosphotransferase activity (intermolecular or intermolecular), translocation, etc of one or more PAK isoforms.

As used herein, a "PAK inhibitor" refers to any molecule, compound, or composition that directly or indirectly decreases the PAK activity. In some embodiments, PAK inhibitors inhibit, decrease, and/or abolish the level of a PAK mRNA and/or protein or the half-life of PAK mRNA and/or protein, such inhibitors are referred to as "clearance agents". In some embodiments, a PAK inhibitor is a PAK antagonist that inhibits, decreases, and/or abolishes an activity of PAK. In some embodiments, a PAK inhibitor also disrupts, inhibits, or abolishes the interaction between PAK and its natural binding partners (e.g., a substrate for a PAK kinase, a Rac protein, a cdc42 protein, LIM kinase) or a protein that is a binding partner of PAK in a pathological condition, as measured using standard methods. In some embodiments, the PAK inhibitor is a Group I PAK inhibitor that inhibits, for example, one or more Group I PAK polypeptides, for example, PAK1, PAK2, and/or PAK3. In some embodiments, the PAK inhibitor is a PAK1 inhibitor. In some embodiments, the PAK inhibitor is a PAK2 inhibitor. In some embodiments, the PAK inhibitor is a PAK3 inhibitor. In some embodiments, the PAK inhibitor is a mixed PAK1/PAK3 inhibitor. In some embodiments, the PAK inhibitor inhibits all three Group I PAK isoforms (PAK1,2 and PAK3) with equal or similar potency. In some embodiments, the PAK inhibitor is a Group II PAK inhibitor that inhibits one or more Group II PAK polypeptides, for example PAK4, PAK5, and/or PAK6. In some embodiments, the PAK inhibitor is a PAK4 inhibitor. In some embodiments, the PAK inhibitor is a PAK5 inhibitor. In some embodiments, the PAK inhibitor is a PAK6 inhibitor. In some embodiments, the PAK inhibitor is a PAK7 inhibitor. As used herein, a PAK5 polypeptide is substantially homologous to a PAK7 polypeptide.

In some embodiments, PAK inhibitors reduce, abolish, and/or remove the binding between PAK and at least one of its natural binding partners (e.g., Cdc42 or Rac). In some instances, binding between PAK and at least one of its natural binding partners is stronger in the absence of a PAK inhibitor (by e.g., 90%, 80%, 70%, 60%, 50%, 40%, 30% or 20%) than in the presence of a PAK inhibitor. In some embodiments, PAK inhibitors prevent, reduce, or abolish binding between PAK and a protein that abnormally accumulates or aggregates in cells or tissue in a disease state. In some instances, binding between PAK and at least one of the proteins that aggregates or accumulates in a cell or tissue is stronger in the absence of a PAK inhibitor (by e.g., 90%, 80%, 70%, 60%, 50%, 40%, 30% or 20%) than in the presence of an inhibitor.

A "individual" or an "individual," as used herein, is a mammal. In some embodiments, an individual is an animal, for example, a rat, a mouse, a dog or a monkey. In some embodiments, an individual is a human patient. In some embodiments a "individual" or an "individual" is a human. In some embodiments, an individual suffers from a neuropsychiatric condition or is suspected to be suffering from a neuropsychiatric condition or is pre-disposed to a neuropsychiatric condition.

In some embodiments, a pharmacological composition comprising a PAK inhibitor is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, intra-arterial, subcutaneous, intramuscular, intraperitoneal, transdermal, by inhalation, transbuccal, intranasal, rectal, oral, parenteral, sublingual, or trans-nasal. In some embodiments, a PAK inhibitor is administered by an intracerebral route.

The terms "polypeptide," and "protein" are used interchangeably herein to refer to a polymer of amino acid residues. That is, a description directed to a polypeptide applies equally to a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly to accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Cassol et al. (1992); Rossolini et al., Mol. Cell. Probes 8:91-98 (1994)).

The terms "isolated" and "purified" refer to a material that is substantially or essentially removed from or concentrated in its natural environment. For example, an isolated nucleic acid is one that is separated from the nucleic acids that normally flank it or other nucleic acids or components (proteins, lipids, etc.) in a sample. In another example, a polypeptide is purified if it is substantially removed from or concentrated in its natural environment. Methods for purification and isolation of nucleic acids and proteins are documented methodologies.

The term "antibody" describes an immunoglobulin whether natural or partly or wholly synthetically produced. The term also covers any polypeptide or protein having a binding domain which is, or is homologous to, an antigen-binding domain. CDR grafted antibodies are also contemplated by this term.

The term antibody as used herein will also be understood to mean one or more fragments of an antibody that retain the ability to specifically bind to an antigen, (see generally, Holliger et al., Nature Biotech. 23 (9) 1126-1129 (2005)). Non-limiting examples of such antibodies include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544 546), which consists of a VH domain; and (vi) an isolated complementarity determining region (CDR). Furthermore, although the two domains of the Fv fragment, VL and VH, are coded for by separate genes, they are optionally joined, using recombinant methods, by a synthetic linker that enables them to be made as a single protein chain in which the VL and VH regions pair to form monovalent molecules (known as single chain Fv (scFv); see e.g., Bird et al. (1988) Science 242:423 426; and Huston et al. (1988) Proc. Natl. Acad. Sci. USA 85:5879 5883; and Osbourn et al. (1998) Nat. Biotechnol. 16:778). Such single chain antibodies are also intended to be encompassed within the term antibody. Any VH and VL sequences of specific scFv is optionally linked to human immunoglobulin constant region cDNA or genomic sequences, in order to generate expression vectors encoding complete IgG molecules or other isotypes. VH and VL are also optionally used in the generation of Fab, Fv or other fragments of immunoglobulins using either protein chemistry or recombinant DNA technology. Other forms of single chain antibodies, such as diabodies are also encompassed.

"F(ab')2" and "Fab" moieties are optionally produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CHγ1 (γ1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')2.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are documented.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise a VH, a VL, or both a VH and VL domain of an antibody, wherein both domains are present in a single polypeptide chain. In some embodiments, the Fv polypeptide further comprises a polypeptide linker between the VH and VL domains which enables the sFv to form the desired structure for antigen binding. For a review of sFv see, e.g., Pluckthun in The-Pharmacology of Monoclonal Antibodies, Vol. 113, Rosenburg and Moore eds. Springer-Verlag, New York, pp. 269 315 (1994).

A "chimeric" antibody includes an antibody derived from a combination of different mammals. The mammal is, for example, a rabbit, a mouse, a rat, a goat, or a human. The combination of different mammals includes combinations of fragments from human and mouse sources.

In some embodiments, an antibody described or described herein is a monoclonal antibody (MAb), typically a chimeric human-mouse antibody derived by humanization of a mouse monoclonal antibody. Such antibodies are obtained from, e.g., transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. In some embodiments, the transgenic mice synthesize human antibodies specific for human antigens, and the mice are used to produce human antibody-secreting hybridomas.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heteroalicyclic, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, amido, carbonyl, sulfonyl, or the like.

As used herein, where a subsituent is attached to a ring "via a carbon atom," the bond between the substituent and the ring is a carbon-carbon bond.

An "alkyl" group refers to an aliphatic hydrocarbon group. An "alkyl" group includes substituted and unsubstituted alkyl groups. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$ alkyl. A "heteroalkyl" group substitutes any one of the carbons of the alkyl group with a heteroatom having the appropriate number of hydrogen atoms attached (e.g., a $CH_2$ group to an NH group or an O group).

An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula C(O)NHR or NHC(O)R, where R is selected from alkyl, cycloalkyl, aryl, heteroaryl (bonded through a ring carbon) and heteroalicyclic (bonded through a ring carbon).

The term "ester" refers to a chemical moiety with formula —C(=O)OR, where R is selected from the group consisting of alkyl, cycloalkyl, aryl, heteroaryl and heteroalicyclic.

As used herein, the term "aryl" refers to an aromatic ring wherein each of the atoms forming the ring is a carbon atom.

An "aryl" group includes substituted and unsubstituted aryl groups. Aryl rings described herein include rings having five, six, seven, eight, nine, or more than nine carbon atoms. Aryl groups are optionally substituted. Examples of aryl groups include, but are not limited to phenyl, and naphthalenyl.

The term "cycloalkyl" refers to a monocyclic or polycyclic non-aromatic radical, wherein each of the atoms forming the ring (i.e. skeletal atoms) is a carbon atom. A "cycloalkyl" group includes substituted and unsubstituted cycloalkyl groups. In various embodiments, cycloalkyls are saturated, or partially unsaturated. In some embodiments, cycloalkyls are fused with an aromatic ring. In some embodiments, cycloalkyls are fused with a heteroaryl ring. Cycloalkyl groups include groups having from 3 to 10 ring atoms. Illustrative examples of cycloalkyl groups include, but are not limited to, the following moieties:

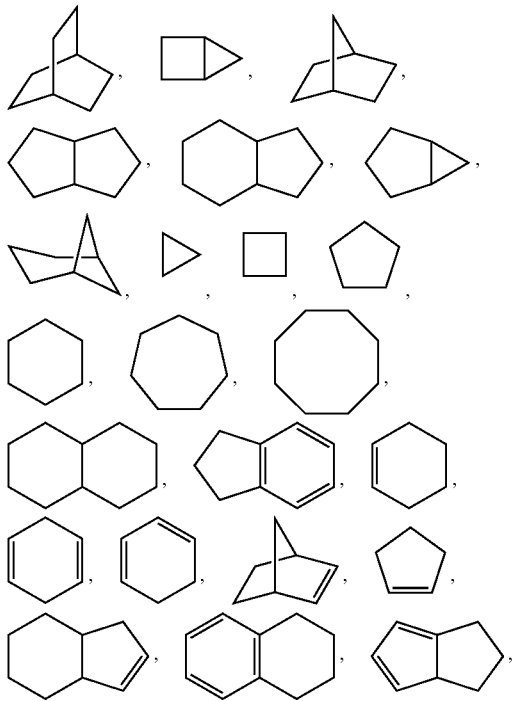

and the like. Monocyclic cycloalkyls include, but are not limited to, cyclopropyl, cyclobutyl, cyclopentyl, cyclohexyl, cycloheptyl, and cyclooctyl. Dicylclic cycloalkyls include, but are not limited to tetrahydronaphthyl, indanyl, tetrahydropentalene or the like. Polycyclic cycloalkyls include admantane, norbornane or the like. The term cycloalkyl includes "unsaturated nonaromatic carbocyclyl" or "nonaromatic unsaturated carbocyclyl" both of which refer to a nonaromatic carbocyclyle, as defined herein, that contains at least one carbon carbon double bond or one carbon carbon triple bond.

The term "heterocycle" refers to heteroaromatic and heteroalicyclic groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. A "heteroaryl" group includes substituted and unsubstituted heteroaryl groups. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Illustrative examples of heteroaryl groups include the following moieties:

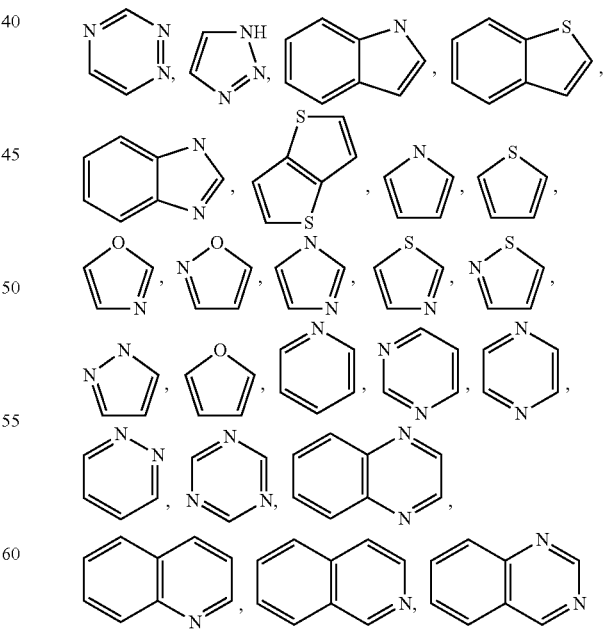

and the like.

A "heteroalicyclic" group or "heterocyclo" group or "heterocycloalkyl" group refers to a cycloalkyl group, wherein at least one skeletal ring atom is a heteroatom selected from nitrogen, oxygen and sulfur. A "heterocycloalkyl" group includes substituted and unsubstituted heterocycloalkyl groups. In various embodiments, the radicals are fused with an aryl or heteroaryl. Illustrative examples of heterocyclo groups, also referred to as non-aromatic heterocycles, include:

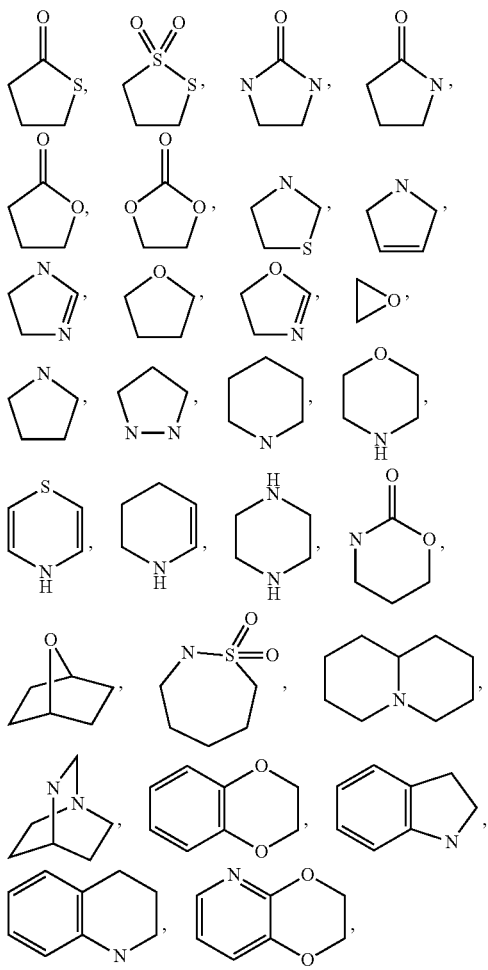

and the like. The term heteroalicyclic also includes all ring forms of the carbohydrates, including but not limited to the monosaccharides, the disaccharides and the oligosaccharides.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —C$_{1-12}$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. In some embodiments, up to two heteroatoms are consecutive, such as, by way of example, —CH$_2$—NH—OCH$_3$ and —CH$_2$—O—Si(CH$_3$)$_3$.

A "cyano" group refers to a CN group.

An "isocyanato" group refers to a NCO group.

A "thiocyanato" group refers to a CNS group.

An "isothiocyanato" group refers to a NCS group.

"Alkoyloxy" refers to a RC(═O)O— group.

"Alkoyl" refers to a RC(═O)— group.

Synthesis of Compounds

In some embodiments, compounds of Formula V are synthesized according to procedures described in Scheme 1 and in the Examples section.

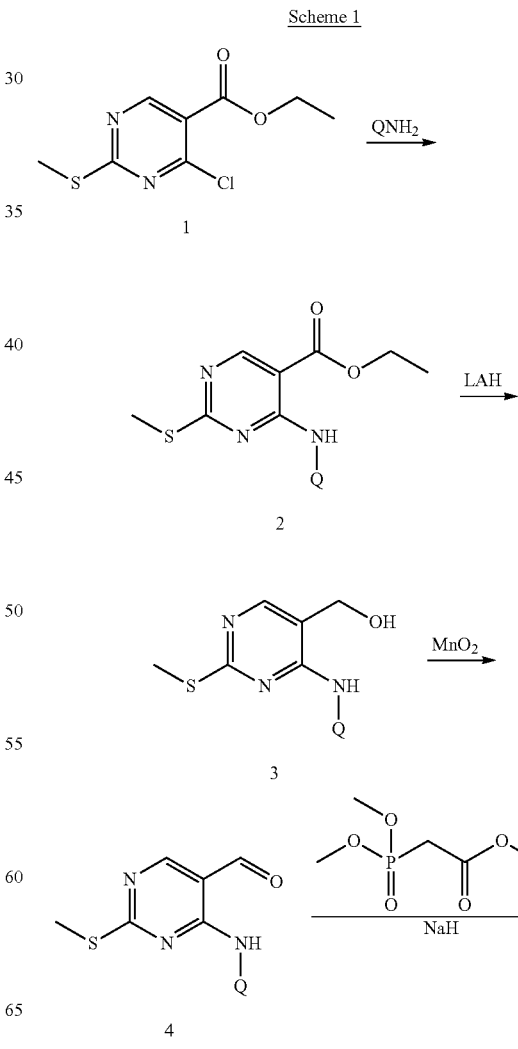

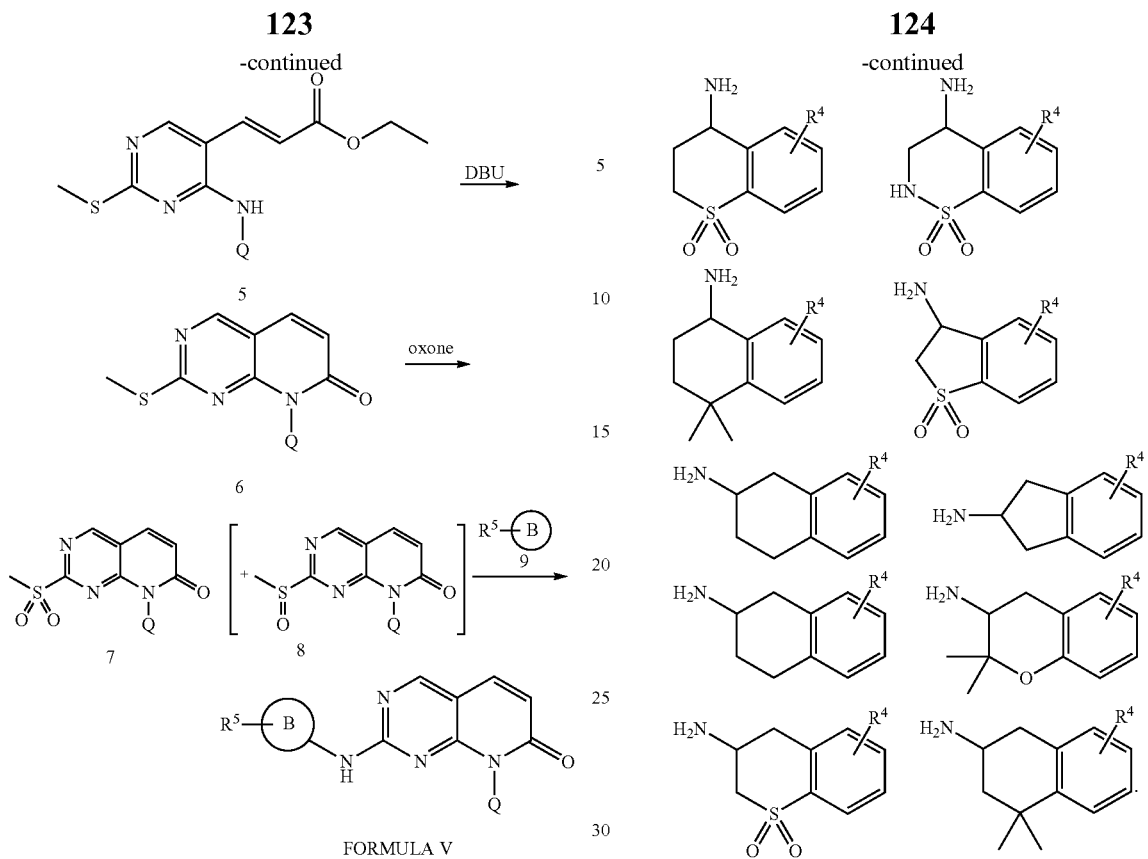

A reaction of an appropriate amine with ethyl 4-chloro-2-(methylthio)pyrimidine-5-carboxylate (1) furnishes a compound (2) as shown in Scheme 1. Reduction of the ester to an alcohol followed by oxidation of the alcohol to an aldehyde furnishes the intermediate (4). A Horner-Wadsworth Emmons reaction furnishes compound (5) which is cyclized in the presence of DBU to provide intermediate (6). Oxidation of the thiomethyl moiety in the presence of oxone furnishes a mixture of the sulfone and sulfoxide intermediates (7) and (8). Reaction of the sulfonyl compound with an amine (9) furnishes compounds of Formula V.

Amines Q-NH$_2$ that are compatible with the procedures described herein include and are not limited to In some embodiments, amines Q-NH$_2$ are synthesized according to procedures described in Scheme 2 and in the Examples section. Borane reduction of oxime (11) furnishes amine (12). In some embodiments, spiroborate-catalyzed borane reduction of an oxime (11) provides a chiral amine (13).

Scheme 2

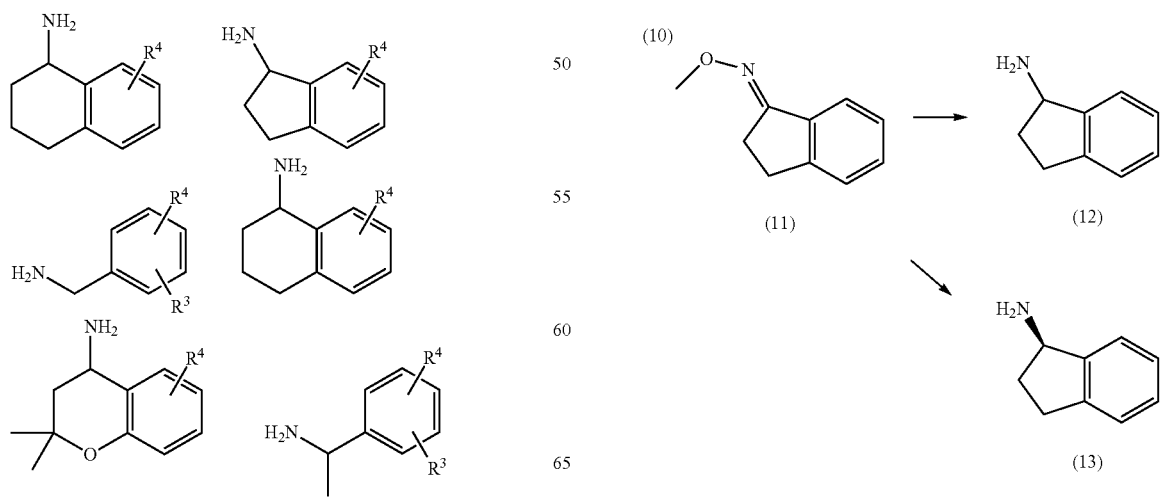

In some embodiments, compounds of Formulae VIII are synthesized according to procedures described in Scheme 3 and in the Examples section.

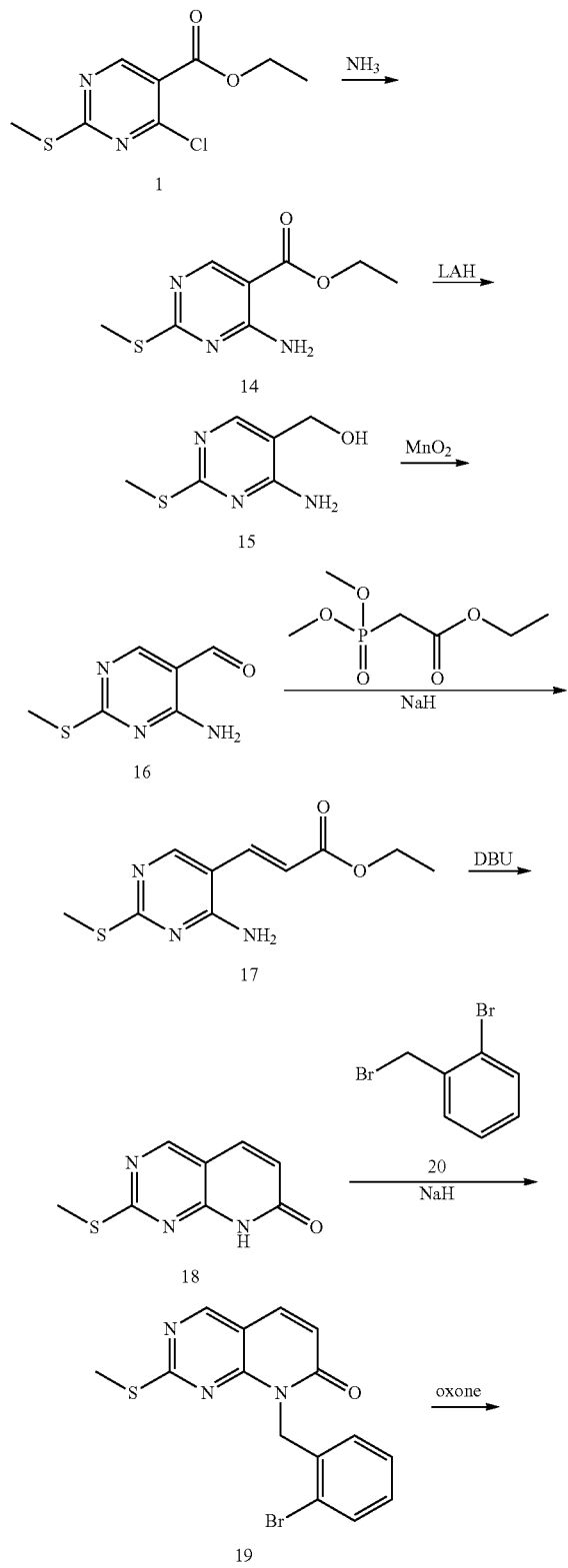

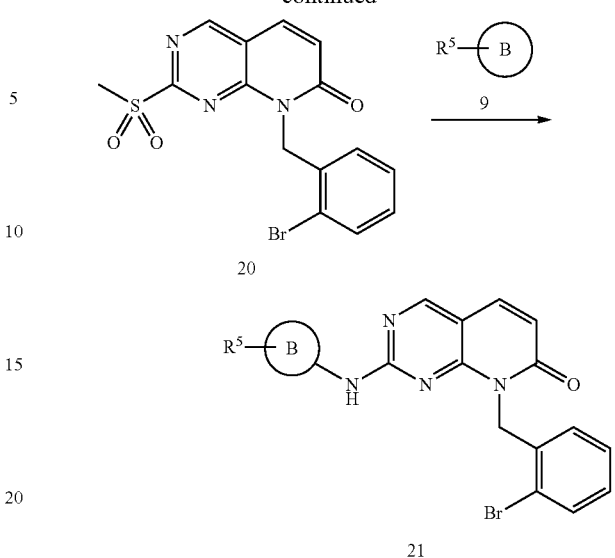

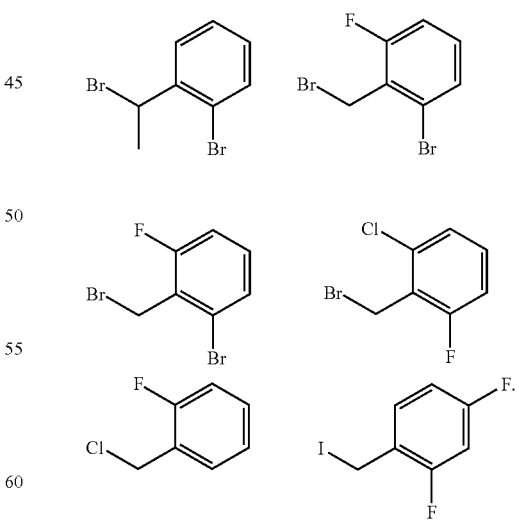

A reaction of ammonia with ethyl 4-chloro-2-(methylthio) pyrimidine-5-carboxylate (1) furnishes compound (14) as shown in Scheme 2. The ester moiety in compound 14 is reduced to an alcohol and oxidized to an aldehylde to yield compound 16. A Horner Wadsworth Emmons reaction furnishes compound 17 which is then cyclized in the presence of DBU to furnish compound 18. Compound 18 is alkylated with an appropriate benzyl halide, such as, for example, compound 20 in the presence of a strong base such as, for example, sodium hydride to yield compound 19. The thiomethyl group is oxidized in the presence of oxone and the methyl sulfone group in compound 20 is subjected to a displacement reaction with an appropriate amine 9 to yield compound 21. Other benzyl halides are compatible with the procedure described in Scheme 2 include and are not limited to As shown in Scheme 4 below, the bromide group in compound 19 is optionally subjected to further reactions such as, for example, a Suzuki reaction with an appropriate boronic acid to yield compounds of Formula X.

Scheme 4
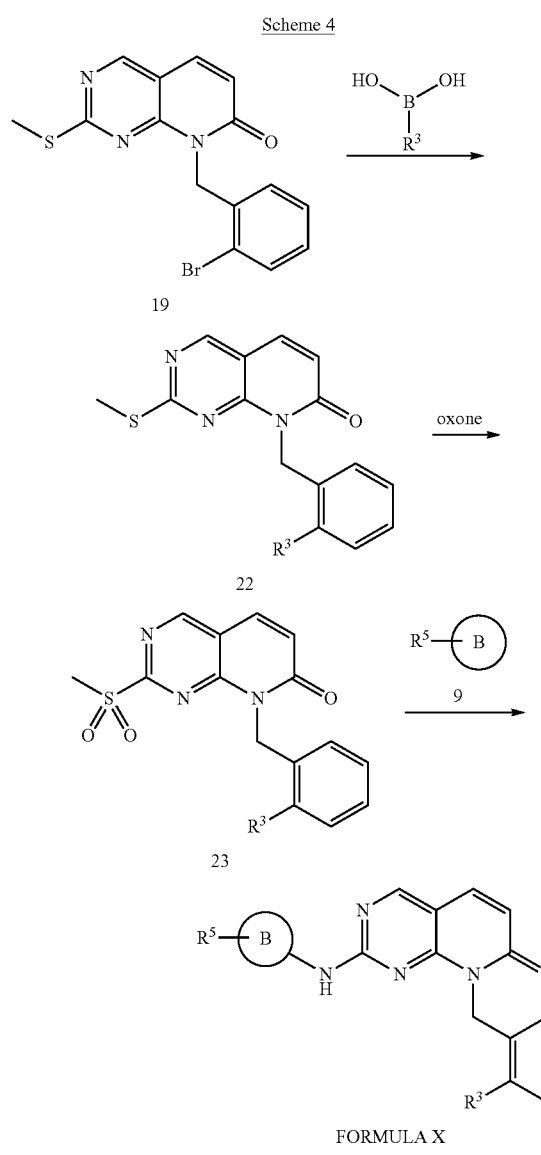
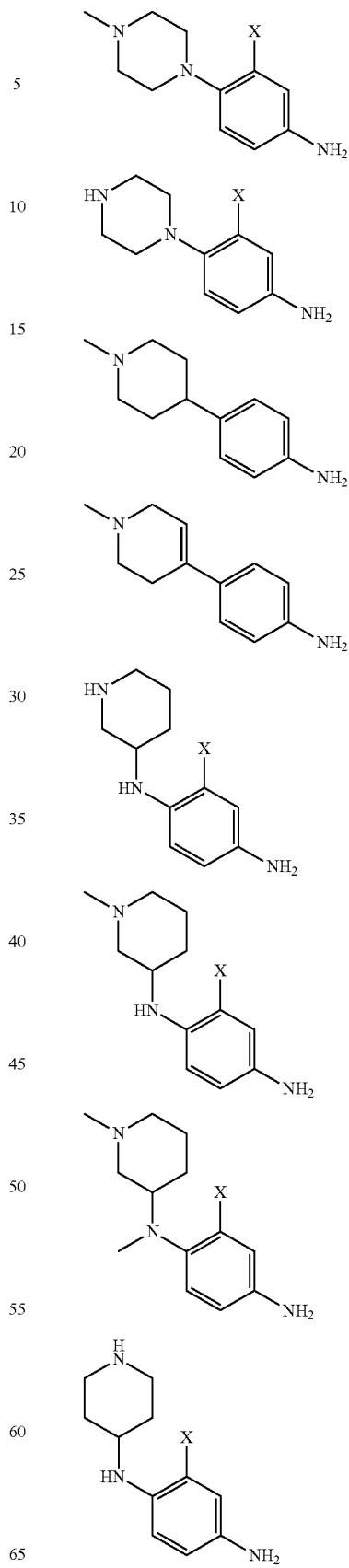
Examples of boronic acids that are compatible with the procedures described in Scheme 4 include and are not limited to
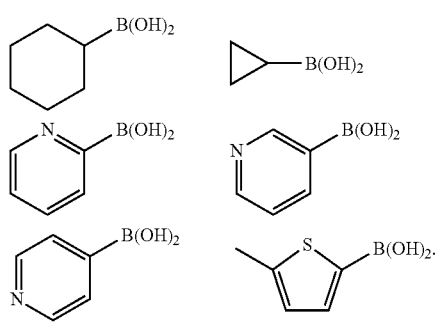
In some embodiments, amines (9) that are compatible with the procedures described herein include and are not limited to 129
-continued
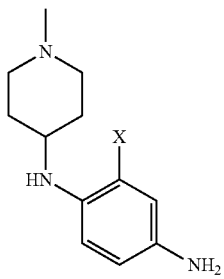
130
-continued
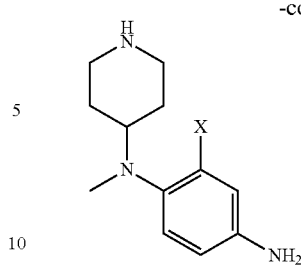
where X is F, Cl, CF$_3$, CHF$_2$, SO$_2$Me, or the like.
In some embodiments, compounds of Formula IIIA are synthesized according to procedures described in Scheme 5 and in the Examples section.
Scheme 5
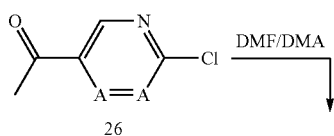
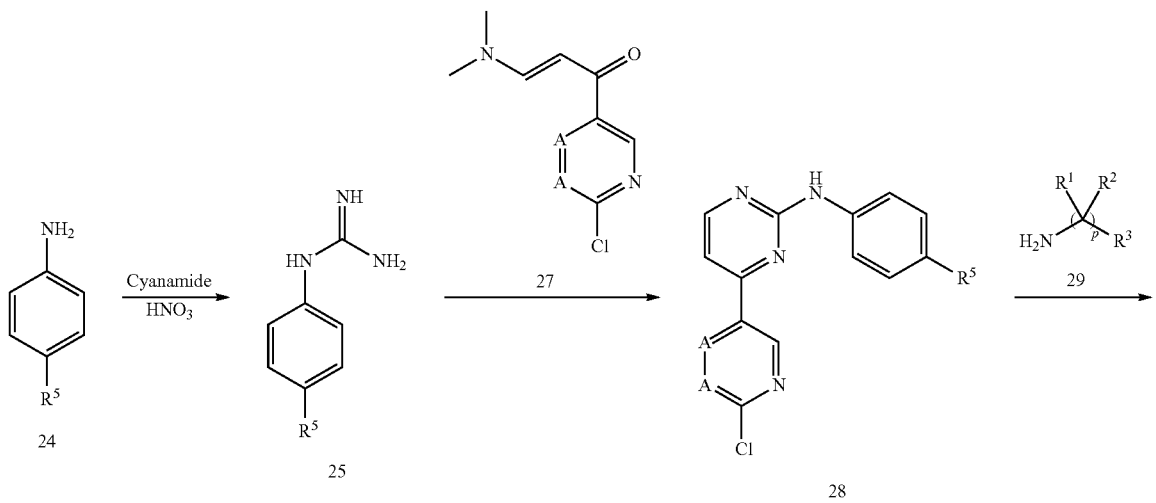
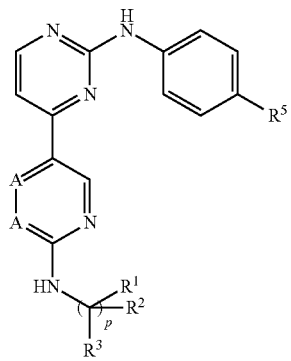
Formula IIIA Reaction of dimethylacetamide with an appropriate ketone 26 provides intermediate 27. Reaction of an aniline 24 with cyanamide provides the guanidine 25. reaction of the guanidine 25 with intermediate 27 provides compounds of structure 28 as shown in Scheme 5. Displacement of the chloride in compound 28 with an appropriate amine 29 furnishes compounds of Formula IIIA.

Methods

Provided herein are methods for treating neuropsychiatric conditions comprising administration of a therapeutically effective amount of a p21-activated kinase inhibitor (e.g., a compound of Formula I-X) to an individual in need thereof. In some embodiments of the methods provided herein, administration of a p21-activated kinase inhibitor alleviates or reverses one or more behavioral symptoms (e.g., social withdrawal, depersonalization, loss of appetite, loss of hygiene, delusions, hallucinations, depression, blunted affect, avolition, anhedonia, alogia, the sense of being controlled by outside forces or the like) of the neuropsychiatric condition (e.g. negative symptoms of schizophrenia). In some embodiments of the methods provided herein, administration of a p21-activated kinase inhibitor (e.g., a compound of Formula I-X) alleviates or reverses one or more negative symptoms and/or cognition impairment associated with a neuropsychiatric condition (e.g., impairment in executive function, comprehension, inference, decision-making, planning, learning or memory associated with schizophrenia, Alzheimer's disease, FXS, autism or the like).

Also provided herein are methods for modulation of dendritic spine morphology and/or synaptic function comprising administering to an individual in need thereof (e.g., an individual suffering from or suspected of having schizophrenia, Parkinson's disease, Alzheimer's disease, epilepsy or the like) a therapeutically effective amount of a PAK inhibitor (e.g., a compound of Formula I-X). In some embodiments, modulation of dendritic spine morphology and/or synaptic function alleviates or reverses negative symptoms and/or cognitive impairment associated with neuropsychiatric conditions. In some embodiments, modulation of dendritic spine morphology and/or synaptic function halts or delays further deterioration of neuropsychiatric symptoms (e.g., progression of cognitive impairments and/or loss of bodily functions). In some embodiments, modulation of dendritic spine morphology and/or synaptic function stabilizes or reverses symptoms of disease (e.g., reduces frequency of epileptic seizures, stabilizes mild cognitive impairment and prevents progression to early dementia). In some embodiments of the methods provided herein, administration of a p21-activated kinase inhibitor halts or delays progressive loss of memory and/or cognition associated with a neuropsychiatric condition (e.g., Alzheimer's disease).

Provided herein are methods for modulation of synaptic function or synaptic plasticity comprising administering to an individual in need thereof (e.g., an individual suffering from or suspected of having any neuropsychiatric condition described herein) a therapeutically effective amount of a PAK inhibitor (e.g., a compound of Formula I-X). Modulation of synaptic function or plasticity includes, for example, alleviation or reversal of defects in LTP, LTD or the like.

Defects in LTP include, for example, an increase in LTP or a decrease in LTP in any region of the brain in an individual suffering from or suspected of having a neuropsychiatric condition. Defects in LTD include for example a decrease in LTD or an increase in LTD in any region of the brain (e.g., the temporal lobe, parietal lobe, the frontal cortex, the cingulate gyrus, the prefrontal cortex, the cortex, or the hippocampus or any other region in the brain or a combination thereof) in an individual suffering from or suspected of having a neuropsychiatric condition.

In some embodiments of the methods, administration of a PAK inhibitor (e.g., a compound of Formula I-X) modulates synaptic function (e.g., synaptic transmission and/or plasticity) by increasing long term potentiation (LTP) in an individual suffering from or suspected of having a neuropsychiatric condition. In some embodiments of the methods described herein, administration of a PAK inhibitor (e.g., a compound of Formula I-X) to an individual in need thereof modulates synaptic function (e.g., synaptic transmission and/or plasticity) by increasing long term potentiation (LTP) in the prefrontal cortex, or the cortex, or the hippocampus or any other region in the brain or a combination thereof. In some embodiments of the methods described herein, administration of a PAK inhibitor modulates synaptic function (e.g., synaptic transmission and/or plasticity) by decreasing long term depression (LTD) in an individual suffering from or suspected of having a neuropsychiatric condition. In some embodiments of the methods described herein, administration of a PAK inhibitor to an individual in need thereof modulates synaptic function (e.g., synaptic transmission and/or plasticity) by decreasing long term depression (LTD) in the temporal lobe, parietal lobe, the frontal cortex, the cingulate gyrus, the prefrontal cortex, the cortex, or the hippocampus or any other region in the brain or a combination thereof.

In some embodiments of the methods described herein, administration of a PAK inhibitor reverses defects in synaptic function (i.e. synaptic transmission and/or synaptic plasticity, induced by soluble Abeta dimers or oligomers. In some embodiments of the methods described herein, administration of a PAK inhibitors reverses defects in synaptic function (i.e. synaptic transmission and/or synaptic plasticity, induced by insoluble Abeta oligomers and/or Abeta-containing plaques.

Provided herein are methods for stabilization of synaptic plasticity comprising administering to an individual in need thereof (e.g., an individual suffering from or suspected of having a neuropsychiatric condition) a therapeutically effective amount of a PAK inhibitor (e.g., a compound of Formula I-X). In some embodiments of the methods described herein, administration of a PAK inhibitor stabilizes LTP or LTD following induction (e.g., by theta-burst stimulation, high-frequency stimulation for LTP, low-frequency (e.g., 1 Hz) stimulation for LTD).

Provided herein are methods for stabilization of synaptic transmission comprising administering to an individual in need thereof (e.g., an individual suffering from or suspected of having a neuropsychiatric condition) a therapeutically effective amount of a PAK inhibitor (e.g., a compound of Formula I-X). In some embodiments of the methods described herein, administration of a PAK inhibitor stabilizes LTP or LTD following induction (e.g., by theta-burst stimulation, high-frequency stimulation for LTP, low-frequency (e.g., 1 Hz) stimulation for LTD).

Also provided herein are methods for alleviation or reversal of cortical hypofrontality during performance of a cognitive task comprising administering to an individual in need thereof (e.g., an individual suffering from or suspected of having a neuropsychiatric condition) a therapeutically effective amount of a PAK inhibitor (e.g., a compound of Formula I-X). In some embodiments of the methods described herein, administration of a PAK inhibitor to an individual suffering from or suspected of having a neuropsychiatric condition alleviates deficits in the frontal cortex, for example deficits in frontal cortical activation, during the performance of a cognitive task (e.g., a Wisconsin Card Sort test, Mini-Mental State Examination (MMSE), MATRICS cognitive battery, BACS score, Alzheimer's disease Assessment Scale—Cognitive Subscale (ADAS-Cog), Alzheimer's disease Assessment Scale—Behavioral Subscale (ADAS-Behav), Hopkins Verbal Learning Test-Revised or the like) and improves cognition scores of the individual.

Provided herein are methods for reversing abnormalities in dendritic spine morphology or synaptic function that are caused by mutations in high-risk genes (e.g. mutations in Amyloid Precursor Protein (APP), mutations in presenilin 1 and 2, the epsilon4 allele, the 91 by allele in the telomeric region of 12q, Apolipoprotein E-4 (APOE4) gene, SORL1 gene, reelin gene, DISC1 gene, or any other high-risk allele) comprising administering to an individual in need thereof a therapeutically effective amount of a PAK inhibitor (e.g., a compound of Formula I-X). In some embodiments of the methods described herein, prophylactic administration of a PAK inhibitor to an individual at a high risk for developing a neuropsychiatric condition (e.g., a mutation in a DISC1 gene pre-disposes the individual to schizophenia, a mutation in an APOE4 gene pre-disposes the individual to Alzheimer's disease) reverses abnormalities in dendritic spine morphology and/or synaptic function and prevents development of the neuropsychiatric condition.

Provided herein are methods for stabilizing, reducing or reversing abnormalities in dendritic spine morphology or synaptic function that are caused by increased activation of PAK at the synapse, comprising administration of a therapeutically effective amount of a PAK inhibitor (e.g., a compound of Formula I-X) to an individual in need thereof (e.g., an individual suffering from or suspected of having a neuropsychiatric condition). In some embodiments of the methods described herein, increased activation of PAK at the synapse is caused by Abeta. In some instances, increased activation of PAK at the synapse is caused by redistribution of PAK from the cytosol to the synapse. In some embodiments of the methods described herein, administration of a therapeutically effective amount of a PAK inhibitor (e.g., a compound of Formula I-X) to an individual in need thereof (e.g., an individual suffering from or suspected of having a neuropsychiatric condition) reduces or prevents redistribution of PAK from the cytosol to the synapse in neurons, thereby stabilizing, reducing or reversing abnormalities in dendritic spine morphology or synaptic function that are caused by increased activation of PAK at the synapse.

Provided herein are methods for delaying the onset of a neuropsychiatric condition comprising administering to an individual in need thereof (e.g., an individual with a high-risk allele for a NC) a therapeutically effective amount of a PAK inhibitor (e.g., a compound of Formula I-X). Provided herein are methods for delaying the loss of dendritic spine density comprising administering to an individual in need thereof (e.g., an individual with a high-risk allele for a NC) a therapeutically effective amount of a PAK inhibitor. Provided herein are methods for modulation of spine density, shape, spine length, spine head volume, or spine neck diameter or the like comprising administering to an individual in need thereof (e.g., an individual suffering from or suspected of having a neuropsychiatric condition) a therapeutically effective amount of a PAK inhibitor (e.g., a compound of Formula I-X). Provided herein are methods of modulating the ratio of mature dendritic spines to immature dendritic spines comprising administering to an individual in need thereof (e.g., an individual suffering from or suspected of having a neuropsychiatric condition) a therapeutically effective amount of a PAK inhibitor. Provided herein are methods of modulating the ratio of dendritic spines head volume to dendritic spines length comprising administering to an individual in need thereof (e.g., an individual suffering from or suspected of having a neuropsychiatric condition) a therapeutically effective amount of a PAK inhibitor (e.g., a compound of Formula I-X).

In some embodiments of the methods described herein, administration of a PAK inhibitor (e.g., a maintenance dose of a PAK inhibitor) reduces the incidence of recurrence of one or more symptoms or pathologies in an individual (e.g., recurrence of psychotic episodes, epileptic seizures or the like). In some embodiments of the methods described herein, administration of a PAK inhibitor causes substantially complete inhibition of PAK and restores dendritic spine morphology and/or synaptic function to normal levels. In some embodiments of the methods described herein, administration of a PAK inhibitor causes partial inhibition of PAK and restores dendritic spine morphology and/or synaptic function to normal levels.

Provided herein are methods for stabilizing, reducing or reversing neuronal withering and/or atrophy or nervous tissue and/or degeneration of nervous tissue that is associated with a neuropsychiatric condition. In some embodiments of the methods described herein, administration of a PAK inhibitor to an individual suffering from or suspected of having a neuropsychiatric condition (e.g., Alzheimer's disease, Parkinson's disease or the like) stabilizes, alleviates or reverses neuronal withering and/or atrophy and/or degeneration in the temporal lobe, parietal lobe, the frontal cortex, the cingulate gyrus or the like. In some embodiments of the methods described herein, administration of a PAK inhibitor to an individual suffering from or suspected of having a neuropsychiatric condition stabilizes, reduces or reverses deficits in memory and/or cognition and/or control of bodily functions.

In some instances, an NC is associated with a decrease in dendritic spine density. In some embodiments of the methods described herein, administration of a PAK inhibitor increases dendritic spine density. In some instances, an NC is associated with an increase in dendritic spine length. In some embodiments of the methods described herein, administration of a PAK inhibitor decreases dendritic spine length. In some instances, an NC is associated with a decrease in dendritic spine neck diameter. In some embodiments of the methods described herein, administration of a PAK inhibitor increases dendritic spine neck diameter. In some instances, an NC is associated with a decrease in dendritic spine head diameter and/or dendritic spine head surface area and/or dendritic spine head volume. In some embodiments of the methods described herein, administration of a PAK inhibitor increases dendritic spine head diameter and/or dendritic spine head volume and/or dendritic spine head surface area.

In some instances, an NC is associated with an increase in immature spines and a decrease in mature spines. In some embodiments of the methods described herein, administration of a PAK inhibitor modulates the ratio of immature spines to mature spines. In some instances, an NC is associated with an increase in stubby spines and a decrease in mushroom-shaped spines. In some embodiments of the methods described herein, administration of a PAK inhibitor modulates the ratio of stubby spines to mushroom-shaped spines.

In some embodiments of the methods described herein, administration of a PAK inhibitor modulates a spine:head ratio, e.g., ratio of the volume of the spine to the volume of the head, ratio of the length of a spine to the head diameter of the spine, ratio of the surface area of a spine to the surface area of the head of a spine, or the like, compared to a spine:head ratio in the absence of a PAK inhibitor. In certain embodiments, a PAK inhibitor suitable for the methods described herein modulates the volume of the spine head, the width of the spine head, the surface area of the spine head, the length of the spine shaft, the diameter of the spine shaft, or a combination thereof. In some embodiments, provided herein is a method of modulating the volume of a spine head, the width of a spine head, the surface area of a spine head, the length of a spine shaft, the diameter of a spine shaft, or a combination thereof, by contacting a neuron comprising the dendritic spine with an effective amount of a PAK inhibitor described herein. In specific embodiments, the neuron is contacted with the PAK inhibitor in vivo.

In certain embodiments, a compound or a composition comprising a compound described herein is administered for prophylactic and/or therapeutic treatments. In therapeutic applications, the compositions are administered to an individual already suffering from a disease or condition, in an amount sufficient to cure or at least partially arrest the symptoms of the disease or condition. In various instances, amounts effective for this use depend on the severity and course of the disease or condition, previous therapy, an individual's health status, weight, and response to the drugs, and the judgment of the treating physician.

In some embodiments, a composition containing a therapeutically effective amount of a PAK inhibitor is administered prophylactically to an individual that while not overtly manifesting symptoms of a neuropsychiatric condition has been identified as having a high risk of developing a neuropsychiatric condition, e.g., an individual is identified as being a carrier of a mutation or polymorphism associated with a higher risk to develop a neuropsychiatric condition (see, e.g., Hall et al (2006), *Nat. Neurosci.*, 9(12):1477-8), or an individual that is from a family that has a high incidence of neuropsychiatric conditions. In some embodiments, MRI is used to detect brain morphological changes in individuals prior to the onset of disease (see, e.g., Toga et al (2006), *TINS*, 29(3):148-159). For example, in some instances, the typical age of onset for schizophrenia is post-puberty. In some instances, the typical age of onset for schizophrenia is between 20-28 for males and 26-32 for females. For example, in some instances, a typical age of onset for Alzheimer's disease is about 55-80 years. Accordingly, in some embodiments, a PAK inhibitor is administered prophylactically to an individual at risk between about 1 to about 10 years, e.g., 1, 2, 3, 4, 5, 6, 7, 8, 9, or 10 years prior to an established and/or typical age range of onset for a neuropsychiatric condition.

In prophylactic applications, compounds or compositions containing compounds described herein are administered to an individual susceptible to or otherwise at risk of a particular disease, disorder or condition. In certain embodiments of this use, the precise amounts of compound administered depend on an individual's state of health, weight, and the like. Furthermore, in some instances, when a compound or composition described herein is administered to an individual, effective amounts for this use depend on the severity and course of the disease, disorder or condition, previous therapy, an individual's health status and response to the drugs, and the judgment of the treating physician.

In certain instances, wherein following administration of a selected dose of a compound or composition described herein, an individual's condition does not improve, upon the doctor's discretion the administration of a compound or composition described herein is optionally administered chronically, that is, for an extended period of time, including throughout the duration of an individual's life in order to ameliorate or otherwise control or limit the symptoms of an individual's disorder, disease or condition.

In certain embodiments, an effective amount of a given agent varies depending upon one or more of a number of factors such as the particular compound, disease or condition and its severity, the identity (e.g., weight) of an individual or host in need of treatment, and is determined according to the particular circumstances surrounding the case, including, e.g., the specific agent being administered, the route of administration, the condition being treated, and an individual or host being treated. In some embodiments, doses administered include those up to the maximum tolerable dose. In certain embodiments, about 0.02-5000 mg per day, from about 1-1500 mg per day, about 1 to about 100 mg/day, about 1 to about 50 mg/day, or about 1 to about 30 mg/day, or about 5 to about 25 mg/day of a compound described herein is administered. In various embodiments, the desired dose is conveniently be presented in a single dose or in divided doses administered simultaneously (or over a short period of time) or at appropriate intervals, for example as two, three, four or more sub-doses per day.

In certain instances, there are a large number of variables in regard to an individual treatment regime, and considerable excursions from these recommended values are considered within the scope described herein. Dosages described herein are optionally altered depending on a number of variables such as, by way of non-limiting example, the activity of the compound used, the disease or condition to be treated, the mode of administration, the requirements of an individual individual, the severity of the disease or condition being treated, and the judgment of the practitioner.

Toxicity and therapeutic efficacy of such therapeutic regimens are optionally determined by pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. In certain embodiments, data obtained from cell culture assays and animal studies are used in formulating a range of dosage for use in human. In specific embodiments, the dosage of compounds described herein lies within a range of circulating concentrations that include the $ED_{50}$ with minimal toxicity. The dosage optionally varies within this range depending upon the dosage form employed and the route of administration utilized.

Combination Therapy

In some embodiments, one or more PAK inhibitors are used in combination with one or more other therapeutic agents to treat an individual suffering from a neuropsychiatric condition. The combination of PAK inhibitors with a second therapeutic agent (e.g., a typical or atypical antipsychotic agent, an mGluR1 antagonist, an mGluR5 antagonist, an mGluR5 potentiator, a mGluR2 agonist, an alpha7 nicotinic receptor agonist or potentiator, an antioxidant, a neuroprotectant, a trophic factor, an anticholinergic, a beta-secretase inhibitor or the like) allows a reduced dose of both agents to be used thereby reducing the likelihood of side effects associated with higher dose monotherapies. In one embodiment, the dose of a second active agent is reduced in the combination therapy by at least 50% relative to the corresponding monotherapy dose, whereas the PAK inhibitor dose is not reduced relative to the monotherapy dose; in further embodiments, the reduction in dose of a second active agent is at least 75%; in yet a further embodiment, the reduction in dose of a second active agent is at least 90%. In some embodiments, the second therapeutic agent is administered at the same dose as a monotherapy dose, and the addition of a PAK inhibitor to the treatment regimen alleviates symptoms of an NC that are not treated by monotherapy with the second therapeutic agent. Symptoms and diagnostic criteria for all of the conditions mentioned above are described in detail in the Diagnostic and Statistical Manual of Mental Disorders, fourth edition, American Psychiatric Association (2005) (DSM-IV).

In some embodiments, the combination of a PAK inhibitor and a second therapeutic agent is synergistic (e.g., the effect of the combination is better than the effect of each agent alone). In some embodiments, the combination of a PAK inhibitor and a second therapeutic agent is additive (e.g., the effect of the combination of active agents is about the same as the effect of each agent alone). In some embodiments, an additive effect is due to the PAK inhibitor and the second therapeutic agent modulating the same regulatory pathway. In some embodiments, an additive effect is due to the PAK inhibitor and the second therapeutic agent modulating different regulatory pathways. In some embodiments, an additive effect is due to the PAK inhibitor and the second therapeutic agent treating different symptom groups of the NC (e.g., a PAK inhibitor treats negative symptoms and the second therapeutic agent treats positive symptoms of schizophrenia). In some embodiments, administration of a second therapeutic agent treats the remainder of the same or different symptoms or groups of symptoms that are not treated by administration of a PAK inhibitor alone.

In some embodiments, administration of a combination of a PAK inhibitor and a second therapeutic agent alleviates side effects that are caused by the second therapeutic agent (e.g., side effects caused by an antipsychotic agent or a nootropic agent). In some embodiments, administration of the second therapeutic agent inhibits metabolism of an administered PAK inhibitor (e.g., the second therapeutic agent blocks a liver enzyme that degrades the PAK inhibitor) thereby increasing efficacy of a PAK inhibitor. In some embodiments, administration of a combination of a PAK inhibitor and a second therapeutic agent (e.g. a second agent that modulates dendritic spine morphology (e.g., minocycline)) improves the therapeutic index of a PAK inhibitor.

Agents for Treating Psychotic Disorders

Where a subject is suffering from or at risk of suffering from a psychotic disorder (e.g., schizophrenia), a PAK inhibitor composition described herein is optionally used together with one or more agents or methods for treating a psychotic disorder in any combination. Alternatively, a PAK inhibitor composition described herein is administered to a patient who has been prescribed an agent for treating a psychotic disorder. In some embodiments, administration of a PAK inhibitor in combination with an antipsychotic agent has a synergistic effect and provides an improved therapeutic outcome compared to monotherapy with antipsychotic agent or monotherapy with PAK inhibitor. Alternatively, a PAK inhibitor composition described herein is administered to a patient who is non-responsive to, or being unsatisfactorily treated with an antipsychotic agent.

Examples of therapeutic agents/treatments for treating a psychotic disorder include, but are not limited to, any of the following: typical antipsychotics, e.g., Chlorpromazine (Largactil, Thorazine), Fluphenazine (Prolixin), Haloperidol (Haldol, Serenace), Molindone, Thiothixene (Navane), Thioridazine (Mellaril), Trifluoperazine (Stelazine), Loxapine, Perphenazine, Prochlorperazine (Compazine, Buccastem, Stemetil), Pimozide (Orap), Zuclopenthixol; and atypical antipsychotics, e.g., LY2140023, Clozapine, Risperidone, Olanzapine, Quetiapine, Ziprasidone, Aripiprazole, Paliperidone, Asenapine, Iloperidone, Sertindole, Zotepine, Amisulpride, Bifeprunox, and Melperone.

Agents for Treating Mood Disorders

Where a subject is suffering from or at risk of suffering from a mood disorder (e.g., clinical depression), a PAK inhibitor composition described herein is optionally used together with one or more agents or methods for treating a mood disorder in any combination. Alternatively, a PAK inhibitor composition described herein is administered to a patient who has been prescribed an agent for treating a mood disorder. Alternatively, a PAK inhibitor composition described herein is administered to a patient who is non-responsive to or being unsatisfactorily treated with an agent for treating a mood disorder.

Examples of therapeutic agents/treatments for treating a mood disorder include, but are not limited to, any of the following: selective serotonin reuptake inhibitors (SSRIs) such as citalopram (Celexa), escitalopram (Lexapro, Esipram), fluoxetine (Prozac), paroxetine (Paxil, Seroxat), sertraline (Zoloft), fluvoxamine (Luvox); serotonin-norepinephrine reuptake inhibitors (SNRIs) such as venlafaxine (Effexor), desvenlafaxine, nefazodone, milnacipran, duloxetine (Cymbalta), bicifadine; tricyclic antidepressants such as amitriptyline, amoxapine, butriptyline, clomipramine, desipramine, dosulepin, doxepin, imipramine, lofepramine, nortriptyline; monoamine oxidase inhibitors (MAOIs) such as isocarboxazid, linezolid, moclobemide, nialamide, phenelzine, selegiline, tranylcypromine, trimipramine; and other agents such as mirtazapine, reboxetine, viloxazine, malprotiline, and bupropion.

Agents for Treating Epilepsy

Where a subject is suffering from or at risk of suffering from epilepsy, a PAK inhibitor composition described herein is optionally used together with one or more agents or methods for treating epilepsy in any combination. Alternatively, a PAK inhibitor composition described herein is administered to a patient who has been prescribed an agent for treating epilepsy. Alternatively, a PAK inhibitor composition described herein is administered to a patient who is refractory to or being unsatisfactorily treated with an agent for treating epilepsy.

Examples of therapeutic agents/treatments for treating epilepsy include, but are not limited to, any of the following: carbamazepine, clobazam, clonazepam, ethosuximide, felbamate, fosphenyloin, gabapentin, lamotrigine, levetiracetam, oxcarbazepine, phenobarbital, phenyloin, pregabalin, primidone, sodium valproate, tiagabine, topiramate, valproate semisodium, valproic acid, vigabatrin, and zonisamide.

Agents for Treating Huntington's Disease

Where a subject is suffering from or at risk of suffering from Huntingtin's disease, a PAK inhibitor composition described herein is optionally used together with one or more agents or methods for treating Huntingtin's disease in any combination. Alternatively, a PAK inhibitor composition described herein is administered to a patient who has been prescribed an agent for treating Huntington's disease. Alternatively, a PAK inhibitor composition described herein is administered to a patient who is refractory to or being unsatisfactorily treated with an agent for treating Huntington's disease.

Examples of therapeutic agents/treatments for treating Huntingtin's disease include, but are not limited to, any of the following: omega-3 fatty acids, miraxion, Haloperidol, dopamine receptor blockers, creatine, cystamine, cysteamine, clonazepam, clozapine, Coenzyme Q10, minocycline, antioxidants, antidepressants (notably, but not exclusively, selective serotonin reuptake inhibitors SSRIs, such as sertraline, fluoxetine, and paroxetine), select dopamine antagonists, such as tetrabenazine; and RNAi knockdown of mutant huntingtin (mHtt).

Agents for Treating Parkinson's Disease

Where a subject is suffering from or at risk of suffering from Parkinson's Disease, a PAK inhibitor composition described herein is optionally used together with one or more agents or methods for treating Parkinson's disease in any combination. Alternatively, a PAK inhibitor composition described herein is administered to a patient who has been prescribed an agent for treating Parkinson's disease. Alternatively, a PAK inhibitor composition described herein is administered to a patient who is refractory to or being unsatisfactorily treated with an agent for treating Parkinson's disease.

Examples of therapeutic agents/treatments for treating Parkinson's Disease include, but are not limited to any of the following: L-dopa, carbidopa, benserazide, tolcapone, entacapone, bromocriptine, pergolide, pramipexole, ropinirole, cabergoline, apomorphine, lisuride, selegiline, or rasagiline Group I mGluR Antagonists In some embodiments, one or more PAK inhibitors are used in combination with one or more Group I metabotropic glutamate receptor (mGluR) antagonists (e.g., mGluR5 antagonists) to treat an individual suffering from a neuropsychiatric condition. The combination of PAK inhibitors with Group I mGluR antagonists allows a reduced dose of both agents to be used thereby reducing the likelihood of side effects associated with higher dose monotherapies.

In some embodiments, reduction of signaling from a Group I mGluR (mGluR5) in vivo by genetic engineering (using mGluR5 knock-out heterozygote animals) leads to a reversal of the dendritic spine and behavioral defects. In some instances, where an individual is suffering from or at risk of suffering from a neuropsychiatric condition, a PAK inhibitor composition described herein is optionally used together with one or Group I mGluR antagonists. Group I mGluR antagonists include antagonists that are mGluR1-selective antagonists, mGluR5-selective antagonists, or antagonists that antagonize both mGluR1 and mGluR5. In some embodiments, a PAK inhibitor composition is used in combination with an mGluR5-selective antagonist. In some embodiments, a PAK inhibitor composition is used in combination with an mGluR1selective antagonist. In some embodiments, a PAK inhibitor composition is used in combination with a Group I mGluR antagonist that antagonizes both mGluR1 and mGluR5 (i.e., an antagonist that is not selective for mGluR1 or mGluR5). As used herein, the term "selective antagonist" indicates that the antagonist has an $ED_{50}$ for antagonizing a first receptor (e.g., mGluR5) that is at least about 10 fold to about 1000 fold lower, e.g., 11, 20, 30, 40, 50, 100, 105, 125, 135, 150, 200, 300, 400, 500, 600, 700, 800, 900, or any other fold lower from about 10 fold to about 1000 fold lower than the $ED_{50}$ for antagonism of a second receptor (e.g., mGluR1).

Examples of Group I mGluR antagonists include, but are not limited to, any of the following (E)-6-methyl-2-styryl-pyridine (SIB 1893), 6-methyl-2-(phenylazo)-3-pyridinol, .alpha.-methyl-4-carboxyphenylglycine (MCPG), or 2-methyl-6-(phenylethynyl)-pyridine (MPEP). Examples of Group I mGluR antagonists also include those described in, e.g., U.S. patent application Ser. Nos. 10/076,618; 10/211,523; and 10/766,948. Examples of mGluR5-selective antagonists include, but are not limited to those described in, e.g., U.S. Pat. No. 7,205,411 and U.S. patent application Ser. No. 11/523,873. Examples of mGluR1-selective antagonists include, but are not limited to, those described in, e.g., U.S. Pat. No. 6,482,824.

In some embodiments, the mGluR Group I antagonist is AIDA (1-aminoindan-1,5-dicarboxylic acid); ACDPP (3-Amino-6-chloro-5-dimethylamino-N-2-pyridinylpyrazine carboxamide hydrochloride; DL-AP3 (DL-2-Amino-3-phosphonopropionic acid); BAY-36-7620 ((3aS,6aS)-Hexahydro-5-methylene-6a-(2-naphthalenylmethyl)-1H-cyclopenta[c]furan-1-one); Fenobam; 4 CPG ((S)-4-carboxyphenylglycine); (S)-4C3HPG ((S)-4-carboxy-3-hydroxyphenylglycine); CPCCOEt (7-hydroxyiminocyclopropan[b]chromen-1a-carboxylic acid ethyl ester); LY 367385 ((S)-(+)-a-Amino-4-carboxy-2-methylbenzeneacetic acid); LY 456236 hydrochloride (6-methoxy-N-(4-methoxyphenyl) quinazolin-4-amine, MPMQ hydrochloride); 3-MATIDA (a-Amino-5-carboxy-3-methyl-2-thiopheneacetic acid); MCPG (α-methyl-4-carboxyphenylglycine); MPEP (2-methyl-6-(phenylethynyl)-pyridine); (MTEP) 3-[(2-methyl-1,3-thiazol-4-yl)ethynyl]-pyridine; PHCCC(N-Phenyl-7-(hydroxyimino)cyclopropa[b]chromen-1a-carbox amide; SIB 1757 (6-Methyl-2-(phenylazo)-3-pyridinol; SIB 1893 (2-Methyl-6-(2-phenylethenyl)pyridine; YM 298198 hydrochloride (6-Amino-N-cyclohexyl-N,3-dimethylthiazolo[3,2-a]benzimidazole-2-carboxamidehydrochloride); (YM-193167 (6-amino-N-cyclohexyl-N,3-dimethylthiazolo[3,2-a]benzimidazole-2-carboxamide); (NPS 2390 (Quinoxaline-2-carboxylic acid adamantan-1-ylamide); 3-(5-(pyridin-2-yl)-2H-tetrazol-2-yl)benzonitrile; 3-[3-fluoro-5-(5-pyridin-2-yl-2H-tetrazol-2-yl)phenyl]-4-methylpyridine; 3-fluoro-5-(5-pyridin-2-yl-2H-tetrazol-2-yl)benzonitrile; N-cyclohexyl-6-{[(2-methoxyethyl)(methyl)amino]methyl}-N-methylthiazolo[3,2-a]benzimidazole-2-carboxamide (YM-202074); Desmethyl-YM298198 (6-Amino-N-cyclohexyl-3-methylthiazolo[3,2-a]benzimidazole-2-carboxamide hydrochloride); MPEP hydrochloride (2-Methyl-6-(phenylethynyl)pyridine hydrochloride); (S)-MCPG ((S)-a-Methyl-4-carboxyphenylglycine); (RS)-MCPG ((RS)-a-Methyl-4-carboxyphenylglycine); E4CPG ((RS)-a-Ethyl-4-carboxyphenylglycine); Hexylhomoibotenic acid (a-Amino-4-hexyl-2,3-dihydro-3-oxo-5-isoxazolepropanoic acid; HexylHIBO); (S)-Hexylhomoibotenic acid ((S)-a-Amino-4-hexyl-2,3-dihydro-3-oxo-5-isoxazolepropanoic acid; (S)-HexylHIBO); EMQMCM (3-ethyl-2-methyl-quinolin-6-yl)-(4-methoxy-cyclohexyl)-methanone methanesulfonate); JNJ 16259685; R214127 (1-(3,4-dihydro-2H-pyrano[2,3-b] quinolin-7-yl)-2-phenyl-1-ethanone); (S)-3-Carboxy-4-hydroxyphenylglycine ((S)-3C4HPG); Anti-mGlu5 blocking peptide ([K]-SSPKYDTLIIRDYTQSSSSL); DFB (3,3'-Difluorobenzaldazine); DMeOB ([(3-Methoxyphenyl)methylene]hydrazone-3-methoxybenzalde hyde); Anti-mGlu$_5$ (([K]-SSPKYDTLIIRDYTQSSSSL); reluzole; or combinations thereof.

In some embodiments, the modulator of a Group I mGluR is S-(4-Fluoro-phenyl)-{3-[3-(4-fluoro-phenyl)-[1,2,4]oxadiazol-5-yl]-piperidin-1-yl}-methanone (ADX47273) (Positive allosteric modulator); 4-[1-(2-fluoropyridin-3-yl)-5-methyl-1H-1,2,3-triazol-4-yl]-N-isopropyl-N-methyl-3,6-dihydropyridine-1(2H)-carboxamide (FTIDC); 6-(3-methoxy-4-(pyridin-2-yl)phenyl)imidazole[2,1-b]thiazole; 2-(2-methoxy-4-(4-(pyridin-2-yl)oxazol-2-yl)phenyl)acetonitrile; 2-(4-(benzo[d]oxazol-2-yl)-2-methoxyphenyl)acetonitrile; 2-(4-(2,3-dihydro-1H-inden-2-ylamino)4a,5,6,7,8,8a-hexahydroquinazolin-2ylthio)ethanol; or combinations thereof.

In some embodiments, where a Group I mGluR antagonist (e.g., an mGluR5 antagonist) is administered in combination with a PAK inhibitor, the dose of the Group I mGluR antagonist ranges from about 0.001 mg/kg/day to about 30.0 mg/kg/day, e.g., about 0.005 mg/kg/day, 0.009 mg/kg/day, 0.010 mg/kg/day, 0.050 mg/kg/day, 0.20 mg/kg/day, 0.50 mg/kg/day, 0.75 mg/kg/day, 1.0 mg/kg/day, 2.0 mg/kg/day, 3.5 mg/kg/day, 4.5 mg/kg/day, 5.0 mg/kg/day, 6.2 mg/kg/day, 6.8 mg/kg/day, 7.0 mg/kg/day, 10.0 mg/kg/day, 15 mg/kg/day, 20 mg/kg/day, 25 mg/kg/day, or any other dose from about 0.001 mg/kg/day to about 10.0 mg/kg/day, from about 0.001 mg/kg/day to about 20.0 mg/kg/day, or from about 0.01 mg/kg/day to about 20.0 mg/kg/day.

In some embodiments, the combination treatment comprises administering a combined dosage form that is a pharmacological composition comprising a therapeutically effective amount of a PAK inhibitor and a Group I mGluR antagonist (e.g., an mGluR5-selective antagonist) as described herein. In some embodiments, the pharmacological composition comprises a PAK inhibitor compound and an mGluR5-selective antagonist selected from U.S. Pat. No. 7,205,411.

mGluR Agonists

In some embodiments, a second therapeutic agent used in combination with a PAK inhibitor is a Group I mGluR1 agonist. Examples of mGluR1 agonists and/or mGluR1 potentiators include and are not limited to ACPT-I ((1S,3R,4S)-1-aminocyclopentane-1,3,4-tricarboxylic acid); L-AP4 (L-(+)-2-Amino-4-phosphonobutyric acid); (S)-3,4-DCPG ((S)-3,4-dicarboxyphenylglycine); (RS)-3,4-DCPG ((RS)-3,4-dicarboxyphenylglycine); (RS)-4-phosphonophenylglycine ((RS)PPG); AMN082 (N'-bis(diphenylmethyl)-1,2-ethanediamine dihydrochloride); DCG-IV ((2S,2'R,3'R)-2-(2',3'-dicarboxycyclopropyl)glycine) or the like. In some embodiments, an mGluR1 agonist is AMN082. In some embodiments, a second therapeutic agent is a mGluR2/3 agonist or mGluR2/3 potentiator. Examples of mGluR2/3 agonists include and are not limited to LY389795 ((−)-2-thia-4-aminobicyclo-hexane-4,6-dicarboxylate); LY379268 ((−)-2-oxa-4-aminobicyclo-hexane-4,6-dicarboxylate); LY354740 ((+)-2-aminobicyclo-hexane-2,6dicarboxylate); DCG-IV ((2S,2'R,3'R)-2-(2',3'-dicarboxycyclopropyl)glycine); 2R,4R-APDC (2R,4R-4-aminopyrrolidine-2,4-dicarboxylate), (S)-3C4HPG ((S)-3-carboxy-4-hydroxyphenylglycine); (S)-4C3HPG ((S)-4-carboxy-3-hydroxyphenylglycine); L-CCG-I ((2S,1'S,2'S)-2-(carboxycyclopropyl)glycine); and/or combinations thereof. Examples of mGluR2 agonists or mGluR2 potentiators include and are not limited to positive allosteric modulators of mGluR2, including ADX71149 (Addex Partner). Examples of mGluR5 agonists or mGluR5 potentiators include and are not limited to MPEP, (RS)-2-chloro-5-hydroxyphenylglycine (CHPG), 1S,3R-1-amino-1,3-cyclopentanedicarboxylate (ACPD) or the like.

Apha7 Nicotinic Receptor Modulators

In some embodiments, one or more PAK inhibitors are used in combination with one or more alpha7 nicotinic receptor modulators to treat an individual suffering from a neuropsychiatric condition. Alpha7 nicotinic receptor modulators include alpha7 nicotinic receptor agonists, alpha7 nicotinic receptor antagonists, and/or alpha7 nicotinic receptor modulators positive allosteric potentiators. The combination of PAK inhibitors with alpha7 nicotinic receptor modulators allows a reduced dose of both agents to be used thereby reducing the likelihood of side effects associated with higher dose monotherapies.

Examples of alpha7 nicotinic receptor agonists include and are not limited to (+)—N-(1-azabicyclo[2.2.2]oct-3-yl)benzo[b]furan-2-carboxamide, PHA-709829, PNU-282,987, A-582941, TC-1698, TC-5619, GTS-21, SSR180711, tropisetron or the like. Examples of alpha7 nicotinic receptor antagonists include α-conotoxin, quinolizidine or the like. Alpha7 nicotinic receptor allosteric potentiators include PNU-120596, NS-1738, XY4083, A-867744, EVP-6124 (Envivo), or the like.

Anticholinergic Agents

Where a subject is suffering from or at risk of suffering from Alzheimer's disease, a PAK inhibitor composition described herein is optionally used together with one or more agents or methods for treating Alzheimer's disease in any combination. In some embodiments, a PAK inhibitor composition described herein is administered to a patient who has been prescribed an anticholinergic agent. In some embodiments, administration of a PAK inhibitor in combination with an anticholinergic agent has a synergistic effect and provides an improved therapeutic outcome compared to monotherapy with anticholinergic agent or monotherapy with PAK inhibitor. Alternatively, a PAK inhibitor composition described herein is administered to an individual who is non-responsive to, or being unsatisfactorily treated with an anticholinergic agent. Example of anticholinergic drugs include ipratropium bromide (Atrovent), oxitropium bromide (Oxivent), tiotropium (Spiriva), are donepezil (Aricept), galantamine (Razadyne), rivastigmine (Exelon and Exelon Patch), physostigimine, scopolamine, orphenadrine, dicycloverine/dicyclomine or the like.

NMDA Receptor Antagonists

Where a subject is suffering from or at risk of suffering from Alzheimer's disease, a PAK inhibitor composition described herein is optionally used together with one or more agents or methods for treating Alzheimer's disease in any combination. In some embodiments, a PAK inhibitor composition described herein is administered to a patient who has been prescribed an NMDA receptor antagonist. Examples of NMDA receptor antagonists useful in the methods and compositions described herein include and are not limited to memantine.

Neuroprotectants

In some embodiments, a PAK inhibitor or a composition thereof described herein is administered in combination with a neuroprotectant such as, for example, minocycline, resveratrol or the like.

Trophic Factors

In some embodiments, a PAK inhibitor or a composition thereof described herein is administered in combination with a trophic agent including, by way of example, glial derived nerve factor (GDNF), brain derived nerve factor (BDNF) or the like.

Antioxidants

Where a subject is suffering from or at risk of suffering from a neuropsychiatric condition (e.g., Alzheimer's disease, Mild Cognitive Impairment), a PAK inhibitor composition described herein is optionally used together with one or more agents or methods for treating the neuropsychiatric condition in any combination. In some embodiments, a PAK inhibitor composition described herein is administered to a patient who is taking or has been prescribed an antioxidant. Examples of antioxidants useful in the methods and compositions described herein include and are not limited to ubiquinone, aged garlic extract, curcumin, lipoic acid, beta-carotene, melatonin, resveratrol, *Ginkgo biloba* extract, vitamin C, viatmin E or the like.

Metal Protein Attenuating Compounds

Where a subject is suffering from or at risk of suffering from a neuropsychiatric condition (e.g., Alzheimer's disease, Parkinson's disease), a PAK inhibitor composition described herein is optionally used together with one or more agents or methods for treating the neuropsychiatric condition in any combination. In some embodiments, a PAK inhibitor composition described herein is administered to a patient who has been prescribed a Metal Protein Attenuating agent. Examples of Metal Protein Attenuating agents useful in the methods and compositions described herein include and are not limited to 8-Hydroxyquinoline, iodochlorhydroxyquin or the like and derivatives thereof.

Beta-Secretase Inhibitors

Where a subject is suffering from or at risk of suffering from a neuropsychiatric condition (e.g., Alzheimer's disease), a PAK inhibitor composition described herein is optionally used together with one or more agents or methods for treating the neuropsychiatric condition in any combination. In some embodiments, a PAK inhibitor composition described herein is administered to a patient who has been prescribed a beta secretase inhibitor. Examples of beta secretase inhibitors useful in the methods and compositions described herein include and are not limited to LY450139, 2-Aminoquinazolines compounds described in J. Med. Chem. 50 (18): 4261-4264, beta secretase inhibitors described therein are incorporated herein by reference, or the like.

Gamma Secretase Inhibitors

Where a subject is suffering from or at risk of suffering from a neuropsychiatric condition (e.g., Alzheimer's disease), a PAK inhibitor composition described herein is optionally used together with one or more agents or methods for treating the neuropsychiatric condition in any combination. In some embodiments, a PAK inhibitor composition described herein is administered to a patient who has been prescribed a beta secretase inhibitor. Examples of beta secretase inhibitors useful in the methods and compositions described herein include and are not limited to LY-411575, (2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide (semagacestat), (R)-2-(3-Fluoro-4-phenylphenyl)propanoic acid (Tarenflurbil), or the like.

Antibodies

Where a subject is suffering from or at risk of suffering from a neuropsychiatric condition (e.g., Alzheimer's disease), a PAK inhibitor composition described herein is optionally used together with one or more agents or methods for treating the neuropsychiatric condition in any combination. In some embodiments, a PAK inhibitor composition described herein is administered to a patient who has been prescribed an Abeta antibody. Examples of antibodies useful in the methods and compositions described herein include and are not limited an Abeta antibody (e.g., bapineuzumab), PAK antibodies (e.g., ABIN237914) or the like.

Other Agents

In some embodiments, one or more PAK inhibitors are used in combination with one or more agents that modulate dendritic spine morphology or synaptic function. Examples of agents that modulate dendritic spine morphology include minocycline, trophic factors (e.g., brain derived neutrophic factor, glial cell-derived neurtrophic factor), or anesthetics that modulate spine motility, or the like. In some embodiments, one or more PAK inhibitors are used in combination with one or more agents that modulate cognition. In some embodiments, a second therapeutic agent is a nootropic agent that enhances cognition. Examples of nootropic agents include and are not limited to piracetam, pramiracetam, oxiracetam, and aniracetam.

Blood Brain Barrier Facilitators

In some instances, a PAK inhibitor is optionally administered in combination with a blood brain barrier facilitator. In certain embodiments, an agent that facilitates the transport of a PAK inhibitor is covalently attached to the PAK inhibitor. In some instances, PAK inhibitors described herein are modified by covalent attachment to a lipophilic carrier or co-formulation with a lipophilic carrier. In some embodiments, a PAK inhibitor is covalently attached to a lipophilic carrier, such as e.g., DHA, or a fatty acid. In some embodiments, a PAK inhibitor is covalently attached to artificial low density lipoprotein particles. In some instances, carrier systems facilitate the passage of PAK inhibitors described herein across the blood-brain barrier and include but are not limited to, the use of a dihydropyridine pyridinium salt carrier redox system for delivery of drug species across the blood brain barrier. In some instances a PAK inhibitor described herein is coupled to a lipophilic phosphonate derivative. In certain instances, PAK inhibitors described herein are conjugated to PEG-oligomers/polymers or aprotinin derivatives and analogs. In some instances, an increase in influx of a PAK inhibitor described herein across the blood brain barrier is achieved by modifying A PAK inhibitor described herein (e.g., by reducing or increasing the number of charged groups on the compound) and enhancing affinity for a blood brain barrier transporter. In certain instances, a PAK inhibitor is co-administered with an an agent that reduces or inhibits efflux across the blood brain barrier, e.g. an inhibitor of P-glycoprotein pump (PGP) mediated efflux (e.g., cyclosporin, SCH66336 (lonafarnib, Schering)).

In some embodiments, compounds of Formulae (I-X) are optionally administered in combination with, e.g., compounds described in U.S. Pat. Nos. 5,863,532, 6,191,169, 6,248,549, and 6,498,163; U.S. Patent Applications 200200045564, 20020086390, 20020106690, 20020142325, 20030124107, 20030166623, 20040091992, 20040102623, 20040208880, 200500203114, 20050037965, 20050080002, and 20050233965, 200.60088897; EP Patent Publication 1492871; PCT patent publication WO 9902701; PCT patent publication WO 2008/047307; Kumar et al., (2006), *Nat. Rev. Cancer*, 6:459; and Eswaran et al., (2007), Structure, 15:201-213, all of which are incorporated herein by reference for disclosure of kinase inhibitors and/or PAK inhibitors described therein.

In some embodiments, compounds of Formulae (I-X) are optionally administered in combination with compounds including and not limited to BMS-387032; SNS-032; CHI4-258; TKI-258; EKB-569; JNJ-7706621; PKC-412; staurosporine; SU-14813; sunitinib; N-(3-chloro-4-fluoro-phenyl)-7-methoxy-6-(3-morpholin-4-ylpropoxy)quinazolin-4-amine (gefitinib), VX-680; MK-0457; combinations thereof; or salts, prodrugs thereof.

In some embodiments, compounds of Formulae (I-X) are optionally administered in combination with a polypeptide comprising an amino acid sequence about 80% to about 100% identical, e.g., 85%, 90%, 92%, 93%, 95%, 96%, 97%, 98%, 99%, or any other percent from about 80% to about 100% identical the following amino acid sequence:

HTIHVGFDAVTGEFTGMPEQWARLLQTSNITKSEQKKNPQAVLDVLE

FYNSKKTSNSQ KYMSFTDKS

The above sequence corresponds to the PAK autoinhibitory domain (PAD) polypeptide amino acids 83-149 of PAK1 polypeptide as described in, e.g., Zhao et al (1998). In some embodiments, the PAK inhibitor is a fusion protein comprising the above-described PAD amino acid sequence. In some embodiments, in order to facilitate cell penetration the fusion polypeptide (e.g., N-terminal or C-terminal) further comprises a polybasic protein transduction domain (PTD) amino acid sequence, e.g.: RKKRRQRR; YARAAARQARA; THRLPRRRRRR; or GGRRARRRRRR.

In some embodiments, in order to enhance uptake into the brain, the fusion polypeptide further comprises a human insulin receptor antibody as described in U.S. patent application Ser. No. 11/245,546.

In some embodiments, compounds of Formulae (I-X) are optionally administered in combination with a peptide inhibitor comprising a sequence at least 60% to 100%, e.g., 65%, 70%, 75%, 80%, 85%, 90%, 92%, 93%, 95%, 96%, 97%, 98%, 99%, or any other percent from about 60% to about 100% identical the following amino acid sequence: PPVIAPREHTKSVYTRS as described in, e.g., Zhao et al (2006), *Nat Neurosci*, 9(2):234-242. In some embodiments, the peptide sequence further comprises a PTD amino acid sequence as described above.

In some embodiments, compounds of Formulae (I-X) are optionally administered in combination with a polypeptide comprising an amino acid sequence at least 80% to 100%, e.g., 85%, 90%, 92%, 93%, 95%, 96%, 97%, 98%, 99%, or any other percent from about 80% to about 100% identical to the FMRP1 protein (GenBank Accession No. Q06787), where the polypeptide is able to bind with a PAK (for example, PAK1, PAK2, PAK3, PAK4, PAK5 and/or PAK6). In some embodiments compounds of Formulae (I-X) are optionally administered in combination with a polypeptide comprising an amino acid sequence at least 80% to 100%, e.g., 85%, 90%, 92%, 93%, 95%, 96%, 97%, 98%, 99%, or any other percent from about 80% to about 100% identical to the FMRPI protein (GenBank Accession No. Q06787), where the polypeptide is able to bind with a Group I PAK, such as, for example PAK I (see, e.g., Hayashi et al (2007), *Proc Natl Acad Sci USA*, 104(27):11489-11494. In some embodiments, compounds of Formulae (I-X) are optionally administered in combination with a polypeptide comprising a fragment of human FMRP1 protein with an amino acid sequence at least 80% to 100%, e.g., 85%, 90%, 92%, 93%, 95%, 96%, 97%, 98%, 99%, or any other percent from about 80% to about 100% identical to the sequence of amino acids 207-425 of the human FMRPI protein (i.e., comprising the KH1 and KH2 domains), where the polypeptide is able to bind to PAK1.

In some embodiments, compounds of Formulae (I-X) are optionally administered in combination with a polypeptide comprising an amino acid sequence at least 80% to 100%, e.g., 85%, 90%, 92%, 93%, 95%, 96%, 97%, 98%, 99%, or any other percent from about 80% to about 100% identical to at least five, at least ten at least twenty, at least thirty, at least forty, at least fifty, at least sixty, at least seventy, at least eighty, at least ninety contiguous amino acids of the huntingtin (htt) protein (GenBank Accession No. NP 002102, gi 90903231), where the polypeptide is able to bind to a Group I PAK (for example, PAK1, PAK2, and/or PAK3). In some embodiments, compounds of Formulae (I-X) are optionally administered in combination with a polypeptide comprising an amino acid sequence at least 80% to 100%, e.g., 85%, 90%, 92%, 93%, 95%, 96%, 97%, 98%, 99%, or any other percent from about 80% to about 100% identical to at least a portion of the huntingtin (htt) protein (GenBank Accession No. NP 002102, gi 90903231), where the polypeptide is able to bind to PAK1. In some embodiments, compounds of Formulae (I-X) are optionally administered in combination with a polypeptide comprising a fragment of human huntingtin protein with an amino acid sequence at least 80% to 100%, e.g., 85%, 90%, 92%, 93%, 95%, 96%, 97%, 98%, 99%, or any other percent from about 80% to about 100% identical to a sequence of at least five, at least ten, at least twenty, at least thirty, at least forty, at least fifty, at least sixty, at least seventy, at least eighty, at least ninety, or at least 100 contiguous amino acids of the human huntingtin protein that is outside of the sequence encoded by exon 1 of the htt gene (i.e., a fragment that does not contain poly glutamate domains), where the polypeptide binds a PAK. In some embodiments, compounds of Formulae (I-X) are optionally administered in combination with a polypeptide comprising a fragment of human huntingtin protein with an amino acid sequence at least 80% identical to a sequence of the human huntingtin protein that is outside of the sequence encoded by exon 1 of the htt gene (i.e., a fragment that does not contain poly glutamate domains), where the polypeptide binds PAKI.

Upstream Regulators of p21 Activated Kinases

In certain embodiments, compounds of Formulae (I-X) are optionally administered in combination with an indirect PAK modulator (e.g., an indirect PAK inhibitor) that affects the activity of a molecule that acts in a signaling pathway upstream of PAK (upstream regulators of PAK). Upstream effectors of PAK include, but are not limited to: TrkB receptors; NMDA receptors; EphB receptors; adenosine receptors; estrogen receptors; integrins; FMRP; Rho-family GTPases, including Cdc42, Rac (including but not limited to Rac1 and Rac2), CDK5, PI3 kinases, NCK, PDK1, EKT, GRB2, Chp, TC10, Tcl, and Wrch-1; guanine nucleotide exchange factors ("GEFs"), such as but not limited to GEFT, members of the Dbl family of GEFs, p21-activated kinase interacting exchange factor (PIX), DEF6, Zizimin 1, Vav1, Vav2, Dbs, members of the DOCK180 family, Kalirin-7, and Tiaml; G protein-coupled receptor kinase-interacting protein 1 (GIT1), CIB1, filamin A, Etk/Bmx, and sphingosine.

Modulators of NMDA receptor include, but are not limited to, 1-aminoadamantane, dextromethorphan, dextrorphan, ibogaine, ketamine, nitrous oxide, phencyclidine, riluzole, tiletamine, memantine, neramexane, dizocilpine, aptiganel, remacimide, 7-chlorokynurenate, DCKA (5,7-dichlorokynurenic acid), kynurenic acid, 1-aminocyclopropanecarboxylic acid (ACPC), AP7 (2-amino-7-phosphonoheptanoic acid), APV (R-2-amino-5-phosphonopentanoate), CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4,7-diol; (1R*,2R*)-1-(4-hydroxy-3-methylphenyl)-2-(4-(4-fluoro-phenyl)-4-hydroxypiperidin-1-yl)-propan-1-ol-mesylate; and/or combinations thereof.

Modulators of estrogen receptors include, and are not limited to, PPT (4,4',4"-(4-Propyl-[1H]-pyrazole-1,3,5-triyl) trisphenol); SKF-82958 (6-chloro-7,8-dihydroxy-3-allyl-1-phenyl-2,3,4,5-tetrahydro-1H-3-benzazepine); estrogen; estradiol; estradiol derivatives, including but not limited to 17-☐ estradiol, estrone, estriol, ERβ-131, phytoestrogen, MK 101 (bioNovo); VG-1010 (bioNovo); DPN (diarylpropiolitrile); ERB-041; WAY-202196; WAY-214156; genistein; estrogen; estradiol; estradiol derivatives, including but not limited to 17-β estradiol, estrone, estriol, benzopyrans and triazolo-tetrahydrofluorenones, disclosed in U.S. Pat. No. 7,279,499, and Parker et al., Bioorg. & Med. Chem. Ltrs. 16: 4652-4656 (2006), each of which is incorporated herein by reference for such disclosure.

Modulators of TrkB include by way of example, neutorophic factors including BDNF and GDNF. Modulators of EphB include XL647 (Exelixis), EphB modulator compounds described in WO/2006081418 and US Appl. Pub. No. 20080300245, incorporated herein by reference for such disclosure, or the like.

Modulators of integrins include by way of example, ATN-161, PF-04605412, MEDI-522, Volociximab, natalizumab, Volociximab, Ro 27-2771, Ro 27-2441, etaracizumab, CNTO-95, JSM6427, cilengitide, R411 (Roche), EMD 121974, integrin antagonist compounds described in *J. Med. Chem.*, 2002, 45 (16), pp 3451-3457, incorporated herein by reference for such disclosure, or the like.

Adenosine receptor modulators include, by way of example, theophylline, 8-Cyclopentyl-1,3-dimethylxanthine (CPX), 8-Cyclopentyl-1,3-dipropylxanthine (DPCPX), 8-Phenyl-1,3-dipropylxanthine, PSB 36, istradefylline, SCH-58261, SCH-442,416, ZM-241,385, CVT-6883, MRS-1706, MRS-1754, PSB-603, PSB-0788, PSB-1115, MRS-1191, MRS-1220, MRS-1334, MRS-1523, MRS-3777, MRE3008F20, PSB-10, PSB-11, VUF-5574, N6-Cyclopentyladenosine, CCPA, 2'-MeCCPA, GR 79236, SDZ WAG 99, ATL-146e, CGS-21680, Regadenoson, 5'-N-ethylcarboxamidoadenosine, BAY 60-6583, LUF-5835, LUF-5845, 2-(1-Hexynyl)-N-methyladenosine, CF-101 (IB-MECA), 2-Cl-IB-MECA, CP-532,903, MRS-3558, Rosuvastatin, KW-3902, SLV320, mefloquine, regadenoson, or the like.

In some embodiments, compounds reducing PAK levels decrease PAK transcription or translation or reduce RNA or protein levels. In some embodiments, a compound that decreases PAK levels is an upstream effector of PAK. In some embodiments, a compound that decreases PAK levels is an upstream effector of PAK. In some embodiments, exogenous expression of the activated forms of the Rho family GTPases Chp and cdc42 in cells leads to increased activation of PAK while at the same time increasing turnover of the PAK protein, significantly lowering its level in the cell (Hubsman et al. (2007) *Biochem. J.* 404: 487-497). PAK clearance agents include agents that increase expression of one or more Rho family GTPases and/or one or more guanine nucleotide exchange factors (GEFs) that regulate the activity of Rho family GTPases, in which overexpression of a Rho family GTPase and/or a GEF results in lower levels of PAK protein in cells. PAK clearance agents also include agonists of Rho family GTPases, as well as agonists of GTP exchange factors that activate Rho family GTPases, such as but not limited to agonists of GEFs of the Dbl family that activate Rho family GTPases.

Overexpression of a Rho family GTPase is optionally by means of introducing a nucleic acid expression construct into the cells or by administering a compound that induces transcription of the endogenous gene encoding the GTPase. In some embodiments, the Rho family GTPase is Rac (e.g., Rac1, Rac2, or Rac3), cdc42, Chp, TC10, Tcl, or Wrnch-1. For example, a Rho family GTPase includes Rac1, Rac2, Rac3, or cdc42. A gene introduced into cells that encodes a Rho family GTPase optionally encodes a mutant form of the gene, for example, a more active form (for example, a constitutively active form, Hubsman et al. (2007) *Biochem. J.* 404: 487-497). In some embodiments, a PAK clearance agent is, for example, a nucleic acid encoding a Rho family GTPase, in which the Rho family GTPase is expressed from a constitutive or inducible promoter. PAK levels in some embodiments are reduced by a compound that directly or indirectly enhances expression of an endogenous gene encoding a Rho family GTPase.

In some embodiments, compounds of Formulae (I-X) are optionally administered in combination with a PAK clearance agent. A PAK clearance agent in some embodiments is a Rho family GTPase agonist, or is a compound that directly or indirectly increases the activation level of one or more Rho family GTPases. In some embodiments a PAK clearance agent is a compound that increases the level of an activated Rho family GTPase, such as, but not limited to, Rac or cdc42. The compound is, as nonlimiting examples, a compound that modifies a Rho family GTPase such that it is constitutively activated, or a compound that binds or modifies a Rho family GTPase to increase the longevity or stability of its activated (GTP bound) state. Activating mutations of Rho family GTPases are known (Hubsman et al. (2007) *Biochem. J.* 404: 487-497), as are bacterial toxins such as *E. coli* necrotizing factors 1 and 2 (CNF1 and CNF2) and *Bordetella bronchiseptica* dermonecrotizing toxin (DNT) that modify Rho family GTPases to cause their constitutive activation (Fiorentini et al. (2003) *Cell Death and Differentiation* 10:147-152). Toxins such as CNF1, CNF2, and DNT, fragments thereof that increase the activity of a Rho family GTAPase, or peptides or polypeptides that increase the activity of a Rho family GTAPase having an amino acid sequence at least 80% to 100%, e.g., 85%, 90%, 92%, 93%, 95%, 96%, 97%, 98%, 99%, or any other percent from about 80% to about 100% identical to a sequence of at least ten, at least twenty, at least thirty, at least forty, at least fifty, at least sixty, at least seventy, at least eighty, at least ninety, or at least 100 contiguous amino acids of the toxin are also used as PAK clearance agents. Small molecule inhibitors designed to mimic the effect of activating mutations of GTPases that are upstream regulators of PAK or designed to mimic the effect of bacterial toxins that activate GTPases that bind and activate PAK are also included as compounds that downregulate PAK levels.

In some embodiments, compounds of Formulae (I-X) are optionally administered in combination with a compound that inhibits post-translational modification of a Rho family GTPase. For example, in some embodiments a compound that inhibits prenylation of small Rho-family GTPases such as Rho, Rac, and cdc42 is used to increase GTPase activity and thereby reduce the amount of PAK in the cell. In some embodiments, a compound that decreases PAK levels is a bisphosphonate compound that inhibits prenylation of Rho-family GTPases such as cdc42 and Rac, in which nonprenylated GTPases have higher activity than their prenylated counterparts (Dunford et al. (2006) *J. Bone Miner. Res.* 21: 684-694; Reszka et al. (2004) *Mini Rev. Med. Chem.* 4: 711-719).

In some embodiments, compounds of Formulae (I-X) are optionally administered in combination with a compound that directly or indirectly decreases the activation or activity of the upstream effectors of PAK. For example, in some embodiments a compound that inhibits the GTPase activity of the small Rho-family GTPases such as Rac and cdc42 thereby reduce the activation of PAK kinase. In some embodiments, the compound that decreases PAK activation is by secramine that inhibits cdc42 activation, binding to membranes and GTP in the cell (Pelish et al. (2005) *Nat. Chem. Biol.* 2: 39-46). In some embodiments, PAK activation is decreased by EHT 1864, a small molecule that inhibits Rac1, Rac1b, Rac2 and Rac3 function by preventing binding to guanine nucleotide association and engagement with downstream effectors (Shutes et al. (2007) *J. Biol. Chem.* 49: 35666-35678). In some embodiments, PAK activation is also decreased by the NSC23766 small molecule that binds directly to Rac1 and prevents its activation by Rac-specific RhoGEFs (Gao et al. (2004) *Proc. Natl. Acad. Sci. U.S.A.* 101: 7618-7623). In some embodiments, PAK activation is also decreased by the 16 kDa fragment of prolactin (16 k PRL), generated from the cleavage of the 23 kDa prolactin hormone by matrix metalloproteases and cathepsin D in various tissues and cell types. 16 k PRL down-regulates the Ras-Tiam1-Rac1-Pak1 signaling pathway by reducing Rac1 activation in response to cell stimuli such as wounding (Lee et al. (2007) *Cancer Res* 67:11045-11053). In some embodiments, PAK activation is decreased by inhibition of NMDA and/or AMPA receptors. Examples of modulators of AMPA receptors include and are not limited to ketamine, MK801, CNQX (6-cyano-7-nitroquinoxaline-2,3-dione); NBQX (2,3-dihydroxy-6-nitro-7-sulfamoyl-benzo[f]quinoxaline-2, 3-dione); DNQX (6,7-dinitroquinoxaline-2,3-dione); kynurenic acid; 2,3-dihydroxy-6-nitro-7-sulfamoylbenzo-[f] quinoxaline; PCP or the like. In some embodiments, PAK activation is decreased by inhibition of TrkB activation. In some embodiments, PAK activation is decreased by inhibition of BDNF activation of TrkB. In some embodiments, compounds of Formulae (I-X) are optionally administered in combination with an antibody to BDNF. In some embodiments, PAK activation is decreased by inhibition of TrkB receptors; NMDA receptors; EphB receptors; adenosine receptors; estrogen receptors; integrins; Rho-family GTPases, including Cdc42, Rac (including but not limited to Rac1 and Rac2), CDK5, PI3 kinases, NCK, PDK1, EKT, GRB2, Chp, TC10, Tcl, and Wrch-1; guanine nucleotide exchange factors ("GEFs"), such as but not limited to GEFT, members of the Dbl family of GEFs, p21-activated kinase interacting exchange factor (PIX), DEF6, Zizimin 1, Vav1, Vav2, Dbs, members of the DOCK180 family, Kalirin-7, and Tiam1; G protein-coupled receptor kinase-interacting protein 1 (GIT1), CIB1, filamin A, Etk/Bmx, and/or binding to FMRP and/or sphingosine.

In some embodiments, compounds of Formulae (I-X) are optionally administered in combination with a compound that decreases PAK levels in the cell, e.g., a compound that directly or indirectly increases the activity of a guanine exchange factor (GEF) that promotes the active state of a Rho family GTPase, such as an agonist of a GEF that activates a Rho family GTPase, such as but not limited to, Rac or cdc42. Activation of GEFs is also effected by compounds that activate TrkB, NMDA, or EphB receptors.

In some embodiments, a PAK clearance agent is a nucleic acid encoding a GEF that activates a Rho family GTPase, in which the GEF is expressed from a constitutive or inducible promoter. In some embodiments, a guanine nucleotide exchange factor (GEF), such as but not limited to a GEF that activates a Rho family GTPase is overexpressed in cells to increase the activation level of one or more Rho family GTPases and thereby lower the level of PAK in cells. GEFs include, for example, members of the Dbl family of GTPases, such as but not limited to, GEFT, PIX (e.g., alphaPIX, betaPIX), DEF6, Zizimin 1, Vav1, Vav2, Dbs, members of the DOCK180 family, hPEM-2, FLJ00018, kalirin, Tiam1, STEF, DOCK2, DOCK6, DOCK7, DOCK9, Asf, EhGEF3, or GEF-1. In some embodiments, PAK levels are also reduced by a compound that directly or indirectly enhances expression of an endogenous gene encoding a GEF. A GEF expressed from a nucleic acid construct introduced into cells is in some embodiments a mutant GEF, for example a mutant having enhanced activity with respect to wild type.

The clearance agent is optionally a bacterial toxin such as *Salmonella typhinmurium* toxin SpoE that acts as a GEF to promote Cdc42 nucleotide exchange (Buchwald et al. (2002) *EMBO J.* 21: 3286-3295; Schlumberger et al. (2003) *J. Biological Chem.* 278: 27149-27159). Toxins such as SopE, fragments thereof, or peptides or polypeptides having an amino acid sequence at least 80% to 100%, e.g., 85%, 90%, 92%, 93%, 95%, 96%, 97%, 98%, 99%, or any other percent from about 80% to about 100% identical to a sequence of at least five, at least ten, at least twenty, at least thirty, at least forty, at least fifty, at least sixty, at least seventy, at least eighty, at least ninety, or at least 100 contiguous amino acids of the toxin are also optionally used as downregulators of PAK activity. The toxin is optionally produced in cells from nucleic acid constructs introduced into cells.

Modulators of Upstream Regulators of PAKs

In some embodiments, compounds of Formulae (I-X) are optionally administered in combination with a modulator of an upstream regulator of PAKs. In some embodiments, a modulator of an upstream regulator of PAKs is an indirect inhibitor of PAK. In certain instances, a modulator of an upstream regulator of PAKs is a modulator of PDK1. In some instances, a modulator of PDK1 reduces of inhibits the activity of PDK1. In some instances a PDK1 inhibitor is an antisense compound (e.g., any PDK1 inhibitor described in U.S. Pat. No. 6,124,272, which PDK1 inhibitor is incorporated herein by reference). In some instances, a PDK1 inhibitor is a compound described in e.g., U.S. Pat. Nos. 7,344,870, and 7,041,687, which PDK1 inhibitors are incorporated herein by reference. In some embodiments, an indirect inhibitor of PAK is a modulator of a PI3 kinase. In some instances a modulator of a PI3 kinase is a PI3 kinase inhibitor. In some instances, a PI3 kinase inhibitor is an antisense compound (e.g., any PI3 kinase inhibitor described in WO 2001/018023, which PI3 kinase inhibitors are incorporated herein by reference). In some instances, an inhibitor of a PI3 kinase is 3-morpholino-5-phenylnaphthalen-1(4H)-one (LY294002), or a peptide based covalent conjugate of LY294002, (e.g., SF1126, Semaphore pharmaceuticals). In certain embodiments, an indirect inhibitor of PAK is a modulator of Cdc42. In certain embodiments, a modulator of Cdc42 is an inhibitor of Cdc42. In certain embodiments, a Cdc42 inhibitor is an antisense compound (e.g., any Cdc42 inhibitor described in U.S. Pat. No. 6,410,323, which Cdc42 inhibitors are incorporated herein by reference). In some instances, an indirect inhibitor of PAK is a modulator of GRB2. In some instances, a modulator of GRB2 is an inhibitor of GRB2. In some instances a GRB2 inhibitor is a GRb2 inhibitor described in e.g., U.S. Pat. No. 7,229,960, which GRB2 inhibitor is incorporated by reference herein. In certain embodiments, an indirect inhibitor of PAK is a modulator of NCK. In certain embodiments, an indirect inhibitor of PAK is a modulator of ETK. In some instances, a modulator of ETK is an inhibitor of ETK. In some instances an ETK inhibitor is a compound e.g., α-Cyano-(3, 5-di-t-butyl-4-hydroxy)thiocinnamide (AG 879).

In some embodiments, indirect PAK inhibitors act by decreasing transcription and/or translation of PAK. An indirect PAK inhibitor in some embodiments decreases transcription and/or translation of a PAK. For example, in some embodiments, modulation of PAK transcription or translation occurs through the administration of specific or non-specific inhibitors of PAK transcription or translation. In some embodiments, proteins or non-protein factors that bind the upstream region of the PAK gene or the 5' UTR of a PAK mRNA are assayed for their affect on transcription or translation using transcription and translation assays (see, for example, Baker, et al. (2003) *J. Biol. Chem.* 278: 17876-17884; Jiang et al. (2006) *J. Chromatography A* 1133: 83-94; Novoa et al. (1997) *Biochemistry* 36: 7802-7809; Brandi et al. (2007) *Methods Enzymol.* 431: 229-267). PAK inhibitors include DNA or RNA binding proteins or factors that reduce the level of transcription or translation or modified versions thereof. In other embodiments, compounds of Formulae (I-X) are optionally administered in combination with an agent that is a modified form (e.g., mutant form or chemically modified form) of a protein or other compound that positively regulates transcription or translation of PAK, in which the modified form reduces transcription or translation of PAK. In yet other embodiments, a transcription or translation inhibitor is an antagonist of a protein or compound that positively regulates transcription or translation of PAK, or is an agonist of a protein that represses transcription or translation.

Regions of a gene other than those upstream of the transcriptional start site and regions of an mRNA other than the 5' UTR (such as but not limited to regions 3' of the gene or in the 3' UTR of an mRNA, or regions within intron sequences of either a gene or mRNA) also include sequences to which effectors of transcription, translation, mRNA processing, mRNA transport, and mRNA stability bind. In some embodiments, compounds of Formulae (I-X) are optionally administered in combination with a clearance agent comprising a polypeptide having homology to an endogenous protein that affects mRNA processing, transport, or stability, or is an antagonist or agonist of one or more proteins that affect mRNA processing, transport, or turnover, such that the inhibitor reduces the expression of PAK protein by interfering with PAK mRNA transport or processing, or by reducing the half-life of PAK mRNA. A PAK clearance agents in some embodiments interferes with transport or processing of a PAK mRNA, or by reducing the half-life of a PAK mRNA.

For example, PAK clearance agents decrease RNA and/or protein half-life of a PAK isoform, for example, by directly affecting mRNA and/or protein stability. In certain embodiments, PAK clearance agents cause PAK mRNA and/or protein to be more accessible and/or susceptible to nucleases, proteases, and/or the proteasome. In some embodiments, compounds of Formulae (I-X) are optionally administered in combination with agents that decrease the processing of PAK mRNA thereby reducing PAK activity. For example, PAK clearance agents function at the level of pre-mRNA splicing, 5' end formation (e.g. capping), 3' end processing (e.g. cleavage and/or polyadenylation), nuclear export, and/or association with the translational machinery and/or ribosomes in the cytoplasm. In some embodiments, PAK clearance agents cause a decrease in the level of PAK mRNA and/or protein, the half-life of PAK mRNA and/or protein by at least about 5%, at least about 10%, at least about 20%, at least about 30%, at least about 40%, at least about 50%, at least about 60%, at least about 80%, at least about 90%, at least about 95%, or substantially 100%.

In some embodiments, the clearance agent comprises one or more RNAi or antisense oligonucleotides directed against one or more PAK isoform RNAs. In some embodiments, compounds of Formulae (I-X) are optionally administered in combination with agent that comprise one or more ribozymes directed against one or more PAK isoform RNAs. The design, synthesis, and use of RNAi constructs, antisense oligonucleotides, and ribozymes are found, for example, in Dykxhoorn et al. (2003) *Nat. Rev. Mol. Cell. Biol.* 4: 457-467; Hannon et al. (2004) *Nature* 431: 371-378; Sarver et al. (1990) *Science* 247:1222-1225; Been et al. (1986) Cell 47:207-216). In some embodiments, nucleic acid constructs that induce triple helical structures are also introduced into cells to inhibit transcription of the PAK gene (Helene (1991) *Anticancer Drug Des.* 6:569-584).

For example, a clearance agent is in some embodiments an RNAi molecule or a nucleic acid construct that produces an RNAi molecule. An RNAi molecule comprises a double-stranded RNA of at least about seventeen bases having a 2-3 nucleotide single-stranded overhangs on each end of the double-stranded structure, in which one strand of the double-stranded RNA is substantially complementary to the target PAK RNA molecule whose downregulation is desired. "Substantially complementary" means that one or more nucleotides within the double-stranded region are not complementary to the opposite strand nucleotide(s). Tolerance of mismatches is optionally assessed for individual RNAi structures based on their ability to downregulate the target RNA or protein. In some embodiments, RNAi is introduced into the cells as one or more short hairpin RNAs ("shRNAs") or as one or more DNA constructs that are transcribed to produce one or more shRNAs, in which the shRNAs are processed within the cell to produce one or more RNAi molecules.

Nucleic acid constructs for the expression of siRNA, shRNA, antisense RNA, ribozymes, or nucleic acids for generating triple helical structures are optionally introduced as RNA molecules or as recombinant DNA constructs. DNA constructs for reducing gene expression are optionally designed so that the desired RNA molecules are expressed in the cell from a promoter that is transcriptionally active in mammalian cells, such as, for example, the SV40 promoter, the human cytomegalovirus immediate-early promoter (CMV promoter), or the pol III and/or pol II promoter using known methods. For some purposes, it is desirable to use viral or plasmid-based nucleic acid constructs. Viral constructs include but are not limited to retroviral constructs, lentiviral constructs, or based on a pox virus, a herpes simplex virus, an adenovirus, or an adeno-associated virus (AAV).

In other embodiments, compounds of Formulae (I-X) are optionally administered in combination with a polypeptide that decreases the activity of PAK. Protein and peptide inhibitors of PAK are optionally based on natural substrates of PAK, e.g., Myosin light chain kinase (MLCK), regulatory Myosin light chain (R-MLC), Myosins I heavy chain, myosin II heavy chain, Myosin VI, Caldesmon, Desmin, Op18/stathmin, Merlin, Filamin A, LIM kinase (LIMK), cortactin, cofilin, Ras, Raf, Mek, p47(phox), BAD, caspase 3, estrogen and/or progesterone receptors, NET1, Gaz, phosphoglycerate mutase-B, RhoGDI, prolactin, p41Arc, cortactin and/or Aurora-A. In some embodiments, compounds of Formulae (I-X) are optionally administered in combination with an agent that is based on a sequence of PAK itself, for example, the autoinhibitory domain in the N-terminal portion of the PAK protein that binds the catalytic domain of a partner PAK molecule when the PAK molecule is in its homodimeric state (Zhao et al. (1998) *Mol. Cell. Biol.* 18:2153-2163; Knaus et al. (1998) *J. Biol. Chem.* 273: 21512-21518; Hofman et al. (2004) *J. Cell Sci.* 117: 4343-4354). In some embodiments, polypeptide inhibitors of PAK comprise peptide mimetics, in which the peptide has binding characteristics similar to a natural binding partner or substrate of PAK.

In some embodiments, provided herein are compounds that downregulate PAK protein level. In some embodiments, the compounds described herein activate or increase the activity of an upstream regulator or downstream target of PAK. In some embodiments, compounds described herein downregulate protein level of a PAK. In some instances compounds described herein reduce at least one of the symptoms related a neuropsychiatric condition by reducing the amount of PAK in a cell. In some embodiments a compound that decreases PAK protein levels in cells also decreases the activity of PAK in the cells. In some embodiments a compound that decreases PAK protein levels does not have a substantial impact on PAK activity in cells. In some embodiments a compound that increases PAK activity in cells decreases PAK protein levels in the cells.

In some embodiments, a compound that decreases the amount of PAK protein in cells decreases transcription and/or translation of PAK or increases the turnover rate of PAK mRNA or protein by modulating the activity of an upstream effector or downstream regulator of PAK. In some embodiments, PAK expression or PAK levels are influenced by feedback regulation based on the conformation, chemical modification, binding status, or activity of PAK itself. In some embodiments, PAK expression or PAK levels are influenced by feedback regulation based on the conformation, chemical modification, binding status, or activity of molecules directly or indirectly acted on by PAK signaling pathways. As used herein "binding status" refers to any or a combination of whether PAK, an upstream regulator of PAK, or a downstream effector of PAK is in a monomeric state or in an oligomeric complex with itself, or whether it is bound to other polypeptides or molecules. For example, a downstream target of PAK, when phosphorylated by PAK, in some embodiments directly or indirectly downregulates PAK expression or decrease the half-life of PAK mRNA or protein. Downstream targets of PAK include but are not limited to: Myosin light chain kinase (MLCK), regulatory Myosin light chain (R-MLC), Myosins I heavy chain, myosin II heavy chain, Myosin VI, Caldesmon, Desmin, Op18/stathmin, Merlin, Filamin A, LIM kinase (LIMK), Ras, Raf, Mek, $p47^{phox}$, BAD, caspase 3, estrogen and/or progesterone receptors, NET1, Gaz, phosphoglycerate mutase-B, RhoGDI, prolactin, $p41^{Arc}$, cortactin and/or Aurora-A. Downregulators of PAK levels include downstream targets of PAK or fragments thereof in a phosphorylated state and downstream targets of PAK or fragments thereof in a hyperphosphorylated state.

A fragment of a downstream target of PAK includes any fragment with an amino acid sequence at least 80% to 100%, e.g., 85%, 90%, 92%, 93%, 95%, 96%, 97%, 98%, 99%, or any other percent from about 80% to about 100% identical to a sequence of at least five, at least ten, at least twenty, at least thirty, at least forty, at least fifty, at least sixty, at least seventy, at least eighty, at least ninety, or at least 100 contiguous amino acids of the downstream regulator, in which the fragment of the downstream target of PAK is able to downregulate PAK mRNA or protein expression or increase turnover of PAK mRNA or protein. In some embodiments, the fragment of a downstream regulator of PAK comprises a sequence that includes a phosphorylation site recognized by PAK, in which the site is phosphorylated.

In some embodiments, compounds of Formulae (I-X) are optionally administered in combination with a compound that decreases the level of PAK including a peptide, polypeptide, or small molecule that inhibits dephosphorylation of a downstream target of PAK, such that phosphorylation of the downstream target remains at a level that leads to downregulation of PAK levels.

In some embodiments, PAK activity is reduced or inhibited via activation and/or inhibition of an upstream regulator and/or downstream target of PAK. In some embodiments, the protein expression of a PAK is downregulated. In some embodiments, the amount of PAK in a cell is decreased. In some embodiments a compound that decreases PAK protein levels in cells also decreases the activity of PAK in the cells. In some embodiments a compound that decreases PAK protein levels does not decrease PAK activity in cells. In some embodiments a compound that increases PAK activity in cells decreases PAK protein levels in the cells.

In some instances, compounds of Formulae (I-X) are optionally administered in combination with a polypeptide that is delivered to one or more brain regions of an individual by administration of a viral expression vector, e.g., an AAV vector, a lentiviral vector, an adenoviral vector, or a HSV vector. A number of viral vectors for delivery of therapeutic proteins are described in, e.g., U.S. Pat. Nos., 7,244,423, 6,780,409, 5,661,033. In some embodiments, the PAK inhibitor polypeptide to be expressed is under the control of an inducible promoter (e.g., a promoter containing a tet-operator). Inducible viral expression vectors include, for example, those described in U.S. Pat. No. 6,953,575. Inducible expression of a PAK inhibitor polypeptide allows for tightly controlled and reversible increases of PAK inhibitor polypeptide expression by varying the dose of an inducing agent (e.g., tetracycline) administered to an individual.

Any combination of one or more PAK inhibitors and a second therapeutic agent is compatible with any method described herein. The PAK inhibitor compositions described herein are also optionally used in combination with other therapeutic reagents that are selected for their therapeutic value for the condition to be treated. In general, the compositions described herein and, in embodiments where combinational therapy is employed, other agents do not have to be administered in the same pharmaceutical composition, and, because of different physical and chemical characteristics, are optionally to administered by different routes. The initial administration is generally made according to established protocols, and then, based upon the observed effects, the dosage, modes of administration and times of administration subsequently modified.

In certain instances, it is appropriate to administer at least one PAK inhibitor composition described herein in combination with another therapeutic agent. By way of example only, if one of the side effects experienced by a patient upon receiving one of the PAK inhibitor compositions described herein is nausea, then it is appropriate to administer an anti-nausea agent in combination with the initial therapeutic agent. Or, by way of example only, the therapeutic effectiveness of a PAK inhibitor is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering a PAK inhibitor with another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a synergistic benefit.

Therapeutically-effective dosages vary when the drugs are used in treatment combinations. Suitable methods for experimentally determining therapeutically-effective dosages of drugs and other agents include, e.g., the use of metronomic dosing, i.e., providing more frequent, lower doses in order to minimize toxic side effects. Combination treatment further includes periodic treatments that start and stop at various times to assist with the clinical management of the patient.

In any case, the multiple therapeutic agents (one of which is a PAK inhibitor described herein) is administered in any order, or even simultaneously. If simultaneously, the multiple therapeutic agents are optionally provided in a single, unified form, or in multiple forms (by way of example only, either as a single pill or as two separate pills). In some embodiments, one of the therapeutic agents is given in multiple doses, or both are given as multiple doses. If not simultaneous, the timing between the multiple doses optionally varies from more than zero weeks to less than four weeks. In addition, the combination methods, compositions and formulations are not to be limited to the use of only two agents; the use of multiple therapeutic combinations are also envisioned.

The pharmaceutical agents which make up the combination therapy disclosed herein are optionally a combined dosage form or in separate dosage forms intended for substantially simultaneous administration. The pharmaceutical agents that make up the combination therapy are optionally also be administered sequentially, with either therapeutic compound being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration are optionally used to determine the optimal dose interval.

In addition, a PAK inhibitor is optionally used in combination with procedures that provide additional or synergistic benefit to the patient. By way of example only, patients are expected to find therapeutic and/or prophylactic benefit in the methods described herein, wherein pharmaceutical composition of a PAK inhibitor and/or combinations with other therapeutics are combined with genetic testing to determine whether that individual is a carrier of a mutant gene that is correlated with certain diseases or conditions.

A PAK inhibitor and the additional therapy(ies) are optionally administered before, during or after the occurrence of a disease or condition, and the timing of administering the composition containing a PAK inhibitor varies in some embodiments. Thus, for example, the PAK inhibitor is used as a prophylactic and administered continuously to individuals with a propensity to develop conditions or diseases in order to prevent the occurrence of the disease or condition. The PAK inhibitors and compositions are optionally administered to an individual during or as soon as possible after the onset of the symptoms. The administration of the compounds are optionally initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration is optionally via any route practical, such as, for example, an intravenous injection, a bolus injection, infusion over 5 minutes to about 5 hours, a pill, a capsule, transdermal patch, buccal delivery, and the like, or combination thereof. A PAK inhibitor is optionally administered as soon as is practicable after the onset of a disease or condition is detected or suspected, and for a length of time necessary for the treatment of the disease, such as, for example, from about 1 month to about 3 months. The length of treatment optionally varies for each individual, and the length is then determined using the known criteria. For example, the PAK inhibitor or a formulation containing the PAK inhibitor is administered for at least 2 weeks, preferably about 1 month to about 5 years, and more preferably from about 1 month to about 3 years.

In some embodiments, the particular choice of compounds depends upon the diagnosis of the attending physicians and their judgment of the condition of an individual and the appropriate treatment protocol. The compounds are optionally administered concurrently (e.g., simultaneously, essentially simultaneously or within the same treatment protocol) or sequentially, depending upon the nature of the disease, disorder, or condition, the condition of an individual, and the actual choice of compounds used. In certain instances, the determination of the order of administration, and the number of repetitions of administration of each therapeutic agent during a treatment protocol, is based on an evaluation of the disease being treated and the condition of an individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g., from more than zero weeks to less than four weeks. In some embodiments, the additional therapeutic agent is utilized to achieve reversal or amelioration of symptoms of a neuropsychiatric condition, whereupon the therapeutic agent described herein (e.g., a compound of any one of Formulas I-X) is subsequently administered. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors.

These factors include the disorder from which an individual suffers, as well as the age, weight, sex, diet, and medical condition of an individual. Thus, in various embodiments, the dosage regimen actually employed varies and deviates from the dosage regimens set forth herein.

Examples of Pharmaceutical Compositions and Methods of Administration

Provided herein, in certain embodiments, are compositions comprising a therapeutically effective amount of any compound described herein (e.g., a compound of Formula I-X).

Pharmaceutical compositions are formulated using one or more physiologically acceptable carriers including excipients and auxiliaries which facilitate processing of the active compounds into preparations which are used pharmaceutically. Proper formulation is dependent upon the route of administration chosen. A summary of pharmaceutical compositions is found, for example, in Remington: The Science and Practice of Pharmacy, Nineteenth Ed (Ea hston, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Provided herein are pharmaceutical compositions that include one or more PAK inhibitors and a pharmaceutically acceptable diluent(s), excipient(s), or carrier(s). In addition, the PAK inhibitor is optionally administered as pharmaceutical compositions in which it is mixed with other active ingredients, as in combination therapy. In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

A pharmaceutical composition, as used herein, refers to a mixture of a PAK inhibitor with other chemical components, such as carriers, stabilizers, diluents, dispersing agents, suspending agents, thickening agents, and/or excipients. The pharmaceutical composition facilitates administration of the PAK inhibitor to an organism. In practicing the methods of treatment or use provided herein, therapeutically effective amounts of a PAK inhibitor are administered in a pharmaceutical composition to a mammal having a condition, disease, or disorder to be treated. Preferably, the mammal is a human. A therapeutically effective amount varies depending on the severity and stage of the condition, the age and relative health of an individual, the potency of the PAK inhibitor used and other factors. The PAK inhibitor is optionally used singly or in combination with one or more therapeutic agents as components of mixtures.

The pharmaceutical formulations described herein are optionally administered to an individual by multiple administration routes, including but not limited to, oral, parenteral (e.g., intravenous, subcutaneous, intramuscular), intranasal, buccal, topical, rectal, or transdermal administration routes. By way of example only, Example 131a is describes a parenteral formulation, Example 131f describes a rectal formulation. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

The pharmaceutical compositions will include at least one PAK inhibitor, as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these PAK inhibitors having the same type of activity. In some situations, PAK inhibitors exist as tautomers. All tautomers are included within the scope of the compounds presented herein. Additionally, the PAK inhibitor exists in unsolvated as well as solvated forms with pharmaceutically acceptable solvents such as water, ethanol, and the like. The solvated forms of the PAK inhibitors presented herein are also considered to be disclosed herein.

"Carrier materials" include any commonly used excipients in pharmaceutics and should be selected on the basis of compatibility with compounds disclosed herein, such as, a PAK inhibitor, and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

Moreover, the pharmaceutical compositions described herein, which include a PAK inhibitor, are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, a formulation comprising a PAK inhibitor is a solid drug dispersion. A solid dispersion is a dispersion of one or more active ingredients in an inert carrier or matrix at solid state prepared by the melting (or fusion), solvent, or melting-solvent methods. (Chiou and Riegelman, Journal of Pharmaceutical Sciences, 60, 1281 (1971)). The dispersion of one or more active agents in a solid diluent is achieved without mechanical mixing. Solid dispersions are also called solid-state dispersions. In some embodiments, any compound described herein (e.g., a compound of Formula I-X) is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion. In some embodiments, such amorphous dispersions are filled in capsules and/or constituted into oral powders for reconstitution. Solubility of an SDD comprising a drug is higher than the solubility of a crystalline form of a drug or a non-SDD amorphous form of a drug. In some embodiments of the methods described herein, PAK inhibitors are administered as SDDs constituted into appropriate dosage forms described herein.

Pharmaceutical preparations for oral use are optionally obtained by mixing one or more solid excipient with a PAK inhibitor, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross linked croscarmellose sodium, polyvinylpyrrolidone, agar, or alginic acid or a salt thereof such as sodium alginate.

Dragee cores are provided with suitable coatings. For this purpose, concentrated sugar solutions are generally used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are optionally added to the tablets or dragee coatings for identification or to characterize different combinations of active compound doses.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. By way of example, Example 131b describes a solid dosage formulation that is a capsule. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of a PAK inhibitor are optionally administered as a single capsule or in multiple capsule dosage form. In some embodiments, the pharmaceutical formulation is administered in two, or three, or four, capsules or tablets.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary microencapsulation materials useful for delaying the release of the formulations including a PAK inhibitor, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, Prima-Flo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

The pharmaceutical solid oral dosage forms including formulations described herein, which include a PAK inhibitor, are optionally further formulated to provide a controlled release of the PAK inhibitor. Controlled release refers to the release of the PAK inhibitor from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to an individual over an extended period of time according to a predetermined profile. Such release rates provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In other embodiments, the formulations described herein, which include a PAK inhibitor, are delivered using a pulsatile dosage form. A pulsatile dosage form is capable of providing one or more immediate release pulses at predetermined time points after a controlled lag time or at specific sites. Pulsatile dosage forms including the formulations described herein, which include a PAK inhibitor, are optionally administered using a variety of pulsatile formulations that include, but are not limited to, those described in U.S. Pat. Nos. 5,011,692, 5,017,381, 5,229,135, and 5,840,329. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the PAK inhibitor, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Suitable intranasal formulations include those described in, for example, U.S. Pat. Nos. 4,476,116, 5,116,817 and 6,391,452. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present.

For administration by inhalation, the PAK inhibitor is optionally in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit is determined by providing a valve to deliver a metered amount. Capsules and cartridges of, such as, by way of example only, gelatin for use in an inhaler or insufflator are formulated containing a powder mix of the PAK inhibitor and a suitable powder base such as lactose or starch. By way of example, Example 131e describes an inhalation formulation.

Buccal formulations that include a PAK inhibitor include, but are not limited to, U.S. Pat. Nos. 4,229,447, 4,596,795, 4,755,386, and 5,739,136. In addition, the buccal dosage forms described herein optionally further include a bioerodible (hydrolysable) polymeric carrier that also serves to adhere the dosage form to the buccal mucosa. The buccal dosage form is fabricated so as to erode gradually over a predetermined time period, wherein the delivery of the PAK inhibitor, is provided essentially throughout. Buccal drug delivery avoids the disadvantages encountered with oral drug administration, e.g., slow absorption, degradation of the active agent by fluids present in the gastrointestinal tract and/or first-pass inactivation in the liver. The bioerodible (hydrolysable) polymeric carrier generally comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components also be incorporated into the buccal dosage forms described herein include, but are not limited to, disintegrants, diluents, binders, lubricants, flavoring, colorants, preservatives, and the like. For buccal or sublingual administration, the compositions optionally take the form of tablets, lozenges, or gels formulated in a conventional manner. By way of example, Examples 135c and 135d describe sublingual formulations.

Transdermal formulations of a PAK inhibitor are administered for example by those described in U.S. Pat. Nos. 3,598, 122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144. By way of example, Example 131g describes a topical formulation.

The transdermal formulations described herein include at least three components: (1) a formulation of a PAK inhibitor; (2) a penetration enhancer; and (3) an aqueous adjuvant. In addition, transdermal formulations include components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein maintain a saturated or supersaturated state to promote diffusion into the skin.

In some embodiments, formulations suitable for transdermal administration of a PAK inhibitor employ transdermal delivery devices and transdermal delivery patches and are lipophilic emulsions or buffered, aqueous solutions, dissolved and/or dispersed in a polymer or an adhesive. Such patches are optionally constructed for continuous, pulsatile, or on demand delivery of pharmaceutical agents. Still further, transdermal delivery of the PAK inhibitor is optionally accomplished by means of iontophoretic patches and the like. Additionally, transdermal patches provide controlled delivery of the PAK inhibitor. The rate of absorption is optionally slowed by using rate-controlling membranes or by trapping the PAK inhibitor within a polymer matrix or gel. Conversely, absorption enhancers are used to increase absorption. An absorption enhancer or carrier includes absorbable pharmaceutically acceptable solvents to assist passage through the skin. For example, transdermal devices are in the form of a bandage comprising a backing member, a reservoir containing the PAK inhibitor optionally with carriers, optionally a rate controlling barrier to deliver the PAK inhibitor to the skin of the host at a controlled and predetermined rate over a prolonged period of time, and means to secure the device to the skin.

Formulations that include a PAK inhibitor suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, a PAK inhibitor is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or non-aqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of the PAK inhibitor in water soluble form. Additionally, suspensions of the PAK inhibitor are optionally prepared as appropriate oily injection suspensions.

In some embodiments, the PAK inhibitor is administered topically and formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

The PAK inhibitor is also optionally formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The PAK inhibitor is optionally used in the preparation of medicaments for the prophylactic and/or therapeutic treatment of a neuropsychiatric condition that would benefit, at least in part, from amelioration of symptoms. In addition, a method for treating any of the diseases or conditions described herein in an individual in need of such treatment, involves administration of pharmaceutical compositions containing at least one PAK inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

In the case wherein the patient's condition does not improve, upon the doctor's discretion the administration of the PAK inhibitor is optionally administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the PAK inhibitor is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

In some embodiments, the pharmaceutical compositions described herein are in unit dosage forms suitable for single administration of precise dosages. In unit dosage form, the formulation is divided into unit doses containing appropriate quantities of one or more PAK inhibitor. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

The daily dosages appropriate for the PAK inhibitor are from about 0.01 to 2.5 mg/kg per body weight. An indicated daily dosage in the larger mammal, including, but not limited to, humans, is in the range from about 0.5 mg to about 1000 mg, conveniently administered in divided doses, including, but not limited to, up to four times a day or in extended release form. Suitable unit dosage forms for oral administration include from about 1 to 500 mg active ingredient, from about 1 to 250 mg of active ingredient, or from about 1 to about 100 mg active ingredient. The foregoing ranges are merely suggestive, as the number of variables in regard to an individual treatment regime is large, and considerable excursions from these recommended values are not uncommon. Such dosages are optionally altered depending on a number of variables, not limited to the activity of the PAK inhibitor used, the disease or condition to be treated, the mode of administration, the requirements of an individual individual, the severity of the disease or condition being treated, and the judgment of the practitioner.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. PAK inhibitors exhibiting high therapeutic indices are preferred. The data obtained from cell culture assays and animal studies is optionally used in formulating a range of dosage for use in human. The dosage of such PAK inhibitors lies preferably within a range of circulating concentrations that include the ED50 with minimal toxicity. The dosage optionally varies within this range depending upon the dosage form employed and the route of administration utilized.

Assays for Identification and Characterization of PAK Inhibitors

Small molecule PAK inhibitors are optionally identified in high-throughput in vitro or cellular assays as described in, e.g., Yu et al (2001), *J Biochem* (Tokyo); 129(2):243-251; Rininsland et al (2005), BMC *Biotechnol*, 5:16; and Allen et al (2006), *ACS Chem Biol;* 1(6):371-376. PAK inhibitors suitable for the methods described herein are available from a variety of sources including both natural (e.g., plant extracts) and synthetic. For example, candidate PAK inhibitors are isolated from a combinatorial library, i.e., a collection of diverse chemical compounds generated by either chemical synthesis or biological synthesis by combining a number of chemical "building blocks." For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks, as desired. Theoretically, the systematic, combinatorial mixing of 100 interchangeable chemical building blocks results in the synthesis of 100 million tetrameric compounds or 10 billion pentameric compounds. See Gallop et al. (1994), *J. Med. Chem.* 37(9), 1233. Each member of a library may be singular and/or may be part of a mixture (e.g. a "compressed library"). The library may comprise purified compounds and/or may be "dirty" (i.e., containing a quantity of impurities). Preparation and screening of combinatorial chemical libraries are documented methodologies. See Cabilly, ed., *Methods in Molecular Biology*, Humana Press, Totowa, N.J., (1998). Combinatorial chemical libraries include, but are not limited to: diversomers such as hydantoins, benzodiazepines, and dipeptides, as described in, e.g., Hobbs et al. (1993), *Proc. Natl. Acad. Sci. U.S.A.* 90, 6909; analogous organic syntheses of small compound libraries, as described in Chen et al. (1994), *J. Amer. Chem. Soc.*, 116: 2661; Oligocarbamates, as described in Cho, et al. (1993), *Science* 261, 1303; peptidyl phosphonates, as described in Campbell et al. (1994), *J. Org. Chem.*, 59: 658; and small organic molecule libraries containing, e.g., thiazolidinones and metathiazanones (U.S. Pat. No. 5,549,974), pyrrolidines (U.S. Pat. Nos. 5,525,735 and 5,519, 134), benzodiazepines (U.S. Pat. No. 5,288,514). In addition, numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.).

Devices for the preparation of combinatorial libraries are commercially available (see, e.g., 357 MPS, 390 MPS from Advanced Chem Tech, Louisville, Ky.; Symphony from Rainin, Woburn, Mass.; 433A from Applied Biosystems, Foster City, Calif.; and 9050 Plus from Millipore, Bedford, Mass.). A number of robotic systems have also been developed for solution phase chemistries. These systems include automated workstations like the automated synthesis apparatus developed by Takeda Chemical Industries, LTD (Osaka, Japan), and many robotic systems utilizing robotic arms (Zymate II). Any of the above devices are optionally used to generate combinatorial libraries for identification and characterization of PAK inhibitors which mimic the manual synthetic operations performed by small molecule PAK inhibitors suitable for the methods described herein. Any of the above devices are optionally used to identify and characterize small molecule PAK inhibitors suitable for the methods disclosed herein. In many of the embodiments disclosed herein, PAK inhibitors, PAK binding molecules, and PAK clearance agents are disclosed as polypeptides or proteins (where polypeptides comprise two or more amino acids). In these embodiments, the inventors also contemplate that PAK inhibitors, binding molecules, and clearance agents also include peptide mimetics based on the polypeptides, in which the peptide mimetics interact with PAK or its upstream or downstream regulators by replicating the binding or substrate interaction properties of PAK or its regulators. Nucleic acid aptmers are also contemplated as PAK inhibitors, binding molecules, and clearance agents, as are small molecules other than peptides or nucleic acids. For example, in some embodiments small molecule PAK binding partners, inhibitors, or clearance agents, or small molecule agonists or antagonists of PAK modulators or targets, are designed or selected based on analysis of the structure of PAK or its modulators or targets and binding interactions with interacting molecules, using "rational drug design" (see, for example Jacobsen et al. (2004) *Molecular Interventions* 4:337-347; Shi et al. (2007) *Bioorg. Med. Chem. Lett.* 17:6744-6749).

The identification of potential PAK inhibitors is determined by, for example, assaying the in vitro kinase activity of PAK in the presence of candidate inhibitors. In such assays, PAK and/or a characteristic PAK fragment produced by recombinant means is contacted with a substrate in the presence of a phosphate donor (e.g., ATP) containing radiolabeled phosphate, and PAK-dependent incorporation is measured. "Substrate" includes any substance containing a suitable hydroxyl moiety that can accept the γ-phosphate group from a donor molecule such as ATP in a reaction catalyzed by PAK. The substrate may be an endogenous substrate of PAK, i.e. a naturally occurring substance that is phosphorylated in unmodified cells by naturally-occurring PAK or any other substance that is not normally phosphorylated by PAK in physiological conditions, but may be phosphorylated in the employed conditions. The substrate may be a protein or a peptide, and the phosphrylation reaction may occur on a serine and/or threonine residue of the substrate. For example, specific substrates, which are commonly employed in such assays include, but are not limited to, histone proteins and myelin basic protein. In some embodiments, PAK inhibitors are identified using IMAP® technology.

Detection of PAK dependent phosphorylation of a substrate can be quantified by a number of means other than measurement of radiolabeled phosphate incorporation. For example, incorporation of phosphate groups may affect physiochemical properties of the substrate such as electrophoretic mobility, chromatographic properties, light absorbance, fluorescence, and phosphorescence. Alternatively, monoclonal or polyclonal antibodies can be generated which selectively recognize phosphorylated forms of the substrate from non-phosphorylated forms whereby allowing antibodies to function as an indicator of PAK kinase activity.

High-throughput PAK kinase assays can be performed in, for example, microtiter plates with each well containing PAK kinase or an active fragment thereof, substrate covalently linked to each well, $P^{32}$ radiolabled ATP and a potential PAK inhibitor candidate. Microtiter plates can contain 96 wells or 1536 wells for large scale screening of combinatorial library compounds. After the phosphorylation reaction has completed, the plates are washed leaving the bound substrate. The plates are then detected for phosphate group incorporation via autoradiography or antibody detection. Candidate PAK inhibitors are identified by their ability to decease the amount of PAK phosphotransferase ability upon a substrate in comparison with PAK phosphotransferase ability alone.

The identification of potential PAK inhibitors may also be determined, for example, via in vitro competitive binding assays on the catalytic sites of PAK such as the ATP binding site and/or the substrate binding site. For binding assays on the ATP binding site, a known protein kinase inhibitor with high affinity to the ATP binding site is used such as staurosporine. Staurosporine is immobolized and may be fluorescently labeled, radiolabeled or in any manner that allows detection. The labeled staurosporine is introduced to recombinantly expressed PAK protein or a fragment thereof along with potential PAK inhibitor candidates. The candidate is tested for its ability to compete, in a concentration-dependant manner, with the immobolized staurosporine for binding to the PAK protein. The amount of staurosporine bound PAK is inversely proportional to the affinity of the candidate inhibitor for PAK. Potential inhibitors would decrease the quantifiable binding of staurosporine to PAK. See e.g., Fabian et al (2005) *Nat. Biotech.*, 23:329. Candidates identified from this competitive binding assay for the ATP binding site for PAK would then be further screened for selectivity against other kinases for PAK specificity.

The identification of potential PAK inhibitors may also be determined, for example, by in cyto assays of PAK activity in the presence of the inhibitor candidate. Various cell lines and tissues may be used, including cells specifically engineered for this purpose. In cyto screening of inhibitor candidates may assay PAK activity by monitoring the downstream effects of PAK activity. Such effects include, but are not limited to, the formation of peripheral actin microspikes and or associated loss of stress fibers as well as other cellular responses such as growth, growth arrest, differentiation, or apoptosis. See e.g., Zhao et al., (1998) *Mol. Cell. Biol.* 18:2153. For example in a PAK yeast assay, yeast cells grow normally in glucose medium. Upon exposure to galactose however, intracellular PAK expression is induced, and in turn, the yeast cells die. Candidate compounds that inhibit PAK activity are identified by their ability to prevent the yeast cells from dying from PAK activation.

Alternatively, PAK-mediated phosphorylation of a downstream target of PAK can be observed in cell based assays by first treating various cell lines or tissues with PAK inhibitor candidates followed by lysis of the cells and detection of PAK mediated events. Cell lines used in this experiment may include cells specifically engineered for this purpose. PAK mediated events include, but are not limited to, PAK mediated phosphorylation of downstream PAK mediators. For example, phosphorylation of downstream PAK mediators can be detected using antibodies that specifically recognize the phosphorylated PAK mediator but not the unphosphorylated form. These antibodies have been described in the literature and have been extensively used in kinase screening campaigns. In some instances a phospho LIMK antibody is used after treatment of HeLa cells stimulated with EGF or sphingosine to detect downstream PAK signaling events.

The identification of potential PAK inhibitors may also be determined, for example, by in vivo assays involving the use of animal models, including transgenic animals that have been engineered to have specific defects or carry markers that can be used to measure the ability of a candidate substance to reach and/or affect different cells within the organism. For example, DISC1 knockout mice have defects in synaptic plasticity and behavior from increased numbers of dendritic spines and an abundance of long and immature spines. Thus, identification of PAK inhibitors can comprise administering a candidate to DISC1 knockout mice and observing for reversals in synaptic plasticity and behavior defects as a readout for PAK inhibition.

For example, fragile X mental retardation 1 (FMR1) knockout mice have defects in synaptic plasticity and behavior from increased numbers of dendritic spines and an abundance of long and immature spines. See e.g., Comery et al., (1997) Proc. Natl. Acad. Sci. USA, 94:5401-04. As PAK is a downstream effector of the FMR1 gene, the defects are reversed upon the use of dominant negative transgenes of PAK that inhibit endogenous PAK activity. See Hayashi et al. (2007) Proc. Natl. Acad. Sci. USA, 104:11489-94. Thus, identification of PAK inhibitors can comprise administering a candidate to FMR1 knockout mice and observing for reversals in synaptic plasticity and behavior defects as a readout for PAK inhibition.

For example, suitable animal models for Alzheimer's diseases are knock-ins or transgenes of the human mutated genes including transgenes of the "swedish" mutation of APP (APPswe), transgenes expressing the mutant form of presenilin 1 and presenilin 2 found in familial/early onset AD. Thus, identification of PAK inhibitors can comprise administering a candidate to a knock-in animal and observing for reversals in synaptic plasticity and behavior defects as a readout for PAK inhibition.

Administration of the candidate to the animal is via any clinical or non-clinical route, including but not limited to oral, nasal, buccal and/or topical adiminstrations. Additionally or alternatively, administration may be intratracheal instillation, bronchial instillation, intradermal, subcutaneous, intramuscular, intraperitoneal, inhalation, and/or intravenous injection.

Changes in spine morphology are detected using any suitable method, e.g., by use of 3D and/or 4D real time interactive imaging and visualization. In some instances, the Imaris suite of products (available from Bitplane Scientific Solutions) provides functionality for visualization, segmentation and interpretation of 3D and 4D microscopy datasets obtained from confocal and wide field microscopy data.

EXAMPLES

The following specific examples are to be construed as merely illustrative, and not imitative of the remainder of the disclosure in any way whatsoever.

All synthetic chemistry was performed in standard laboratory glassware unless indicated otherwise in the examples. Commercial reagents were used as received. Analytical LC/MS was performed on an Agilent 1200 system with a variable wavelength detector and Agilent 6140 Single quadrupole mass spectrometer, alternating positive and negative ion scans. Retention times were determined from the extracted 220 nm chromatogram. $^1$H NMR was performed on a Bruker DRX-400 at 400 MHz. Microwave reactions were performed in a Biotage Initiator using the instrument software to control heating time and pressure. Hydrogenation reactions were performed on a H-Cube using the commercially available catalyst cartridges. Silica gel chromatography was performed manually.

Preparative HPLC was performed on a Waters 1525/2487 with UV detection at 220 nm and manual collection.

Analytical LC/MS Method:

HPLC column: Zorbax SB-C18, 3.5 µm, 2.1 mm×30 mm, maintained at 40° C. HPLC Gradient: 0.4 mL/min, 95:5:0.1 water:acetonitrile:formic acid for 0.1 min then to 5:95:0.1 water:acetonitrile:formic acid in 3.9 min, maintaining for 0.5 min.

Preparative HPLC Method:

HPLC column: Zorbax SB-C18 21.2×100 mm.

HPLC Gradient: 20 mL/min, 95:5:0.1 water:methanol:formic acid to 5:95:0.1 water:methanol:formic acid; the gradient shape was optimized for individual separations.

Example 1

Synthesis of 8-(7-methoxy-2,3-dihydro-1H-inden-1-yl)-2-(4-(4-methylpiperazin-1-yl)phenylamino)pyrido[2,3-d]pyrimidin-7(8H)-one

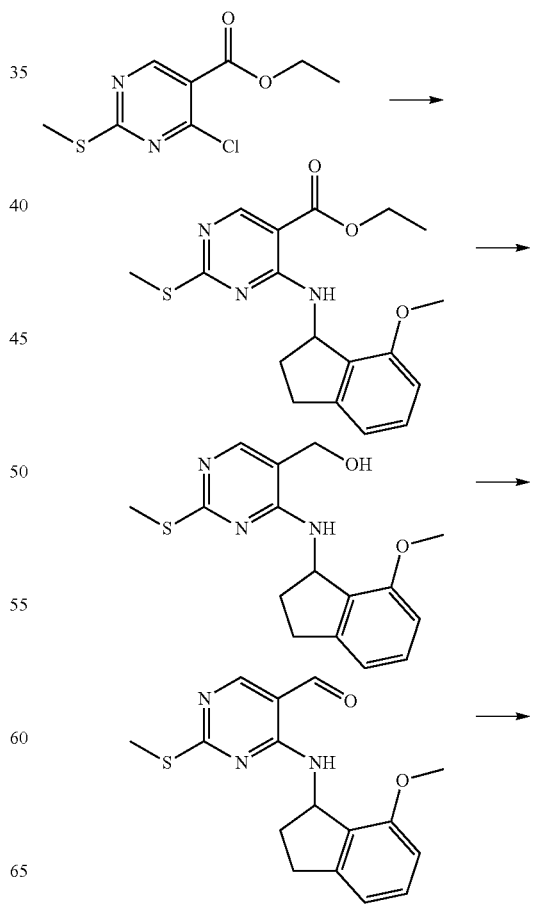

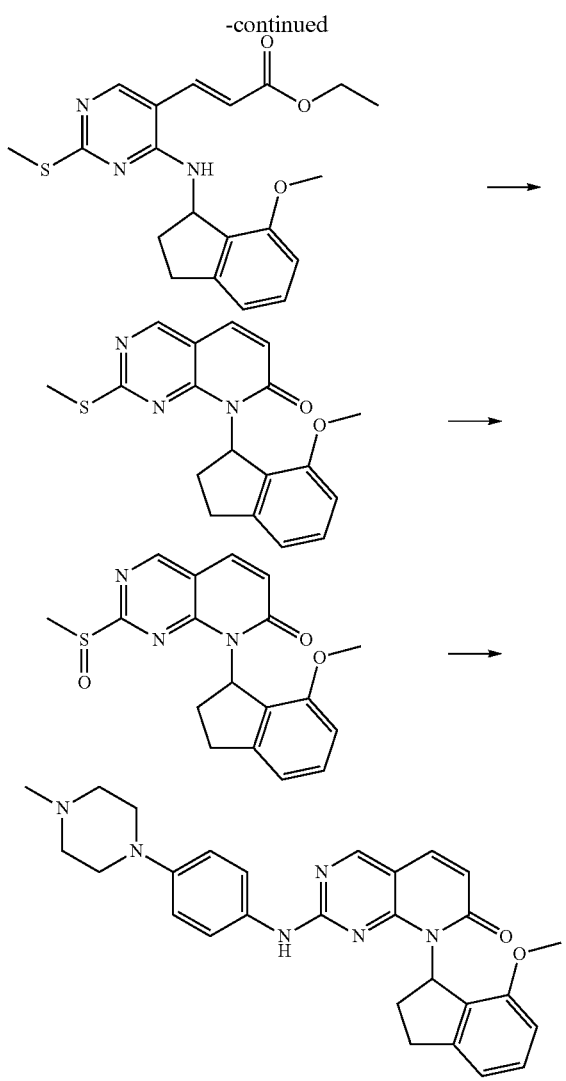

Intermediate 1: Synthesis of
7-methoxy-1-aminoindane hydrochloride

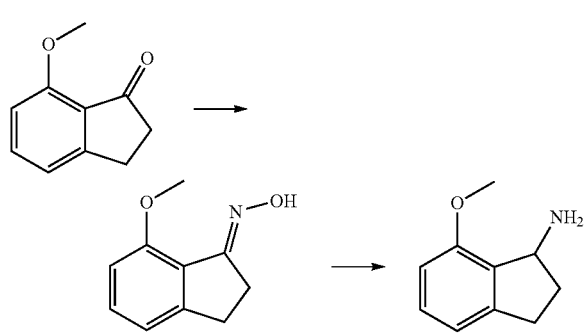

Step 1: Synthesis of 7-methoxyindan-1-one oxime

To a suspension of 7-methoxyindanone (5.0 g, 31 mmol) and hydroxylamine hydrochloride (12.9 g, 185 mmol) in 100 mL ethanol was added the solution of sodium acetate (11.4 g, 139 mmol) in 35 mL water at room temperature. The reaction mixture was heated at reflux for 4 h, then stirred at room temperature for 18 h. The suspension was filtered, the white solid was washed with water, ethanol and diethyl ether to give the title compound (5.4 g, 31 mmol, 98%). ESMS m/z 178 $(M+H)^+$.

Step 2: Synthesis of 7-methoxy-1-aminoindane hydrochloride 7-methoxyindan-1-one oxime (2.92 g, 16 mmol) was dissolved in acetic acid (150 mL) and hydrogenated on the H-Cube: 1 mL/min flow rate, 80° C., 100 bar with 10% Pd/C. The reaction mixture was evaporated, the residue was dissolved in methanol and 1 equivalent of hydrochloric acid in methanol was added. The solvent was evaporated and the residue was triturated with diethyl ether to give 7-methoxy-1-aminoindane hydrochloride (2.38 g, 12 mmol, 75%). ESMS m/z 147 $(M+H)^+$.

Step 3: Synthesis of ethyl 4-(7-methoxy-2,3-dihydro-1H-inden-1-ylamino)-2-(methylthio)pyrimidine-5-carboxylate To a stirred solution of ethyl 4-chloro-2-methylthiopyrimidine-5-carboxylate (2.24 g, 9.62 mmol) in 35 mL of anhydrous tetrahydrofuran was added triethylamine (4.00 mL, 2.90 g, 28.72 mmol). The solution was cooled to 0-5° C. and 7-methoxy-1-aminoindane hydrochloride (2.00 g, 10.01 mmol) was added. The reaction mixture was allowed to warm to room temperature and stirred 48 h. The precipitate was filtered off, washed with ethyl acetate (1×25 mL), and the combined filtrates were evaporated to dryness. The residue was dissolved in dichloromethane (35 mL) washed with saturated sodium bicarbonate solution (1×17 mL), dried over magnesium sulfate, filtered and concentrated to give 4-(7-methoxy-2,3-dihydro-1H-inden-1-ylamino)-2-(methylthio)pyrimidine-5-carboxylate as an oil (3.31 g, 9.21 mmol, 95%). ESMS m/z 360 $(M+H)^+$; $^1H$ NMR (400 MHz, CDCl$_3$) δ ppm 8.63 (s, 1H), 8.43 (d, J=6.5 Hz, 1H), 7.21-7.26 (m, 1H), 6.88 (d, J=7.5 Hz, 1H), 6.72 (d, J=8.3 Hz, 1H), 5.69-5.78 (m, 1H), 4.26 (q, J=7.2 Hz, 2H), 3.78 (s, 3H), 3.01-3.13 (m, 1H), 2.82-2.94 (m, 1H), 2.59-2.67 (m, 1H), 2.56 (s, 3H), 2.04-2.14 (m, 1H), 1.33 (t, J=7.2 Hz, 3H).

Step 4: Synthesis of (4-(7-methoxy-2,3-dihydro-1H-inden-1-ylamino)-2-(methylthio)pyrimidin-5-yl)methanol A solution of 4-(7-methoxy-2,3-dihydro-1H-inden-1-ylamino)-2-(methylthio)pyrimidine-5-carboxylate (3.25 g, 9.04 mmol) in anhydrous tetrahydrofuran (30 mL) was added dropwise to a suspension of lithium aluminum hydride (0.54 g, 14.25 mmol) in anhydrous tetrahydrofuran (8 mL) at 0-5° C. The reaction mixture was allowed to slowly warm to room temperature and stirred for 18 h, then the mixture was cooled to 0-5° C. and quenched with water:tetrahydrofuran (15 mL:5 mL), followed by a 10% sodium hydroxide solution (11 mL). After stirring for 1 h, the precipitate was filtered off and washed with ethyl acetate (5×25 mL). The combined filtrates were diluted with saturated brine solution (20 mL) and water (15 mL), the two phases were separated, and the organic layer was washed with water (1×25 mL), dried over magnesium sulfate, filtered and evaporated to a light brown solid (2.43 g, 7.65 mmol, 84%). ESMS m/z 318 $(M+H)^+$.

Step 5: Synthesis of 4-(7-methoxy-2,3-dihydro-1H-inden-1-ylamino)-2-(methylthio)pyrimidine-5-carbaldehyde To a solution of (4-(7-methoxy-2,3-dihydro-1H-inden-1-ylamino)-2-(methylthio)pyrimidin-5-yl)methanol (2.36 g, 7.43 mmol) in dichloromethane (80 mL) was added manganese dioxide (90%, 3.87 g, 40 mmol) in small portions. The resulting suspension was stirred for 18 h. Additional manganese dioxide (90%, 3.87 g, 40 mmol) was added and the mixture was stirred for an additional 18 h. The mixture was filtered through Celite and washed with dichloromethane (5×10 mL). The combined filtrates were evaporated in vacuo to give 4-(7-methoxy-2,3-dihydro-1H-inden-1-ylamino)-2-(methylthio)pyrimidine-5-carbaldehyde as a light brown solid (1.89 g, 5.99 mmol, 80%). ESMS m/z 316 (M+H)$^+$.

Step 6: Synthesis of (E)-ethyl 3-(4-(7-methoxy-2,3-dihydro-1H-inden-1-ylamino)-2-(methylthio)pyrimidin-5-yl)acrylate To a suspension of sodium hydride (60% dispersion, 0.21 g, 5.25 mmol) in anhydrous tetrahydrofuran (21 mL) was added dropwise a solution of triethyl phosphonoacetate (1.03 mL, 1.16 g, 5.19 mmol) in anhydrous tetrahydrofuran (5 mL) at 0-5° C. and the reaction mixture was stirred for 30 min at this temperature. To this suspension was added carefully 4-(7-methoxy-2,3-dihydro-1H-inden-1-ylamino)-2-(methylthio)pyrimidine-5-carbaldehyde (1.48 g, 4.69 mmol) in anhydrous tetrahydrofuran (25 mL) below 5° C. The reaction mixture was allowed to warm to room temperature and stirred for 18 h. The mixture was cooled to below 5° C. and water (22 mL) was added dropwise. It was diluted further with ethyl acetate (25 mL) and saturated brine solution (15 mL), the two phases were separated, and the organic layer was washed with saturated sodium carbonate solution (1×30 mL), water (1×30 mL), dried over sodium sulfate, filtered and evaporated to give (E)-ethyl 3-(4-(7-methoxy-2,3-dihydro-1H-inden-1-ylamino)-2-(methylthio)pyrimidin-5-yl)acrylate as a light brown solid (2.26 g, 5.86 mmol, quant.). ESMS m/z 386 (M+H)$^+$; $^1$H NMR (400 MHz, CDCl$_3$), E/Z isomers in a ratio of 90:10, δ ppm 8.15 (s, 0.9H, E), 8.13 (s, 0.1H, Z), 7.46 (d, J=16. e.g., 1 Hz, 0.9H, E), 7.27-7.31 (m, 1H, E+Z), 6.92 (d, J=7.5 Hz, 1H, E+Z), 6.76 (d, J=8.3 Hz, 0.9H, E), 6.73 (d, J=8.3 Hz, 0.1H, Z), 6.57 (d, J=11.8 Hz, 0.1H, Z) 6.27 (d, J=16. e.g., 1 Hz, 0.9H, E), 5.98 (d, J=11.8 Hz, 0.1H, Z) 5.77 (d, J=4.5 Hz, 0.9H, E), 5.58-5.65 (m, 1H, E+Z), 5.17 (d, J=4.5 Hz, 0.1H, Z) 4.23 (q, J=7.2 Hz, 2H, E+Z), 3.83 (s, 2.7H, E), 3.78 (s, 0.3H, Z), 2.99-3.11 (m, 1H, E+Z), 2.85-2.95 (m, 1H, E+Z), 2.71-2.82 (m, 1H, E+Z), 2.57 (s, 2.9H, E), 2.56 (s, 0.3H, Z) 1.99-2.11 (m, 1H, E+Z), 1.30 (t, J=7.2 Hz, 3H, E+Z).

Step 7: Synthesis of 8-(7-methoxy-2,3-dihydro-1H-inden-1-yl)-2-(methylthio)pyrido[2,3-d]pyrimidin-7(8H)-one To a solution of (E)-ethyl 3-(4-(7-methoxy-2,3-dihydro-1H-inden-1-ylamino)-2-(methylthio)pyrimidin-5-yl)acrylate (0.30 g, 0.78 mmol) in N-methylpyrrolidinone (1.8 mL) was added 1,8-diazabicyclo[5.4.0]undec-7-ene (0.35 mL, 0.35 g, 2.29 mmol) and the reaction was stirred for 4 h at 120° C. The reaction mixture was poured onto ice water and diluted with ethyl acetate (8 mL) and saturated brine solution (2.5 mL). The two phases were separated, and the organic layer was washed with 1 M hydrochloric acid (1×7 mL), water (1×7 mL), dried over sodium sulfate, filtered and evaporated to 8-(7-methoxy-2,3-dihydro-1H-inden-1-yl)-2-(methylthio)pyrido[2,3-d]pyrimidin-7(8H)-one as a brown oil (0.40 g, 1.18 mmol, quant.). ESMS m/z 340 (M+H)$^+$.

Step 8: Synthesis of 8-(7-methoxy-2,3-dihydro-1H-inden-1-yl)-2-(methylsulfinyl)pyrido[2,3-d]pyrimidin-7(8H)-one To a solution of 8-(7-methoxy-2,3-dihydro-1H-inden-1-yl)-2-(methylthio)pyrido[2,3-d]pyrimidin-7(8H)-one (0.32 g, 0.94 mmol) in dichloromethane (3 mL) was added 3-chloroperbenzoic acid (70%, 0.18 g, 0.73 mmol) and the mixture was stirred at room temperature for 5 h. The reaction mixture was extracted with saturated sodium bicarbonate solution (2×1.5 mL), the organic layer was dried over sodium sulfate, then filtered and evaporated to give 8-(7-methoxy-2,3-dihydro-1H-inden-1-yl)-2-(methylsulfinyl)pyrido[2,3-d]pyrimidin-7(8H)-one as a light brown oil (0.29 g, 0.82 mmol, 87%). ESMS m/z 356 (M+H)$^+$.

Step 9: Synthesis of 8-(7-methoxy-2,3-dihydro-1H-inden-1-yl)-2-(4-(4-methylpiperazin-1-yl)phenylamino)pyrido[2,3-d]pyrimidin-7(8H)-one 8-(7-methoxy-2,3-dihydro-1H-inden-1-yl)-2-(methylsulfinyl)pyrido[2,3-d]pyrimidin-7(8H)-one (0.29 g, 0.81 mmol) and 4-(4-methylpiperazino)aniline (0.15 g, 0.81 mmol) were stirred at 140° C. for 4 h. The reaction mixture was dissolved in dichloromethane (35 mL) and washed with 10% sodium hydroxide solution (1×15 mL) then with water (1×15 mL). The organic layer was dried over sodium sulfate, filtered and evaporated. The residue was purified by silica gel column chromatography using dichloromethane:methanol (9:1) to give 8-(7-methoxy-2,3-dihydro-1H-inden-1-yl)-2-(4-(4-methylpiperazin-1-yl)phenylamino)pyrido[2,3-d]pyrimidin-7(8H)-one (32 mg, 0.07 mmol, 8.6%) as the major product. ESMS m/z 483 (M+H)$^+$; $^1$H NMR (400 MHz, CDCl$_3$) δ ppm 9.81 (br. s., 1H), 8.73 (s, 1H), 7.77 (d, J=9.3 Hz, 1H), 7.61 (d, J=9.0 Hz, 2H), 7.14 (t, J=7.5 Hz, 1H), 6.89 (d, J=9.0 Hz, 2H), 6.87 (br.s., 1H), 6.84 (d, J=7.3 Hz, 1H), 6.65 (d, J=8.3 Hz, 1H), 6.13 (d, J=9.3 Hz, 1H), 3.43 (s, 3H), 3.10-3.00 (m, 4H), 3.00-2.85 (m, 2H), 2.45-2.38 (m, 4H), 2.35-2.25 (m, 2H), 2.20 (s, 3H).

Examples 2-26

The following compounds were made by the method of Example 1 using the appropriate amine at Step 1 and aniline at Step 9. If necessary, the amine was synthesized by the method used for Intermediate 1. Compounds containing secondary amines on the aniline were synthesized using the appropriate Boc protected aminoaniline and in the final step were treated with a solution of hydrogen chloride in an organic solvent to produce the compound, optionally isolated as the hydrochloride salt.

| No. | Structure | MW | LCMS Ion | Rt |
|---|---|---|---|---|
| 2 | 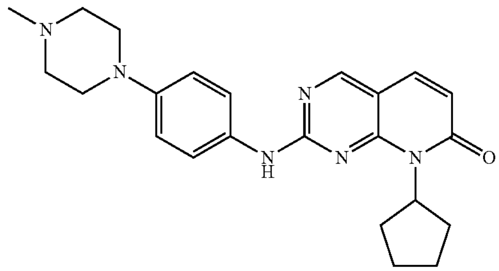 [SMILES: CN1CCN(c2ccc(Nc3ncc4ccc(=O)n(C5CCCC5)c4n3)cc2)CC1] | 404.5 | 405 | 1.87 |
| 3 | 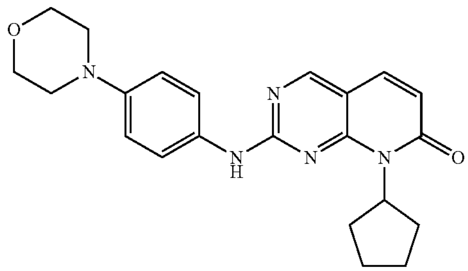 [SMILES: O=c1ccc2cnc(Nc3ccc(N4CCOCC4)cc3)nc2n1C1CCCC1] | 391.5 | 392 | 2.64 |
| 4 | 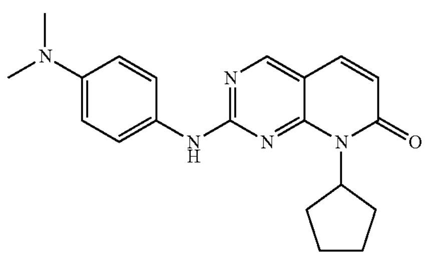 [SMILES: CN(C)c1ccc(Nc2ncc3ccc(=O)n(C4CCCC4)c3n2)cc1] | 349.4 | 350 | 2.68 |
| 5 | 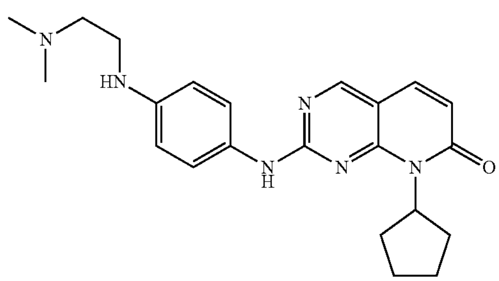 [SMILES: CN(C)CCNc1ccc(Nc2ncc3ccc(=O)n(C4CCCC4)c3n2)cc1] | 392.5 | 393 | 2.48 |
| 6 | 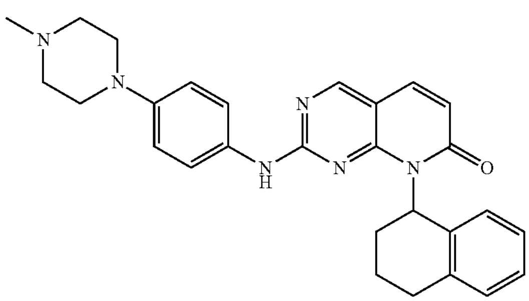 | 466.6 | 467 | 2.88 |

-continued

| No. | Structure | MW | LCMS Ion | Rt |
|---|---|---|---|---|
| 7 | 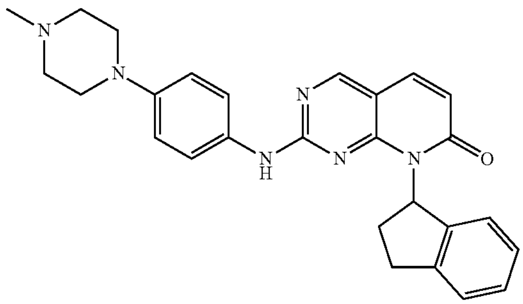 [SMILES: CN1CCN(c2ccc(Nc3ncc4ccc(=O)n(C5CCc6ccccc65)c4n3)cc2)CC1] | 452.6 | 453 | 2.82 |
| 8 | 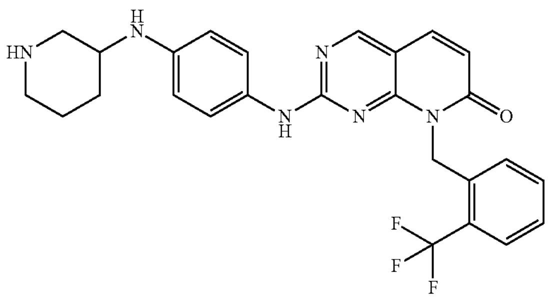 [SMILES: O=c1ccc2cnc(Nc3ccc(NC4CCCNC4)cc3)nc2n1Cc1ccccc1C(F)(F)F] | 494.5 | 495 | 2.89 |
| 9 | 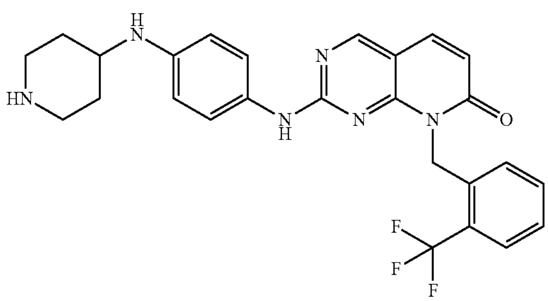 [SMILES: O=c1ccc2cnc(Nc3ccc(NC4CCNCC4)cc3)nc2n1Cc1ccccc1C(F)(F)F] | 494.5 | 495 | 2.75 |
| 10 | 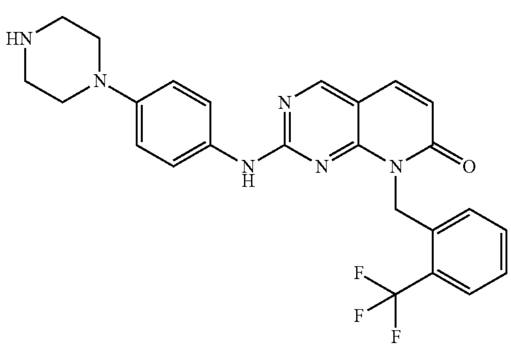 [SMILES: O=c1ccc2cnc(Nc3ccc(N4CCNCC4)cc3)nc2n1Cc1ccccc1C(F)(F)F] | 480.5 | 481 | 2.84 |
| 11 | 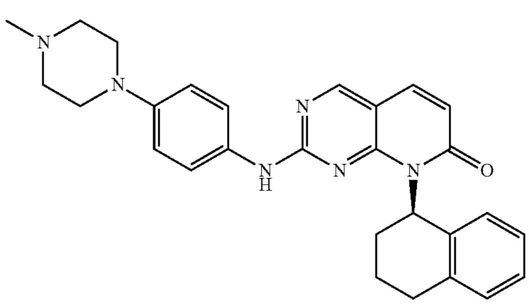 [SMILES: CN1CCN(c2ccc(Nc3ncc4ccc(=O)n([C@@H]5CCCc6ccccc65)c4n3)cc2)CC1] | 466.6 | 467 | 2.90 |

-continued

| No. | Structure | MW | LCMS Ion | Rt |
|---|---|---|---|---|
| 12 | 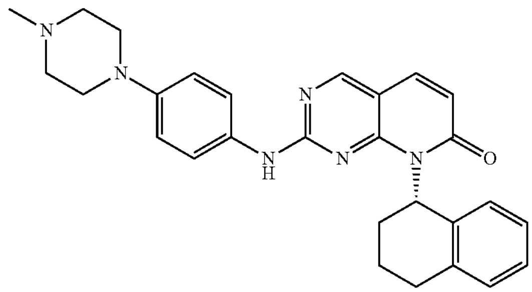 | 466.6 | 467 | 2.91 |
| 13 | 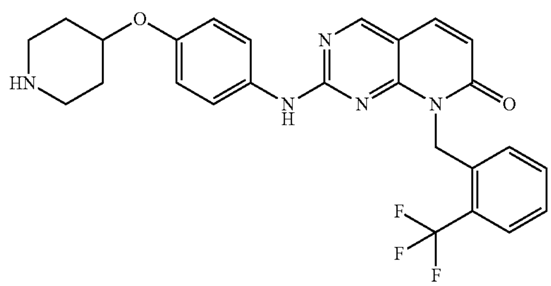 [SMILES: O=c1ccc2cnc(Nc3ccc(OC4CCNCC4)cc3)nc2n1Cc1ccccc1C(F)(F)F] | 495.5 | 496 | 3.66 |
| 14 | 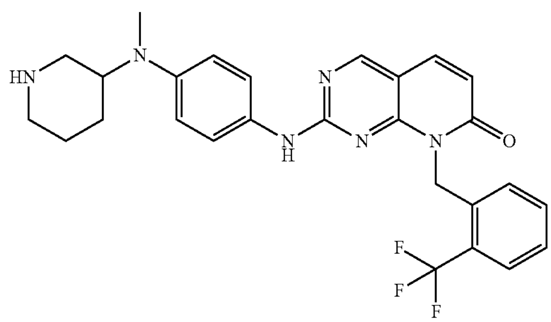 [SMILES: CN(c1ccc(Nc2ncc3ccc(=O)n(Cc4ccccc4C(F)(F)F)c3n2)cc1)C1CCCNC1] | 508.5 | 509 | 2.92 |
| 15 | 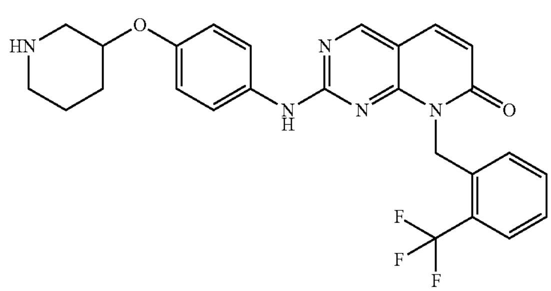 [SMILES: O=c1ccc2cnc(Nc3ccc(OC4CCCNC4)cc3)nc2n1Cc1ccccc1C(F)(F)F] | 495.5 | 496 | 2.95 |
| 16 | 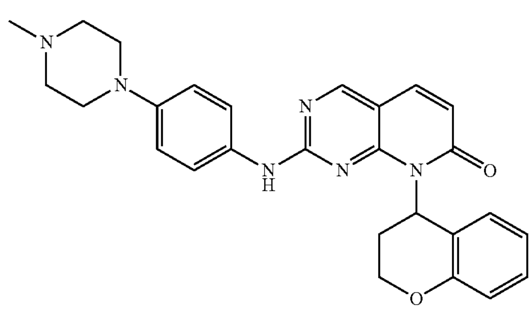 [SMILES: CN1CCN(c2ccc(Nc3ncc4ccc(=O)n(C5CCOc6ccccc65)c4n3)cc2)CC1] | 468.6 | 469 | 2.74 |

-continued
| No. | Structure | MW | LCMS Ion | Rt |
|---|---|---|---|---|
| 17 | 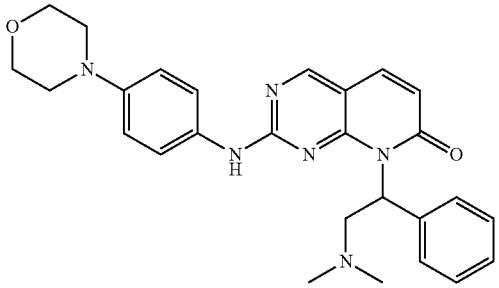 [SMILES: CN(C)CC(c1ccccc1)n1c(=O)ccc2cnc(Nc3ccc(N4CCOCC4)cc3)nc21] | 470.6 | 471 | 2.76 |
| 18 | 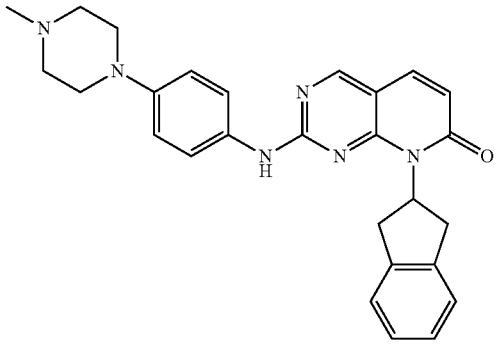 [SMILES: CN1CCN(c2ccc(Nc3ncc4ccc(=O)n(C5Cc6ccccc6C5)c4n3)cc2)CC1] | 452.6 | 453 | 2.92 |
| 19 | 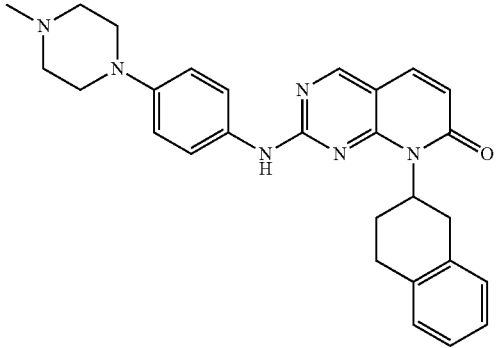 [SMILES: CN1CCN(c2ccc(Nc3ncc4ccc(=O)n(C5CCc6ccccc6C5)c4n3)cc2)CC1] | 466.6 | 465 | 2.97 |
| 20 | 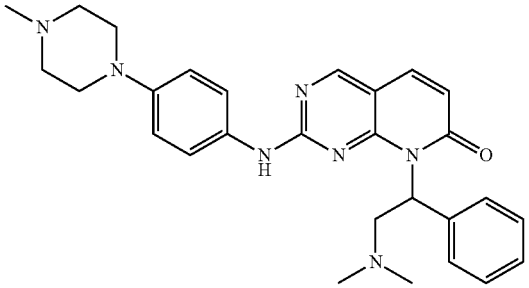 [SMILES: CN(C)CC(c1ccccc1)n1c(=O)ccc2cnc(Nc3ccc(N4CCN(C)CC4)cc3)nc21] | 483.6 | 484 | 2.34 |

| No. | Structure | MW | LCMS Ion | Rt |
|---|---|---|---|---|
| 21 | 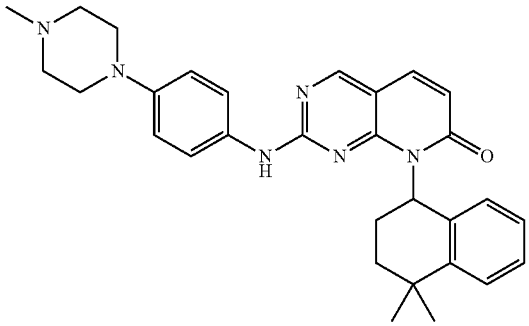 [SMILES: CN1CCN(c2ccc(Nc3ncc4ccc(=O)n(C5CCC(C)(C)c6ccccc65)c4n3)cc2)CC1] | 494.6 | 495 | 3.31 |
| 22 | 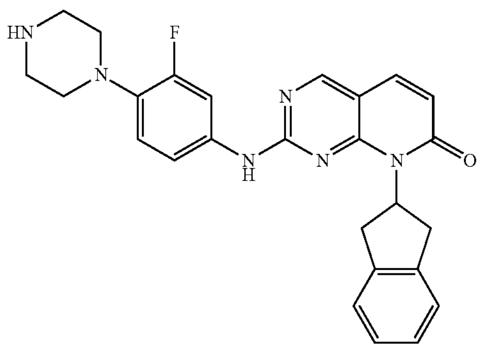 [SMILES: O=c1ccc2cnc(Nc3ccc(N4CCNCC4)c(F)c3)nc2n1C1Cc2ccccc2C1] | 456.5 | 457 | 3.11 |
| 23 | 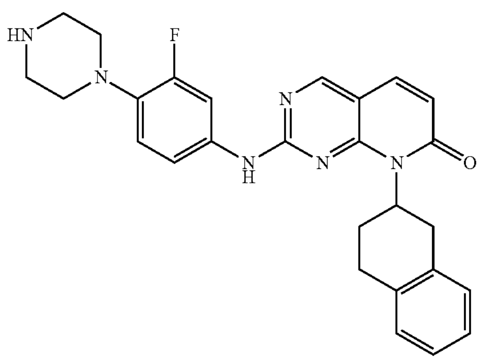 [SMILES: O=c1ccc2cnc(Nc3ccc(N4CCNCC4)c(F)c3)nc2n1C1CCc2ccccc2C1] | 470.6 | 471 | 3.15 |
| 24 | 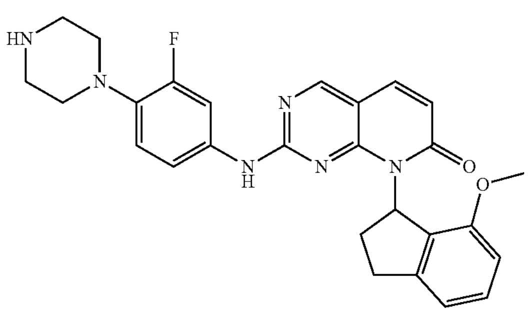 [SMILES: COc1cccc2c1C(n1c(=O)ccc3cnc(Nc4ccc(N5CCNCC5)c(F)c4)nc31)CC2] | 486.6 | 487 | 3.19 |

| No. | Structure | MW | LCMS Ion | Rt |
|---|---|---|---|---|
| 25 | 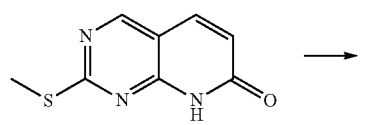 | 487.0 | 487 | 3.20 |
| 26 | 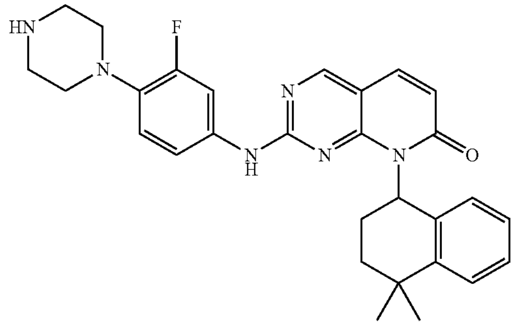 [SMILES: CC1(C)CCC(n2c(=O)ccc3cnc(Nc4ccc(N5CCNCC5)c(F)c4)nc32)c2ccccc21] | 498.6 | 499 | 3.36 |

Example 27

Synthesis of 8-(2-bromobenzyl)-2-(4-(4-methylpiperazin-1-yl)phenylamino)pyrido[2,3-d]pyrimidin-7(8H)-one

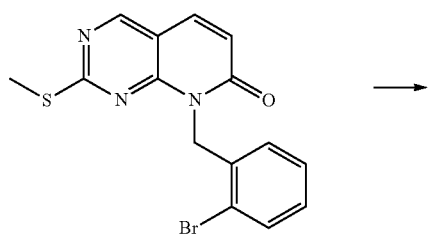

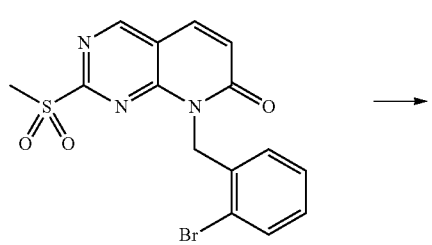

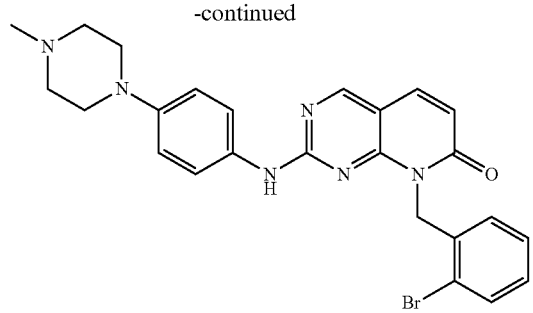

Step 1: Synthesis of 8-(2-bromobenzyl)-2-(methylthio)pyrido[2,3-d]pyrimidin-7(8H)-one To a suspension of NaH (60%, 47 mg, 1.19 mmol) in anhydrous dimethylformamide (2 mL) was added 2-(methylthio)pyrido[2,3-d]pyrimidin-7(8H)-one (150 mg, 0.78 mmol, prepared by the method in example 1, Steps 1-5, using ammonia in the first step) at room temperature and stirred at 60° C. for 0.5 h. The reaction mixture was cooled down to room temperature and 2-bromobenzyl bromide was added and stirred for 48 h. The mixture was diluted with ethyl acetate (20 mL) and 10% brine solution (10 mL), the two phases were separated, the aqueous layer was washed with ethyl acetate (1×20 mL), the combined organic layer was dried over sodium sulfate, filtered and evaporated to give 8-(2-bromobenzyl)-2-(methylthio)pyrido[2,3-d]pyrimidin-7(8H)-one, an orange oil (0.24 g, 0.66 mmol, 84%). ESMS m/z 362 (M+H)$^+$; $^1$H NMR (400 MHz, CDCl$_3$) δ ppm 8.63 (s, 1H), 7.69 (d, J=9.5 Hz, 1H), 7.59 (dd, J=7.4, 1.4 Hz, 1H), 7.05-7.15 (m, 2H), 6.74 (d, J=9.5 Hz, 1H), 6.65 (d, J=7.0 Hz, 1H), 5.69 (s, 2H), 2.38 (s, 3H).

Step 2: Synthesis of 8-(2-bromobenzyl)-2-(methylsulfonyl)pyrido[2,3-d]pyrimidin-7(8H)-one To a solution of 8-(2-bromobenzyl)-2-(methylthio)pyrido[2,3-d]pyrimidin-7(8H)-one (0.24 g, 0.66 mmol) in methanol (20 mL) was added the solution of Oxone (720 mg, 1.17 mmol) in water (10 mL). The mixture was stirred for 18 h, then evaporated to dryness. The residue was dissolved in the mixture of dichloromethane (20 mL) and water (20 mL), separated, and the aqueous layer was extracted with dichloromethane (1×20 mL), and the combined organic layers were dried over sodium sulfate, filtered and concentrated in vacuo to give 8-(2-bromobenzyl)-2-(methylsulfonyl)pyrido[2,3-d]pyrimidin-7(8H)-one as a beige solid (0.17 g, 0.43 mmol, 65%). ESMS m/z 394 (M+H)+.

Step 3: Synthesis of 8-(2-bromobenzyl)-2-(4-(4-methylpiperazin-1-yl)phenylamino)pyrido[2,3-d]pyrimidin-7(8H)-one 8-(2-bromobenzyl)-2-(methylsulfonyl)pyrido[2,3-d]pyrimidin-7(8H)-one (0.17 g, 0.43 mmol) and 4-(4-methylpiperazino)aniline (0.08 g, 0.43 mmol) were stirred at 140° C. for 4 h. The reaction mixture was dissolved in dichloromethane (20 mL) and washed with 10% sodium hydroxide solution (1×10 mL) then with water (1×10 mL). The organic layer was dried over sodium sulfate, filtered and evaporated. The residue was purified by silica gel column chromatography using dichloromethane:methanol (95:5) and the product was recrystallized from isopropanol to give the title compound (19 mg, 0.04 mmol, 9.3%). ESMS m/z 505 (M+H)+; 1H NMR (400 MHz, CDCl3) δ ppm 8.53 (s, 1H), 7.64 (dd, J=7.7, 1.4 Hz, 1H), 7.61 (d, J=9.3 Hz, 1H), 7.06-7.25 (m, 5H), 6.82 (d, J=8.8 Hz, 2H), 6.66 (br. s., 1H), 6.54 (d, J=9.3 Hz, 1H), 5.59 (s, 2H), 3.14-3.21 (m, 4H), 2.55-2.63 (m, 4H), 2.36 (s, 3H).

Examples 28-80

The following compounds were made by the method of Example 30 using the appropriate benzyl bromide, benzyl chloride or phenethyl bromide at Step 1 and aniline at Step 3. If necessary, the benzyl chloride was made by reduction of the appropriate acid or aldehyde to the alcohol followed by conversion to the benzyl chloride with thionyl chloride. Compounds containing secondary amines on the aniline were synthesized using the appropriate Boc protected aminoaniline and in the final step were treated with a solution of hydrogen chloride in an organic solvent to produce the compound, optionally isolated as the hydrochloride salt.

| No. | Structure | MW | LCMS Ion | Rt |
|---|---|---|---|---|
| 28 | 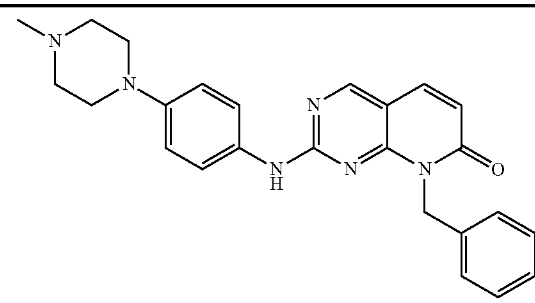 | 426.5 | 427 | 2.42 |
| 29 | 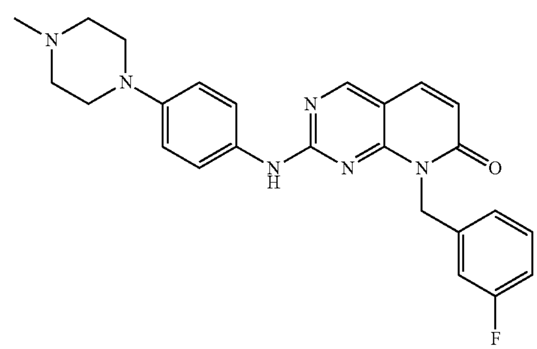 [SMILES: CN1CCN(c2ccc(Nc3ncc4ccc(=O)n(Cc5cccc(F)c5)c4n3)cc2)CC1] | 444.5 | 445 | 2.77 |
| 30 | 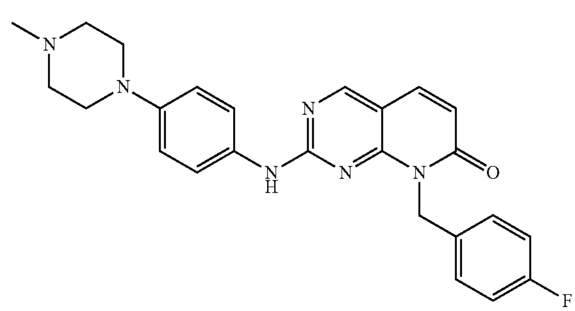 [SMILES: CN1CCN(c2ccc(Nc3ncc4ccc(=O)n(Cc5ccc(F)cc5)c4n3)cc2)CC1] | 444.5 | 445 | 2.79 |

-continued

| No. | Structure | MW | LCMS Ion | Rt |
|---|---|---|---|---|
| 31 | 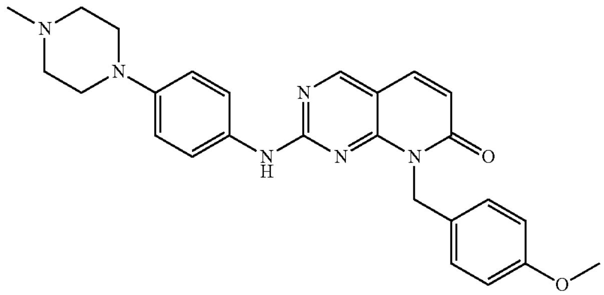 | 456.5 | 457 | 2.78 |
| 32 | 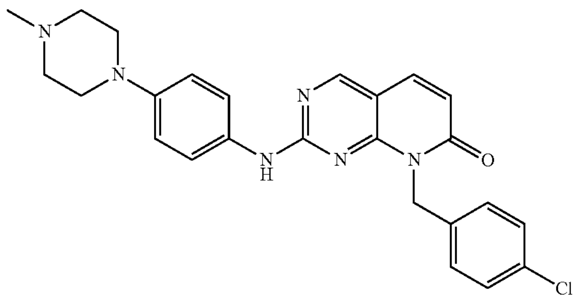 [SMILES: CN1CCN(c2ccc(Nc3ncc4ccc(=O)n(Cc5ccc(Cl)cc5)c4n3)cc2)CC1] | 461.0 | 461 | 2.91 |
| 33 | 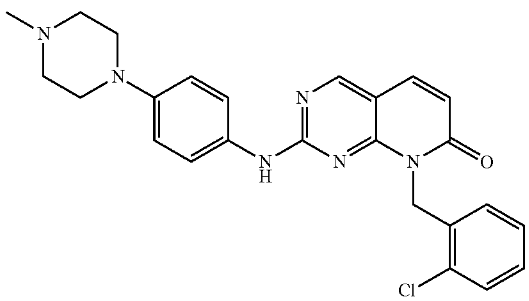 | 461.0 | 461 | 2.84 |
| 34 | 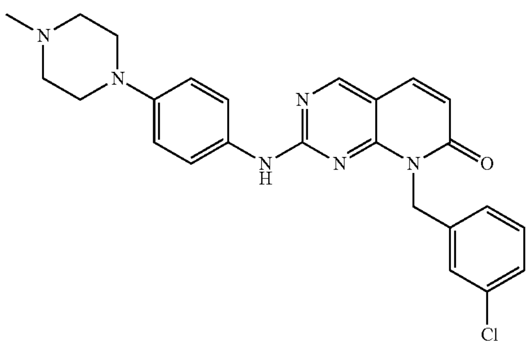 | 461.0 | 461 | 2.90 |
| 35 | 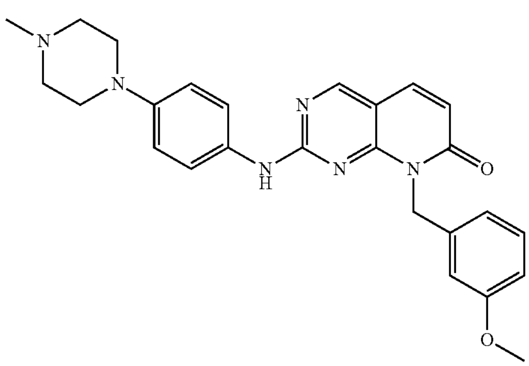 | 456.5 | 457 | 2.78 |

-continued
| No. | Structure | MW | LCMS Ion | Rt |
|---|---|---|---|---|
| 36 | 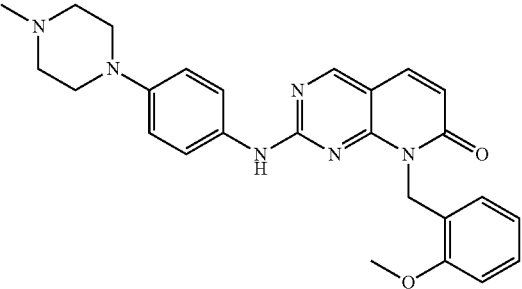 [SMILES: COc1ccccc1Cn1c(=O)ccc2cnc(Nc3ccc(N4CCN(C)CC4)cc3)nc21] | 456.5 | 457 | 2.78 |
| 37 | 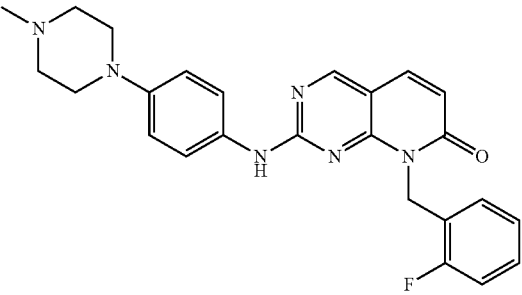 [SMILES: CN1CCN(c2ccc(Nc3ncc4ccc(=O)n(Cc5ccccc5F)c4n3)cc2)CC1] | 444.5 | 445 | 2.75 |
| 38 | 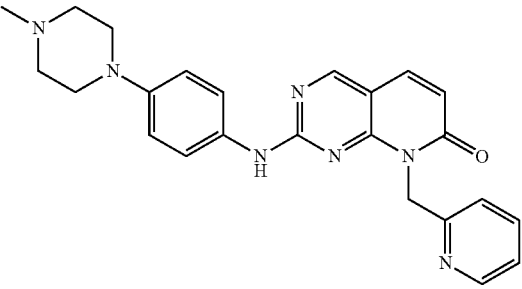 [SMILES: CN1CCN(c2ccc(Nc3ncc4ccc(=O)n(Cc5ccccn5)c4n3)cc2)CC1] | 427.5 | 428 | 2.32 |
| 39 | 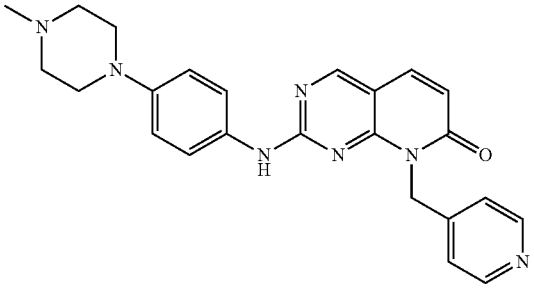 [SMILES: CN1CCN(c2ccc(Nc3ncc4ccc(=O)n(Cc5ccncc5)c4n3)cc2)CC1] | 427.5 | 428 | 1.88 |
| 40 | 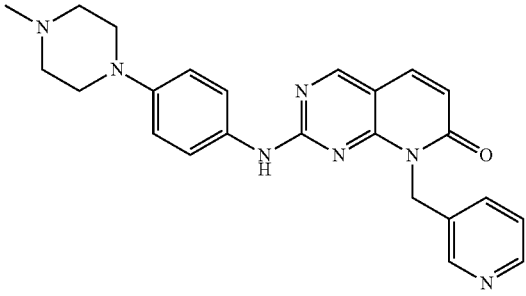 [SMILES: CN1CCN(c2ccc(Nc3ncc4ccc(=O)n(Cc5cccnc5)c4n3)cc2)CC1] | 427.5 | 428 | 2.08 |

-continued
| No. | Structure | MW | LCMS Ion | Rt |
|---|---|---|---|---|
| 41 | 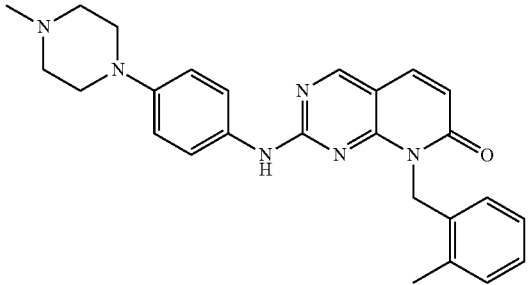 [SMILES: Cc1ccccc1Cn1c(=O)ccc2cnc(Nc3ccc(N4CCN(C)CC4)cc3)nc21] | 440.6 | 441 | 2.74 |
| 42 | 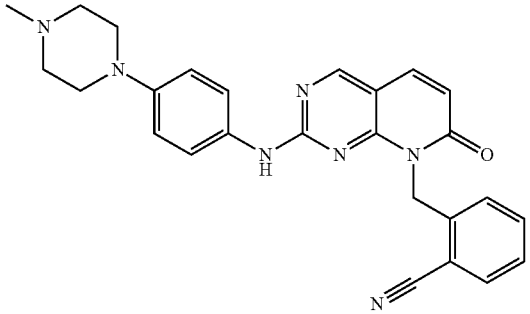 [SMILES: CN1CCN(c2ccc(Nc3ncc4ccc(=O)n(Cc5ccccc5C#N)c4n3)cc2)CC1] | 451.5 | 452 | 2.63 |
| 43 | 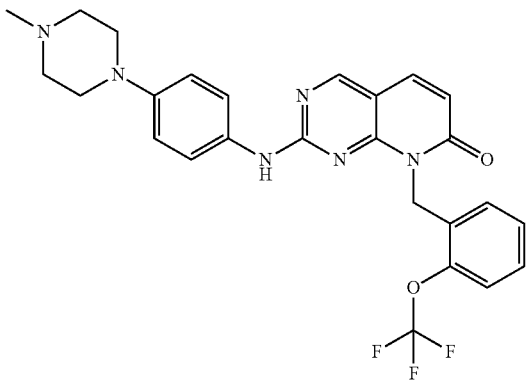 [SMILES: CN1CCN(c2ccc(Nc3ncc4ccc(=O)n(Cc5ccccc5OC(F)(F)F)c4n3)cc2)CC1] | 510.5 | 511 | 2.91 |
| 44 | 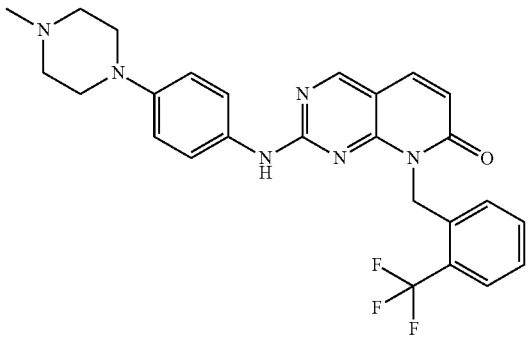 [SMILES: CN1CCN(c2ccc(Nc3ncc4ccc(=O)n(Cc5ccccc5C(F)(F)F)c4n3)cc2)CC1] | 494.5 | 495 | 2.87 |

-continued

| No. | Structure | MW | LCMS Ion | Rt |
|---|---|---|---|---|
| 45 | 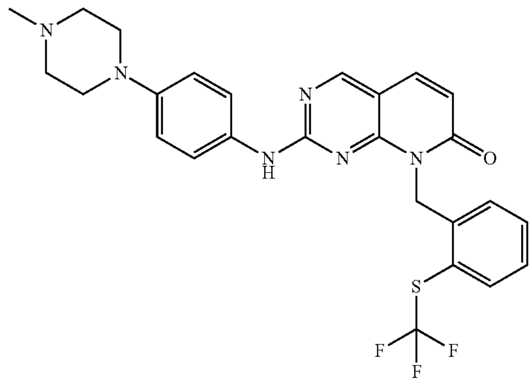 | 526.6 | 527 | 3.01 |
| 46 | 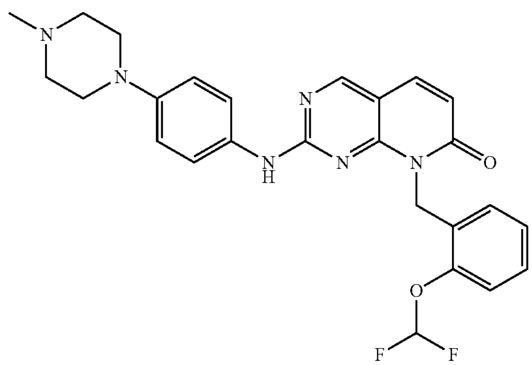 [SMILES: CN1CCN(c2ccc(Nc3ncc4ccc(=O)n(Cc5ccccc5OC(F)F)c4n3)cc2)CC1] | 492.5 | 493 | 2.79 |
| 47 | 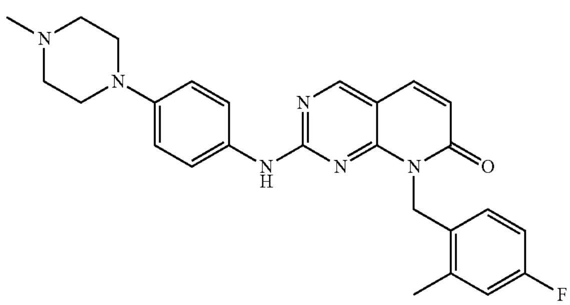 [SMILES: Cc1cc(F)ccc1Cn1c(=O)ccc2cnc(Nc3ccc(N4CCN(C)CC4)cc3)nc21] | 458.5 | 459 | 2.78 |
| 48 | 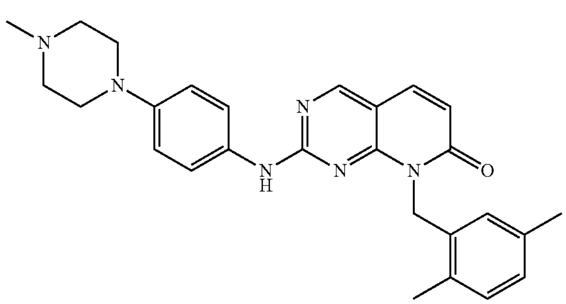 | 454.6 | 455 | 2.81 |

-continued

| No. | Structure | MW | LCMS Ion | Rt |
|---|---|---|---|---|
| 49 | 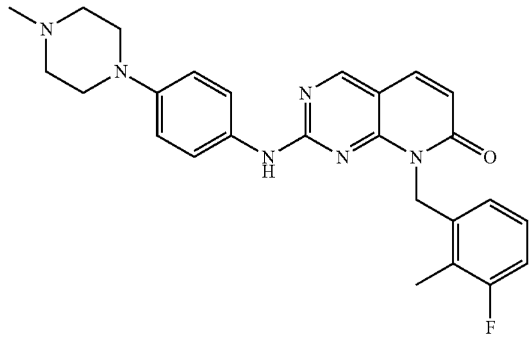 [SMILES: Cc1c(F)cccc1Cn1c(=O)ccc2cnc(Nc3ccc(N4CCN(C)CC4)cc3)nc21] | 458.5 | 459 | 2.79 |
| 50 | 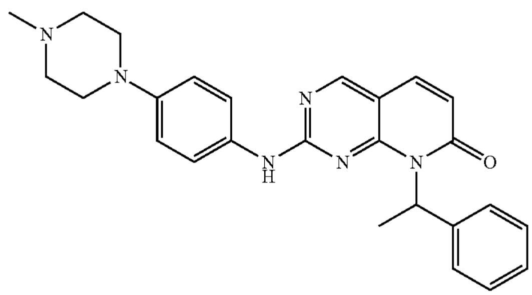 [SMILES: CC(c1ccccc1)n1c(=O)ccc2cnc(Nc3ccc(N4CCN(C)CC4)cc3)nc21] | 440.6 | 441 | 2.72 |
| 51 | 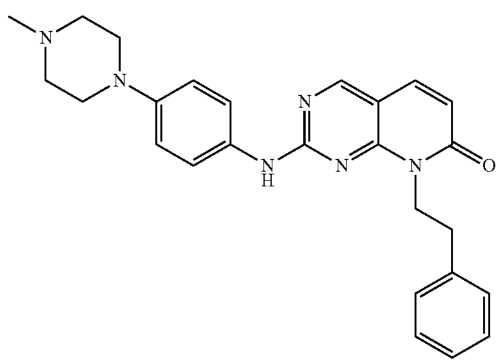 [SMILES: CN1CCN(c2ccc(Nc3ncc4ccc(=O)n(CCc5ccccc5)c4n3)cc2)CC1] | 440.6 | 441 | 2.79 |
| 52 | 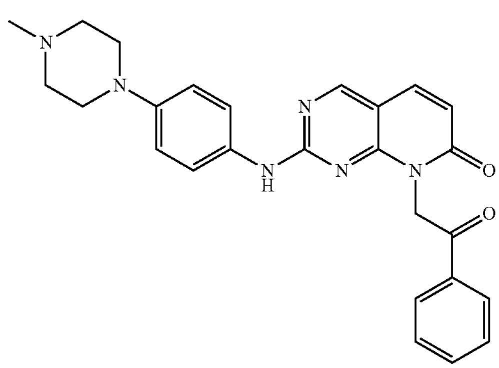 [SMILES: CN1CCN(c2ccc(Nc3ncc4ccc(=O)n(CC(=O)c5ccccc5)c4n3)cc2)CC1] | 454.5 | 455 | 2.55 |

-continued
| No. | Structure | MW | LCMS Ion | Rt |
|---|---|---|---|---|
| 53 | 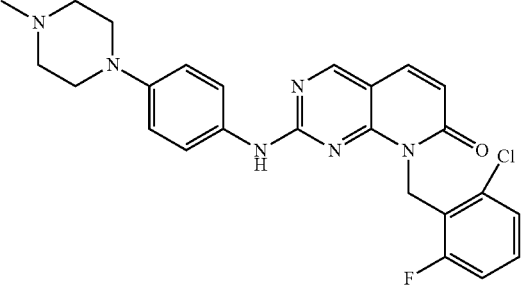 [SMILES: CN1CCN(c2ccc(Nc3ncc4ccc(=O)n(Cc5c(F)cccc5Cl)c4n3)cc2)CC1] | 479.0 | 479 | 2.77 |
| 54 | 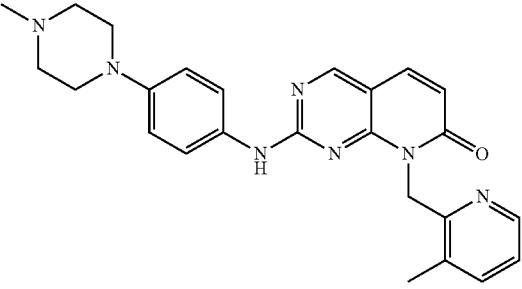 [SMILES: Cc1cccnc1Cn1c(=O)ccc2cnc(Nc3ccc(N4CCN(C)CC4)cc3)nc21] | 441.5 | 442 | 2.23 |
| 55 | 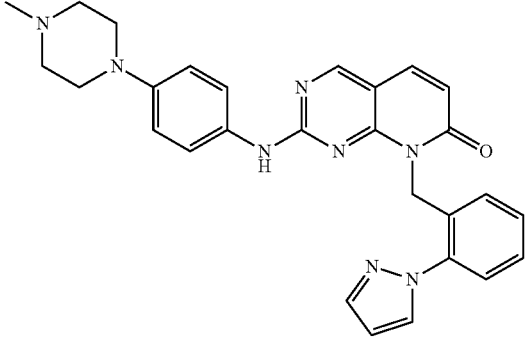 [SMILES: CN1CCN(c2ccc(Nc3ncc4ccc(=O)n(Cc5ccccc5-n5cccn5)c4n3)cc2)CC1] | 492.6 | 493 | 2.65 |
| 56 | 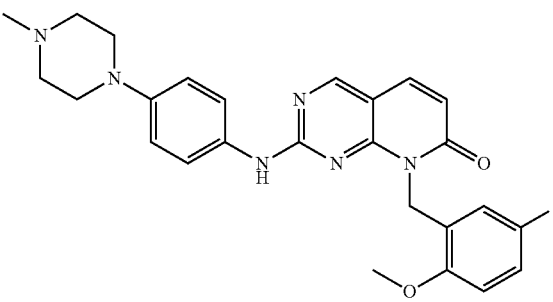 | 474.5 | 475 | 2.75 |
| 57 | 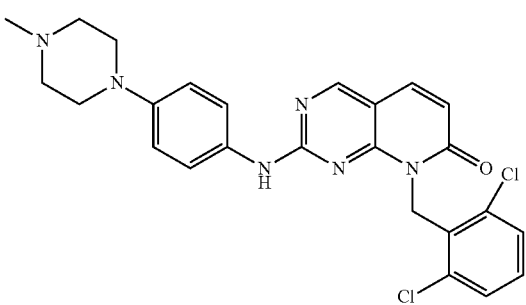 | 495.4 | 495 | 2.84 |

| No. | Structure | MW | LCMS Ion | Rt |
|---|---|---|---|---|
| 58 | 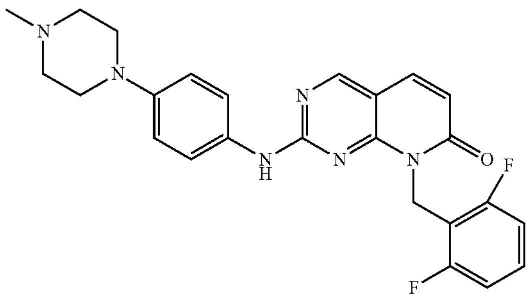 | 462.5 | 463 | 2.72 |
| 59 | 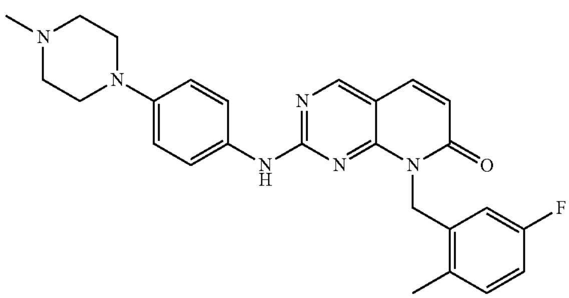 [SMILES: Cc1ccc(F)cc1Cn1c(=O)ccc2cnc(Nc3ccc(N4CCN(C)CC4)cc3)nc21] | 458.5 | 459 | 2.78 |
| 60 | 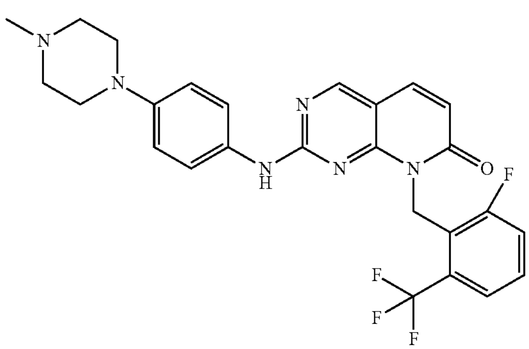 [SMILES: CN1CCN(c2ccc(Nc3ncc4ccc(=O)n(Cc5c(F)cccc5C(F)(F)F)c4n3)cc2)CC1] | 512.5 | 513 | 2.91 |
| 61 | 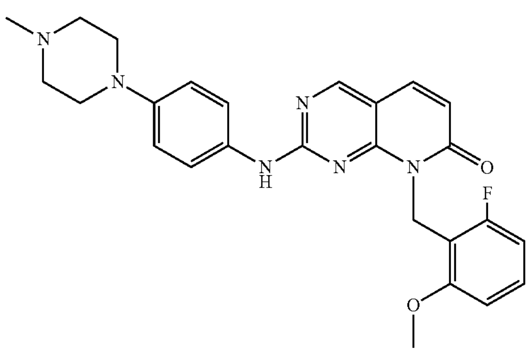 [SMILES: COc1cccc(F)c1Cn1c(=O)ccc2cnc(Nc3ccc(N4CCN(C)CC4)cc3)nc21] | 474.5 | 475 | 2.74 |

-continued

| No. | Structure | MW | LCMS Ion | Rt |
|---|---|---|---|---|
| 62 | 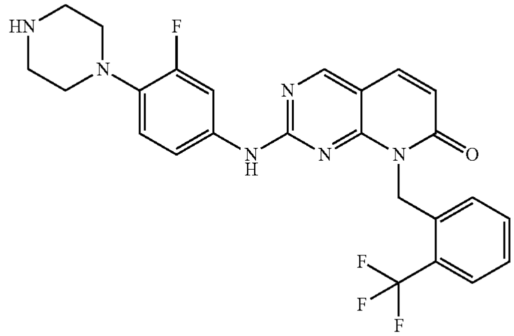 [SMILES: O=c1ccc2cnc(Nc3ccc(N4CCNCC4)c(F)c3)nc2n1Cc1ccccc1C(F)(F)F] | 498.5 | 499 | 2.85 |
| 63 | 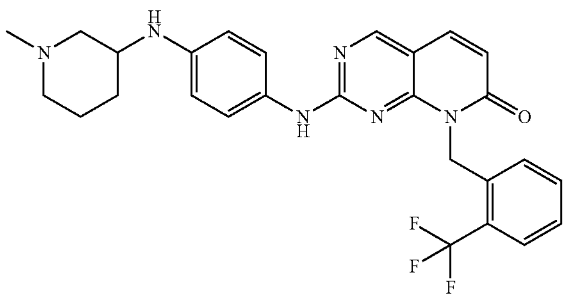 [SMILES: CN1CCCC(Nc2ccc(Nc3ncc4ccc(=O)n(Cc5ccccc5C(F)(F)F)c4n3)cc2)C1] | 508.5 | 509 | 2.90 |
| 64 | 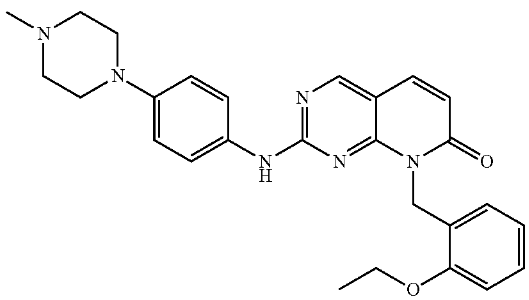 [SMILES: CCOc1ccccc1Cn1c(=O)ccc2cnc(Nc3ccc(N4CCN(C)CC4)cc3)nc21] | 470.6 | 471 | 2.83 |
| 65 | 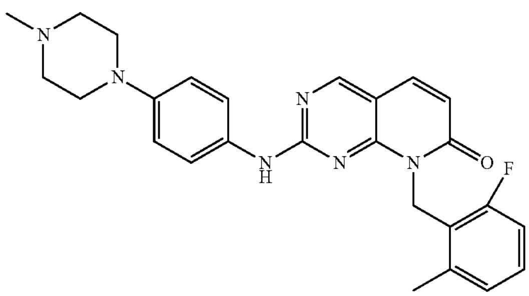 | 458.5 | 459 | 2.75 |
| 66 | 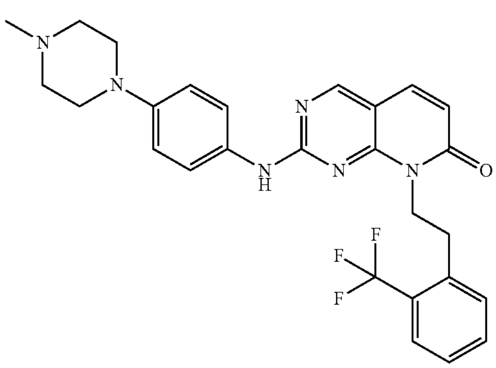 [SMILES: CN1CCN(c2ccc(Nc3ncc4ccc(=O)n(CCc5ccccc5C(F)(F)F)c4n3)cc2)CC1] | 508.5 | 509 | 2.98 |

| No. | Structure | MW | LCMS Ion | Rt |
|---|---|---|---|---|
| 67 | 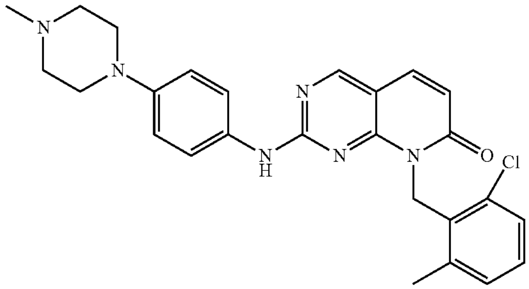 [SMILES: Cc1cccc(Cl)c1Cn1c(=O)ccc2cnc(Nc3ccc(N4CCN(C)CC4)cc3)nc21] | 475.0 | 475 | 2.88 |
| 68 | 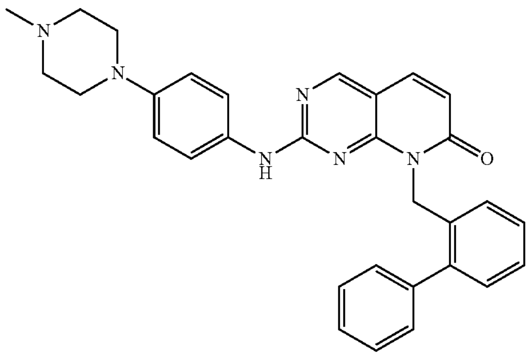 [SMILES: CN1CCN(c2ccc(Nc3ncc4ccc(=O)n(Cc5ccccc5-c5ccccc5)c4n3)cc2)CC1] | 502.6 | 503 | 2.99 |
| 69 | 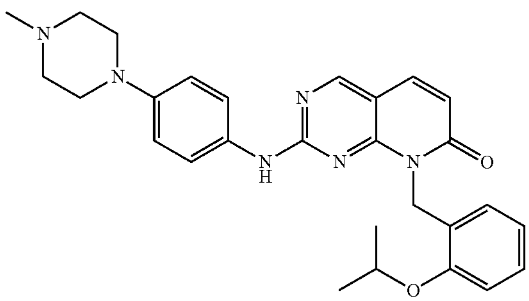 [SMILES: CC(C)Oc1ccccc1Cn1c(=O)ccc2cnc(Nc3ccc(N4CCN(C)CC4)cc3)nc21] | 484.6 | 485 | 2.92 |
| 70 | 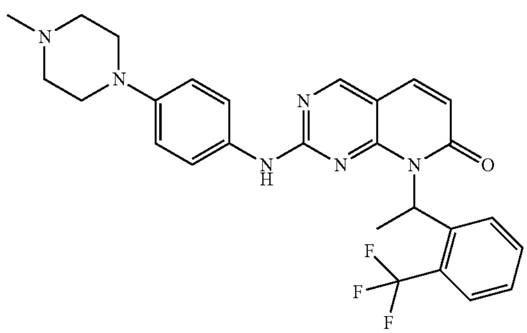 [SMILES: CC(c1ccccc1C(F)(F)F)n1c(=O)ccc2cnc(Nc3ccc(N4CCN(C)CC4)cc3)nc21] | 508.5 | 509 | 2.95 |
| 71 | 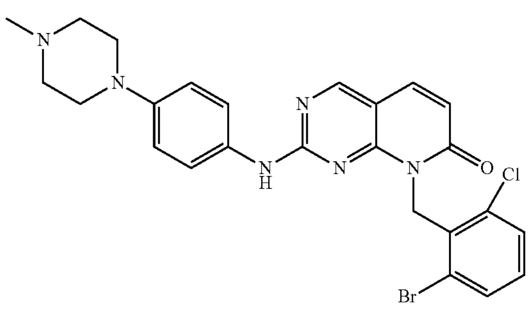 [SMILES: CN1CCN(c2ccc(Nc3ncc4ccc(=O)n(Cc5c(Cl)cccc5Br)c4n3)cc2)CC1] | 539.9 | 539 | 2.97 |

| No. | Structure | MW | LCMS Ion | Rt |
|---|---|---|---|---|
| 72 | 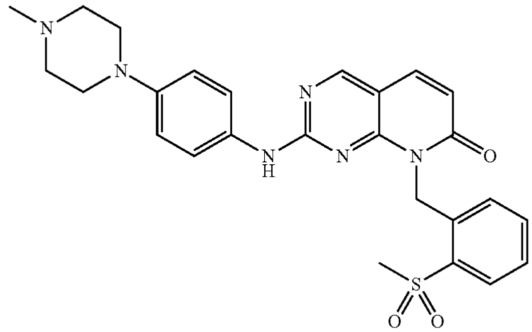 [SMILES: CN1CCN(c2ccc(Nc3ncc4ccc(=O)n(Cc5ccccc5S(C)(=O)=O)c4n3)cc2)CC1] | 504.6 | 505 | 2.61 |
| 73 | 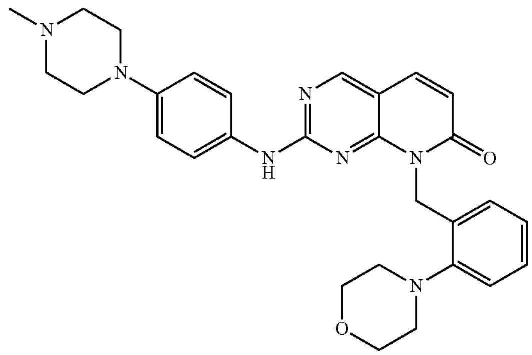 [SMILES: CN1CCN(c2ccc(Nc3ncc4ccc(=O)n(Cc5ccccc5N5CCOCC5)c4n3)cc2)CC1] | 511.6 | 512 | 2.80 |
| 74 | 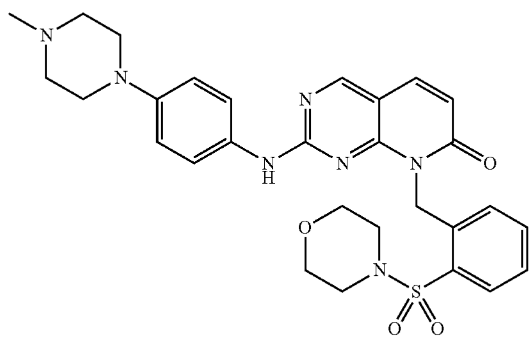 [SMILES: CN1CCN(c2ccc(Nc3ncc4ccc(=O)n(Cc5ccccc5S(=O)(=O)N5CCOCC5)c4n3)cc2)CC1] | 575.7 | 576 | 2.71 |
| 75 | 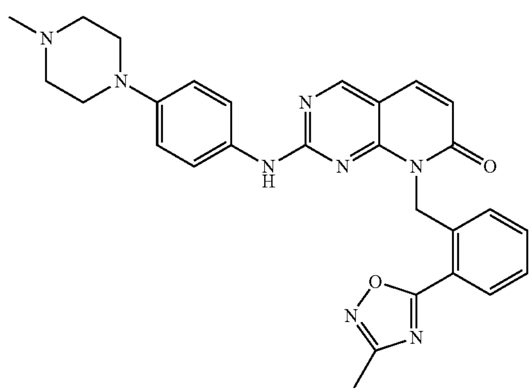 [SMILES: Cc1noc(-c2ccccc2Cn2c(=O)ccc3cnc(Nc4ccc(N5CCN(C)CC5)cc4)nc32)n1] | 508.6 | 509 | 2.86 |

-continued

| No. | Structure | MW | LCMS Ion | Rt |
|---|---|---|---|---|
| 76 | 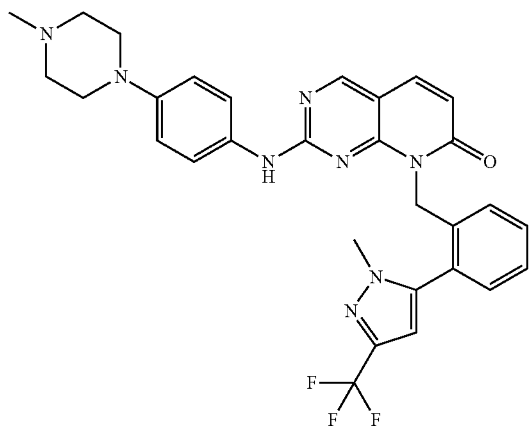 [SMILES: CN1CCN(c2ccc(Nc3ncc4ccc(=O)n(Cc5ccccc5-c5cc(C(F)(F)F)nn5C)c4n3)cc2)CC1] | 574.6 | 575 | 3.15 |
| 77 | 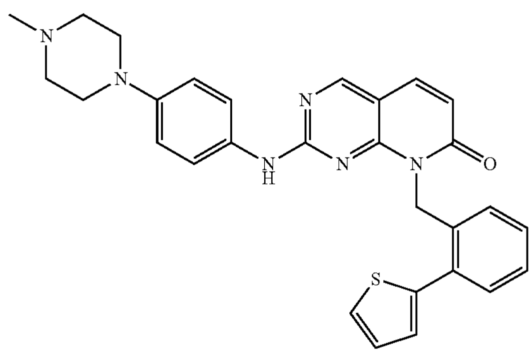 [SMILES: CN1CCN(c2ccc(Nc3ncc4ccc(=O)n(Cc5ccccc5-c5cccs5)c4n3)cc2)CC1] | 508.6 | 509 | 3.06 |
| 78 | 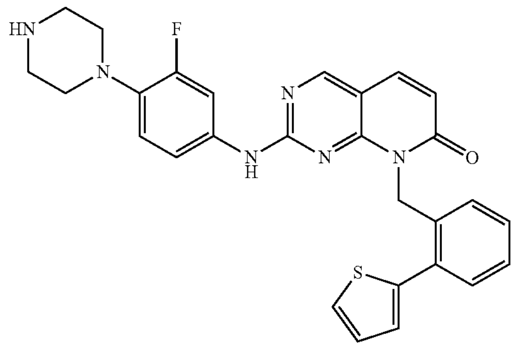 [SMILES: O=c1ccc2cnc(Nc3ccc(N4CCNCC4)c(F)c3)nc2n1Cc1ccccc1-c1cccs1] | 512.6 | 513 | 3.11 |
| 79 | 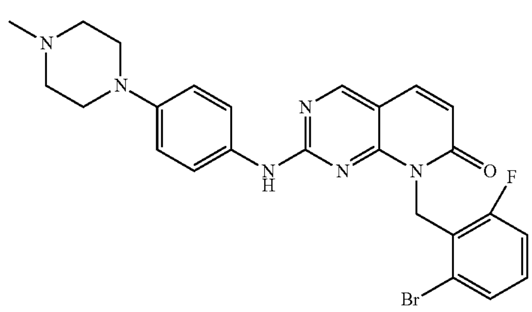 | 523.4 | 523 | 2.96 |

| No. | Structure | MW | LCMS Ion | Rt |
|---|---|---|---|---|
| 80 | 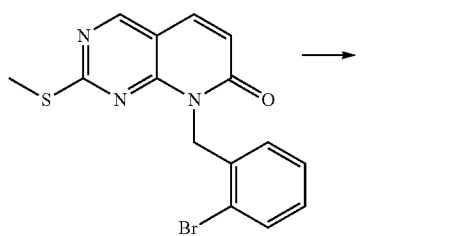 | 512.5 | 513 | 2.96 |

Example 81

Synthesis of 8-(2-cyclopropylbenzyl)-2-(4-(4-methylpiperazin-1-yl)phenylamino)pyrido[2,3-d]pyrimidin-7(8H)-one

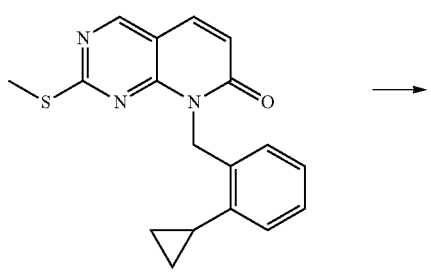

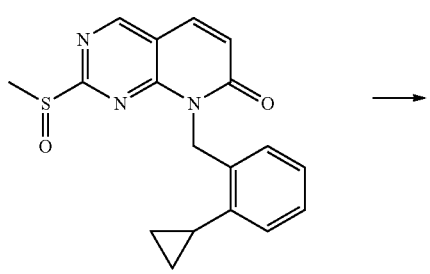

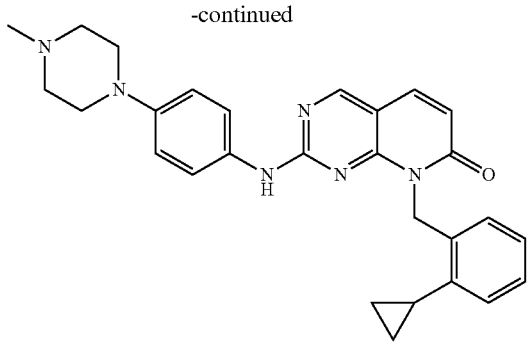

Step 1: Synthesis of 8-(2-cyclopropylbenzyl)-2-(methylthio)pyrido[2,3-d]pyrimidin-7(8H)-one 8-(2-bromobenzyl)-2-(methylthio)pyrido[2,3-d]pyrimidin-7(8H)-one (150 mg, 0.41 mmol, Example 30), cyclopropylboronic acid (107 mg, 1.25 mmol), $K_3PO_4$ (264 mg, 1.24 mmol) and $PdCl_2(Pcy_3)_2$ (15 mg, 0.02 mmol) were mixed as solids and placed under argon. Argon was bubbled through a mixture of toluene:water (20:1, 1.5 mL) for 20 min. The solvent was added to the solid and the suspension was heated under microwave irradiation at 140° C. for 1.5 h. The reaction mixture was then diluted with toluene (10 mL) and water (1×5 mL), the two phases were separated, and the aqueous layer was extracted with toluene (1×10 mL). The combined organic layers were washed with water (1×10 mL) and evaporated to dryness. The crude compound was purified by silica gel column chromatography using dichloromethane:methanol (100:0.5) to yield 8-(2-cyclopropylbenzyl)-2-(methylthio)pyrido[2,3-d]pyrimidin-7(8H)-one as an off-white solid (88 mg, 0.27 mmol, 66%). ESMS m/z 324 (M+H)$^+$.

Step 2: Synthesis of 8-(2-cyclopropylbenzyl)-2-(methylsulfinyl)pyrido[2,3-d]pyrimidin-7(8H)-one To a solution of 8-(2-cyclopropylbenzyl)-2-(methylthio)pyrido[2,3-d]pyrimidin-7(8H)-one (88 mg, 0.27 mmol) in dichloromethane (1 mL) was added 3-chloroperbenzoic acid (70%, 67 mg, 0.27 mmol) at 0-5° C. and the mixture was stirred at room temperature for 18 h. After completion, it was diluted with dichloromethane (10 mL) and washed with saturated sodium bicarbonate solution (1×5 mL) then with water (1×5 mL). The organic layer was dried over sodium sulfate, filtered and evaporated to give 8-(2-cyclopropylbenzyl)-2-(methylsulfinyl)pyrido[2,3-d]pyrimidin-7(8H)-one as a pale yellow solid (80 mg, 0.23 mmol, 85%). ESMS m/z 340 (M+H)⁺.

Step 3: Synthesis of 8-(2-cyclopropylbenzyl)-2-(4-(4-methylpiperazin-1-yl)phenylamino)pyrido[2,3-d]pyrimidin-7(8H)-one 8-(2-cyclopropylbenzyl)-2-(methylsulfinyl)pyrido[2,3-d]pyrimidin-7(8H)-one (80 mg, 0.24 mmol) and 4-(4-methylpiperazino)aniline (45 mg, 0.24 mmol) were stirred at 140° C. for 3 h. After completion, the reaction mixture was purified by silica gel column chromatography using chloroform:methanol (100:3). The crude product was recrystallized from acetonitrile to give the title compound (31 mg, 0.07 mmol, 29%). ESMS m/z 467 (M+H)⁺; ¹H NMR (400 MHz, CDCl₃) δ ppm 8.53 (s, 1H), 7.60 (d, J=9.3 Hz, 1H), 7.14-7.20 (m, 2H), 6.99-7.13 (m, 4H), 6.71 (br. s., 2H), 6.63 (d, J=7.5 Hz, 1H), 6.54 (d, J=9.3 Hz, 1H), 5.72 (s, 2H), 3.12-3.18 (m, 4H), 2.54-2.64 (m, 4H), 2.36 (s, 3H), 2.00-2.11 (m, 1H), 0.90-0.99 (m, 2H), 0.69-0.77 (m, 2H).

Examples 82-85

The following compounds were made by the method of Example 81 using the appropriate 8-(2-bromobenzyl)-2-(methylthio)pyrido[2,3-d]pyrimidin-7(8H)-one starting material and boronic acid at Step 1 and aniline at Step 3. Compounds containing secondary amines on the aniline were synthesized using the appropriate Boc protected aminoaniline and in the final step were treated with a solution of hydrogen chloride in an organic solvent to produce the compound, optionally isolated as the hydrochloride salt.

| No. | Structure | MW | LCMS Ion | Rt |
|---|---|---|---|---|
| 82 | 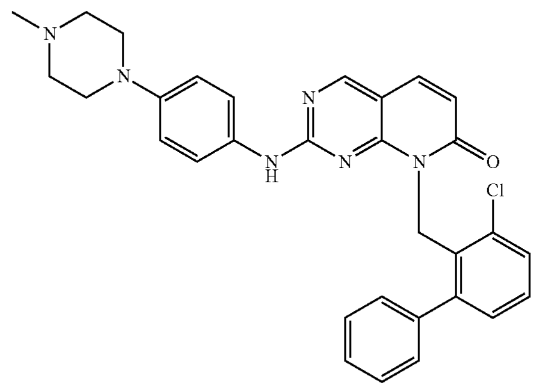 [SMILES: CN1CCN(c2ccc(Nc3ncc4ccc(=O)n(Cc5c(Cl)cccc5-c5ccccc5)c4n3)cc2)CC1] | 537.1 | 537 | 3.12 |
| 83 | 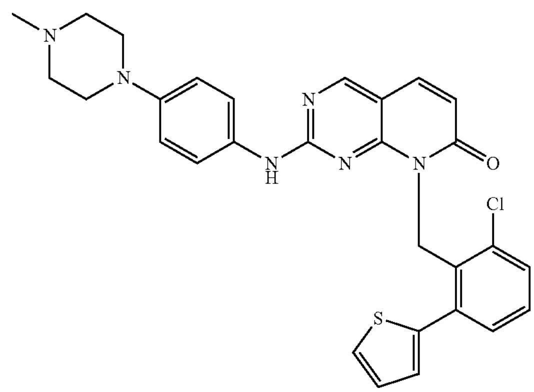 [SMILES: CN1CCN(c2ccc(Nc3ncc4ccc(=O)n(Cc5c(Cl)cccc5-c5cccs5)c4n3)cc2)CC1] | 543.1 | 543 | 3.29 |
| 84 | 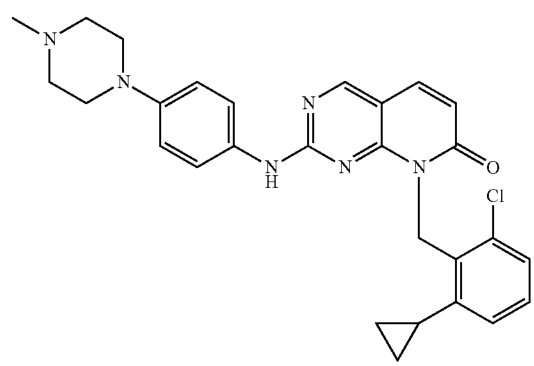 [SMILES: CN1CCN(c2ccc(Nc3ncc4ccc(=O)n(Cc5c(Cl)cccc5C5CC5)c4n3)cc2)CC1] | 501.0 | 501 | 3.24 |

-continued
| No. | Structure | MW | LCMS Ion | Rt |
|---|---|---|---|---|
| 85 | 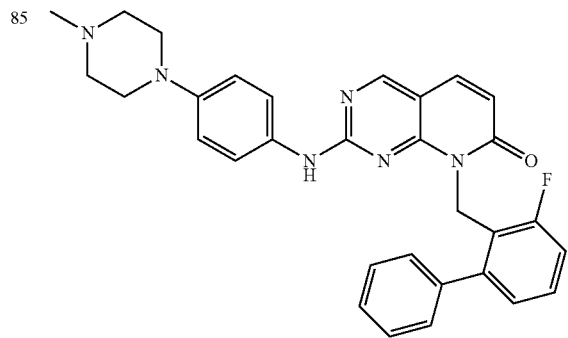 | | | |
| 86 | 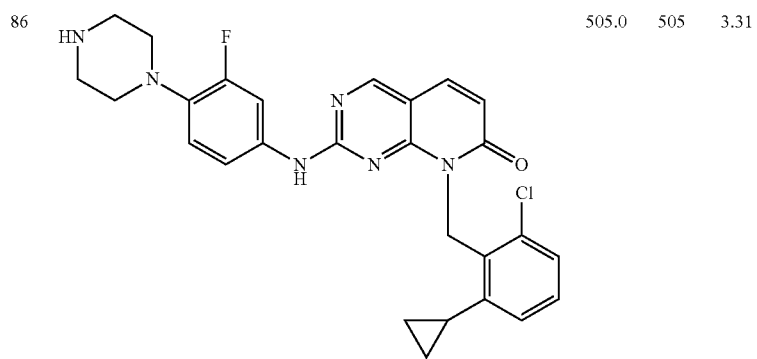 | 505.0 | 505 | 3.31 |
| 87 | 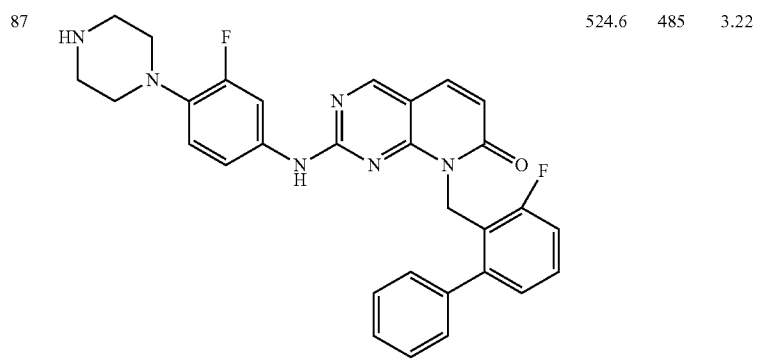 | 524.6 | 485 | 3.22 |

Examples 88-90

The following compounds were made by using the method of Example 81 Step 1 as the last step starting with 8-(2-Bromo-6-fluoro-benzyl)-2-[4-(4-methyl-piperazin-1-yl)-phenylamino]-8H-pyrido[2,3-d]pyrimidin-7-one and the appropriate boronic acid.

| No. | Structure | MW | LCMS Ion | Rt |
|---|---|---|---|---|
| 88 | 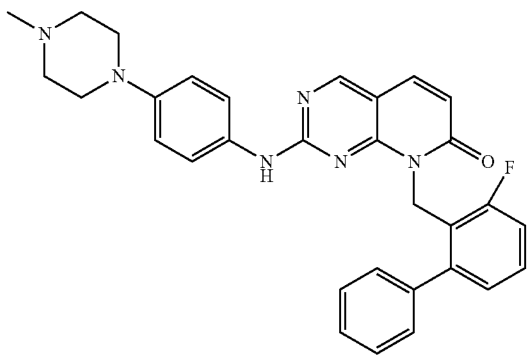 [SMILES: CN1CCN(c2ccc(Nc3ncc4ccc(=O)n(Cc5c(F)cccc5-c5ccccc5)c4n3)cc2)CC1] | 520.6 | 521 | 3.26 |
| 89 | 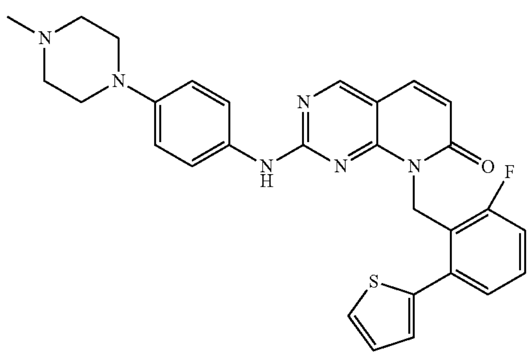 [SMILES: CN1CCN(c2ccc(Nc3ncc4ccc(=O)n(Cc5c(F)cccc5-c5cccs5)c4n3)cc2)CC1] | 526.6 | 527 | 3.28 |
| 90 | 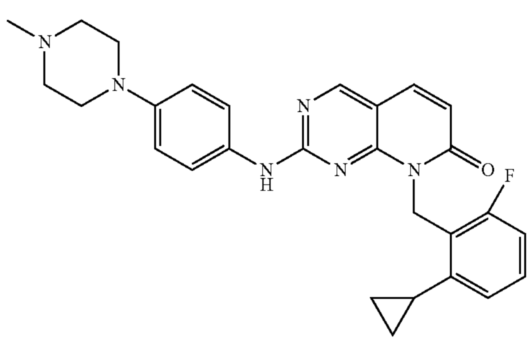 [SMILES: CN1CCN(c2ccc(Nc3ncc4ccc(=O)n(Cc5c(F)cccc5C5CC5)c4n3)cc2)CC1] | 484.6 | 485 | 3.22 |

Example 91

Synthesis of 8-(2-fluoro-6-(methylthio)benzyl)-2-(4-(4-methylpiperazin-1-yl)phenylamino)pyrido[2,3-d]pyrimidin-7(8H)-one

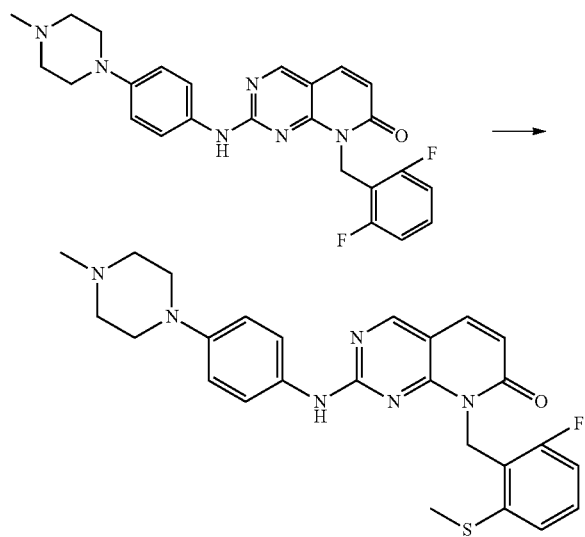

Step 1: Synthesis of 8-(2-fluoro-6-(methylthio)benzyl)-2-(4-(4-methylpiperazin-1-yl)phenylamino)pyrido[2,3-d]pyrimidin-7(8H)-one 8-(2,6-difluorobenzyl)-2-(4-(4-methylpiperazin-1-yl)phenylamino)pyrido[2,3-d]pyrimidin-7(8H)-one (23 mg, 0.05 mmol, Example 61) was treated with NaSMe (5 mg, 0.06 mmol) in DMSO (0.2 mL) at 100° C. for 2 h. The reaction mixture was diluted with water, the precipitated product was filtered off, then purified by silica gel column chromatography using dichloromethane:methanol (95:5) to give 8-(2-fluoro-6-(methylthio)benzyl)-2-(4-(4-methylpiperazin-1-yl)phenylamino)pyrido[2,3-d]pyrimidin-7(8H)-one (22 mg, Y=90%). ESMS m/z 491 (M+H)$^+$.

Examples 92-93

Synthesis of 8-(2-fluoro-6-(methylsulfinyl)benzyl)-2-(4-(4-methylpiperazin-1-yl)phenylamino)pyrido[2,3-d]pyrimidin-7(8H)-one and 8-(2-fluoro-6-(methylsulfonyl)benzyl)-2-(4-(4-methylpiperazin-1-yl)phenylamino)pyrido[2,3-d]pyrimidin-7(8H)-one

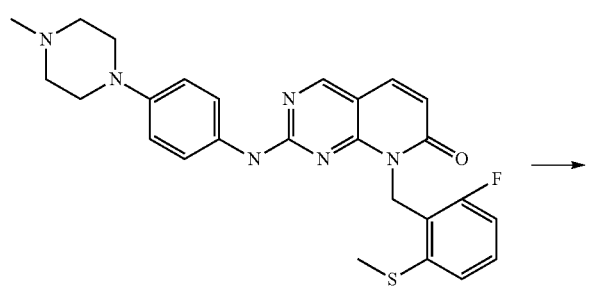

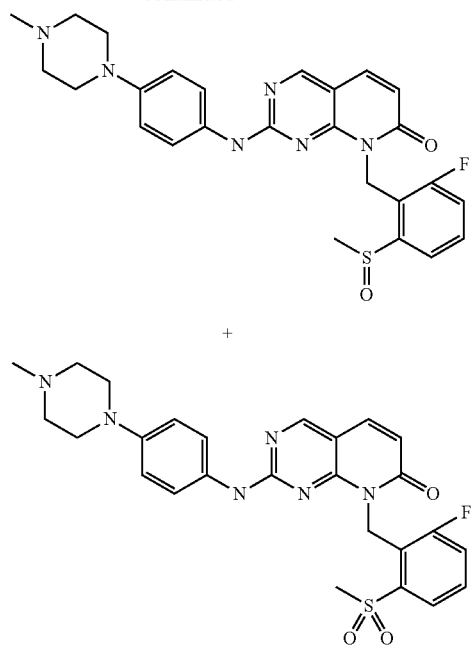

Step 1: Synthesis of 8-(2-fluoro-6-(methylsulfinyl)benzyl)-2-(4-(4-methylpiperazin-1-yl)phenylamino)pyrido[2,3-d]pyrimidin-7(8H)-one and 8-(2-fluoro-6-(methylsulfonyl)benzyl)-2-(4-(4-methylpiperazin-1-yl)phenylamino)pyrido[2,3-d]pyrimidin-7(8H)-one 8-(2-fluoro-6-(methylthio)benzyl)-2-(4-(4-methylpiperazin-1-yl)phenylamino)pyrido[2,3-d]pyrimidin-7(8H)-one (15 mg, 0.03 mmol, Example 94) was reacted with mCPBA (8 mg, 0.05 mmol) in dichloromethane (1 mL) for 2 hours at room temperature. It resulted in the mixture of 8-(2-fluoro-6-(methylsulfinyl)benzyl)-2-(4-(4-methylpiperazin-1-yl)phenylamino)pyrido[2,3-d]pyrimidin-7(8H)-one and 8-(2-fluoro-6-(methylsulfonyl)benzyl)-2-(4-(4-methylpiperazin-1-yl)phenylamino)pyrido[2,3-d]pyrimidin-7(8H)-one; they were separated by preparative HPLC to give (2.5 mg, Y=16%, ESMS m/z 507 (M+H)$^+$) and (1.1 mg; Y=7%, ESMS m/z 523 (M+H)$^+$).

Example 94

Synthesis of N-(5-{2-[4-(4-Methyl-piperazin-1-yl)-phenylamino]-pyrimidin-4-yl}-pyridin-2-yl)-ethane-1,2-diamine hydrochloride

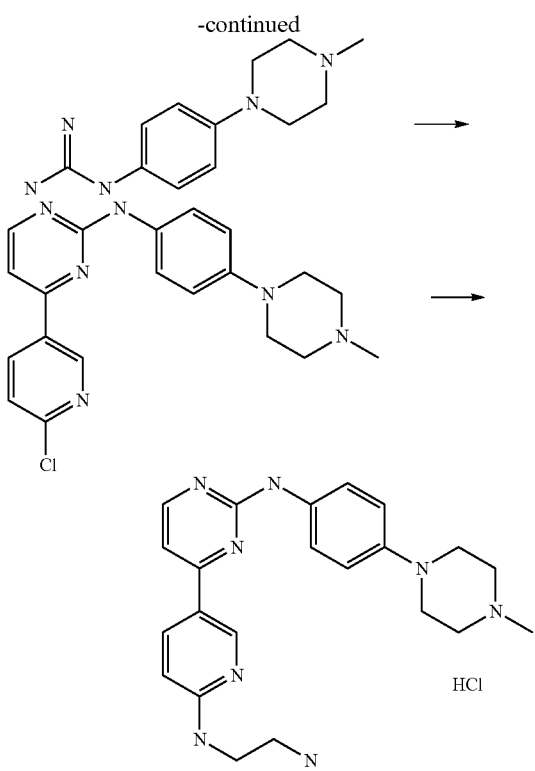

Step 1: Synthesis of 1-(6-Chloro-pyridin-3-yl)-3-dimethylamino-propenone

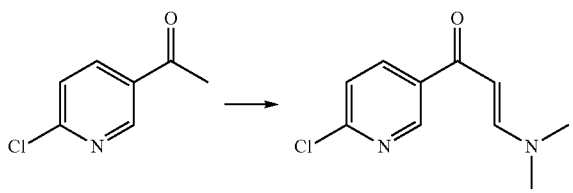

5.00 g (32.2 mmol) 1-(6-Chloro-pyridin-3-yl)-ethanone was dissolved in 40 mL dimethylformamide dimethylacetal, and stirred at 105° C. for 2 h. The solution was cooled to room temperature, and the yellow precipitate was filtered to give 1-(6-Chloro-pyridin-3-yl)-3-dimethylamino-propenone (4.565 g, Y=67%) that was used without further purification.

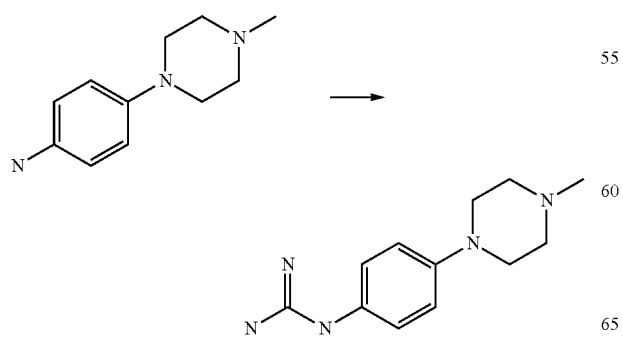

Step 2: Synthesis of N-[4-(4-Methyl-piperazin-1-yl)-phenyl]-guanidine hydrochloride 10.00 g 4-(4-Methyl-piperazin-1-yl)-aniline (52 mmol) was dissolved in 30 mL ethanol, 4.37 g cyanamide (104 mmol) and 7.3 mL of 65% nitric acid (114 mmol) were added. The reaction was stirred at 85° C. for 18 h under a nitrogen atmosphere. It was concentrated in vacuo, and the black residue was washed with isopropanol at reflux (3×25 mL). The solid was cooled to room temperature and ground under isopropanol in a ceramic mortar to give N-[4-(4-Methyl-piperazin-1-yl)-phenyl]-guanidine hydrochloride (12.0 g, Y=77%) as a hygroscopic black powder.

Step 3: Synthesis of [4-(6-Chloro-pyridin-3-yl)-pyrimidin-2-yl]-[4-(4-methyl-piperazin-1-yl)-phenyl]-amine 4.22 g 1-(6-Chloro-pyridin-3-yl)-3-dimethylamino-propenone (20 mmol) was dissolved in 100 mL isopropanol, 5.92 g N-[4-(4-Methyl-piperazin-1-yl)-phenyl]-guanidine hydrochloride (20 mmol) and 0.96 g sodium hydroxide (24 mmol) were added and heated at reflux for 18 h. The mixture was allowed to cool to room temperature and stirred at room temperature for three days. The yellow-green precipitate was filtered to give [4-(6-Chloro-pyridin-3-yl)-pyrimidin-2-yl]-[4-(4-methyl-piperazin-1-yl)-phenyl]-amine (2.50 g, Y=33%). Purity: 94% (LCMS); $^1$H NMR (400 MHz, DMSO-$d_6$) δ ppm 9.49 (s, 1H), 9.14 (d, J=2.5 Hz, 1H), 8.54 (d, J=5.3 Hz, 1H), 8.52 (dd, J=8.5, 2.5 Hz, 1H), 7.70 (d, J=8.5 Hz, 1H), 7.60 (d, J=9.0 Hz, 2H), 7.41 (d, J=5.3 Hz, 1H), 6.91 (d, J=9.0 Hz, 2H), 3.03-3.10 (m, 4H), 2.42-2.47 (m, 4H), 2.22 (s, 3H).

Step 4: Synthesis of N-(5-{2-[4-(4-Methyl-piperazin-1-yl)-phenylamino]-pyrimidin-4-yl}-pyridin-2-yl)-ethane-1,2-diamine 0.15 g (0.39 mmol) of [4-(6-Chloro-pyridin-3-yl)-pyrimidin-2-yl]-[4-(4-methyl-piperazin-1-yl)-phenyl]-amine was dissolved in 2.5 mL ethylenediamine and heated in a sealed tube at 120° C. for 18 h. The reaction was cooled and evaporated to dryness and the crude product was purified by silica gel column chromatography using dichloromethane:methanol:triethylamine (9:1:0.05 to 1:1:0.05) to give the title compound as a pale yellow solid (58 mg, 0.14 mmol, 36%). The product was dissolved in dichloromethane (2 mL) then 0.51 M hydrochloric acid:diethyl ether (0.275 mL, 0.14 mmol) was added, it was stirred for 0.5 h. The mixture was evaporated and the residue was suspended in methanol and filtered to give N-(5-{2-[4-(4-Methyl-piperazin-1-yl)-phenylamino]-pyrimidin-4-yl}-pyridin-2-yl)-ethane-1,2-diamine hydrochloride (35.5 mg, 0.08 mmol, 21%). ESMS m/z 405 (M+H)$^+$; $^1$H NMR (400 MHz, DMSO-$d_6$) δ ppm 9.23 (s, 1H), 8.84 (d, J=2.0 Hz, 1H), 8.36 (d, J=5.3 Hz, 1H), 8.15 (dd, J=8.8, 2.3 Hz, 1H), 7.87 (br. S., 3H), 7.62 (d, J=9.3 Hz, 2H), 7.33 (t, J=6.3 Hz, 1H), 7.19 (d, J=5.3 Hz, 1H), 6.91 (d, J=9.3 Hz, 2H), 6.65 (d, J=8.5 Hz, 1H), 3.57 (q, J=6.3 Hz, 2H), 3.05-3.12 (m, 4H), 3.01 (t, J=6.3 Hz, 2H), 2.46-2.49 (m, 4H), 2.25 (s, 3H).

Examples 95-115

The following compounds were made by the method of Example 94 using the appropriate guanidine at Step 1, and the appropriate amine at Step 4. Example 110 was synthesized using (2-methylaminoethyl)-carbamic acid tert-butyl ester followed by deprotection with hydrochloric acid in diethyl ether.

| No. | Structure | MW | LCMS Ion | Rt |
|---|---|---|---|---|
| 95 | 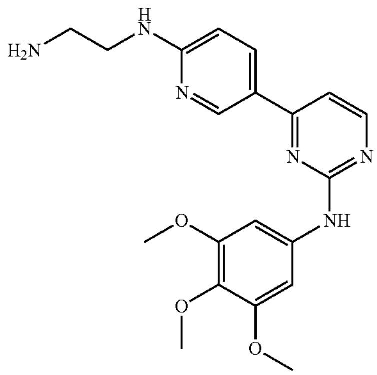 [SMILES: COc1cc(Nc2nccc(-c3ccc(NCCN)nc3)n2)cc(OC)c1OC] | 396.5 | 397 | 2.12 |
| 96 | 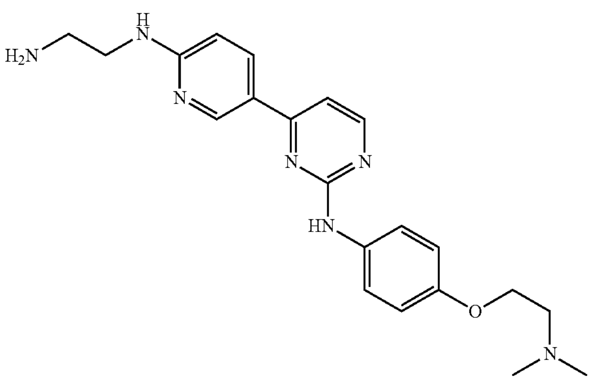 [SMILES: CN(C)CCOc1ccc(Nc2nccc(-c3ccc(NCCN)nc3)n2)cc1] | 393.5 | 394 | 0.93 |
| 97 | 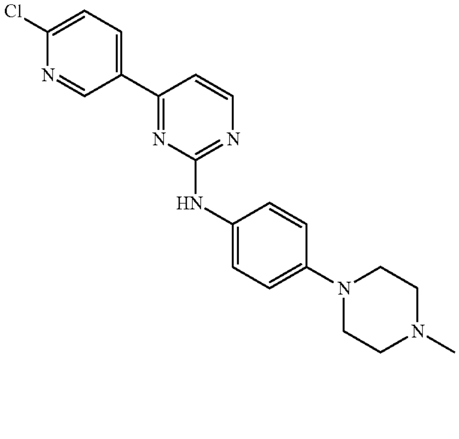 [SMILES: CN1CCN(c2ccc(Nc3nccc(-c4ccc(Cl)nc4)n3)cc2)CC1] | 380.9 | 381 | 2.78 |

-continued

| No. | Structure | MW | LCMS Ion | Rt |
|---|---|---|---|---|
| 98 | 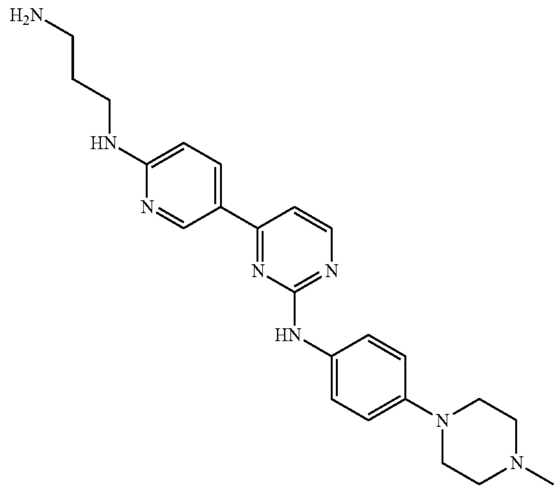 [SMILES: CN1CCN(c2ccc(Nc3nccc(-c4ccc(NCCCN)nc4)n3)cc2)CC1] | 418.5 | 419 | 1.10 |
| 99 | 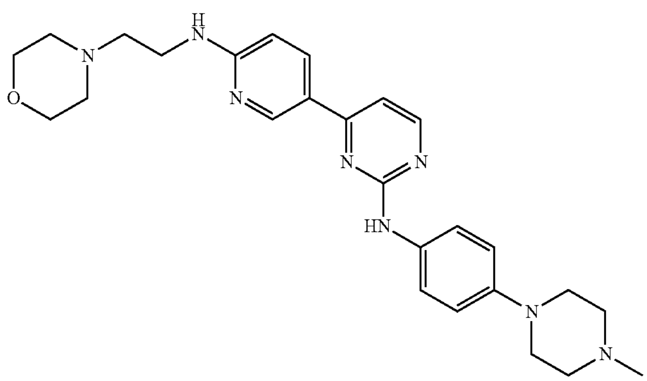 [SMILES: CN1CCN(c2ccc(Nc3nccc(-c4ccc(NCCN5CCOCC5)nc4)n3)cc2)CC1] | 474.6 | 475 | 2.10 |
| 100 | 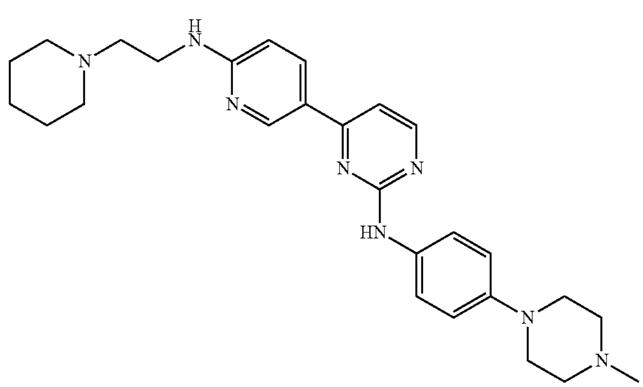 [SMILES: CN1CCN(c2ccc(Nc3nccc(-c4ccc(NCCN5CCCCC5)nc4)n3)cc2)CC1] | 472.6 | 473 | 2.19 |

-continued
| No. | Structure | MW | LCMS Ion | Rt |
|---|---|---|---|---|
| 101 | 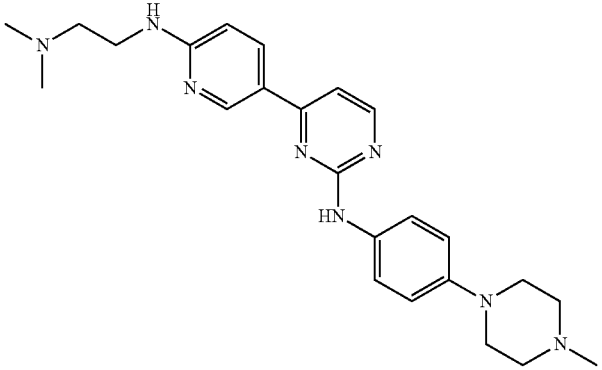 | 432.6 | 433 | 1.29 |
| 102 | 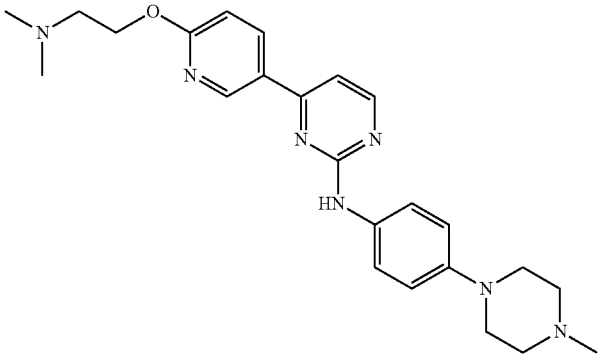 | 433.6 | 434 | 2.17 |
| 103 | 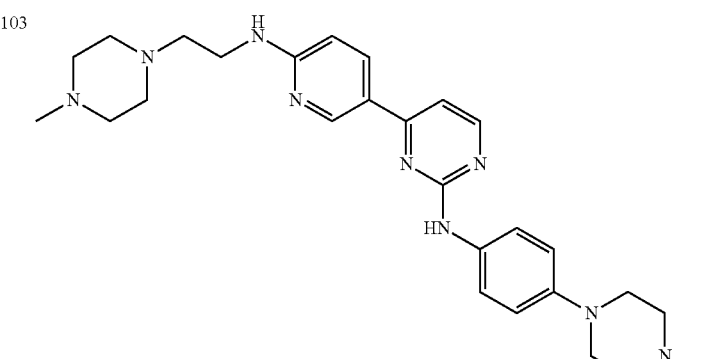 | 487.7 | 488 | 1.14 |
| 104 | 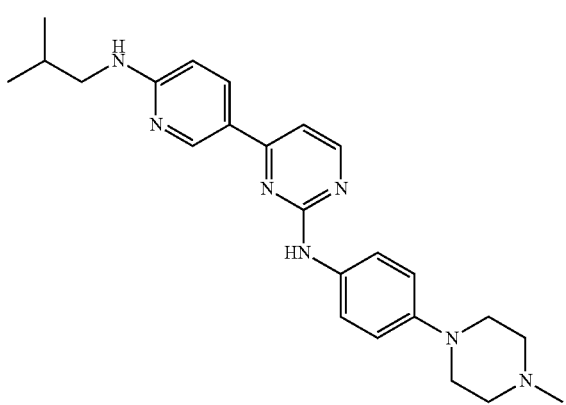 [SMILES: CC(C)CNc1ccc(-c2ccnc(Nc3ccc(N4CCN(C)CC4)cc3)n2)cn1] | 417.6 | 418 | 2.45 |

-continued
| No. | Structure | MW | LCMS Ion | Rt |
|---|---|---|---|---|
| 105 | 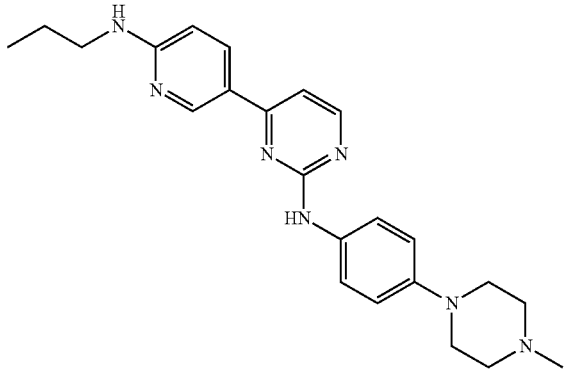 [SMILES: CCCNc1ccc(-c2ccnc(Nc3ccc(N4CCN(C)CC4)cc3)n2)cn1] | 403.5 | 404 | 2.24 |
| 106 | 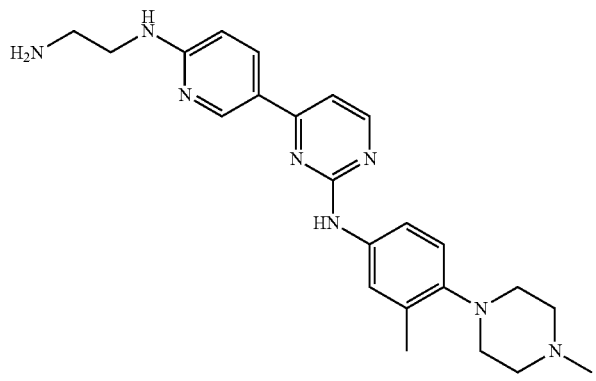 [SMILES: Cc1cc(Nc2nccc(-c3ccc(NCCN)nc3)n2)ccc1N1CCN(C)CC1] | 418.5 | 419 | 2.16 |
| 107 | 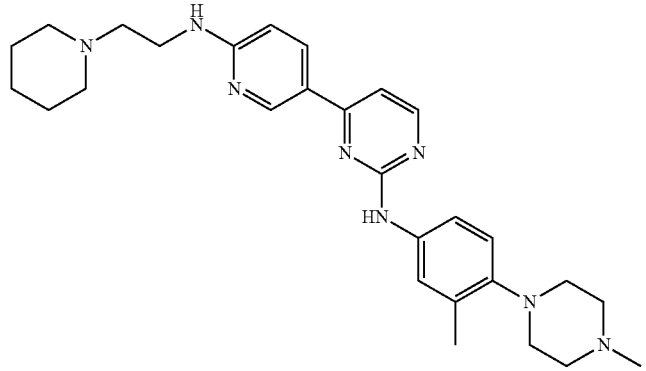 [SMILES: Cc1cc(Nc2nccc(-c3ccc(NCCN4CCCCC4)nc3)n2)ccc1N1CCN(C)CC1] | 486.7 | 487 | 2.32 |
| 108 | 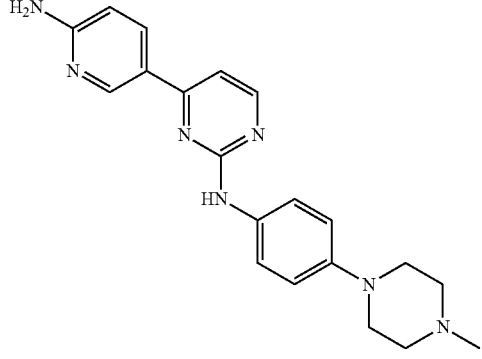 [SMILES: CN1CCN(c2ccc(Nc3nccc(-c4ccc(N)nc4)n3)cc2)CC1] | 361.5 | 362 | 2.31 |

| No. | Structure | MW | LCMS Ion | Rt |
|---|---|---|---|---|
| 109 | 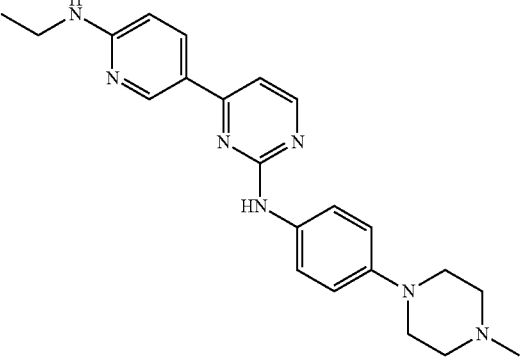 | 389.5 | 390 | 2.17 |
| 110 | 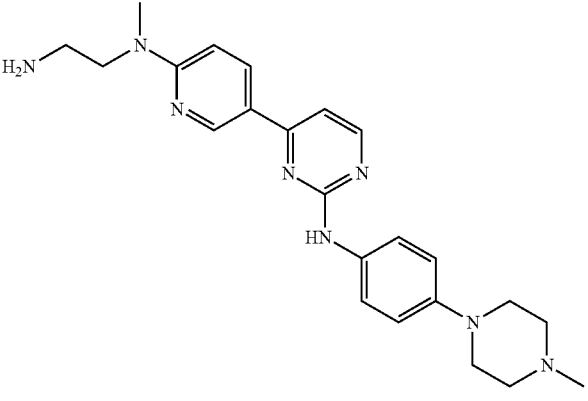 [SMILES: CN1CCN(c2ccc(Nc3nccc(-c4ccc(N(C)CCN)nc4)n3)cc2)CC1] | 418.5 | 419 | 2.11 |
| 111 | 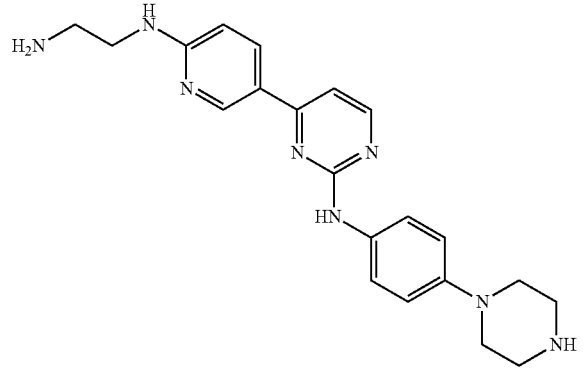 [SMILES: NCCNc1ccc(-c2ccnc(Nc3ccc(N4CCNCC4)cc3)n2)cn1] | 390.5 | 391 | 0.83 |
| 112 | 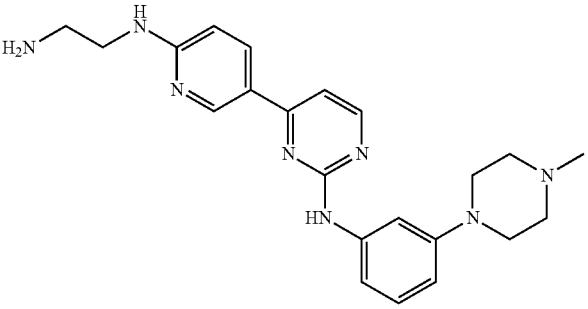 [SMILES: CN1CCN(c2cccc(Nc3nccc(-c4ccc(NCCN)nc4)n3)c2)CC1] | 404.5 | 405 | 3.44 |

-continued
| No. | Structure | MW | LCMS Ion | Rt |
|---|---|---|---|---|
| 113 | 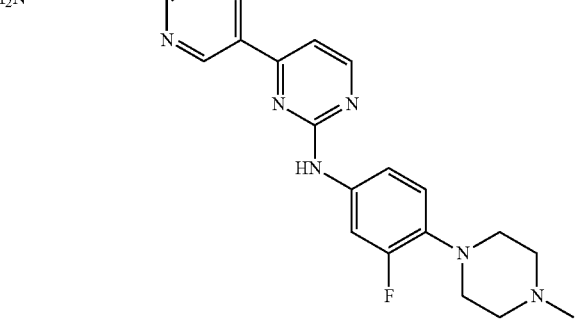 | 422.5 | 423 | 2.02 |
| 114 | 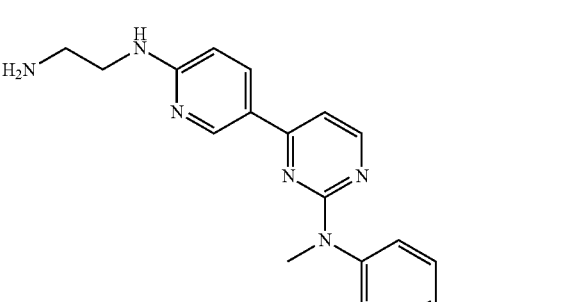 | 418.5 | 419 | 1.35 |
| 115 | 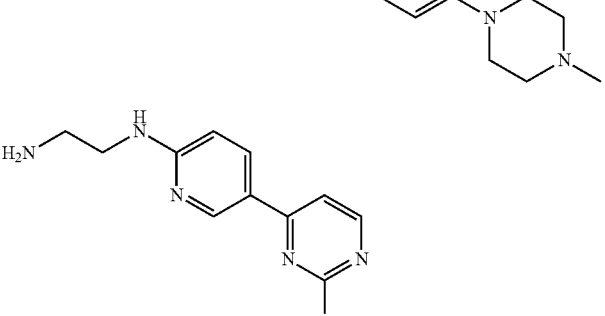 | 432.5 | 433 | 2.23 |
Example 116
Synthesis of 8-ethyl-2-(3-fluoro-4-(piperazin-1-yl)phenylamino)-6-phenylpyrido[2,3-d]pyrimidin-7(8H)-one hydrochloride
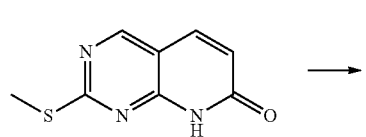
-continued
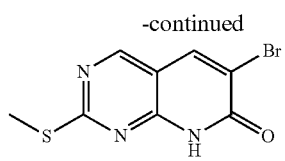
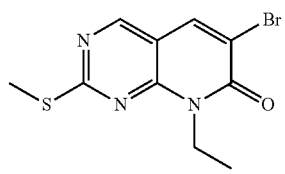

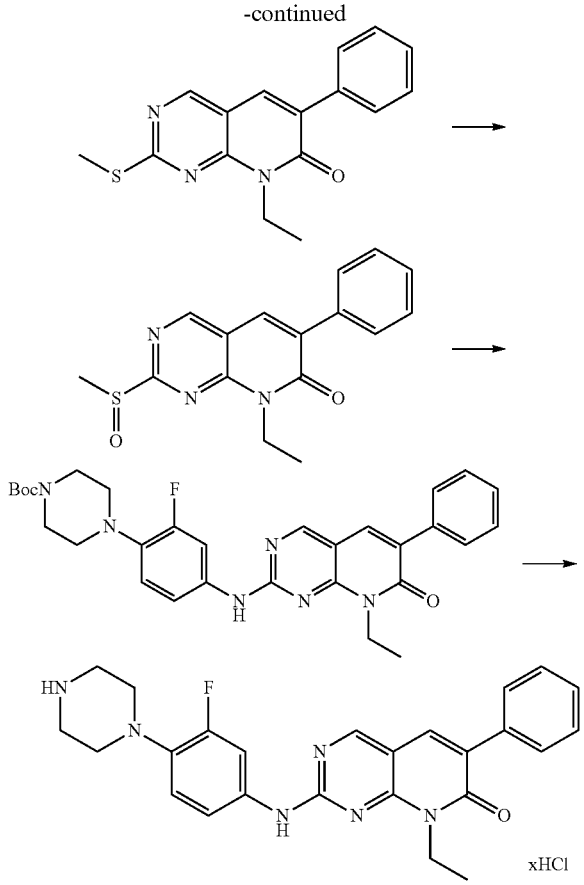

Step 1: Synthesis of 6-bromo-2-(methylthio)pyrido[2,3-d]pyrimidin-7(8H)-one

To a solution of 2-(methylthio)pyrido[2,3-d]pyrimidin-7(8H)-one (1.00 g, 5.18 mmol) in anhydrous dimethylformamide (25 mL) was added N-bromosuccinimide (0.99 g, 5.59 mmol) portionwise at room temperature, and the reaction mixture was stirred for 18 h. The mixture was concentrated, and the solid was triturated with hot water (1×20 mL), filtered, and washed with isopropanol to give title compound as a pale yellow solid (0.68 g, 2.50 mmol, 48%). ESMS m/z 272 (M+H)$^+$; $^1$H NMR (400 MHz, DMSO-d$_6$) δ ppm 12.88 (br. S., 1H), 8.84 (s, 1H), 8.47 (s, 1H), 2.57 (s, 3H).

Step 2: Synthesis of 6-bromo-8-ethyl-2-(methylthio)pyrido[2,3-d]pyrimidin-7(8H)-one To a suspension of NaH (60%, 0.15 g, 3.75 mmol) in anhydrous dimethylformamide (10 mL) was added 6-bromo-2-(methylthio)pyrido[2,3-d]pyrimidin-7(8H)-one (0.68 g, 2.50 mmol) at room temperature and the reaction was stirred at 50° C. for 0.5 h. The reaction mixture was cooled down to room temperature and ethyl bromide (0.22 mL, 0.32 g, 2.93 mmol) was added and stirred at 50° C. for 1.5 h. After completion, the mixture was poured onto ice water (10 g), and the white precipitate was filtered off to give 6-bromo-8-ethyl-2-(methylthio)pyrido[2,3-d]pyrimidin-7(8H)-one (0.57 g, 1.90 mmol, 76%). ESMS m/z 300 (M+H)$^+$.

Step 3: Synthesis of 8-ethyl-2-(methylthio)-6-phenylpyrido[2,3-d]pyrimidin-7(8H)-one 6-bromo-8-ethyl-2-(methylthio)pyrido[2,3-d]pyrimidin-7(8H)-one (150 mg, 0.50 mmol), phenylboronic acid (183 mg, 1.50 mmol), K$_3$PO$_4$ (318 mg, 1.50 mmol) and Pd(PPh$_3$)$_4$ (29 mg, 0.02 mmol) were mixed as solids and placed under argon. Argon was bubbled through the mixture of dimethoxyethane:ethanol:water (1:1:1, 2.0 mL) for 20 min. The solvent was added to the solid and the suspension was heated under microwave irradiation at 120° C. for 1 h. After completion, the reaction mixture evaporated to dryness, the crude product was purified by silica gel column chromatography using dichloromethane:ethyl acetate (100:0.5) to yield 8-ethyl-2-(methylthio)-6-phenylpyrido[2,3-d]pyrimidin-7(8H)-one as an off-white solid (121 mg, 0.41 mmol, 81%). ESMS m/z 298 (M+H)$^+$; $^1$H NMR (400 MHz, CDCl$_3$) δ ppm 8.59 (s, 1H), 8.03 (s, 1H), 4.55 (q, J=7.2 Hz, 2H), 2.63 (s, 3H), 1.35 (t, J=7.2 Hz, 3H).

Step 4: Synthesis of 8-ethyl-2-(methylsulfinyl)-6-phenylpyrido[2,3-d]pyrimidin-7(8H)-one To a solution of 8-ethyl-2-(methylthio)-6-phenylpyrido[2,3-d]pyrimidin-7(8H)-one (127 mg, 0.43 mmol) in dichloromethane (2 mL) was added 3-chloroperbenzoic acid (70%, 95 mg, 0.38 mmol) at 0-5° C. and the mixture was stirred at room temperature for 18 h. The reaction was diluted with dichloromethane (5 mL) and washed with saturated sodium bicarbonate solution (1×3 mL) then with water (1×3 mL). The organic layer was dried over sodium sulfate, filtered and evaporated to get 8-ethyl-2-(methylsulfinyl)-6-phenylpyrido[2,3-d]pyrimidin-7(8H)-one as a pale yellow solid (120 mg, 0.38 mmol, 88%). ESMS m/z 314 (M+H)$^+$.

Step 5: Synthesis of tert-butyl 4-(4-(8-ethyl-7-oxo-6-phenyl-7,8-dihydropyrido[2,3-d]pyrimidin-2-ylamino)-2-fluorophenyl)piperazine-1-carboxylate 8-ethyl-2-(methylsulfinyl)-6-phenylpyrido[2,3-d]pyrimidin-7(8H)-one (120 mg, 0.38 mmol) and 4-(4-amino-2-fluorophenyl)piperazine-1-carboxylic acid tert-butyl ester (113 mg, 0.38 mmol) were stirred at 120° C. for 3 h. The reaction mixture was purified by silica gel column chromatography using hexane:ethyl acetate (3:2). The isolated product was recrystallized from isopropanol to give the title compound (45 mg, 0.08 mmol, 21%) as a pale yellow solid. ESMS m/z 545 (M+H)$^+$.

Step 6: Synthesis of 8-ethyl-2-(3-fluoro-4-(piperazin-1-yl)phenylamino)-6-phenylpyrido[2,3-d]pyrimidin-7(8H)-one hydrochloride To a stirred solution of tert-butyl 4-(4-(8-ethyl-7-oxo-6-phenyl-7,8-dihydropyrido[2,3-d]pyrimidin-2-ylamino)-2-fluorophenyl)piperazine-1-carboxylate (45 mg, 0.08 mmol) in ethyl acetate (5 mL) was added a 4M solution of hydrochloric acid in diethyl ether (5 mL) and the reaction was stirred for 18 h. The precipitate was filtered off to give 8-ethyl-2-(3-fluoro-4-(piperazin-1-yl)phenylamino)-6-phenylpyrido[2,3-d]pyrimidin-7(8H)-one hydrochloride as an off-white solid (36 mg, 0.07 mmol, 87%). ESMS m/z 445 (M+H)$^+$; $^1$H NMR (400 MHz, DMSO-d$_6$) δ ppm 10.21 (br. S., 1H), 9.22 (br. S., 2H), 8.85 (s, 1H), 8.02 (s, 1H), 7.84 (d, J=15.e.g., 1 Hz, 1H), 7.68 (d, J=7.5 Hz, 2H), 7.52 (d, J=8.5 Hz, 1H), 7.43 (t, J=7.3 Hz, 2H), 7.37 (t, J=7.3 Hz, 1H), 7.11 (t, J=8.5 Hz, 1H), 4.41 (q, J=6.7 Hz, 2H), 3.22 (br. S., 8H), 1.31 (t, J=6.7 Hz, 3H).

Examples 117-118

The following compounds were made by the method of Example 120 using the appropriate boronic acid at Step 3 and aniline at Step 5.

| No. | Structure | MW | LCMS Ion | Rt |
|---|---|---|---|---|
| 117 | 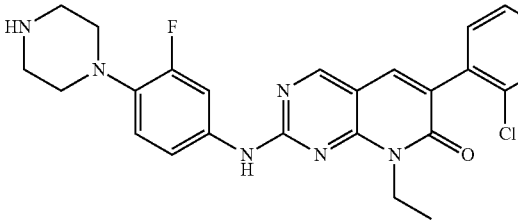 | 513.4 | 513 | 3.62 |
| 118 | 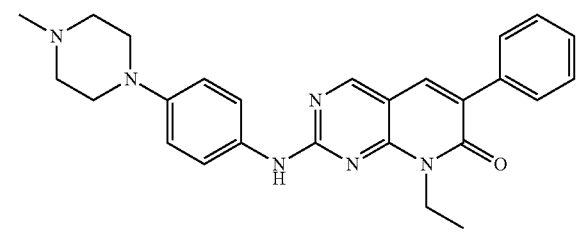 [SMILES: CCn1c(=O)c(-c2ccccc2)cc2cnc(Nc3ccc(N4CCN(C)CC4)cc3)nc21] | 440.6 | 441 | 3.32 |
Examples 119-121
The following compounds were made by the methods of Example 1-26 using the appropriate phenylacetic acid ester at Step 6 in place of the phosphonoacetate ester.
| No. | Structure | MW | LCMS Ion | Rt |
|---|---|---|---|---|
| 119 | 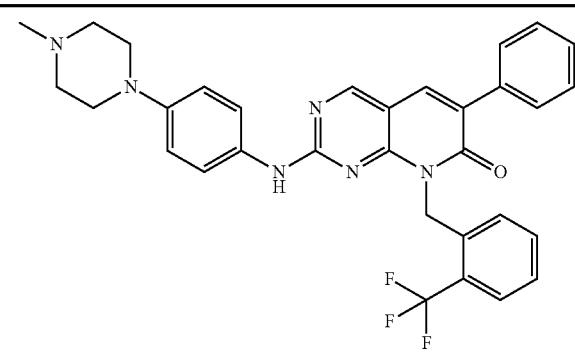 | 570.6 | 571 | 3.46 |
| 120 | 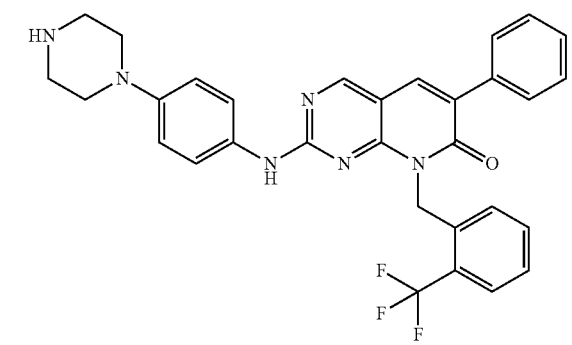 [SMILES: O=c1c(-c2ccccc2)cc2cnc(Nc3ccc(N4CCNCC4)cc3)nc2n1Cc1ccccc1C(F)(F)F] | 556.6 | 557 | 3.37 |

| No. | Structure | MW | LCMS Ion | Rt |
|---|---|---|---|---|
| 121 | 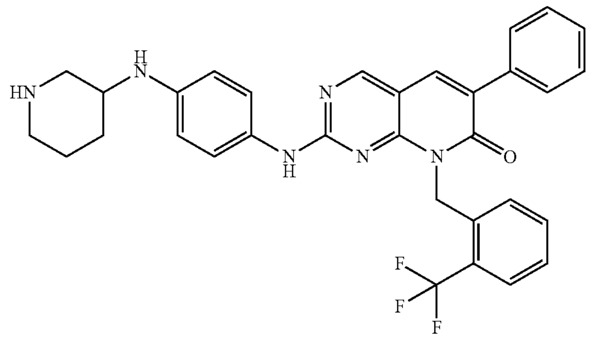 [SMILES: O=c1c(-c2ccccc2)cc2cnc(Nc3ccc(NC4CCCNC4)cc3)nc2n1Cc1ccccc1C(F)(F)F] | 570.6 | 571 | 3.49 |

Example 122

Synthesis of 6-Bromo-8-ethyl-2-[4-(4-methyl-piperazin-1-yl)-phenylamino]-8H-pyrido[2,3-d]pyrimidin-7-one

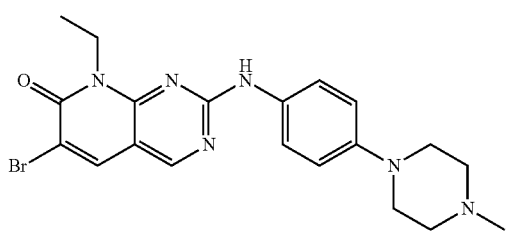 [SMILES: CCn1c(=O)c(Br)cc2cnc(Nc3ccc(N4CCN(C)CC4)cc3)nc21]

8-(2-Fluoro-6-methylsulfanyl-benzyl)-2-(3-fluoro-4-piperazin-1-yl-phenylamino)-8H-pyrido[2,3-d]pyrimidin-7-one was made by the method of Example 120 by reaction with 4-{4-[8-(2,6-Difluoro-benzyl)-7-oxo-7,8-dihydro-pyrido[2,3-d]pyrimidin-2-ylamino]-2-fluoro-phenyl}-piperazine-1-carboxylic acid tert-butyl ester followed by removal of the Boc group by hydrogen chloride in ether in the final step.

Example 123

Identification of Compounds Having High Affinity for PAK Active Sites

A fluorescence-based assay format is used to determine IC50 values of test compounds in vitro. Purified PAK kinase is incubated with ATP, and a test compound at various concentrations and a substrate peptide containing two fluorophores. In a second step, the reaction mix is incubated with a site-specific protease that cleaves non-phosphorylated but not phosphorylated substrate peptide, disrupting the FRET signal generated by the two fluorophores in the cleaved peptide (Z'Lyte™ Kinase assay platform; Life Technologies).

Reagents: 50 mM HEPES, pH 7.5; 0.01% BRIJ-35; 10 mM MgCl$_2$; 1 mM EGTA, 2 uM substrate peptide Ser/Thr20 (proprietary Life Technologies Sequence), PAK enzyme [2.42-30.8 ng for PAK1, 0.29-6 ng for PAK2, 1.5-20 ng for PAK3 and 0.1-0.86 ng for PAK4; actual enzyme amounts depend on lot activity of the enzyme preparation]

Test compounds are dissolved in DMSO at various concentrations; the final DMSO concentration in the assay reaction is 1%.

ATP concentration at Km apparent is used in the assay [50 μM ATP for PAK1 assay, 75 μM ATP for PAK2 assay, 100 μM ATP for PAK3 assay, 5 μM ATP for PAK-4 assay] in a total assay volume of 10 Assay reactions are incubated at room temperature for 1 hr. Following the kinase reaction, 5 μl of 1:256 dilution of development solution A (Life Technologies) is added and the reaction mix is incubated for an additional 1 hr at room temperature.

Plates are analyzed in a standard fluorescence plate reader (Tecan or equivalent) using an excitation wavelength of 400 nm and emission wavelengths of 445 nm and 520 nm. Inhibition of kinase reaction is determined by emission ratio=emission@445 nm/emission@520 nm Based on these data, specific compounds have been identified that have relatively high affinity for the catalytic domain of at least one PAK isoform, and are therefore useful inhibitors, as described herein.

TABLE 8

| No. | Structure | PAK1 IC50 μM | PAK2 IC50 μM | PAK3 IC50 μM | PAK4 IC50 μM |
|---|---|---|---|---|---|
| 1 | 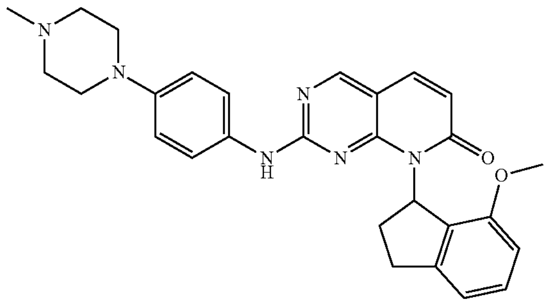 | B | C | C | B |
| 2 | 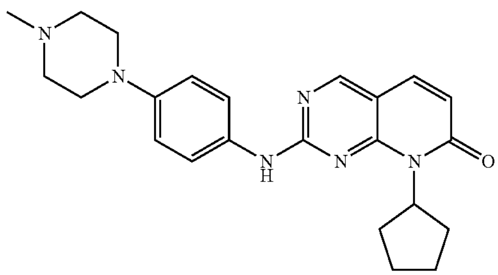 [SMILES: CN1CCN(c2ccc(Nc3ncc4ccc(=O)n(C5CCCC5)c4n3)cc2)CC1] | A | B | B | B |
| 3 | 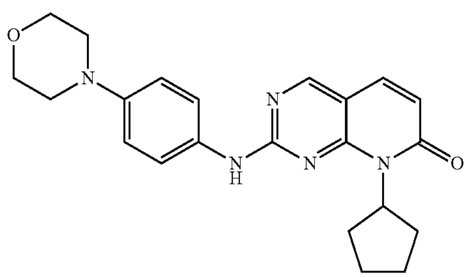 [SMILES: O=c1ccc2cnc(Nc3ccc(N4CCOCC4)cc3)nc2n1C1CCCC1] | C | | C | B |
| 4 | 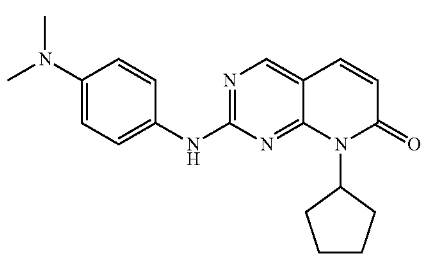 [SMILES: CN(C)c1ccc(Nc2ncc3ccc(=O)n(C4CCCC4)c3n2)cc1] | C | | C | B |
| 5 | 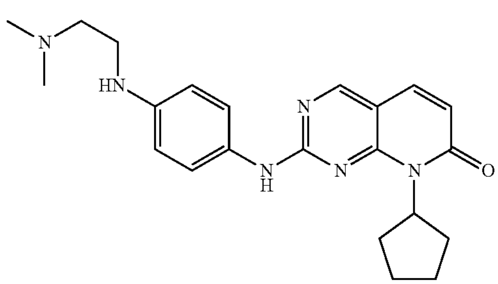 [SMILES: CN(C)CCNc1ccc(Nc2ncc3ccc(=O)n(C4CCCC4)c3n2)cc1] | B | B | | B |

TABLE 8-continued

| No. | Structure | PAK1 IC50 μM | PAK2 IC50 μM | PAK3 IC50 μM | PAK4 IC50 μM |
|---|---|---|---|---|---|
| 6 | 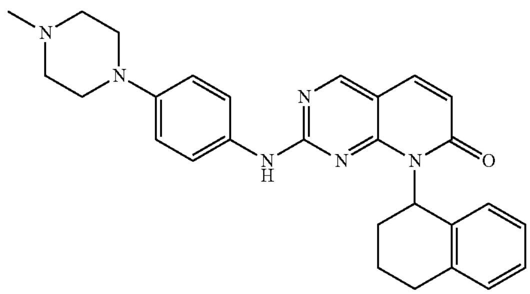 [SMILES: CN1CCN(c2ccc(Nc3ncc4ccc(=O)n(C5CCCc6ccccc65)c4n3)cc2)CC1] | B | B | B | B |
| 7 | 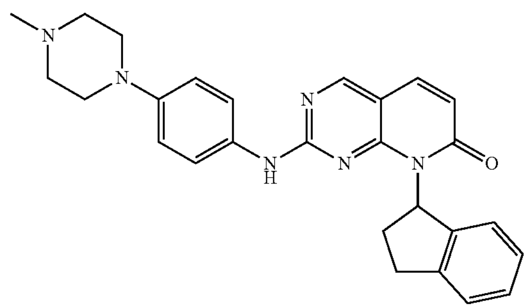 [SMILES: CN1CCN(c2ccc(Nc3ncc4ccc(=O)n(C5CCc6ccccc65)c4n3)cc2)CC1] | A | B | B | B |
| 8 | 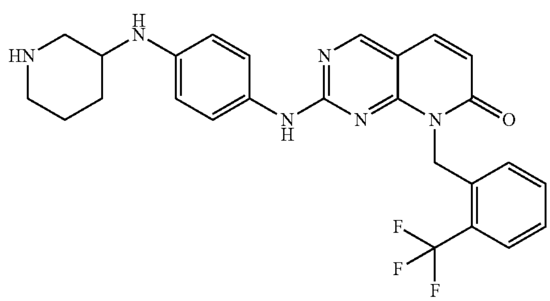 [SMILES: O=c1ccc2cnc(Nc3ccc(NC4CCCNC4)cc3)nc2n1Cc1ccccc1C(F)(F)F] | A | A | A | A |
| 9 | 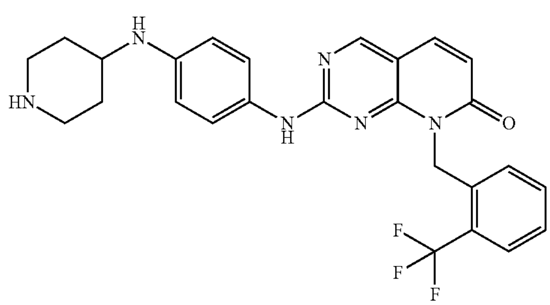 [SMILES: O=c1ccc2cnc(Nc3ccc(NC4CCNCC4)cc3)nc2n1Cc1ccccc1C(F)(F)F] | A | A | A | A |
| 10 | 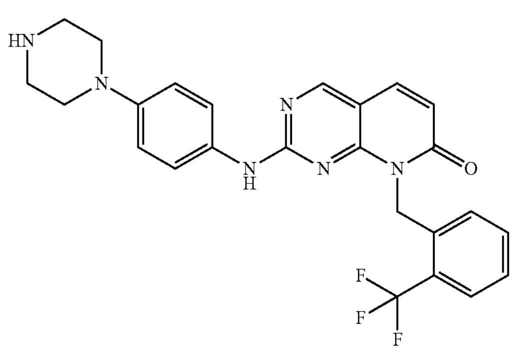 [SMILES: O=c1ccc2cnc(Nc3ccc(N4CCNCC4)cc3)nc2n1Cc1ccccc1C(F)(F)F] | A | A | A | A |

TABLE 8-continued

| No. | Structure | PAK1 IC50 μM | PAK2 IC50 μM | PAK3 IC50 μM | PAK4 IC50 μM |
|---|---|---|---|---|---|
| 11 | 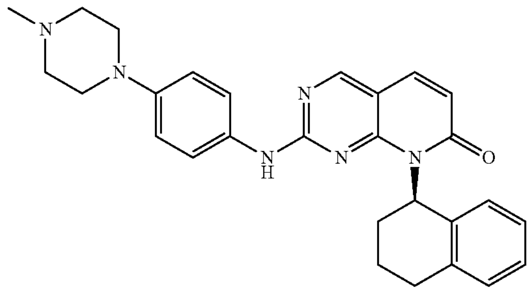 [SMILES: CN1CCN(c2ccc(Nc3ncc4ccc(=O)n([C@@H]5CCCc6ccccc65)c4n3)cc2)CC1] | B | B | B | B |
| 12 | 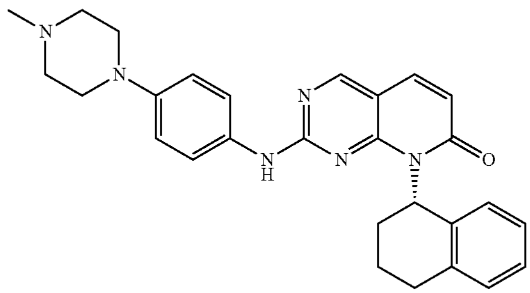 [SMILES: CN1CCN(c2ccc(Nc3ncc4ccc(=O)n([C@H]5CCCc6ccccc65)c4n3)cc2)CC1] | A | B | B | B |
| 13 | 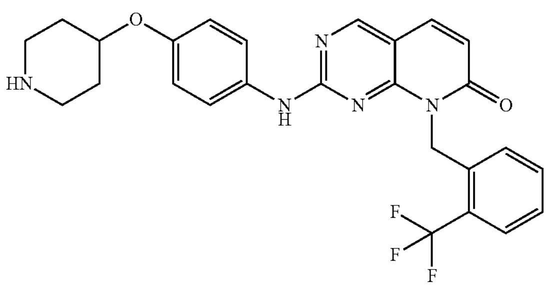 [SMILES: O=c1ccc2cnc(Nc3ccc(OC4CCNCC4)cc3)nc2n1Cc1ccccc1C(F)(F)F] | A | A | A | A |
| 14 | 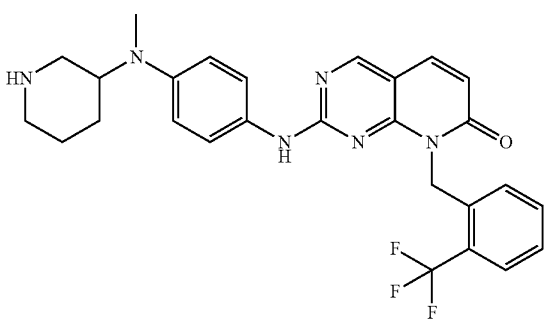 [SMILES: CN(c1ccc(Nc2ncc3ccc(=O)n(Cc4ccccc4C(F)(F)F)c3n2)cc1)C1CCCNC1] | A | A | A | A |
| 15 | 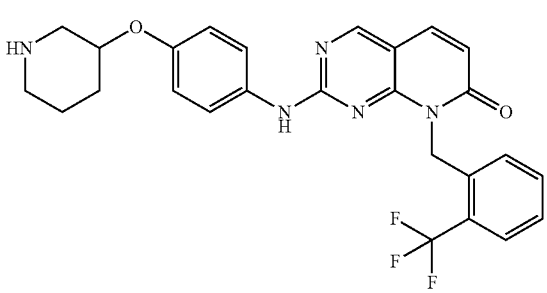 [SMILES: O=c1ccc2cnc(Nc3ccc(OC4CCCNC4)cc3)nc2n1Cc1ccccc1C(F)(F)F] | A | A | A | A |

TABLE 8-continued
| No. | Structure | PAK1 IC50 μM | PAK2 IC50 μM | PAK3 IC50 μM | PAK4 IC50 μM |
|---|---|---|---|---|---|
| 16 | 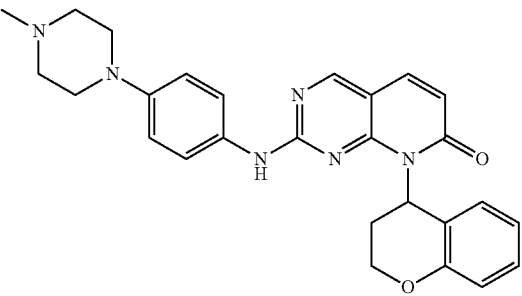 [SMILES: CN1CCN(c2ccc(Nc3ncc4ccc(=O)n(C5CCOc6ccccc65)c4n3)cc2)CC1] | B | B | B | B |
| 17 | 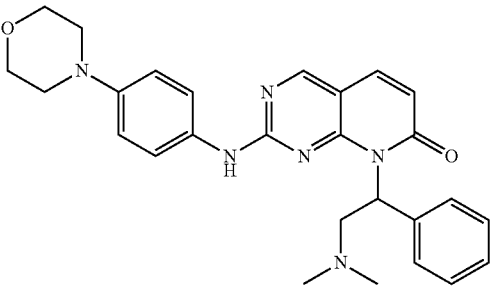 [SMILES: CN(C)CC(c1ccccc1)n1c(=O)ccc2cnc(Nc3ccc(N4CCOCC4)cc3)nc21] | C | C | C | C |
| 18 | 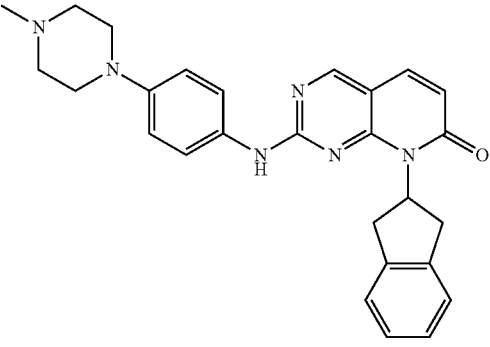 [SMILES: CN1CCN(c2ccc(Nc3ncc4ccc(=O)n(C5Cc6ccccc6C5)c4n3)cc2)CC1] | A | B | B | A |
| 19 | 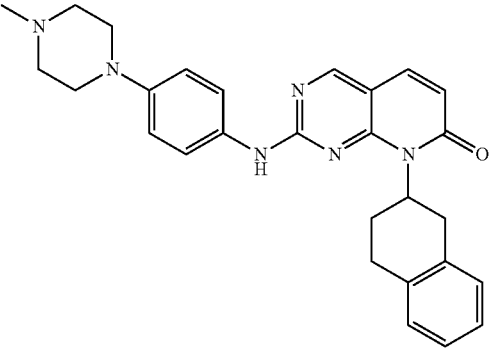 [SMILES: CN1CCN(c2ccc(Nc3ncc4ccc(=O)n(C5CCc6ccccc6C5)c4n3)cc2)CC1] | A | A | A | A |
| 20 | 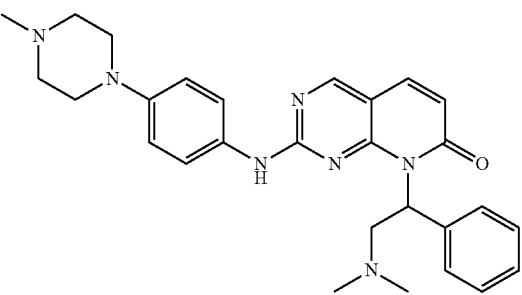 [SMILES: CN(C)CC(c1ccccc1)n1c(=O)ccc2cnc(Nc3ccc(N4CCN(C)CC4)cc3)nc21] | C | C | C | C |

TABLE 8-continued
| No. | Structure | PAK1 IC50 μM | PAK2 IC50 μM | PAK3 IC50 μM | PAK4 IC50 μM |
|---|---|---|---|---|---|
| 21 | 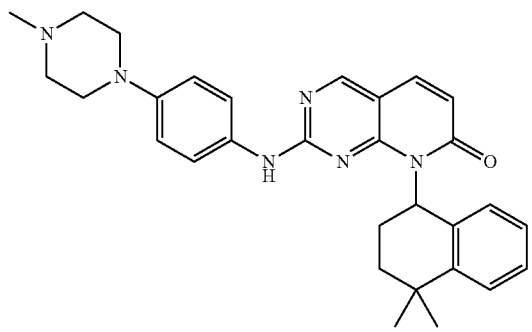 [SMILES: CN1CCN(c2ccc(Nc3ncc4ccc(=O)n(C5CCC(C)(C)c6ccccc65)c4n3)cc2)CC1] | A | A | B | B |
| 22 | 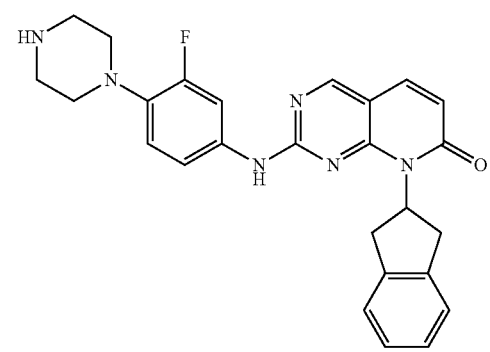 [SMILES: O=c1ccc2cnc(Nc3ccc(N4CCNCC4)c(F)c3)nc2n1C1Cc2ccccc2C1] | A | A | B | A |
| 23 | 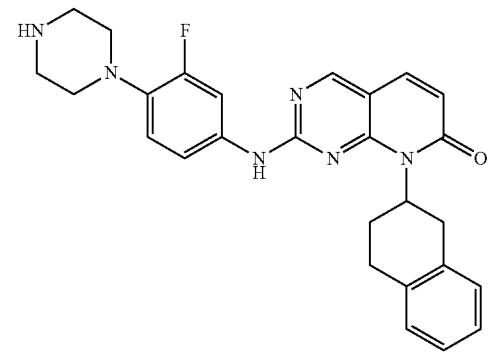 [SMILES: O=c1ccc2cnc(Nc3ccc(N4CCNCC4)c(F)c3)nc2n1C1CCc2ccccc2C1] | A | A | A | A |
| 27 | 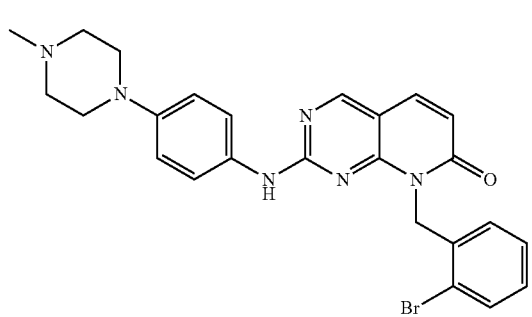 [SMILES: CN1CCN(c2ccc(Nc3ncc4ccc(=O)n(Cc5ccccc5Br)c4n3)cc2)CC1] | A | A | A | A |

TABLE 8-continued

| No. | Structure | PAK1 IC50 μM | PAK2 IC50 μM | PAK3 IC50 μM | PAK4 IC50 μM |
|---|---|---|---|---|---|
| 28 | 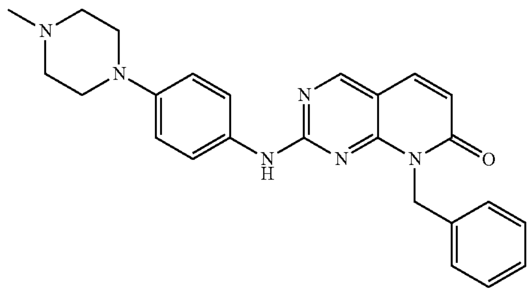 [SMILES: CN1CCN(c2ccc(Nc3ncc4ccc(=O)n(Cc5ccccc5)c4n3)cc2)CC1] | B | B | | C |
| 29 | 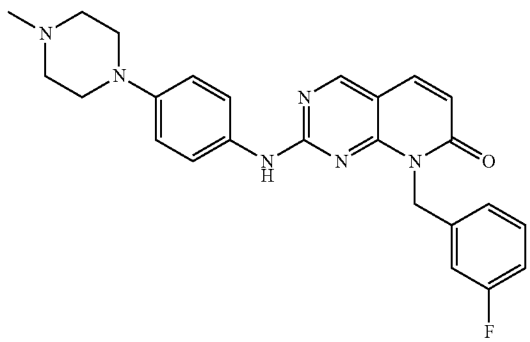 | B | B | | B |
| 30 | 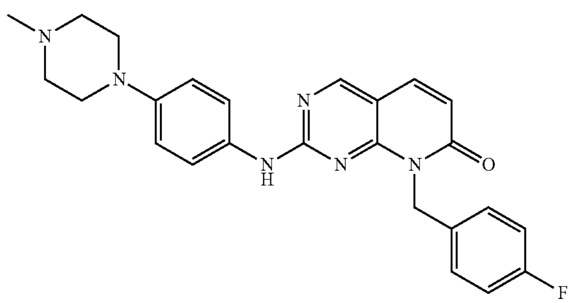 [SMILES: CN1CCN(c2ccc(Nc3ncc4ccc(=O)n(Cc5ccc(F)cc5)c4n3)cc2)CC1] | B | C | | C |
| 31 | 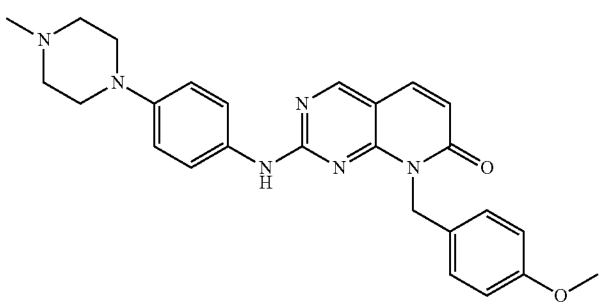 | C | C | | C |
| 32 | 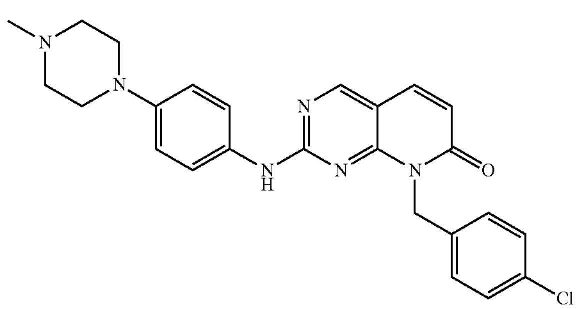 [SMILES: CN1CCN(c2ccc(Nc3ncc4ccc(=O)n(Cc5ccc(Cl)cc5)c4n3)cc2)CC1] | B | C | | C |

TABLE 8-continued

| No. | Structure | PAK1 IC50 μM | PAK2 IC50 μM | PAK3 IC50 μM | PAK4 IC50 μM |
|---|---|---|---|---|---|
| 33 | 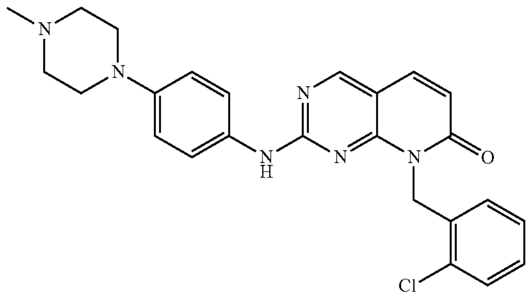 | A | A | | B |
| 34 | 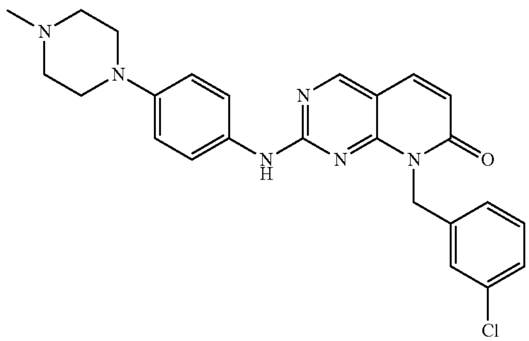 | B | C | | C |
| 35 | 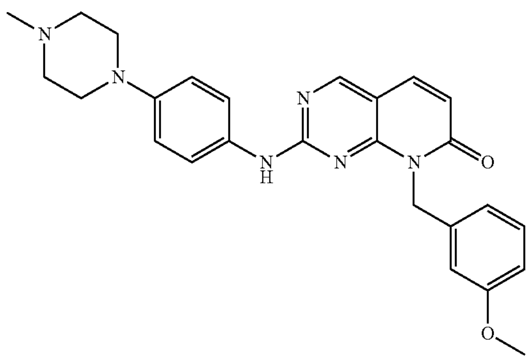 | B | C | | C |
| 36 | 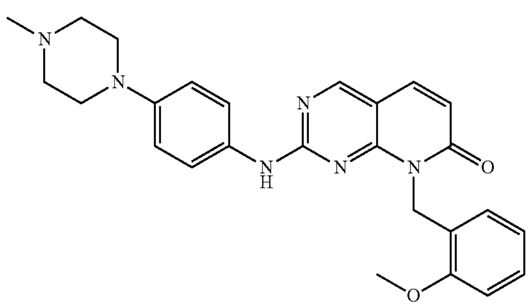 [SMILES: COc1ccccc1Cn1c(=O)ccc2cnc(Nc3ccc(N4CCN(C)CC4)cc3)nc21] | A | B | | B |
| 37 | 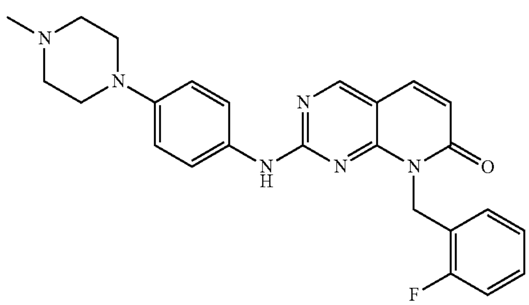 [SMILES: CN1CCN(c2ccc(Nc3ncc4ccc(=O)n(Cc5ccccc5F)c4n3)cc2)CC1] | B | B | | B |

TABLE 8-continued
| No. | Structure | PAK1 IC50 μM | PAK2 IC50 μM | PAK3 IC50 μM | PAK4 IC50 μM |
|---|---|---|---|---|---|
| 38 | 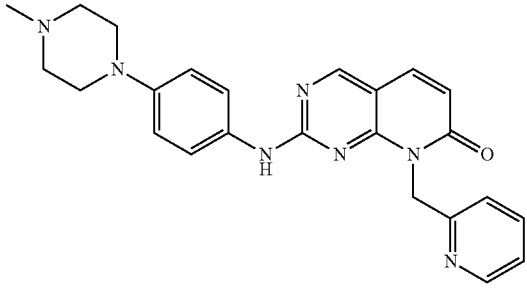 [SMILES: CN1CCN(c2ccc(Nc3ncc4ccc(=O)n(Cc5ccccn5)c4n3)cc2)CC1] | B | C | | B |
| 39 | 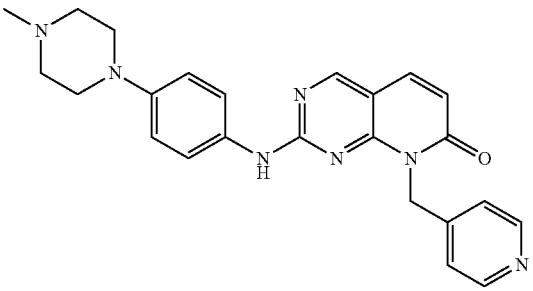 [SMILES: CN1CCN(c2ccc(Nc3ncc4ccc(=O)n(Cc5ccncc5)c4n3)cc2)CC1] | B | C | | C |
| 40 | 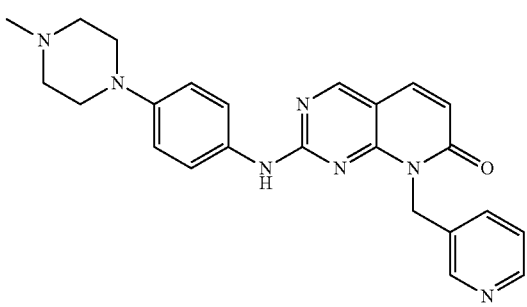 [SMILES: CN1CCN(c2ccc(Nc3ncc4ccc(=O)n(Cc5cccnc5)c4n3)cc2)CC1] | B | C | | C |
| 41 | 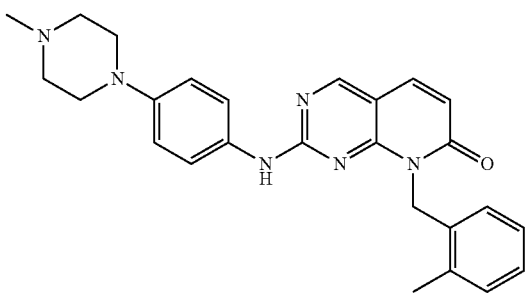 [SMILES: Cc1ccccc1Cn1c(=O)ccc2cnc(Nc3ccc(N4CCN(C)CC4)cc3)nc21] | A | A | | B |
| 42 | 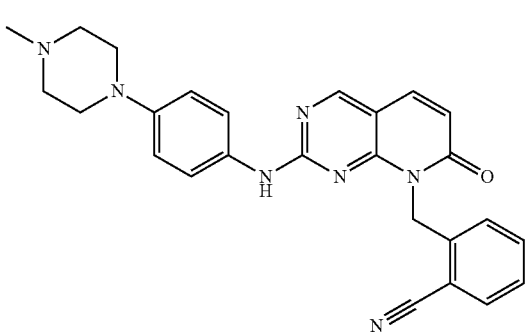 [SMILES: CN1CCN(c2ccc(Nc3ncc4ccc(=O)n(Cc5ccccc5C#N)c4n3)cc2)CC1] | A | A | | B |

TABLE 8-continued
| No. | Structure | PAK1 IC50 μM | PAK2 IC50 μM | PAK3 IC50 μM | PAK4 IC50 μM |
|---|---|---|---|---|---|
| 43 | 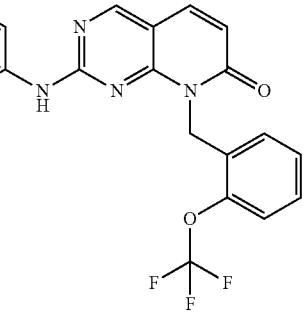 | A | A | | B |
| 44 | 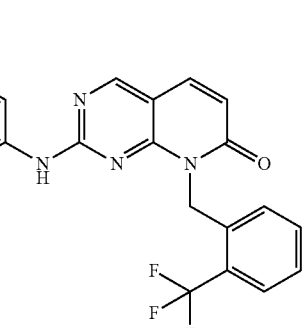 | A | A | A | A |
| 45 | 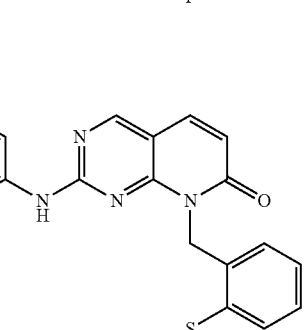 | A | A | A | A |
| 46 | 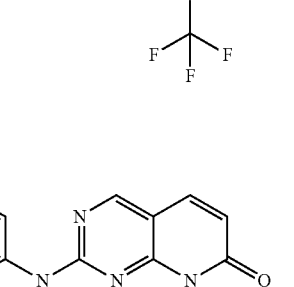 | A | A | A | A |

TABLE 8-continued
| No. | Structure | PAK1 IC50 μM | PAK2 IC50 μM | PAK3 IC50 μM | PAK4 IC50 μM |
|---|---|---|---|---|---|
| 47 | 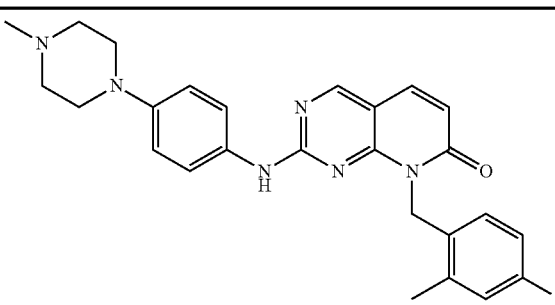 | B | B | B | B |
| 48 | 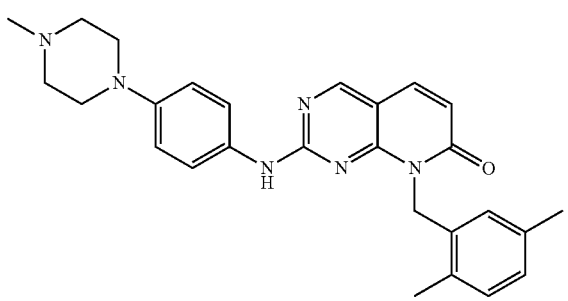 | B | B | B | B |
| 49 | 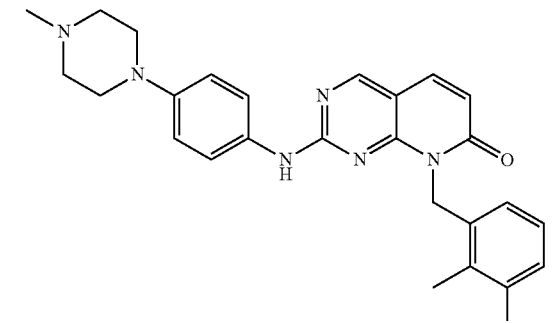 | A | B | C | B |
| 50 | 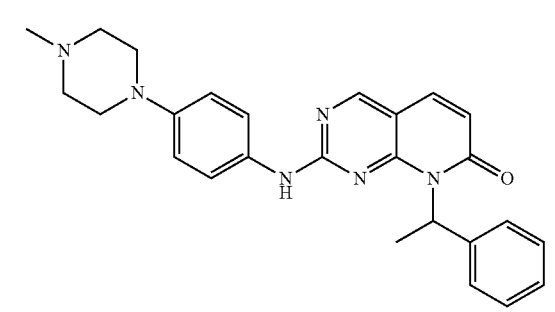 [SMILES: CC(c1ccccc1)n1c(=O)ccc2cnc(Nc3ccc(N4CCN(C)CC4)cc3)nc21] | B | B | C | B |
| 51 | 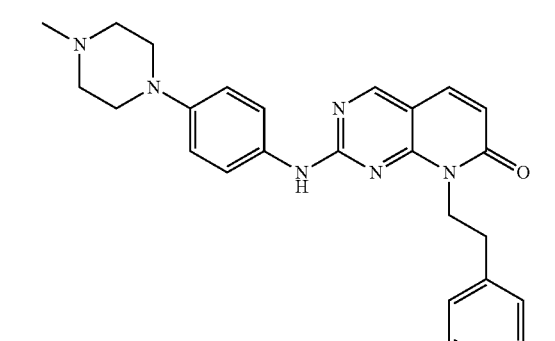 | A | A | B | A |

TABLE 8-continued

| No. | Structure | PAK1 IC50 μM | PAK2 IC50 μM | PAK3 IC50 μM | PAK4 IC50 μM |
|---|---|---|---|---|---|
| 52 | 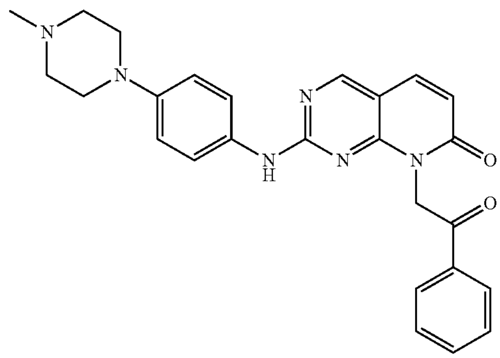 [SMILES: CN1CCN(c2ccc(Nc3ncc4ccc(=O)n(CC(=O)c5ccccc5)c4n3)cc2)CC1] | B | B | B | B |
| 53 | 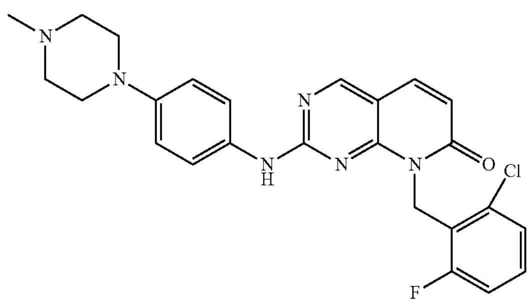 | A | A | A | A |
| 54 | 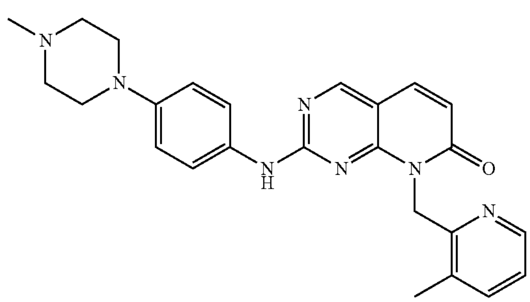 [SMILES: Cc1cccnc1Cn1c(=O)ccc2cnc(Nc3ccc(N4CCN(C)CC4)cc3)nc21] | B | B | C | B |
| 55 | 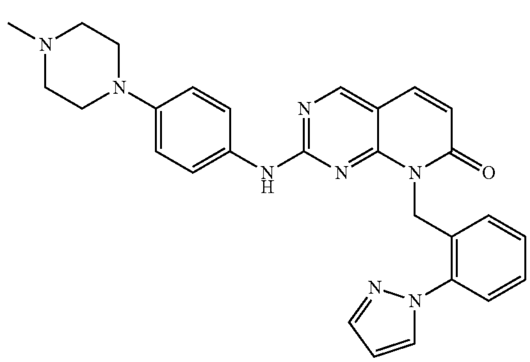 [SMILES: CN1CCN(c2ccc(Nc3ncc4ccc(=O)n(Cc5ccccc5-n5cccn5)c4n3)cc2)CC1] | A | B | B | B |

TABLE 8-continued
| No. | Structure | PAK1 IC50 μM | PAK2 IC50 μM | PAK3 IC50 μM | PAK4 IC50 μM |
|-----|-----------|--------------|--------------|--------------|--------------|
| 56 | 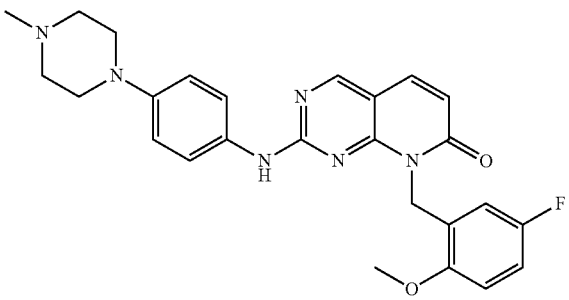 [SMILES: COc1ccc(F)cc1Cn1c(=O)ccc2cnc(Nc3ccc(N4CCN(C)CC4)cc3)nc21] | A | B | B | B |
| 57 | 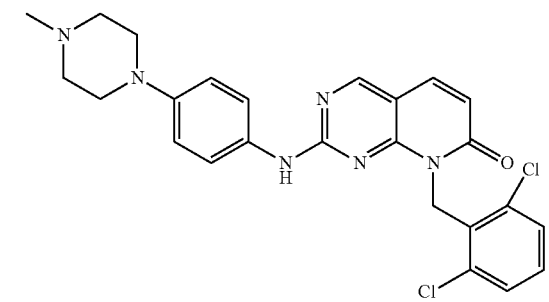 | A | A | B | A |
| 58 | 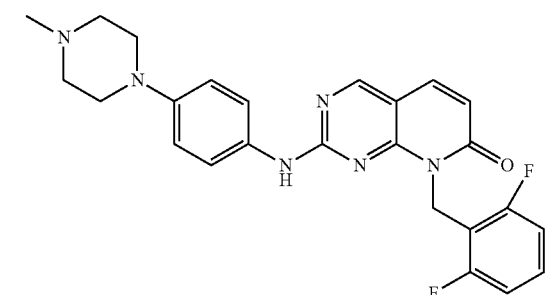 | A | B | B | B |
| 59 | 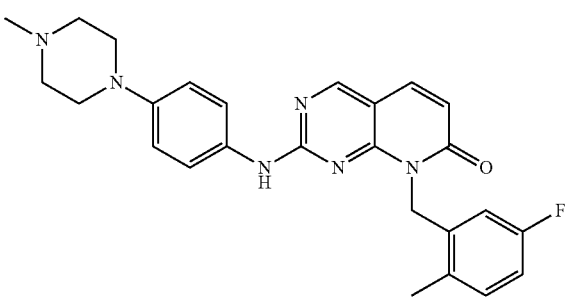 [SMILES: Cc1ccc(F)cc1Cn1c(=O)ccc2cnc(Nc3ccc(N4CCN(C)CC4)cc3)nc21] | A | B | B | A |
| 60 | 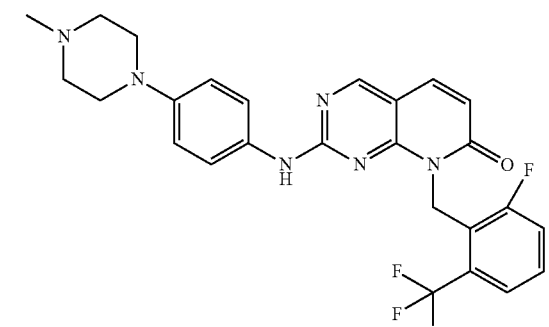 | A | A | A | A |

TABLE 8-continued
| No. | Structure | PAK1 IC50 µM | PAK2 IC50 µM | PAK3 IC50 µM | PAK4 IC50 µM |
|---|---|---|---|---|---|
| 61 | 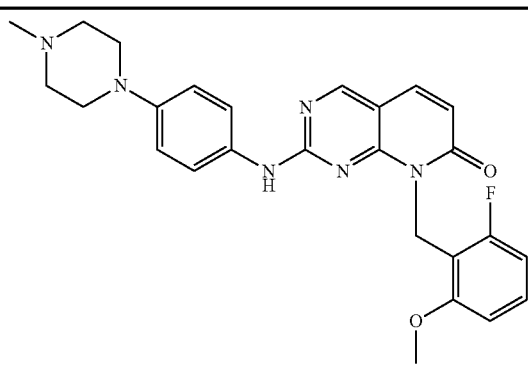 | A | B | B | A |
| 62 | 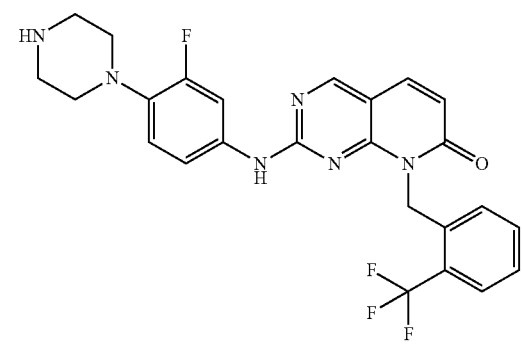 [SMILES: O=c1ccc2cnc(Nc3ccc(N4CCNCC4)c(F)c3)nc2n1Cc1ccccc1C(F)(F)F] | A | A | A | A |
| 63 | 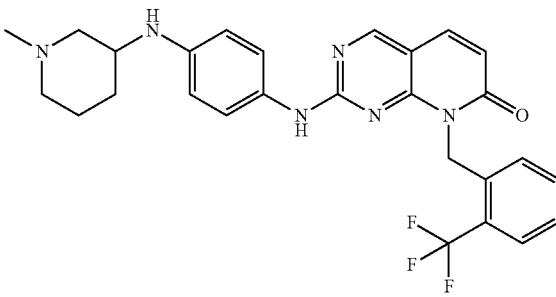 | A | A | A | A |
| 64 | 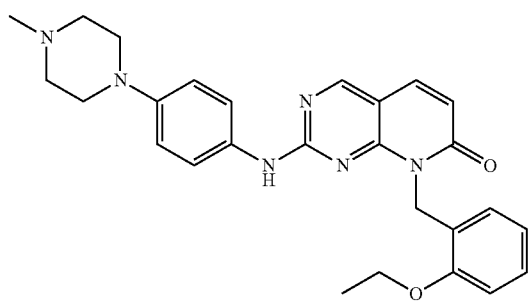 [SMILES: CCOc1ccccc1Cn1c(=O)ccc2cnc(Nc3ccc(N4CCN(C)CC4)cc3)nc21] | A | A | A | B. |
| 65 | 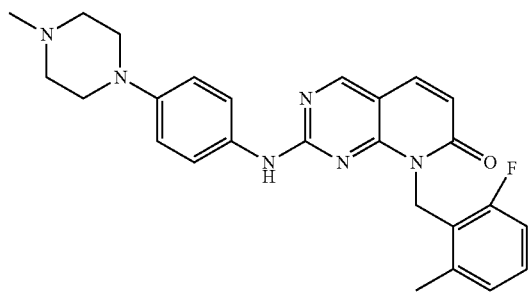 [SMILES: Cc1cccc(F)c1Cn1c(=O)ccc2cnc(Nc3ccc(N4CCN(C)CC4)cc3)nc21] | A | A | A | A |

TABLE 8-continued

| No. | Structure | PAK1 IC50 μM | PAK2 IC50 μM | PAK3 IC50 μM | PAK4 IC50 μM |
|---|---|---|---|---|---|
| 66 | 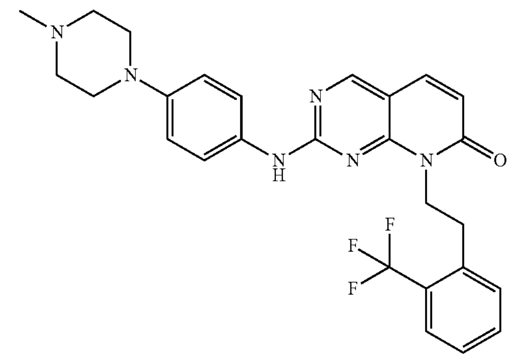 [SMILES: CN1CCN(c2ccc(Nc3ncc4ccc(=O)n(CCc5ccccc5C(F)(F)F)c4n3)cc2)CC1] | A | A | B | A |
| 67 | 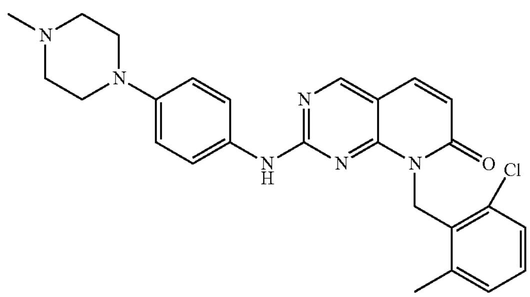 | A | B | B | A |
| 68 | 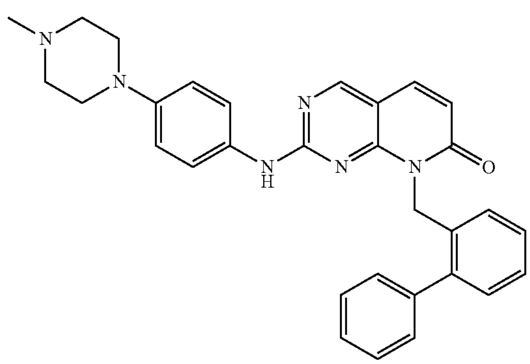 [SMILES: CN1CCN(c2ccc(Nc3ncc4ccc(=O)n(Cc5ccccc5-c5ccccc5)c4n3)cc2)CC1] | A | A | A | B |
| 69 | 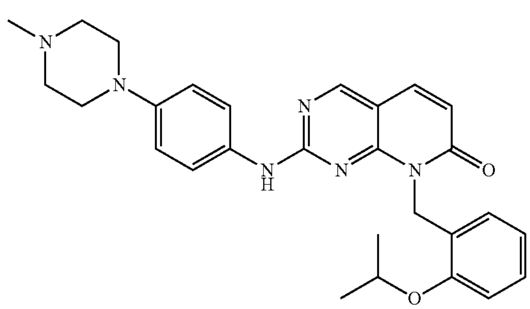 [SMILES: CC(C)Oc1ccccc1Cn1c(=O)ccc2cnc(Nc3ccc(N4CCN(C)CC4)cc3)nc21] | A | A | A | A |

TABLE 8-continued

| No. | Structure | PAK1 IC50 μM | PAK2 IC50 μM | PAK3 IC50 μM | PAK4 IC50 μM |
|---|---|---|---|---|---|
| 70 | 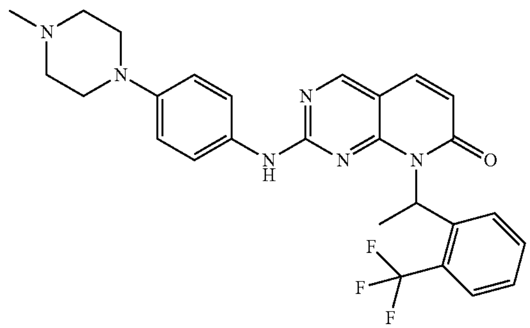 [SMILES: CC(c1ccccc1C(F)(F)F)n1c(=O)ccc2cnc(Nc3ccc(N4CCN(C)CC4)cc3)nc21] | B | C | C | B |
| 71 | 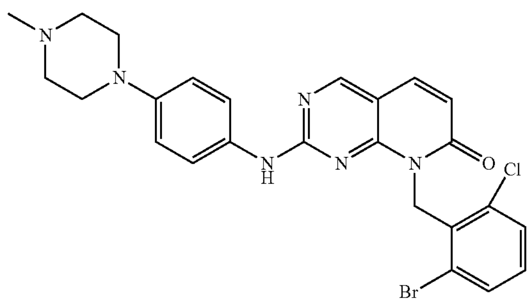 | A | A | A | A |
| 72 | 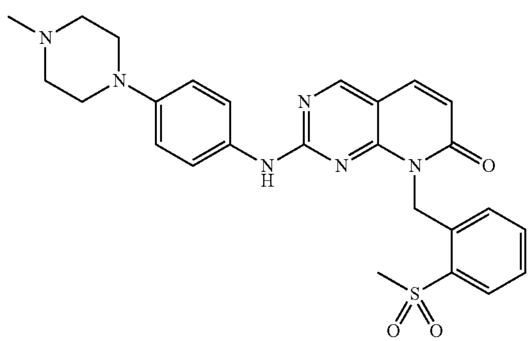 [SMILES: CN1CCN(c2ccc(Nc3ncc4ccc(=O)n(Cc5ccccc5S(C)(=O)=O)c4n3)cc2)CC1] | A | A | A | A |
| 73 | 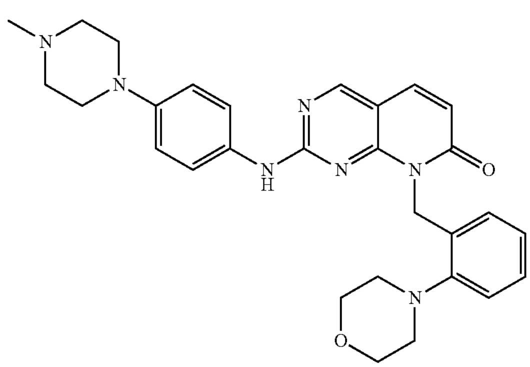 [SMILES: CN1CCN(c2ccc(Nc3ncc4ccc(=O)n(Cc5ccccc5N5CCOCC5)c4n3)cc2)CC1] | A | A | A | A |

TABLE 8-continued

| No. | Structure | PAK1 IC50 μM | PAK2 IC50 μM | PAK3 IC50 μM | PAK4 IC50 μM |
|---|---|---|---|---|---|
| 74 | 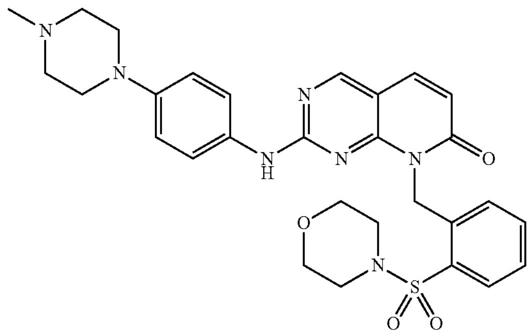 [SMILES: CN1CCN(c2ccc(Nc3ncc4ccc(=O)n(Cc5ccccc5S(=O)(=O)N5CCOCC5)c4n3)cc2)CC1] | A | A | A | A |
| 75 | 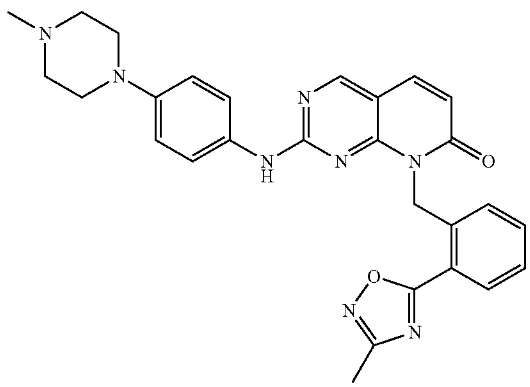 [SMILES: Cc1noc(-c2ccccc2Cn2c(=O)ccc3cnc(Nc4ccc(N5CCN(C)CC5)cc4)nc32)n1] | A | B | B | B |
| 76 | 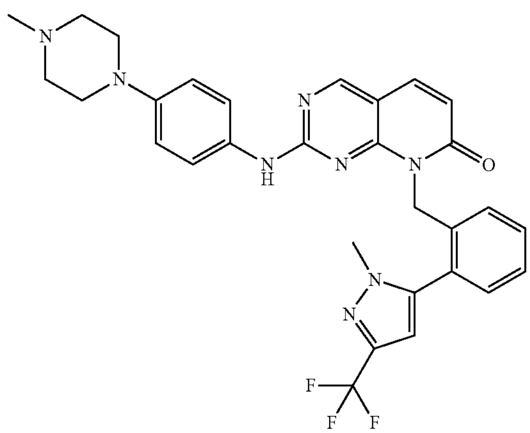 [SMILES: CN1CCN(c2ccc(Nc3ncc4ccc(=O)n(Cc5ccccc5-c5cc(C(F)(F)F)nn5C)c4n3)cc2)CC1] | B | B | B | C |
| 77 | 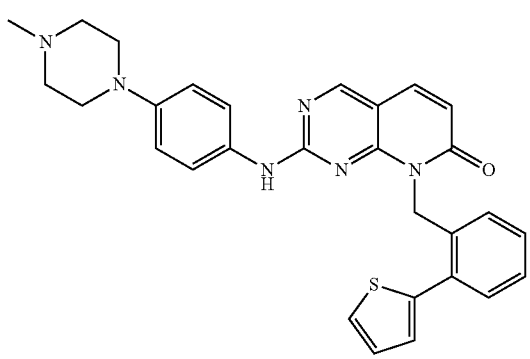 [SMILES: CN1CCN(c2ccc(Nc3ncc4ccc(=O)n(Cc5ccccc5-c5cccs5)c4n3)cc2)CC1] | A | A | A | B |

TABLE 8-continued
| No. | Structure | PAK1 IC50 μM | PAK2 IC50 μM | PAK3 IC50 μM | PAK4 IC50 μM |
|---|---|---|---|---|---|
| 78 | 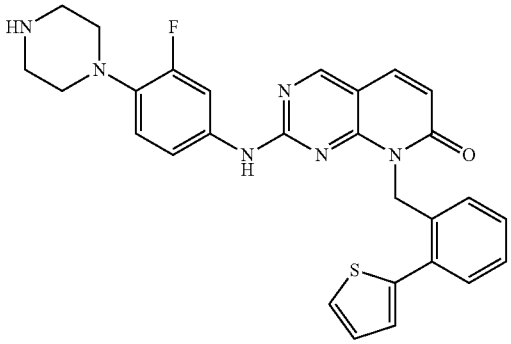 [SMILES: O=c1ccc2cnc(Nc3ccc(N4CCNCC4)c(F)c3)nc2n1Cc1ccccc1-c1cccs1] | A | A | A | A |
| 79 | 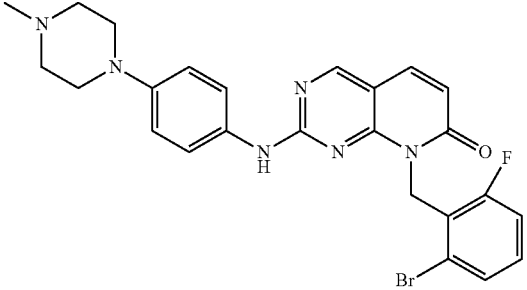 | A | A | A | A |
| 80 | 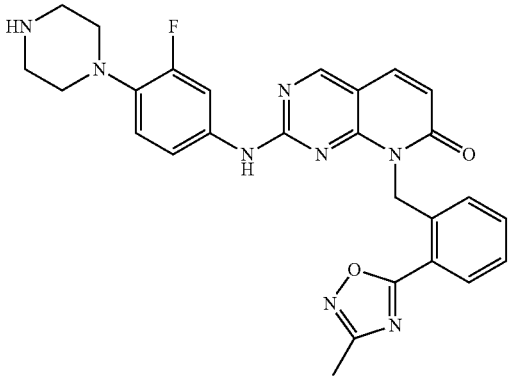 [SMILES: Cc1noc(-c2ccccc2Cn2c(=O)ccc3cnc(Nc4ccc(N5CCNCC5)c(F)c4)nc32)n1] | A | B | B | B |
| 81 | 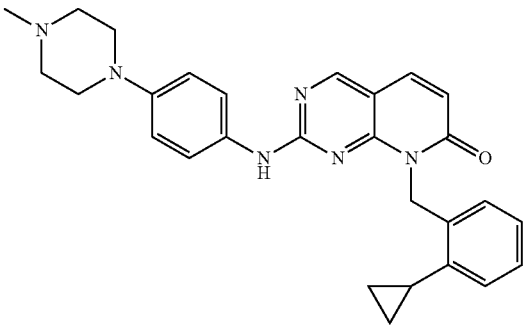 [SMILES: CN1CCN(c2ccc(Nc3ncc4ccc(=O)n(Cc5ccccc5C5CC5)c4n3)cc2)CC1] | A | A | A | A |

TABLE 8-continued

| No. | Structure | PAK1 IC50 μM | PAK2 IC50 μM | PAK3 IC50 μM | PAK4 IC50 μM |
|---|---|---|---|---|---|
| 82 | 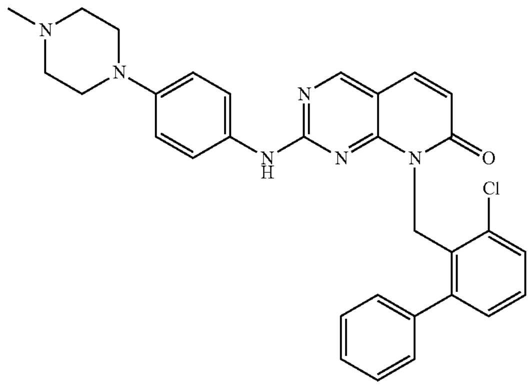 [SMILES: CN1CCN(c2ccc(Nc3ncc4ccc(=O)n(Cc5c(Cl)cccc5-c5ccccc5)c4n3)cc2)CC1] | B | C | C | B |
| 83 | 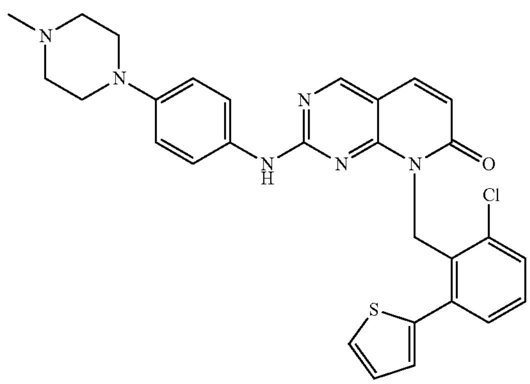 [SMILES: CN1CCN(c2ccc(Nc3ncc4ccc(=O)n(Cc5c(Cl)cccc5-c5cccs5)c4n3)cc2)CC1] | B | C | C | C |
| 84 | 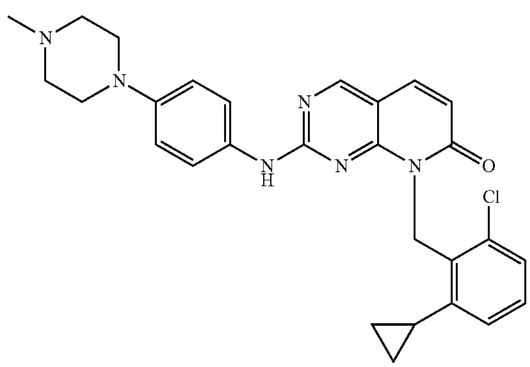 [SMILES: CN1CCN(c2ccc(Nc3ncc4ccc(=O)n(Cc5c(Cl)cccc5C5CC5)c4n3)cc2)CC1] | A | A | A | B |
| 86 | 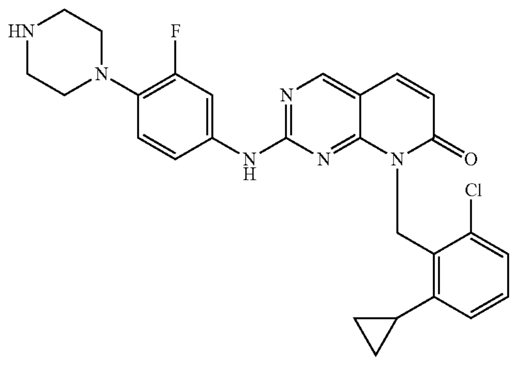 [SMILES: O=c1ccc2cnc(Nc3ccc(N4CCNCC4)c(F)c3)nc2n1Cc1c(Cl)cccc1C1CC1] | A | A | A | B |

TABLE 8-continued
| No. | Structure | PAK1 IC50 μM | PAK2 IC50 μM | PAK3 IC50 μM | PAK4 IC50 μM |
|---|---|---|---|---|---|
| 91 | 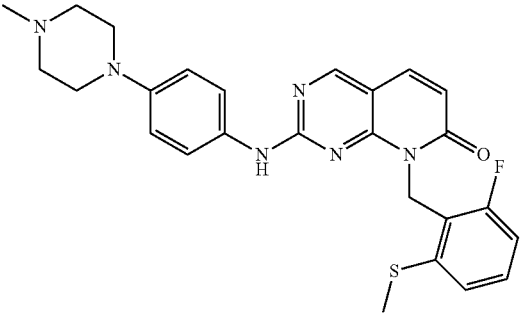 [SMILES: CSc1cccc(F)c1Cn1c(=O)ccc2cnc(Nc3ccc(N4CCN(C)CC4)cc3)nc21] | A | A | A | A |
| 92 | 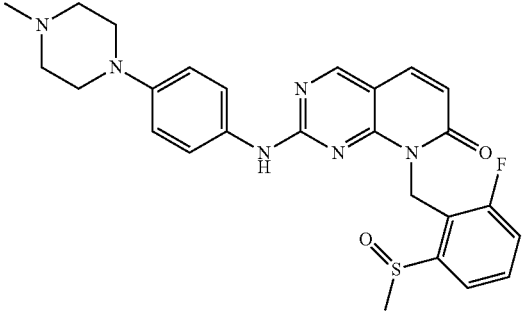 [SMILES: CN1CCN(c2ccc(Nc3ncc4ccc(=O)n(Cc5c(F)cccc5S(C)=O)c4n3)cc2)CC1] | A | B | A | B |
| 94 | 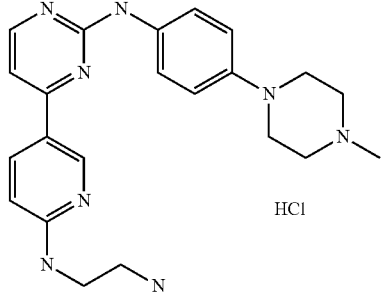 [SMILES: CN1CCN(c2ccc(Nc3nccc(-c4ccc(NCCN)nc4)n3)cc2)CC1 ; Cl] HCl | A | B | B | A |
| 95 | 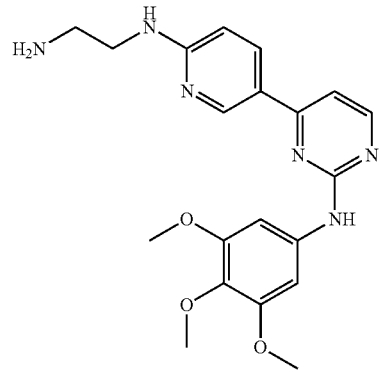 [SMILES: COc1cc(Nc2nccc(-c3ccc(NCCN)nc3)n2)cc(OC)c1OC] | A | B | B | A |

US 8,674,095 B2

277                                                                 278

TABLE 8-continued

| No. | Structure | PAK1 IC50 μM | PAK2 IC50 μM | PAK3 IC50 μM | PAK4 IC50 μM |
|---|---|---|---|---|---|
| 96 | 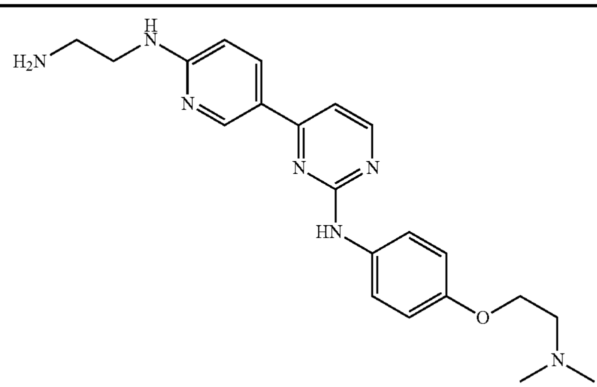 | B | B | | B |
| 97 | 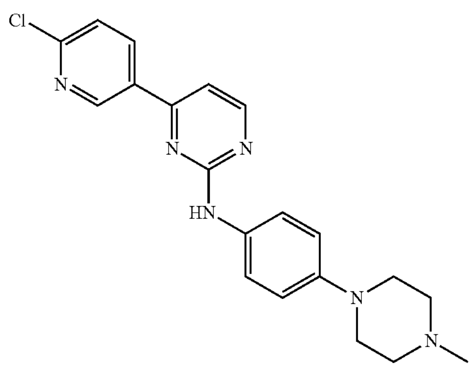 [SMILES: CN1CCN(c2ccc(Nc3nccc(-c4ccc(Cl)nc4)n3)cc2)CC1] | B | C | | C |
| 98 | 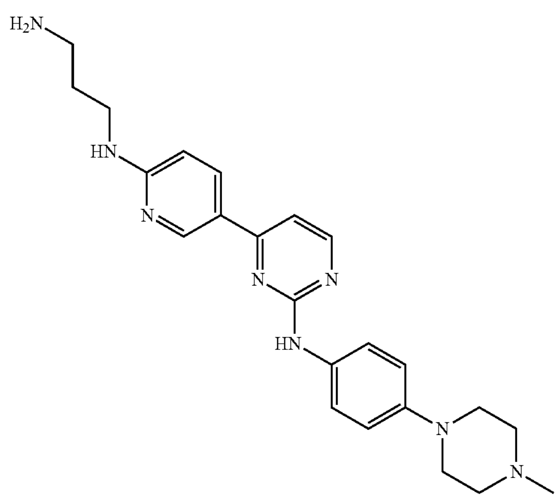 [SMILES: CN1CCN(c2ccc(Nc3nccc(-c4ccc(NCCCN)nc4)n3)cc2)CC1] | A | B | | B |
| 99 | 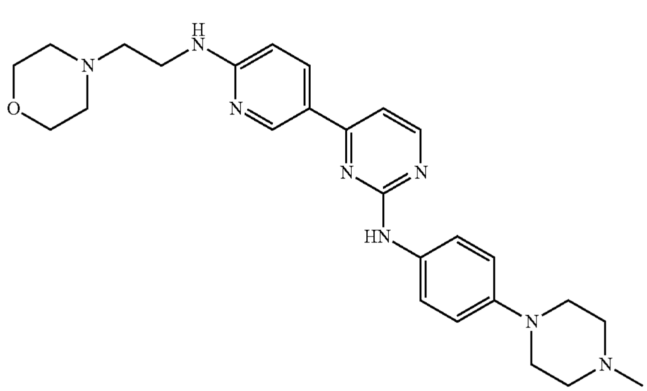 [SMILES: CN1CCN(c2ccc(Nc3nccc(-c4ccc(NCCN5CCOCC5)nc4)n3)cc2)CC1] | B | C | | B |

TABLE 8-continued
| No. | Structure | PAK1 IC50 μM | PAK2 IC50 μM | PAK3 IC50 μM | PAK4 IC50 μM |
|---|---|---|---|---|---|
| 100 | 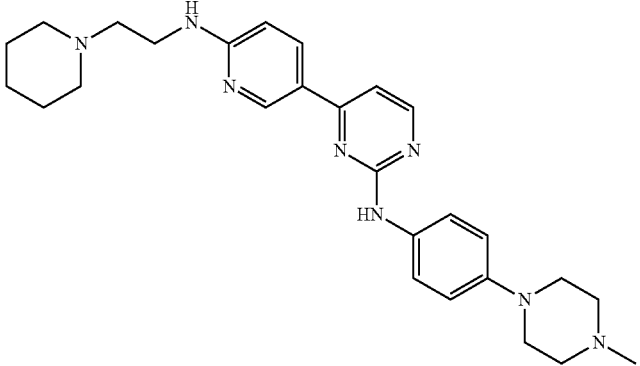 [SMILES: CN1CCN(c2ccc(Nc3nccc(-c4ccc(NCCN5CCCCC5)nc4)n3)cc2)CC1] | B | B | C | A |
| 101 | 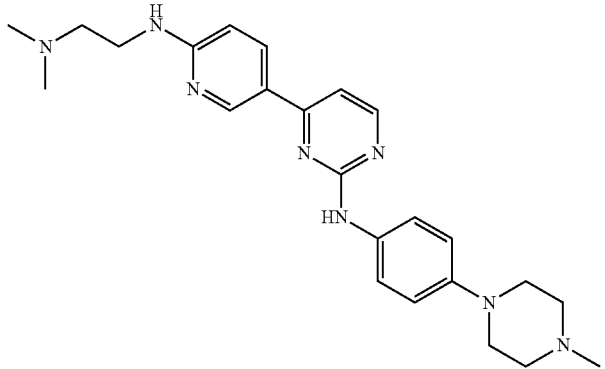 | B | B | | B |
| 102 | 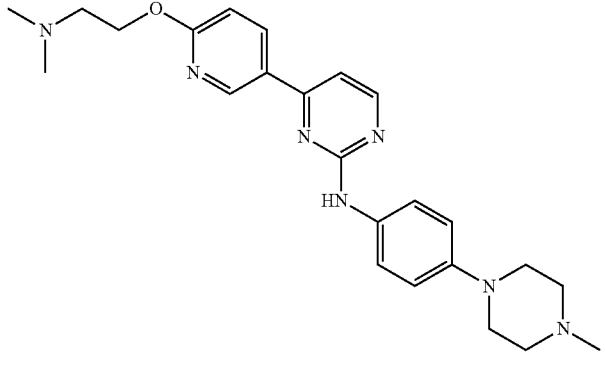 | B | C | | C |
| 103 | 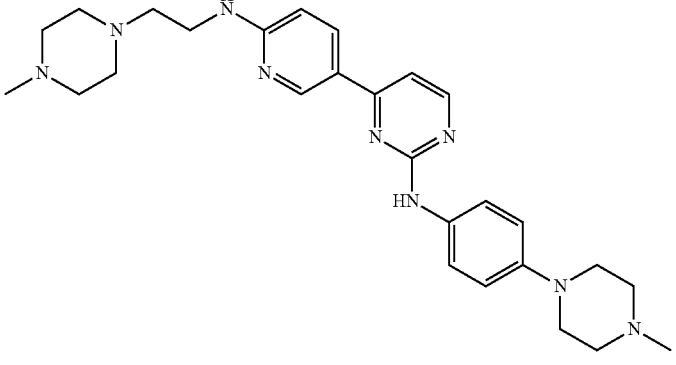 | B | C | | C |

TABLE 8-continued
| No. | Structure | PAK1 IC50 μM | PAK2 IC50 μM | PAK3 IC50 μM | PAK4 IC50 μM |
|---|---|---|---|---|---|
| 104 | 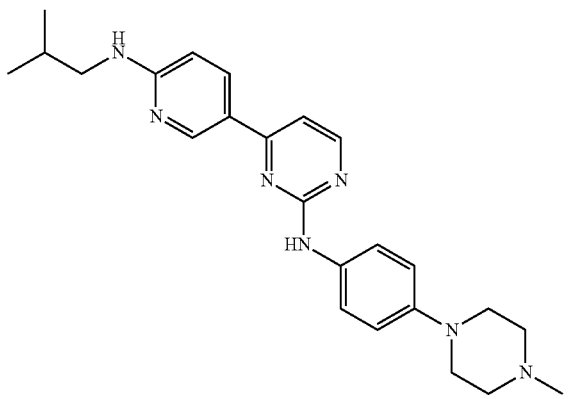 [SMILES: CC(C)CNc1ccc(-c2ccnc(Nc3ccc(N4CCN(C)CC4)cc3)n2)cn1] | B | B | C | A |
| 105 | 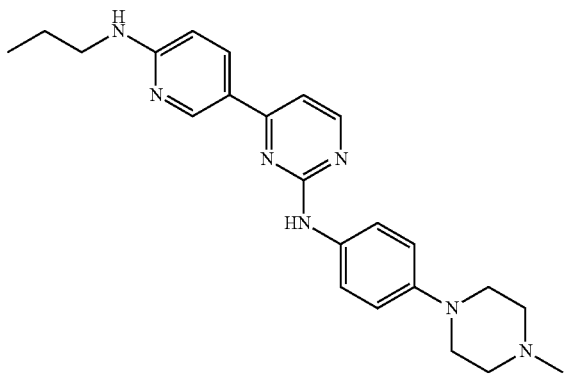 [SMILES: CCCNc1ccc(-c2ccnc(Nc3ccc(N4CCN(C)CC4)cc3)n2)cn1] | B | B | | B |
| 106 | 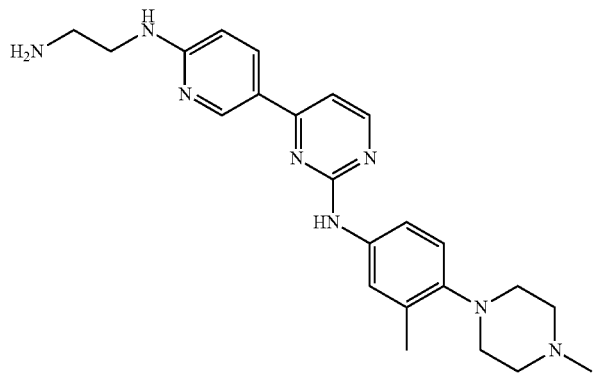 | A | B | B | A |
| 107 | 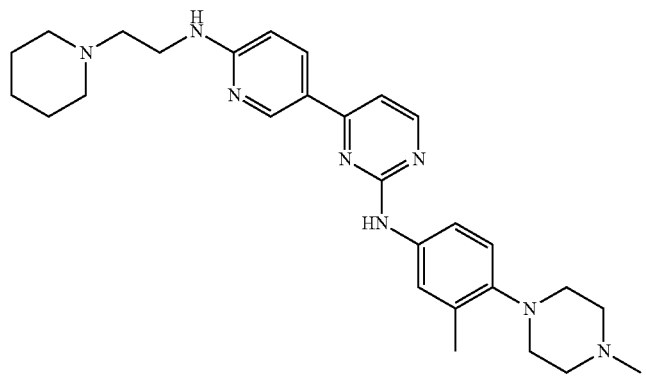 [SMILES: Cc1cc(Nc2nccc(-c3ccc(NCCN4CCCCC4)nc3)n2)ccc1N1CCN(C)CC1] | B | B | C | A |

TABLE 8-continued

| No. | Structure | PAK1 IC50 μM | PAK2 IC50 μM | PAK3 IC50 μM | PAK4 IC50 μM |
|---|---|---|---|---|---|
| 108 | 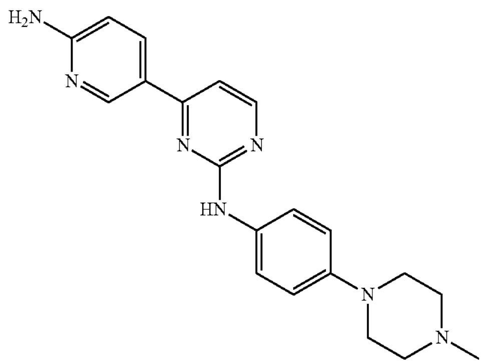 [SMILES: CN1CCN(c2ccc(Nc3nccc(-c4ccc(N)nc4)n3)cc2)CC1] | B | B | C | B |
| 109 | 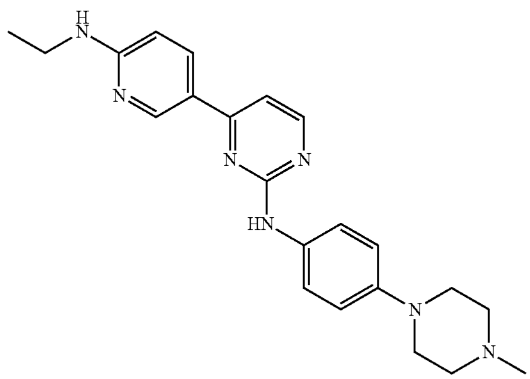 [SMILES: CCNc1ccc(-c2ccnc(Nc3ccc(N4CCN(C)CC4)cc3)n2)cn1] | B | C | C | A |
| 110 | 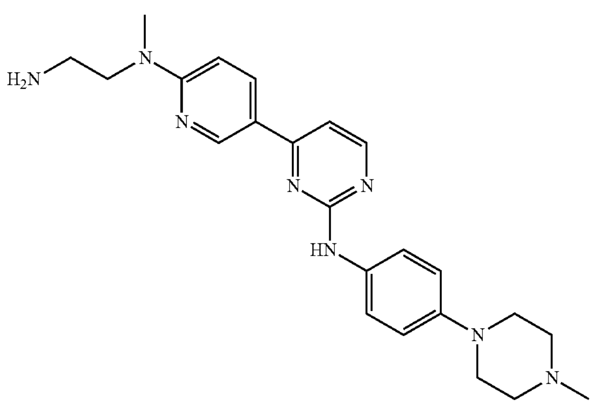 [SMILES: CN1CCN(c2ccc(Nc3nccc(-c4ccc(N(C)CCN)nc4)n3)cc2)CC1] | B | B | C | B |
| 111 | 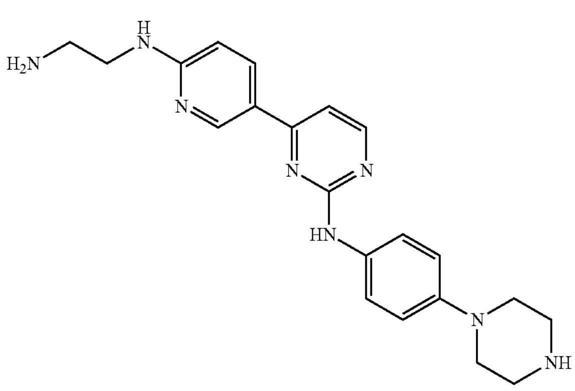 [SMILES: NCCNc1ccc(-c2ccnc(Nc3ccc(N4CCNCC4)cc3)n2)cn1] | A | B | B | A |

TABLE 8-continued

| No. | Structure | PAK1 IC50 μM | PAK2 IC50 μM | PAK3 IC50 μM | PAK4 IC50 μM |
|-----|-----------|--------------|--------------|--------------|--------------|
| 112 | 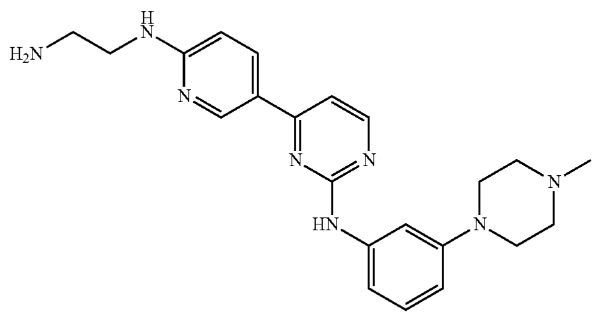 [SMILES: CN1CCN(c2cccc(Nc3nccc(-c4ccc(NCCN)nc4)n3)c2)CC1] | B | B | C | A |
| 113 | 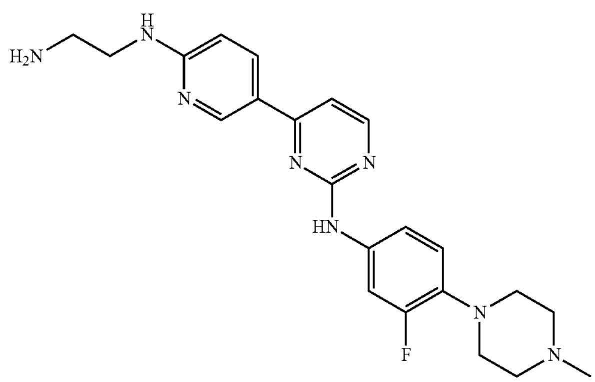 | A | B | B | A |
| 114 | 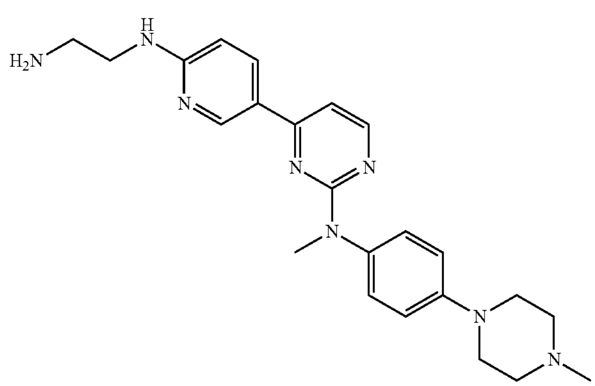 [SMILES: CN1CCN(c2ccc(N(C)c3nccc(-c4ccc(NCCN)nc4)n3)cc2)CC1] | C | C | | C |
| 115 | 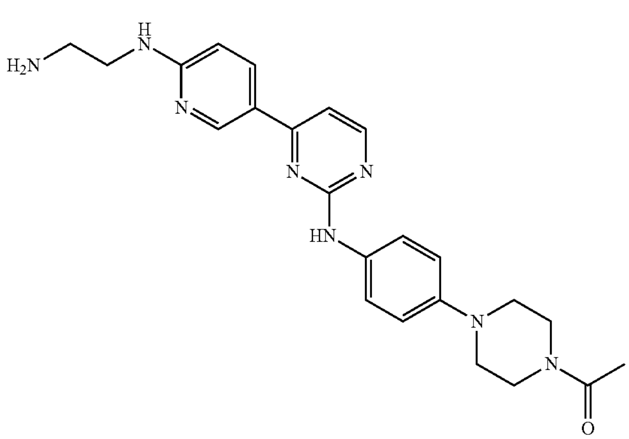 [SMILES: CC(=O)N1CCN(c2ccc(Nc3nccc(-c4ccc(NCCN)nc4)n3)cc2)CC1] | C | C | C | A |

TABLE 8-continued

| No. | Structure | PAK1 IC50 μM | PAK2 IC50 μM | PAK3 IC50 μM | PAK4 IC50 μM |
|---|---|---|---|---|---|
| 119 | 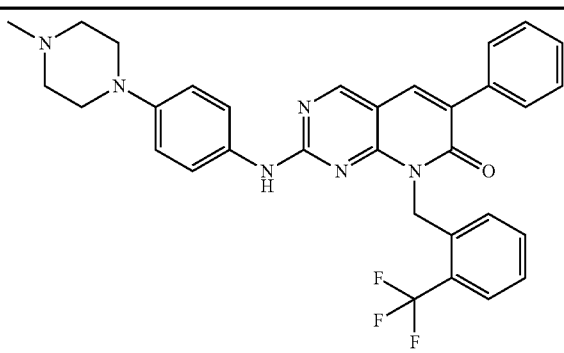 | A | A | A | C |
| 120 | 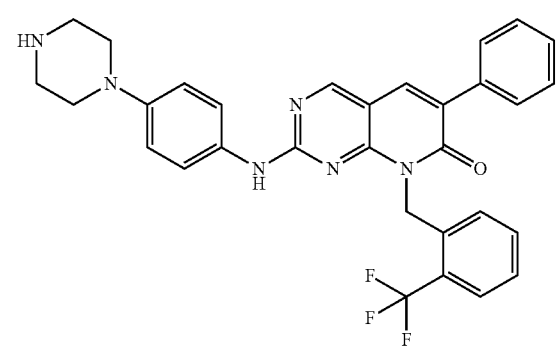 [SMILES: O=c1c(-c2ccccc2)cc2cnc(Nc3ccc(N4CCNCC4)cc3)nc2n1Cc1ccccc1C(F)(F)F] | A | A | A | B |
| 121 | 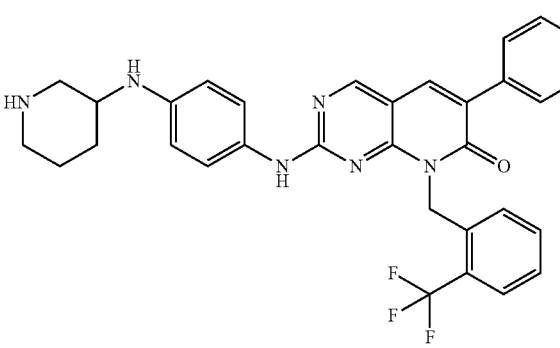 | A | A | A | B |

A: IC50 < 1 μM;
B: IC50 > 1 μM and < 10 μM;
C: IC50 > 10 μM

Example 124

Treatment of Schizophrenia by Administration of a PAK Inhibitor Compound 84 in an Animal Model The ability of a PAK inhibitor to ameliorate behavioral and anatomical symptoms of schizophrenia (i.e., their mouse analogs) is tested in a dominant-negative DISC1 mouse model of schizophrenia (Hikida et al (2007), *Proc Natl Acad Sci USA*, 104(36):14501-14506).

Forty DISC1 mice (ages 5-8 months) on a C57BL6 strain background are divided into treatment group (1 mg/kg Compound 84, oral gavage) and a placebo group (0.1% DMSO in physiological saline solution) and analyzed for behavioral differences in open field, prepulse inhibition, and hidden food behavioral tests, with an interval of about one week between each type of test. In the open field test, each mouse is placed in a novel open field box (40 cm×40 cm; San Diego Instruments, San Diego, Calif.) for two hours. Horizontal and vertical locomotor activities in the periphery as well as the center area are automatically recorded by an infrared activity monitor (San Diego Instruments). Single breaks are reported as "counts." In this behavioral test, a significant reduction in total activity in the treatment group relative to the placebo group indicates a possible treatment effect.

In the hidden food test, mice are food-deprived for 24 h. After habituation to a new cage for 5 min, a food pellet is hidden under the cage bedding. The time it takes for the mouse to find the food pellet is measured until a maximum of 10 min is reached. In this behavioral test, a significant reduction in time to find the food pellet in the treatment group relative to the placebo group is indicative of a successful treatment effect.

In the prepulse inhibition test, acoustic startle and prepulse inhibition responses are measured in a startle chamber (San Diego Instruments). Each mouse is individualed to six sets of seven trail types distributed pseudorandomly: pulse-alone trials, prepulse-pulse trials, and no-stimulus trials. The pulse used is 120 dB and the prepulse is 74 dB. A significant increase in the prepulse inhibition response in the treatment group relative to the placebo group is indicative of a successful treatment effect.

In the forced swim test, each mouse is put in a large plastic cylinder, which is half-filled with room temperature water. The test duration is 6 min, during which the swim/immobility times are recorded. In this behavioral test, a significant reduction in immobility in the treatment group relative to the placebo group is indicative of a successful treatment effect.

In order to evaluate the ability of Compound 84 to alter brain morphology, an MRI study is conducted on placebo-treated and treated groups of DISC1-DN mice. In vivo MRI experiments are performed on an 11.7T Bruker Biospec small animal imaging system. A three-dimensional, fast-spin echo, diffusion weighted (DW) imaging sequence with twin navigation echoes is used to assess the ratio of lateral ventricle volume to total brain volume. A decrease in this ratio in the treated group relative to the ratio observed in the placebo-group is indicative of a successful treatment effect.

Statistical Analysis. Statistical analysis is performed by ANOVA or repeated ANOVA. Differences between groups are considered significant at $p<0.05$.

Example 125

In Vivo Monitoring of Dendritic Spine Plasticity in Double Transgenic GFP-M/DN-DISC1 Mice Treated with a PAK Inhibitor Compound 98

In the following experiment, dendritic spine plasticity is directly monitored in vivo by two photon laser scanning microscopy (TPLSM) in double transgenic GFP-M/DN-DISC1 mice treated with Compound 98 or a placebo. Mice (C57BL/6) expressing GFP in a subset of cortical layer 5 neurons (transgenic line GFP-M described in Feng et al, 2000, *Neuron* 28:41-51) are crossed with DN-DISC1 C57BL/6 DN-DISC1 mice (Hikida et al (2007), *Proc Natl Acad Sci USA*, 104(36):14501-14506) to obtain heterozygous transgenic mice, which are then crossed to obtain homozygous double transgenic GFPM/DN-DISC1 mice used in this study.

GFP-M/DN-DISC1 animals aged 28-61 d are anesthetized using avenin (16 μl/g body weight; Sigma, St. Louis, Mo.). The skull is exposed, scrubbed, and cleaned with ethanol. Primary visual, somatosensory, auditory, and motor cortices are identified based on stereotaxic coordinates, and their location is confirmed with tracer injections (see below).

Long-term imaging experiments are started at P40. The skull is thinned over the imaging area as described in Grutzendler et al, (2002), *Nature*, 420:812-816. A small metal bar is affixed to the skull. The metal bar is then screwed into a plate that connected directly to the microscope stage for stability during imaging. The metal bar also allows for maintaining head angle and position during different imaging sessions. At the end of the imaging session, animals are sutured and returned to their cage. Thirty animals previously imaged at P40 are then divided into a control group receiving a 1% sugar solution (oral gavage once per day) and a treatment group administered Compound 98, in 0.1% DMSO (oral gavage. 1 mg/kg, once per day). During the subsequent imaging sessions (at P45, P50, P55, or P70), animals are reanesthetized and the skull is rethinned. The same imaging area is identified based on the blood vessel pattern and gross dendritic pattern, which generally remains stable over this time period.

At the end of the last imaging session, injections of cholera toxin subunit B coupled to Alexa Fluor 594 are made adjacent to imaged areas to facilitate identification of imaged cells and cortical areas after fixation. Mice are transcardially perfused and fixed with paraformaldehyde, and coronal sections are cut to verify the location of imaged cells. Sections are then mounted in buffer, coverslipped, and sealed. Images are collected using a Fluoview confocal microscope (Olympus Optical, Melville, N.Y.).

For in vivo two photon imaging, a two-photon laser scanning microscope is used as described in Majewska et al, (2000), *pflügers Arch*, 441:398-408. The microscope consists of a modified Fluoview confocal scan head (Olympus Optical) and a titanium/sulphur laser providing 100 fs pulses at 80 MHz at a wavelength of 920 nm (Tsunami; Spectra-Physics, Menlo Park, Calif.) pumped by a 10 W solid-state source (Millenia; Spectra-Physics). Fluorescence is detected using photomultiplier tubes (HC125-02; Hamamatsu, Shizouka, Japan) in whole-field detection mode. The craniotomy over the visual cortex is initially identified under whole-field fluorescence illumination, and areas with superficial dendrites are identified using a 20×, 0.95 numerical aperture lens (IR2; Olympus Optical). Spiny dendrites are further identified under digital zoom (7-10×) using two-photon imaging, and spines 50-200 μm below the pial surface are studied. Image acquisition is accomplished using Fluoview software. For motility measurements, Z stacks taken 0.5-1 μm apart are acquired every 5 min for 2 h. For synapse turnover experiments, Z stacks of dendrites and axons are acquired at P40 and then again at P50 or P70. Dendrites and axons located in layers 1-3 are studied. Although both layer 5 and layer 6 neurons are labeled in the mice used in this study, only layer 5 neurons send a clear apical dendrite close to the pial surface thus, the data will come from spines on the apical tuft of layer 5 neurons and axons in superficial cortical layers.

Images are exported to Matlab (Math Works, Natick, Mass.) in which they are processed using custom-written algorithms for image enhancement and alignment of the time series. For motility measurements (see Majewska et al, (2003), *Proc Nail Acad Sci USA*, 100:16024-16029) spines are analyzed on two-dimensional projections containing between 5 and 30 individual images; therefore, movements in the z dimension are not analyzed. Spine motility is defined as the average change in length per unit time (micrometers per minute). Lengths are measured from the base of the protrusion to its tip. The position of spines are compared on different imaging days. Spines that are farther than 0.5 μm laterally from their previous location are considered to be different spines. Values for stable spines are defined as the percentage of the original spine population present on the second day of imaging. Only areas that show high signal-to-noise ratio in all imaging sessions will be considered for analysis. Analysis is performed blind with respect to animal age and sensory cortical area. Spine motility (e.g., spine turnover), morphology, and density are then compared between control and treatment groups. It is expected that treatment with Compound 98 will rescue defective spine morphology relative to that observed in untreated control animals.

Example 126

Treatment of Clinical Depression by Administration of a PAK Inhibitor Compound 63 in an Animal Model A rat olfactory bulbectomy (OBX) model of clinical depression (see, e.g., van Riezen et al (1990), *Pharmacol*

Ther, 47(1):21-34; and Jarosik et al (2007), *Exp Neurol,* 204 (1):20-28) is used to evaluate treatment of clinical depression with Compound 63. Dendritic spine density and morphology are compared in treated and untreated groups of animals as described below. It is expected that treatment of OBX animals with a PAK inhibitor will cause an increase in spine density relative to that observed in untreated OBX animals.

All experiments are performed in strict accordance with NIH standards for laboratory animal use. The study uses 48 adult male Sprague-Dawley rats (230-280 g) housed in groups of four animals (two sham and two OBX), as indicated in van Riezen et al supra, in a controlled environment with food and water available ad libitum. Half of the experimental animals (n=24) undergo bilateral olfactory bulbectomy (OBX) while the other half undergo sham surgery (n=24). Upon completion of surgery, animals are allowed to recover for 2 weeks prior to behavioral testing. This is necessary to: 1) allow for the recovery of animal body weight which is reduced following surgery, 2) allow complete healing of superficial surgical sites, and) "bulbectomy syndrome" develops during the first 2 weeks postsurgery.

Two weeks after surgery, OBX and sham-operated animals are subdivided into one of four experimental conditions. One group of OBX animals is administered daily injections of saline solution (n=6 for each surgical condition) or Compound 63 (1 mg/kg; oral gavage) (n=6 for each surgical condition). These groups are included to examine the effect of chronic administration of Compound 63 (PAK inhibitor) on olfactory bulbectomized animals (2 weeks postsurgical recovery+2 weeks PAK inhibitor treatment). Administration of the drug or control solution are given at the same time each day and in the home cage of each animal. Groups of OBX and sham-operated animals receive no treatment during this 2-week period and serve as unhandled controls. These groups are necessary to examine the persistence of observed effects of OBX on dendritic spine density (4 weeks postsurgery). Animals receiving postsurgery drug treatment are sacrificed 24 h after the last injection.

Animals are perfused transcardially with 4% formaldehyde (in 0.1 M sodium phosphate buffer, pH=7.4) under deep anesthesia with sodium pentobarbital (60 mg/kg) at the completion of experimental procedures. Following fixation, brains are removed and placed in 4% formaldehyde (freshly depolymerized from para-formaldehyde) overnight. Brains are then sectioned at 100 μm on a vibratome and prepared for Golgi impregnation using a protocol adapted from previously described methods (Izzo et al, 1987). In brief, tissue sections are postfixed in 1% OsO4 for 30 min and then washed in 0.1 M phosphate buffer (3×15 min). Sections are free-floated in 3.5% K2Cr2O7 solution for 90 min, mounted between two microscope slides in a "sandwich" assembly, and rapidly immersed in a 1% AgNO3 solution. The following day, sections are rinsed in ddH 20, dehydrated in 70% and 100% ethanol, cleared with Histoclear™, and mounted on microscope slides with DPX.

Dendritic spines are counted on 1250× camera lucida images that include all spines observable in each focal plane occupied by the dendrite. Cells are analyzed only if they are fully impregnated (CA1: primary apical dendrites extended into stratum lacunosum moleculare and basilar dendrites extended into stratum oriens; CA3: primary apical dendrites extended into stratum lacunosum moleculare and basilar dendrites extended into stratum oriens; dentate gyrus: secondary dendrites extended from primary dendrite within the molecular layer), intact; and occurring in regions of the section that are free of blood vessels, precipitate, and/or other imperfections. Dendritic spines are counted along the entire length of secondary oblique dendritic processes (50-100 μm) extending from the primary apical dendrite within stratum radiatum of area CA1 and CA3. In CA1 and CA3, secondary dendrites are defined as those branches projecting directly from the primary apical dendrite exclusive of tertiary daughter branches. In addition, spines are counted along the length of secondary dendrites of granule cells in the dentate gyrus to determine if effects are limited to CA1 and CA3. In dentate gyrus, secondary dendrites are analyzed in the glutamatergic entorhinal input zone in the outer two-thirds of the molecular layer. Approximately 20 dendritic segments (10 in each cerebral hemisphere; 50-100 μm in length) in each hippocampal subregion (CA1, CA3, and dentate gyrus) are examined for each experimental animal. Treatment conditions are coded throughout the entire process of cell identification, spine counting, dendritic length analysis, and subsequent data analysis. Analysis of variance and Tukey post-hoc pairwise comparisons are used to assess differences between experimental groups.

When significant changes in dendritic spine density are observed, camera lucida images and the Zeiss CLSM measurement program are used to quantify the number and length of secondary dendrites. This analysis is necessary as apparent changes in dendritic spine density can result from an increase or decrease in the length of dendrites and not the formation or loss of spines per se. Photomicrographs are obtained with a helium-neon 633 laser and Zeiss 410 confocal laser scanning microscope.

Example 127

Treatment of Epilepsy by Administration of a PAK Inhibitor Compound 12 in an Animal Model A rat tetanus toxin model of epilepsy is used to evaluate treatment of epilepsy with Compound 12.

Wistar rat pups (Harlan Sprague Dawley, Indianapolis, Ind.), 10 d of age, are anesthetized with an intraperitoneal injection of ketamine and xylazine (33 and 1.5 mg/kg, respectively). When necessary, this is supplemented by inhalation of methoxyflurane (Metofane). Tetanus toxin solution to be injected is generated by dissolving 2.5 or 5 ng of tetanus toxin in 20 or 40 nl of sterile saline solution. Afterwards, the tetanus toxin solution is coinjected into the right hippocampus along with a solution of Compound 12.

To inject tetanus toxin and Compound 12, the pups are placed in an infant rat stereotaxic head holder, a midline incision is made, and a small hole is drilled in the skull. The stereotaxic coordinates for injection are: anteroposterior, −2.1 mm; mediolateral, 3.0 mm from the bregma; and dorsoventral, −2.95 mm from the dural surface. The toxin and Compound 12 are slowly injected at 4 nl/min. After injection, the needle is left in place for 15 min to reduce reflux up the needle track. During injections, the body temperature of rat pups is maintained by a warmed (electrically regulated) metal plate. Littermates, stereotaxically injected with sterile saline, or untreated rats serve as controls.

The frequency of behavioral seizures is monitored for 1 hr/day for 10 consecutive days after tetanus toxin/Compound 12 injections. The types and duration of seizures are scored. Wild running seizures are most easily identified.

After seizure scoring on the 10th day animals are perfused transcardially and dendritic spines in the CA3 region are counted and analyzed as described above.

The t test for comparison of two independent means is used in comparing the number of seizures in treated vs untreated rats and in comparing dendritic and axon arbors in experimental and control rats. When data are not normally distributed, a Mann-Whitney U test is used. Sigma Stat is used to perform all statistical tests. It is expected that treatment with Compound 12 will reduce the frequency and severity of seizures.

Example 128

Clinical Trial: Treatment of Schizophrenia with a PAK Inhibitor Compound 75

The following human clinical trial is performed to determine the safety and efficacy of a PAK inhibitor compound for the treatment of schizophrenia.

Sixty patients are recruited via referrals from community mental health teams, after the patients have been diagnosed with schizophrenia using the Structured Clinical Interview for DSM-IV ("SCID"; First et al., (1995), *Structured Clinical Interview for DSM-IV Axis I Disorders, Patient Edition* (*SCID-P*), version 2, New York State Psychiatric Institute, Biometrics Research, New York).

A screening visit is arranged and a full explanation of the study prior to screening is provided if the patient appeared suitable for and interested in taking part. For inclusion, all patients are required to meet the following criteria: (i) aged between 18 and 60 years, (ii) receiving stable treatment with an atypical (Risperidone, Olanzapine, Quetiapine) antipsychotic and have stable psychotic symptoms (i.e. no change in medication/dose of current medication over last 6 weeks and unlikely to require change in antipsychotic medication), (iii) negative urine screening for illicit drugs and negative pregnancy test for female patients, (iv) cooperative, able to ingest oral medication and willing to undertake repeated cognitive testing, (v) able to provide written informed consent, (vi) reading ability of not more than 40 errors on the National Adult Reading (Nelson et al, (1991)), and (vii) between 1 and 2 standard deviations (S.D.) below expected performance on the basis of age and education level on the California Verbal Learning Test (Delis et al., 1987). In addition, the following criteria are used to define unsuitable patients: (i) concurrent DSM-IV diagnosis, (ii) current treatment with benzodiazepines or antidepressants, (iii) history of neurodegenerative disorder in first degree relative (e.g. AD, Parkinson's disease, Huntington's disease, multiple sclerosis), (iv) history of DSM-IV substance dependence in the last year or substance abuse within last month, (v) lifetime history of trauma resulting in loss of consciousness for 1 h or longer, (vi) participation in another investigational drug trial within 6 weeks prior to study entry, (vii) recent (within last 3 months) history of suicidal or violent acts, and (viii) current diagnosis of uncontrollable seizure disorder, active peptic ulceration, severe and unstable cardiovascular disease or/and acute severe unstable asthma. The study procedures are approved by an institutional ethics review board. All patients in the study must provide written informed consent.

After screening has identified suitable patients that have provided informed consent, patients are placed on a single-blind placebo for 1 week. After 1 week on placebo (baseline), all patients complete a comprehensive cognitive test battery and undergo clinical assessments, and then are randomized into a double-blind protocol so that, half of the sample received Compound 75 capsules and the remaining half received placebo for the next 24 weeks. Cognitive and clinical assessments are carried out again at 12 weeks and 24 weeks.

Patients assigned to the treatment group will receive 1.5 mg twice a day for the first 2 weeks, 3 mg twice a day over the next 2 weeks, 4.5 mg twice a day dose for the next 2 weeks and then 6 mg twice a day for the remaining period so at the time of 12 weeks cognitive assessments all patients are on the maximum dose. The placebo group will receive identical appearing capsules containing ascorbic acid (100 mg).

Symptoms are rated within 4 days of cognitive testing using the Positive and Negative Syndrome scale (PANSS) (Kay et al. (1987), *Schizophr Res,* 13:261-276) on all three occasions. Side effects are also assessed within 4 days of testing using the Abnormal Involuntary Movement Scale (AIMS) (Guy, (1976), *ECCDEU Assessment Manual for Psychopharmacology* (*revised*), DHEW Publication No. (ADM) National Institutes of Mental Health, Rockville, Md., pages 76-338). Inter-rater reliability is carried out for PANSS at 6 monthly intervals by rating exemplar cases based on patient interviews on videotapes.

The cognitive battery includes measures of executive functioning, verbal skills, verbal and spatial working memory, attention and psychomotor speed. The battery is administered to all patients on all three occasions in the same fixed order (e.g., MATRICS cognitive battery, BACS score, and performance in Wisconsin Card Sort Test). Patients are allowed to take breaks as needed in order to obtain maximal performance at all times. Tests are administered and scored by trained psychologists who are blind to patients' group affiliations and are not involved in patients' treatment plan in any way.

Patients are told that the aim of the study is to investigate the cognitive effects of Compound 75. They are requested to abstain from alcohol for at least 24 h prior to their scheduled cognitive testing.

The patients in the treatment and placebo groups are compared on demographic, clinical, and cognitive variables obtained at baseline using independent sample 1-tests.

The effects of Compound 75 on positive symptoms, negative symptoms, general psychopathology score, total PANSS scores, and the scores on the AIMS are analyzed (separately) by 2 (Treatment, placebo)×3 (Time: baseline, 12 weeks, 24 weeks) analysis of variance (ANOVA).

All cognitive variables are first examined for their distribution properties, i.e., to ensure normality. The cognitive effects of Compound 75 over time are then evaluated by Treatment×Time ANOVA, performed separately for each variable, with Time as a within-individuals factor and Treatment as a between-individuals factor, followed by post-hoc mean comparisons wherever appropriate. All cognitive effects are then re-evaluated using ANOVA performed separately on change scores computed for each variable (12 weeks data minus baseline data, 24 weeks data minus baseline data). Alpha level for testing significance of effects is $p=0.05$.

Example 129

Clinical Trial: Treatment of Epilepsy with a PAK1/PAK3 Inhibitor

This is a 24-week study of an oral PAK1/PAK3 inhibitor in symptomatic patients with a diagnosis of epilepsy. This is an open-label, single-arm study to evaluate the dosing, tolerability, effectiveness and safety of a PAK1/PAK3 inhibitor as initial therapy for epilepsy. A total of 30 subjects will enrolled in the study.

Study Type: Interventional
Primary Outcome Measures:
Comparison of the mean stabilized dose of a PAK1/PAK3 inhibitor during the last 28 days of treatment between patients reporting 1 to 3 seizures versus patients reporting more than 3 seizures, during the 3 months prior to study entry Secondary Outcome Measures:

Influence of other patient characteristics on dose; Proportion of subjects remaining seizure-free; Time to stabilized dose; Reduction in seizure frequency.

Inclusion Criteria:

Subjects having new-onset epilepsy or epilepsy relapse characterized by partial-onset seizures or primary generalized tonic-clonic seizures; Having at least 1 seizure within the 3 months prior to entry; Subjects who are previously untreated for epilepsy, previously treated for epilepsy, or if currently taking epilepsy medication, must have been taking it for less than 6 weeks Exclusion Criteria:

Subjects currently on any medication for epilepsy for greater than 6 weeks; Having active liver disease.

Experimental Design

Patients are divided into two groups, a placebo group and a PAK1/PAK3 inhibitor group. Patients are administered tablets starting at 50 milligrams per day and titrated to an individualized optimal dose, up to a maximum of 400 milligrams per day of the PAK1/PAK3 inhibitor by the end of week 6. Patients will take tablets by mouth twice a day (morning and evening) for 24 weeks. Changes to this schedule will be based on a risk-benefit assessment of the patient's clinical condition by the investigator, such as tolerability, or reaching a stable dose sufficient to control their seizures.

Patients are evaluated at weekly visits over a period of 6 weeks. Groups are compared using ANOVA. Single variable differences are analyzed using an independent samples t-test. A Pearson's coefficient is used to determine relationship between seizure frequency and medication dose.

Example 130

Clinical Trial: Treatment of Alzheimer's Disease with a PAK Inhibitor

The following human clinical trial is performed to determine the safety and efficacy of the PAK inhibitor Compound 90 for the treatment of Alzheimer's disease. The study aims to provide preliminary estimates of effect of administration of a PAK inhibitor (Compound 90) in delaying progression of disease over a study period of one year.

Sixty patients between the ages of 55 and 80 are recruited via referrals from hospitals, after the patients have been diagnosed with mid stage Alzheimer's disease using the Mini-Mental State Exam scores and a clinical interview.

A screening visit is arranged and a full explanation of the study prior to screening is provided if the patient appeared suitable for and interested in taking part. For inclusion, all patients are required to meet the following criteria: (i) diagnosis of Alzheimer's disease (ii) a study partner who can attend all study visits (iii) negative urine screening for illicit drugs (iv) cooperative, able to ingest oral medication and willing to undertake repeated cognitive testing, (v) able to provide written informed consent. Exclusion criteria include (i) significant neurological disease other than Alzheimer's disease (ii) significant depression or other psychiatric disorder (iii) unstable medical conditions. The study procedures are approved by an institutional ethics review board. All patients in the study must provide written informed consent.

After screening has identified suitable patients that have provided informed consent, patients are placed on a single-blind placebo for 1 week. After 1 week on placebo (baseline), all patients complete a comprehensive cognitive test battery and undergo clinical assessments, and then are randomized into a double-blind protocol so that, half of the sample received Compound 90 capsules and the remaining half received placebo for the next 52 weeks. Cognitive and clinical assessments are carried out again at 12 weeks, 26 weeks and 52 weeks.

Patients assigned to the Compound 90 group will receive a dose twice a day for 12 weeks at increasing doses. Cognitive assessments for all patients are on the maximum dose. The placebo group will receive identical appearing capsules containing ascorbic acid (100 mg).

The cognitive battery includes measures of executive functioning, verbal skills, verbal and spatial working memory, attention and psychomotor speed. The battery is administered to all patients on all three occasions in the same fixed order (e.g., Mini-Mental State Examination (MMSE), MATRICS cognitive battery, BACS score, and Alzheimer's disease Assessment Scale—Cognitive Subscale (ADAS-Cog)). Patients are allowed to take breaks as needed in order to obtain maximal performance at all times. Tests are administered and scored by trained psychologists who are blind to patients' group affiliations and are not involved in patients' treatment plan in any way. Alzheimer's disease Cooperative Study-Activities of Daily Living (ADCS-ADL) is also recorded.

Patients are told that the aim of the study is to investigate the cognitive effects of Compound 90. They are requested to abstain from alcohol for at least 24 h prior to their scheduled cognitive testing.

The patients in the Compound 90 and placebo groups are compared on demographic, clinical, and cognitive variables obtained at baseline using independent sample 1-tests.

The effects of Compound 90 on Neuropsychological Test Battery and Neuropsychiatric Inventory (NPI) are analyzed (separately) by 2 (Treatment: Compound 90, placebo)×3 (Time: baseline, 12 weeks, 26 weeks, 52 weeks) analysis of variance (ANOVA).

All cognitive variables are first examined for their distribution properties, i.e., to ensure normality. The cognitive effects of Compound 90 over time are then evaluated by Treatment×Time ANOVA, performed separately for each variable, with Time as a within-individuals factor and Treatment as a between-individuals factor, followed by post-hoc mean comparisons wherever appropriate. All cognitive effects are then re-evaluated using ANOVA performed separately on change scores computed for each variable (12 weeks data minus baseline data, 26 weeks, 52 weeks data minus baseline data). Alpha level for testing significance of effects is $p=0.05$.

Primary outcome measure is an improvement in (ADAS-Cog) scores. Secondary outcome measures are improvement in (MMSE) socres and (ADCS-ADL).

Example 131

Pharmaceutical Compositions

Example 131a

Parenteral Composition

To prepare a parenteral pharmaceutical composition suitable for administration by injection, 100 mg of a water-soluble salt of a compound of Formula I-X is dissolved in DMSO and then mixed with 10 mL of 0.9% sterile saline. The mixture is incorporated into a dosage unit form suitable for administration by injection.

Example 131b

Oral Composition

To prepare a pharmaceutical composition for oral delivery, 100 mg of a compound of Formula I-X is mixed with 750 mg of starch. The mixture is incorporated into an oral dosage unit for, e.g., a hard gelatin capsule, which is suitable for oral administration.

Example 131c

Sublingual (Hard Lozenge) Composition

To prepare a pharmaceutical composition for buccal delivery, such as a hard lozenge, mix 100 mg of a compound of Formula I-X with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 131d

Fast-Disintegrating Sublingual Tablet

A fast-disintegrating sublingual tablet is prepared by mixing 48.5% by weigh of a compound of Formula I-X, 44.5% by weight of microcrystalline cellulose (KG-802), 5% by weight of low-substituted hydroxypropyl cellulose (50 μm), and 2% by weight of magnesium stearate. Tablets are prepared by direct compression (*AAPS PharmSciTech*. 2006; 7(2):E41). The total weight of the compressed tablets is maintained at 150 mg. The formulation is prepared by mixing the amount of compound of Formula I-X with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 131e

Inhalation Composition

To prepare a pharmaceutical composition for inhalation delivery, 20 mg of a compound of Formula I-X is mixed with 50 mg of anhydrous citric acid and 100 mL of 0.9% sodium chloride solution. The mixture is incorporated into an inhalation delivery unit, such as a nebulizer, which is suitable for inhalation administration.

Example 131f

Rectal Gel Composition

To prepare a pharmaceutical composition for rectal delivery, 100 mg of a compound of Formula I-X is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 131g

Topical Gel Composition

To prepare a pharmaceutical topical gel composition, 100 mg of a compound of Formula I-X is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 131h

Ophthalmic Solution Composition

To prepare a pharmaceutical opthalmic solution composition, 100 mg of a compound of Formula I-X is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 131i

Nasal Spray Solution

To prepare a pharmaceutical nasal spray solution, 10 g of a compound of Formula I-X is mixed with 30 mL of a 0.05M phosphate buffer solution (pH 4.4). The solution is placed in a nasal administrator designed to deliver 100 μl of spray for each application.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound having the structure of Formula X or a pharmaceutically acceptable salt thereof:

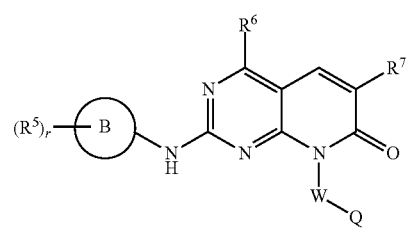

Formula X wherein:

W is a bond;

$R^6$ is H, halogen, —CN, —OH, substituted or unsubstituted alkyl, substituted or unsubstituted alkoxy, —N($R^{10}$)$_2$, substituted or unsubstituted heteroalkyl, substituted or unsubstituted cycloalkyl, substituted or unsubstituted aryl or substituted or unsubstituted heteroaryl;

$R^7$ is H, halogen, —CN, —OH, substituted or unsubstituted alkyl, substituted or unsubstituted alkoxy, —C(=O)N($R^{10}$)$_2$, —CO$_2$$R^{10}$, —N($R^{10}$)$_2$, acyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

Q is

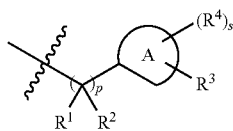

wherein $R^1$ and $R^2$ are each independently H or substituted or unsubstituted alkyl; or $R^1$ and $R^2$ together with the carbon to which they are attached form a $C_3$-$C_6$ cycloalkyl ring;

p is 1, 2 or 3;

ring A is aryl substituted with $R^3$ and $R^4$;

$R^3$ is a substituted or unsubstituted heteroaryl, substituted or unsubstituted cycloalkyl or substituted or unsubstituted heterocycloalkyl attached to ring A via a carbon atom;

each $R^4$ is independently halogen, —CN, —NO$_2$, —OH, —OCF$_3$, —OCF$_2$H, —CF$_3$, —SR$^8$, —S(=O)R$^9$, —S(=O)$_2$R$^9$, —NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$OC(=O)R$^{10}$, —N R$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl;

$R^8$ is H or substituted or unsubstituted alkyl;

$R^9$ is substituted or unsubstituted alkyl, substituted or unsubstituted cycloalkyl, substituted or unsubstituted aryl or substituted or unsubstituted heteroaryl each $R^{10}$ is independently H, substituted or unsubstituted alkyl, substituted or unsubstituted cycloalkyl, substituted or unsubstituted aryl or substituted or unsubstituted heteroaryl, or two $R^{10}$ together with the atoms to which they are attached form a heterocycle;

s is 0-4;

ring B is aryl or heteroaryl substituted with $R^5$;

wherein each $R^5$ is independently halogen, —CN, —NO$_2$, —OH, —SR$^8$, —S(=O)R$^9$, —S(=O)$_2$R$^9$, NR$^{10}$S(=O)$_2$R$^9$, —S(=O)$_2$N(R$^{10}$)$_2$, —C(=O)R$^9$, —OC(=O)R$^9$, —CO$_2$R$^{10}$, —N(R$^{10}$)$_2$, —C(=O)N(R$^{10}$)$_2$, —NR$^{10}$C(=O)R$^{10}$, —NR$^{10}$C(=O)OR$^{10}$, —NR$^{10}$C(=O)N(R$^{10}$)$_2$, substituted or unsubstituted alkyl, substituted or unsubstituted alkoxy, substituted or unsubstituted heteroalkyl, substituted or unsubstituted cycloalkyl or substituted or unsubstituted heterocycloalkyl; and r is 0-8.

2. The compound of claim 1 wherein Q is:

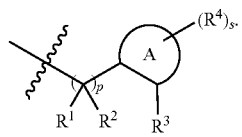

3. The compound of claim 1, wherein Q is

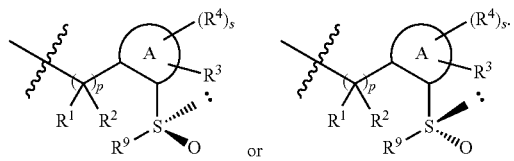

4. The compound of claim 1, wherein $R^3$ is a $C_3$-$C_6$ cycloalkyl ring, a 5-6-membered heteroaryl ring comprising 1-3 nitrogen atoms, an oxygen atom, a sulfur atom, or any combination thereof, or a 3-6-membered heterocycloalkyl ring comprising 1-3 nitrogen atoms, an oxygen atom, a sulfur atom, or any combination thereof, that is attached to ring via a carbon atom and wherein $R^3$ is further substituted by halogen, cyano, alkyl, alkoxy, —SR$^8$, (R) or (S)—S(O)R$^9$ or —S(O)$_2$R$^9$.

5. The compound of claim 4, wherein $R^1$ and $R^2$ are H.

6. The compound of claim 1, wherein variables B, $R^6$, $R^7$, and $R^5$, and substructure

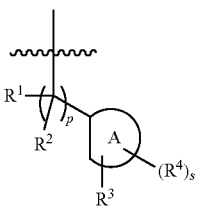

are each defined as shown in the following table:

301 302

| Entry | B | | R⁶ | R⁷ | R⁵ |
|---|---|---|---|---|---|
| 1 | phenyl | 2-isopropyl-6-cyclopropyl-phenyl with CHF₂ | H | OH | p-NH-CH₂CH₂C(CH₃)₂OH, m-F |
| 2 | phenyl | 4-isopropyl-3-(SCF₃)-phenyl with cyclopentyl | H | Me | p-morpholino |
| 3 | phenyl | 4-isopropyl-3-OCF₃-phenyl with azepane-NH | H | H | p-(4-methylpiperazin-1-yl) |
| 4 | phenyl | 2-isopropyl-phenyl with thiazol-5-yl | Cl | H | p-(morpholinobutyl), o-OMe |
| 5 | phenyl | 2-isopropyl-phenyl with 1-methylimidazol-5-yl | H | H | p-O-CH₂-(cyclopentyl)-CH₂OH, o-F |

-continued
| Entry | B | (structure with R¹, R², R³, A, R⁴) | R⁶ | R⁷ | R⁵ |
|---|---|---|---|---|---|
| 6 |  | 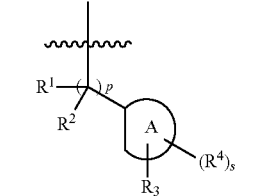 | H | H | 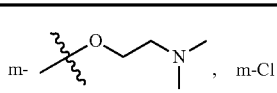 m-, m-Cl |
| 7 |  | 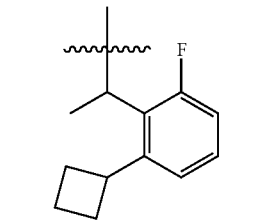 [SMILES: *C(C)c1c(F)cccc1C1CCC1] | H | CONH₂ | 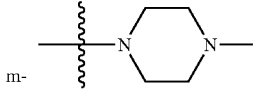 m- |
| 8 |  | 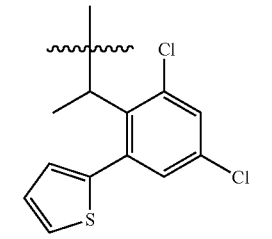 [SMILES: *C(C)c1c(Cl)cc(Cl)cc1-c1cccs1] | H | 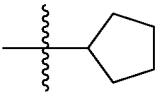 [SMILES: *C1CCCC1] | 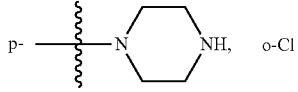 p-, o-Cl |
| 9 |  | 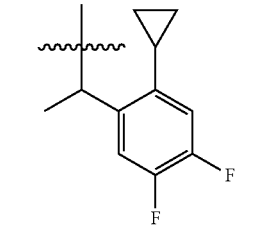 [SMILES: *C(C)c1cc(F)c(F)cc1C1CC1] | Cl | 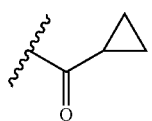 | 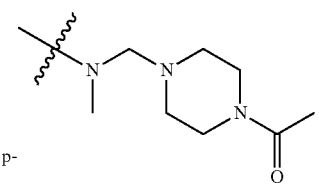 [SMILES: *N(C)CN1CCN(C(C)=O)CC1] p- |
| 10 |  | 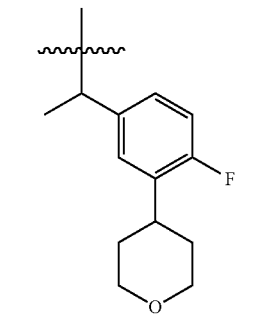 [SMILES: *C(C)c1ccc(F)c(C2CCOCC2)c1] | H | H | 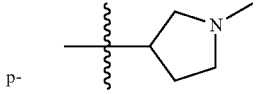 [SMILES: *C1CCN(C)C1] p- |

-continued
| Entry | B | | R⁶ | R⁷ | R⁵ |
|---|---|---|---|---|---|
| 11 |  | 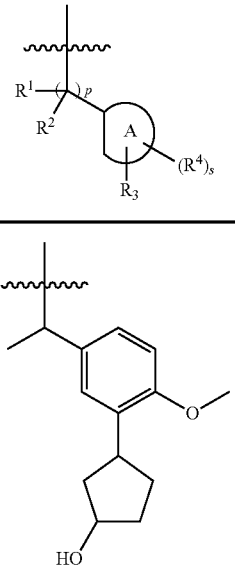 | H | Cl | 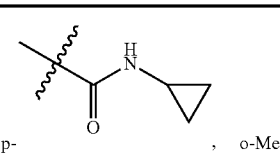 p-, o-Me |
| 12 |  | 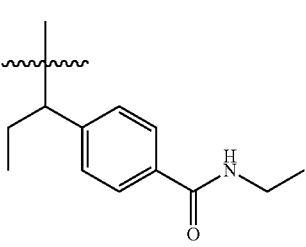 [SMILES: *C(CC)c1ccc(C(=O)NCC)cc1] | Me | H | 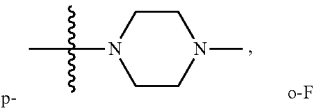 [SMILES: *N1CCN(C)CC1] p-, o-F |
| 13 |  | 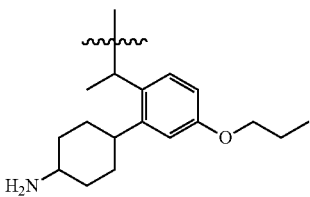 [SMILES: *C(C)c1ccc(OCCC)cc1C1CCC(N)CC1] | H | OMe | 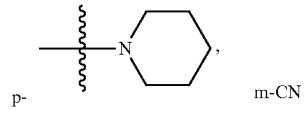 [SMILES: *N1CCCCC1] p-, m-CN |
| 14 |  | 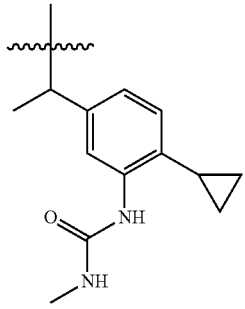 [SMILES: *C(C)c1ccc(C2CC2)c(NC(=O)NC)c1] | H | H | 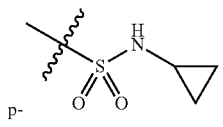 [SMILES: *S(=O)(=O)NC1CC1] p- |
| 15 |  | 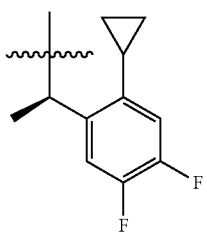 [SMILES: *[C@H](C)c1cc(F)c(F)cc1C1CC1] | H | CN | 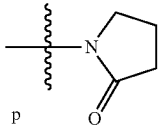 [SMILES: *N1CCCC1=O] p |

-continued
| Entry | B | | R⁶ | R⁷ | R⁵ |
|---|---|---|---|---|---|
| 16 | 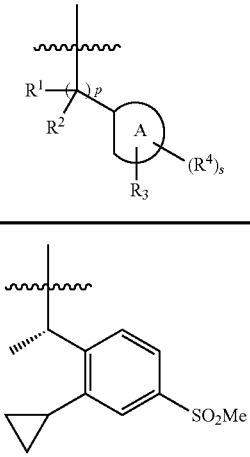 | 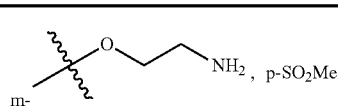 | H | H | , p-SO₂Me |
| 17 | 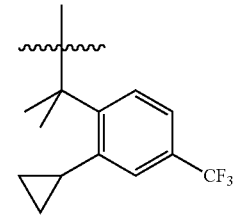 [SMILES: *C(C)(C)c1ccc(C(F)(F)F)cc1C1CC1] | 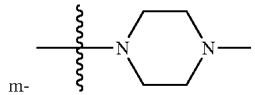 | H | isopropyl |  |
| 18 | 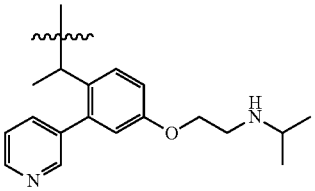 [SMILES: *C(C)c1ccc(OCCNC(C)C)cc1-c1cccnc1] |  | Cl | H | p-SO₂Me |
| 20 | 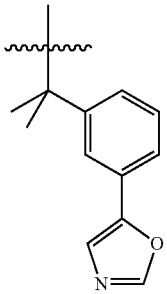 [SMILES: *C(C)(C)c1cccc(-c2cnco2)c1] | 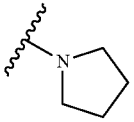 [SMILES: *N1CCCC1] | F | 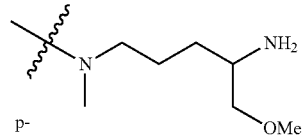 [SMILES: *N(C)CCCC(N)COC] |  |
| 21 | 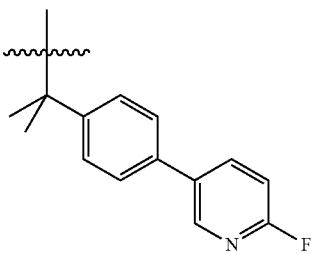 [SMILES: *C(C)(C)c1ccc(-c2ccc(F)nc2)cc1] | 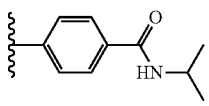 [SMILES: *c1ccc(C(=O)NC(C)C)cc1] | H | 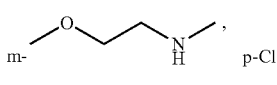 | p-Cl |

-continued

| Entry | B | R3 | R6 | R7 | R5 |
|---|---|---|---|---|---|
| 22 | phenyl | 7-isopropyl-3,5-dichloro-6-(4-methylsulfonylthien-2-yl)phenyl | H | 5-methylthien-2-yl, p- | 4-hydroxypiperidin-1-yl, o-Me |
| 23 | phenyl | 2-isopropyl-4,5-difluoro-(1H-1,2,4-triazol-3-yl)phenyl | H | H | N-phenylurea, m-OMe, p- |
| 24 | phenyl | 2-isopropyl-4,5-difluoro-(5-oxo-2,5-dihydro-1H-pyrrol-3-yl)phenyl | H | H | 1H-1,2,4-triazol-5-yl, p- | or a pharmaceutically acceptable salt thereof.

7. A compound selected from the group consisting of:

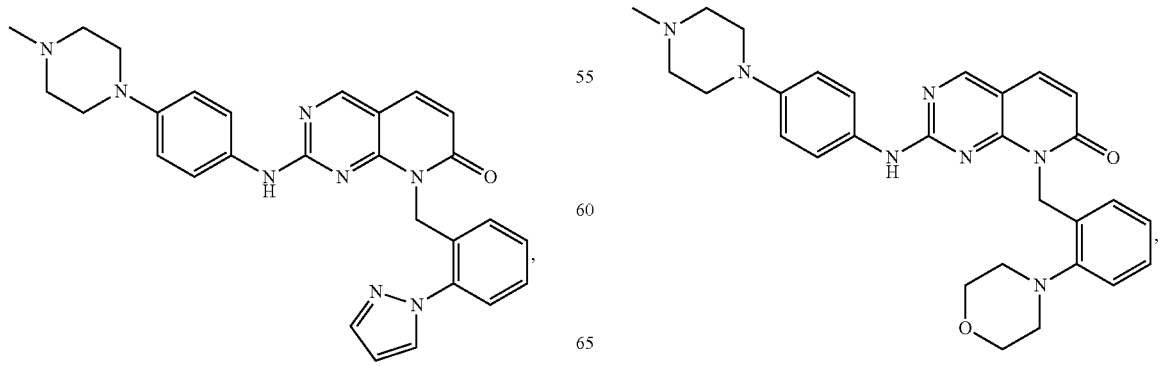

311
-continued
312
-continued
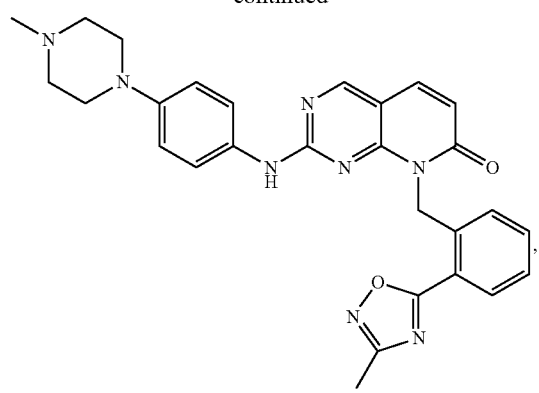
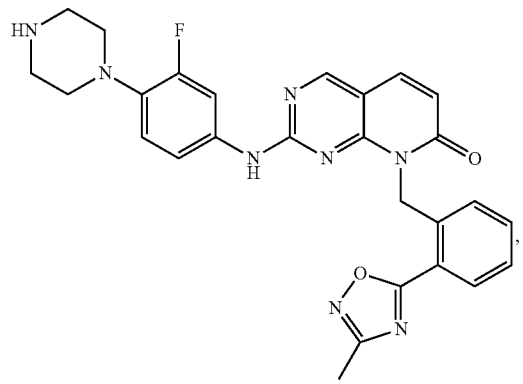
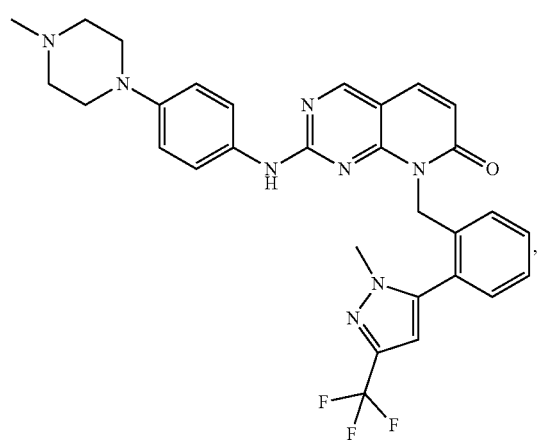
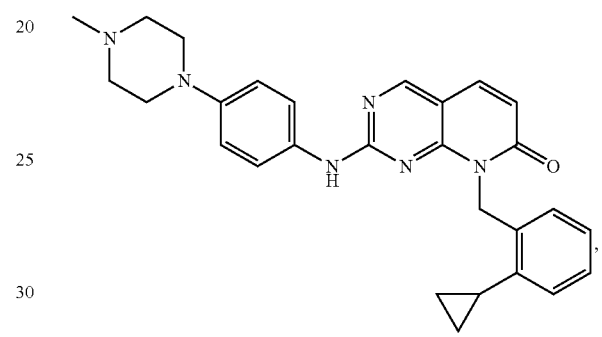
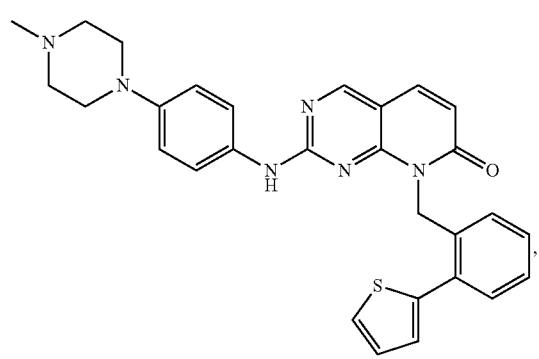
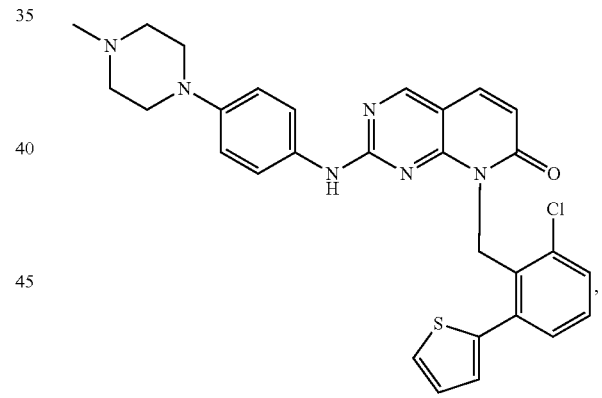
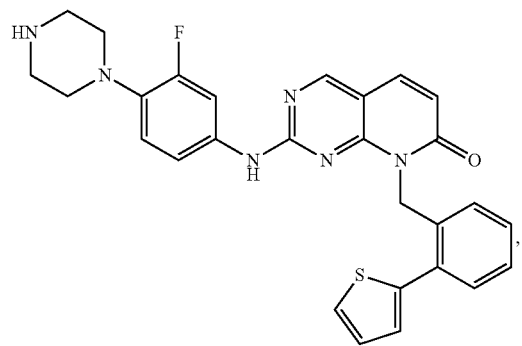
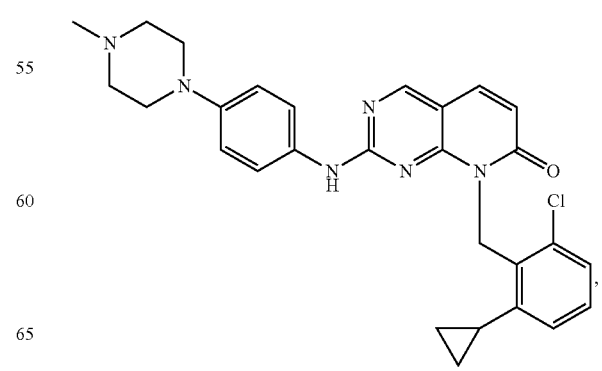

313
-continued
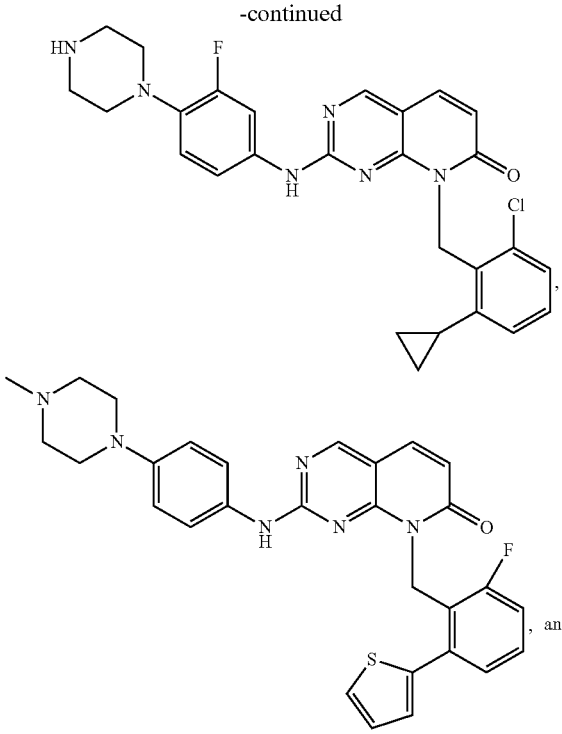
314
-continued
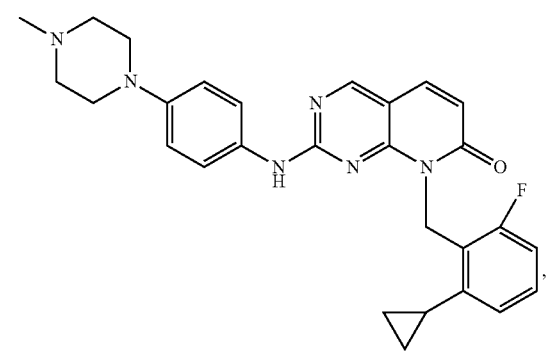
and pharmaceutically acceptable salts thereof.
* * * * *